United States Patent [19]
Beamer et al.

[11] Patent Number: 6,093,573
[45] Date of Patent: Jul. 25, 2000

[54] THREE-DIMENSIONAL STRUCTURE OF BACTERICIDAL/PERMEABILITY-INCREASING PROTEIN (BPI)

[75] Inventors: Lesa J. Beamer, Santa Monica; Stephen F. Carroll, Walnut Creek; David Eisenberg, Los Angeles, all of Calif.

[73] Assignees: XOMA, Berkeley; The Regents of the University of California, Oakland, both of Calif.

[21] Appl. No.: 08/879,565

[22] Filed: Jun. 20, 1997

[51] Int. Cl.[7] ................................................. G01N 33/48
[52] U.S. Cl. .............................. 436/86; 530/350; 702/19; 702/22
[58] Field of Search .............................. 436/86; 530/350; 702/19, 22

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/21 |
| 5,576,292 | 11/1996 | Elsbach et al. | 514/12 |
| 5,578,568 | 11/1996 | Ammons et al. | 514/12 |
| 5,578,572 | 11/1996 | Horwitz et al. | 514/12 |

(List continued on next page.)

FOREIGN PATENT DOCUMENTS

| | | |
|---|---|---|
| WO 89/01486 | 2/1989 | WIPO. |
| WO 90/09183 | 8/1990 | WIPO. |
| WO 92/03535 | 3/1992 | WIPO. |
| WO 92/09621 | 6/1992 | WIPO. |
| WO 93/05797 | 4/1993 | WIPO. |
| WO 93/06228 | 4/1993 | WIPO. |
| WO 93/23434 | 11/1993 | WIPO. |
| WO 93/23540 | 11/1993 | WIPO. |

(List continued on next page.)

OTHER PUBLICATIONS

Elsbach et al., "Oxygen–Independent Antimicrobial Systems of Phagocytes," *Inflammation: Basic Principles and Clinical Correlates*, eds. Gallin et al., Chapter 30, pp. 603–636, Raven Press, Ltd. (1992).

Elsbach et al., "Oxygen–Independent Bactericidal Systems of Polymorphonuclear Leukocytes," *Advances in Inflammation Research*, ed. G. Weissmann, vol. 2, pp. 95–113, Raven Press (1981).

(List continued on next page.)

*Primary Examiner*—Nashaat Nashed
*Attorney, Agent, or Firm*—McAndrews, Held & Malloy, Ltd.

[57] ABSTRACT

The present invention provides a crystallized Bactericidal Permeability-Increasing (BPI) protein; methods for x-ray diffraction analysis to provide x-ray diffraction patterns of sufficiently high resolution for three-dimensional structure determination of the protein, as well as methods for rational drug design, based on using amino acid sequence data and/or x-ray crystallography data provided on computer readable media, as analyzed on a computer system having suitable computer algorithms; and atomic coordinates are provided yielding structural information on the lipid binding and lipid transport protein family that includes BPI, LBP, CETP and PLTP.

6 Claims, 125 Drawing Sheets

(4 of 125 Drawing Sheet(s) Filed in Color)

U.S. PATENT DOCUMENTS

| | | | |
|---|---|---|---|
| 5,627,153 | 5/1997 | Little, II et al. | 514/12 |
| 5,639,727 | 6/1997 | Little, II | 514/12 |
| 5,641,874 | 6/1997 | Elsbach et al. | 536/23.1 |
| 5,643,570 | 7/1997 | Theofan et al. | 424/134.1 |
| 5,643,875 | 7/1997 | Friedmann et al. | 514/12 |
| 5,646,114 | 7/1997 | Lambert, Jr. | 514/12 |
| 5,652,332 | 7/1997 | Little, II | 530/324 |
| 5,674,834 | 10/1997 | Theofan et al. | 514/12 |
| 5,686,414 | 11/1997 | Scannon | 514/12 |
| 5,696,090 | 12/1997 | McGregor et al. | 514/12 |
| 5,703,038 | 12/1997 | Ammons et al. | 514/2 |
| 5,731,415 | 3/1998 | Gazzano-Santoro et al. | 530/350 |
| 5,733,872 | 3/1998 | Little, II | 514/12 |
| 5,741,779 | 4/1998 | White et al. | 514/12 |
| 5,753,620 | 5/1998 | Freidman | 514/12 |
| 5,756,464 | 5/1998 | Scannon et al. | 514/12 |
| 5,763,567 | 6/1998 | Little, II | 530/300 |
| 5,770,561 | 6/1998 | Horwitz et al. | 514/8 |
| 5,770,694 | 6/1998 | Scott et al. | 530/350 |
| 5,783,561 | 7/1998 | Horwitz et al. | 514/12 |
| 5,786,324 | 7/1998 | Gray et al. | 514/9 |
| 5,804,367 | 9/1998 | White et al. | 435/4 |
| 5,807,818 | 9/1998 | Little, II | 514/2 |
| 5,821,064 | 10/1998 | White et al. | 435/7.1 |
| 5,827,816 | 10/1998 | Theofan et al. | 514/2 |
| 5,830,860 | 11/1998 | Gray et al. | 514/12 |
| 5,837,678 | 11/1998 | Little, II | 514/12 |
| 5,851,802 | 12/1998 | Better | 435/69.7 |
| 5,854,214 | 12/1998 | Little, II | 514/12 |
| 5,856,302 | 1/1999 | Ammons et al. | 514/12 |
| 5,856,438 | 1/1999 | Little, II | 530/324 |
| 5,858,974 | 1/1999 | Little, II et al. | 514/12 |
| 5,888,973 | 3/1999 | Lambert | 514/12 |
| 5,888,977 | 3/1999 | Giroir et al. | 514/12 |
| 5,891,618 | 4/1999 | White et al. | 435/4 |
| 5,912,228 | 6/1999 | Lambert | 514/12 |
| 5,932,544 | 8/1999 | Grinna | 514/12 |
| 5,935,930 | 8/1999 | White et al. | 514/12 |
| 5,945,399 | 8/1999 | Scannon et al. | 514/12 |
| 5,952,302 | 9/1999 | Friedmann et al. | 514/12 |
| 5,955,427 | 9/1999 | McGregor et al. | 514/12 |

FOREIGN PATENT DOCUMENTS

| | | |
|---|---|---|
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| WO 94/21280 | 9/1994 | WIPO . |
| WO 94/25476 | 11/1994 | WIPO . |
| WO 95/00641 | 1/1995 | WIPO . |
| WO 95/01428 | 1/1995 | WIPO . |
| WO 95/02414 | 1/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |
| WO 95/19180 | 7/1995 | WIPO . |
| WO 95/19372 | 7/1995 | WIPO . |
| WO 95/19784 | 7/1995 | WIPO . |
| WO 95/20163 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |
| WO 96/30037 | 10/1996 | WIPO . |
| WO 96/34873 | 11/1996 | WIPO . |
| WO 97/04008 | 2/1997 | WIPO . |
| WO 97/17989 | 5/1997 | WIPO . |
| WO 97/17990 | 5/1997 | WIPO . |
| WO 97/35009 | 9/1997 | WIPO . |
| WO 97/42966 | 11/1997 | WIPO . |
| WO 97/42967 | 11/1997 | WIPO . |
| WO 97/44056 | 11/1997 | WIPO . |
| WO 98/06415 | 2/1998 | WIPO . |
| WO 98/19694 | 5/1998 | WIPO . |
| WO 98/58961 | 12/1998 | WIPO . |

OTHER PUBLICATIONS

Elsbach, et al., "Separation and Purification of a Potent Bactericidal/Permeability–Increasing Protein and a Closely Associated Phospholipase $A_2$ from Rabbit Polymorphonuclear Leukocytes," *J. Biol. Chem.*, 254(21):11000–11009 (Nov. 10, 1979).

Gazzano–Santoro, et al., "High–Affinity Binding of the Bactericidal/Permeability–Increasing Protein and a Recombinant Amino–Terminal Fragment to the Lipid A Region of Lipopolysaccharide," *Infect. Immun.*, 60:4754–4761 (Nov., 1992).

Gray, et al., "Cloning of the cDNA of a Human Neutrophil Bactericidal Protein," *J. Biol. Chem.*, 264(16):9505–9509 (Jun. 5, 1989).

In't Veld, et al., "Effects of the Bactericidal/Permeability–Increasing Protein of Polymorphonuclear Leukocytes on Isolated Bacterial Cytoplasmic Membrane Vesicles," *Infection and Immunity*, 56:1203–1208 (May, 1988).

Weiss et al., "Cellular and Subcellular Localization of the Bactericidal/Permeability Increasing Protein of Neutrophils," Blood, 69(2):652–659 (Feb. 1987).

Little, et al., "Functional Domains of Recombinant Bactericidal/Permeabilty Increasing Protein ($rBPI_{23}$)," *J. Biol. Chem.*), 269(3)1865–1872 (Jan. 21, 1994).

Mannion, et al., "Separation of Sublethal and Lethal Effects of the Bactericidal/Permeability Increasing Protein on *Escherichia coli*," *J. Clin. Invest.*, 85:853–860 (Mar., 1990).

Mannion, et al., "Separation of Sublethal and Lethal Effects of Polymorphonuclear Leukocytes on *Escherichia coli*," *J. Clin. Invest.* 86:631–641 (Aug., 1990).

Ooi, et al., "A 25–kDa $NH_2$–terminal Fragment Carries All the Antibacterial Activities of the Human Neutrophil 60–KDa Bactericidal/Permeability–increasing Protein," *J. Bio. Chem.*, 262:14891–14894 (1987).

Ooi, et al., "Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils," *J. Exp. Med.*, 174:649–655 (Sep., 1991).

Weiss, et al., "Resistance of Gram–negative Bacteria to Purified Bactericidal Leukocyte Proteins," *J. Clin. Invest.* 65:619–628 (Mar., 1980).

Weiss, et al., "The Role of Lipopolysaccharides in the Action of the Bactericidal/Permeability–Increasing Neutrophil Protein on the Bacterial Envelope," *J. Immunol. 132*:3109–3115 (1984).

Weiss, et al., "Human Bactericidal/ Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria," *J. Clin. Invest.*, 90:1122–1130 (Sep., 1992).

Beamer, et al., "Crystal Structure of BPI, The Human Bactericidal/Permeability–Increasing Protein," Abstract/Poster, Keystone Meeting, Jan. 1997, Park City, Utah.

Beamer, "Crystal Structure of BPI, the Human Bactericidal Permeability–Increasing Protein," Invited Speaker, West Coast Crystallography Workshop, Mar. 1997, Monterey, California.

Beamer, et al., "Crystal Structure of Human BPI and Two Bound Phospholipids at 2.4 Angstrom Resolution," *Science* 276:1861–1864 (Jun., 1997).

Beamer, et al., "The BPI/LBP family of proteins: A structural analysis of conserved regions," *Protein Sci.*, 7:906–914 (1998).

Beamer, et al., "Detecting distant relatives of mammalian LPS–binding and lipid transport proteins," *Protein Sci.*, 7:1643–1646 (1998).

Bruce, et al., "The implications of the structure of the bactericidal/permeability–increasing protein on the lipid–transfer function of the cholesteryl ester transfer protein," *Current Opinion in Struc. Biol.* 8:426–434 (1998).

Beamer, et al., "The Three–Dimensional Structure of Human Bactericidal/Permeability–Increasing Protein," *Biochem. Pharm,*, 57:225–229 (1999).

A

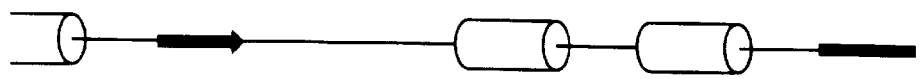

```
BPI   LVYQEAGVLKMTLRDDMIPKESKFRLTTKFFGT---FLPEVAKKFPNMKIQIHVS   319
LBP   LVYHEEGYLNFSITDDMIPPDSNIRLTTKSFRP---FVPRLARLYPNMNLELQGS   317
PLTP  ESYFRAGALQLLLVGDKVPHDLDMLLRATYFGS---IV-LLSPAVIDSPLKLELR   311
CETP  KVAFQDGRLMLSLMGD----EFKAVLETWGFNTNQEIFQEVVGGFPS-QAQVTVH   318
         .*    .  . .        .        .        .      .  ..
```

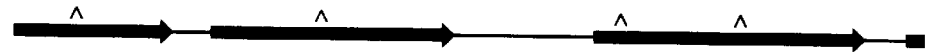

```
BPI   ASTPPHLSVQPTGLTFYPAVDVQAFAVLPNSSLASLFLIGMHTTGSMEVSAESNR
LBP   VPSAPLLNFSPGNLSVDPYMEIDAFVLLPSSSKEPVFRLSVATNVSATLTFNTSK
PLTP  VLAPPRCTIKPSGTTISVTASVTIALVPPDQPEVQLSSMTMDARLSAKMALRGKA
CETP  CLKMPKISCQNKGVVVNSSVMVKFLFPRPDQQHSVAYTFEEDIVTTVQASYSKKK
                             *
```

```
BPI   L-VGBLKLDRLLLELKHSNIGPFPVEL---------------LQDIMNYIVPI   411
LBP   I-TGFLKPGKVKVELKESKVGLFNAEL---------------LEALLNYYILN   409
PLTP  L-RTQLDLRRFRIYSNHSALESLALIP---------------LQAPLKTMLQI   403
CETP  LFLSLLDFQITP------------------KTVSNLTESSSESIQSFLQSMITA  409
         .    *                                  . ..  .
```

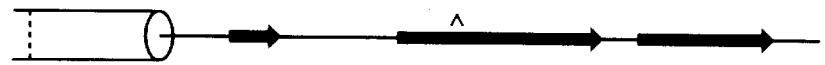

```
BPI   LVLPRVNEKLQKGF-PLPTPARVQLYNVV---LQPHQNFLLFGADVVYK------
LBP   TFYPKFNDKLAEGF-PLPLLKRVQLYDLG---LQIHKDFLFLGANVQYMR-----
PLTP  GVMPMLNERTWRGV-QIPLPEGINFVHEV---VTNHAGFLTIGADLHFAKGLREV
CETP  VGIPEVMSRLEVVFTALMNSKGVSLFDIINPEIITRDGFLLLQMDFGFPEHL--L
         *                             .  .   .     .    .
```

```
BPI   --------------------   456
LBP   -------------------V   456
PLTP  IEKNRPADVRASTAPTPSTAAV  476
CETP  VDFLQSLS------------   470
```

Fig. 5b

| ATOM | 1 | CB | VAL A | 1 | 95.942 | 11.564 | 18.390 | 1.00 | 51.23 |
| ATOM | 2 | CG1 | VAL A | 1 | 97.217 | 12.313 | 18.805 | 1.00 | 48.90 |
| ATOM | 3 | CG2 | VAL A | 1 | 94.694 | 12.383 | 18.720 | 1.00 | 50.67 |
| ATOM | 4 | C | VAL A | 1 | 96.124 | 12.502 | 16.083 | 1.00 | 47.46 |
| ATOM | 5 | O | VAL A | 1 | 97.238 | 12.990 | 15.911 | 1.00 | 49.54 |
| ATOM | 8 | N | VAL A | 1 | 97.161 | 10.372 | 16.554 | 1.00 | 51.03 |
| ATOM | 10 | CA | VAL A | 1 | 95.982 | 11.216 | 16.876 | 1.00 | 48.79 |
| ATOM | 11 | N | ASN A | 2 | 95.020 | 13.016 | 15.554 | 1.00 | 42.80 |
| ATOM | 13 | CA | ASN A | 2 | 95.067 | 14.266 | 14.810 | 1.00 | 38.18 |
| ATOM | 14 | CB | ASN A | 2 | 93.709 | 14.566 | 14.185 | 1.00 | 39.01 |
| ATOM | 15 | CG | ASN A | 2 | 93.494 | 13.831 | 12.892 | 1.00 | 40.06 |
| ATOM | 16 | OD1 | ASN A | 2 | 94.323 | 13.020 | 12.487 | 1.00 | 42.94 |
| ATOM | 17 | ND2 | ASN A | 2 | 92.380 | 14.108 | 12.228 | 1.00 | 39.49 |
| ATOM | 20 | C | ASN A | 2 | 95.439 | 15.376 | 15.786 | 1.00 | 34.97 |
| ATOM | 21 | O | ASN A | 2 | 94.946 | 15.399 | 16.916 | 1.00 | 37.36 |
| ATOM | 22 | N | PRO A | 3 | 96.373 | 16.260 | 15.397 | 1.00 | 30.80 |
| ATOM | 23 | CD | PRO A | 3 | 97.144 | 16.244 | 14.143 | 1.00 | 28.90 |
| ATOM | 24 | CA | PRO A | 3 | 96.806 | 17.367 | 16.252 | 1.00 | 28.19 |
| ATOM | 25 | CB | PRO A | 3 | 98.083 | 17.830 | 15.571 | 1.00 | 26.30 |
| ATOM | 26 | CG | PRO A | 3 | 97.765 | 17.619 | 14.128 | 1.00 | 26.17 |
| ATOM | 27 | C | PRO A | 3 | 95.765 | 18.482 | 16.283 | 1.00 | 28.00 |
| ATOM | 28 | O | PRO A | 3 | 95.104 | 18.758 | 15.275 | 1.00 | 28.89 |
| ATOM | 29 | N | GLY A | 4 | 95.615 | 19.108 | 17.444 | 1.00 | 26.31 |
| ATOM | 31 | CA | GLY A | 4 | 94.653 | 20.182 | 17.588 | 1.00 | 25.44 |
| ATOM | 32 | C | GLY A | 4 | 95.178 | 21.508 | 17.091 | 1.00 | 25.34 |
| ATOM | 33 | O | GLY A | 4 | 94.407 | 22.425 | 16.831 | 1.00 | 28.37 |
| ATOM | 34 | N | VAL A | 5 | 96.494 | 21.621 | 16.981 | 1.00 | 23.98 |
| ATOM | 36 | CA | VAL A | 5 | 97.134 | 22.842 | 16.519 | 1.00 | 21.80 |
| ATOM | 37 | CB | VAL A | 5 | 97.671 | 23.681 | 17.689 | 1.00 | 18.63 |
| ATOM | 38 | CG1 | VAL A | 5 | 98.573 | 24.785 | 17.171 | 1.00 | 20.04 |
| ATOM | 39 | CG2 | VAL A | 5 | 96.526 | 24.283 | 18.468 | 1.00 | 20.89 |
| ATOM | 40 | C | VAL A | 5 | 98.308 | 22.436 | 15.660 | 1.00 | 24.04 |
| ATOM | 41 | O | VAL A | 5 | 99.014 | 21.486 | 15.984 | 1.00 | 27.65 |
| ATOM | 42 | N | VAL A | 6 | 98.492 | 23.139 | 14.551 | 1.00 | 25.94 |

Figure 6

| | | | | | | | | | |
|---|---|---|---|---|---|---|---|---|---|
| ATOM | 44 | CA | VAL | A | 6 | 99.589 | 22.874 | 13.633 | 1.00 26.54 |
| ATOM | 45 | CB | VAL | A | 6 | 99.082 | 22.292 | 12.294 | 1.00 29.26 |
| ATOM | 46 | CG1 | VAL | A | 6 | 100.253 | 22.038 | 11.357 | 1.00 31.93 |
| ATOM | 47 | CG2 | VAL | A | 6 | 98.318 | 21.001 | 12.535 | 1.00 30.52 |
| ATOM | 48 | C | VAL | A | 6 | 100.289 | 24.191 | 13.355 | 1.00 24.99 |
| ATOM | 49 | O | VAL | A | 6 | 99.638 | 25.202 | 13.135 | 1.00 26.97 |
| ATOM | 50 | N | VAL | A | 7 | 101.611 | 24.183 | 13.416 | 1.00 26.91 |
| ATOM | 52 | CA | VAL | A | 7 | 102.404 | 25.371 | 13.156 | 1.00 27.18 |
| ATOM | 53 | CB | VAL | A | 7 | 103.401 | 25.637 | 14.298 | 1.00 27.59 |
| ATOM | 54 | CG1 | VAL | A | 7 | 104.343 | 26.773 | 13.925 | 1.00 27.21 |
| ATOM | 55 | CG2 | VAL | A | 7 | 102.659 | 25.967 | 15.575 | 1.00 27.05 |
| ATOM | 56 | C | VAL | A | 7 | 103.190 | 25.103 | 11.889 | 1.00 29.61 |
| ATOM | 57 | O | VAL | A | 7 | 103.863 | 24.084 | 11.777 | 1.00 32.24 |
| ATOM | 58 | N | ARG | A | 8 | 103.077 | 25.994 | 10.917 | 1.00 33.04 |
| ATOM | 60 | CA | ARG | A | 8 | 103.801 | 25.841 | 9.668 | 1.00 33.25 |
| ATOM | 61 | CB | ARG | A | 8 | 102.842 | 25.631 | 8.494 | 1.00 35.70 |
| ATOM | 62 | CG | ARG | A | 8 | 102.195 | 24.244 | 8.485 | 1.00 41.64 |
| ATOM | 63 | CD | ARG | A | 8 | 101.309 | 24.004 | 7.259 | 1.00 44.24 |
| ATOM | 64 | NE | ARG | A | 8 | 102.049 | 23.578 | 6.073 | 1.00 48.00 |
| ATOM | 66 | CZ | ARG | A | 8 | 101.565 | 23.626 | 4.835 | 1.00 51.86 |
| ATOM | 67 | NH1 | ARG | A | 8 | 100.341 | 24.091 | 4.611 | 1.00 52.72 |
| ATOM | 70 | NH2 | ARG | A | 8 | 102.293 | 23.177 | 3.820 | 1.00 53.10 |
| ATOM | 73 | C | ARG | A | 8 | 104.682 | 27.052 | 9.441 | 1.00 32.06 |
| ATOM | 74 | O | ARG | A | 8 | 104.196 | 28.168 | 9.288 | 1.00 32.62 |
| ATOM | 75 | N | ILE | A | 9 | 105.986 | 26.830 | 9.515 | 1.00 31.21 |
| ATOM | 77 | CA | ILE | A | 9 | 106.955 | 27.888 | 9.315 | 1.00 31.97 |
| ATOM | 78 | CB | ILE | A | 9 | 108.210 | 27.633 | 10.167 | 1.00 32.76 |
| ATOM | 79 | CG2 | ILE | A | 9 | 109.208 | 28.781 | 10.012 | 1.00 29.90 |
| ATOM | 80 | CG1 | ILE | A | 9 | 107.803 | 27.454 | 11.633 | 1.00 32.76 |
| ATOM | 81 | CD1 | ILE | A | 9 | 108.945 | 27.087 | 12.554 | 1.00 36.13 |
| ATOM | 82 | C | ILE | A | 9 | 107.309 | 27.889 | 7.832 | 1.00 34.24 |
| ATOM | 83 | O | ILE | A | 9 | 107.650 | 26.845 | 7.265 | 1.00 37.01 |
| ATOM | 84 | N | SER | A | 10 | 107.179 | 29.045 | 7.195 | 1.00 34.50 |
| ATOM | 86 | CA | SER | A | 10 | 107.473 | 29.173 | 5.774 | 1.00 33.98 |

| | | | | | | | | | |
|---|---|---|---|---|---|---|---|---|---|
| ATOM | 87 | CB | SER | A | 10 | 106.536 | 30.200 | 5.146 | 1.00 33.86 |
| ATOM | 88 | OG | SER | A | 10 | 106.778 | 31.488 | 5.679 | 1.00 36.26 |
| ATOM | 90 | C | SER | A | 10 | 108.922 | 29.563 | 5.500 | 1.00 32.91 |
| ATOM | 91 | O | SER | A | 10 | 109.674 | 29.886 | 6.416 | 1.00 33.57 |
| ATOM | 92 | N | GLN | A | 11 | 109.300 | 29.550 | 4.225 | 1.00 34.16 |
| ATOM | 94 | CA | GLN | A | 11 | 110.653 | 29.912 | 3.811 | 1.00 35.54 |
| ATOM | 95 | CB | GLN | A | 11 | 110.792 | 29.845 | 2.283 | 1.00 35.39 |
| ATOM | 96 | CG | GLN | A | 11 | 112.212 | 30.070 | 1.746 | 1.00 36.23 |
| ATOM | 97 | CD | GLN | A | 11 | 113.164 | 28.920 | 2.040 | 1.00 35.94 |
| ATOM | 98 | OE1 | GLN | A | 11 | 112.880 | 27.774 | 1.716 | 1.00 38.97 |
| ATOM | 99 | NE2 | GLN | A | 11 | 114.310 | 29.230 | 2.624 | 1.00 35.28 |
| ATOM | 102 | C | GLN | A | 11 | 110.991 | 31.312 | 4.316 | 1.00 36.60 |
| ATOM | 103 | O | GLN | A | 11 | 112.116 | 31.559 | 4.740 | 1.00 41.10 |
| ATOM | 104 | N | LYS | A | 12 | 110.013 | 32.216 | 4.305 | 1.00 35.51 |
| ATOM | 106 | CA | LYS | A | 12 | 110.245 | 33.573 | 4.788 | 1.00 31.96 |
| ATOM | 107 | CB | LYS | A | 12 | 109.005 | 34.445 | 4.612 | 1.00 32.24 |
| ATOM | 108 | CG | LYS | A | 12 | 109.226 | 35.876 | 5.065 | 1.00 32.71 |
| ATOM | 109 | CD | LYS | A | 12 | 107.953 | 36.685 | 5.063 | 1.00 31.87 |
| ATOM | 110 | CE | LYS | A | 12 | 108.227 | 38.085 | 5.573 | 1.00 34.67 |
| ATOM | 111 | NZ | LYS | A | 12 | 106.998 | 38.914 | 5.627 | 1.00 37.88 |
| ATOM | 115 | C | LYS | A | 12 | 110.612 | 33.498 | 6.259 | 1.00 30.93 |
| ATOM | 116 | O | LYS | A | 12 | 111.482 | 34.227 | 6.728 | 1.00 32.37 |
| ATOM | 117 | N | GLY | A | 13 | 109.961 | 32.586 | 6.973 | 1.00 30.47 |
| ATOM | 119 | CA | GLY | A | 13 | 110.231 | 32.407 | 8.385 | 1.00 27.64 |
| ATOM | 120 | C | GLY | A | 13 | 111.593 | 31.791 | 8.610 | 1.00 29.49 |
| ATOM | 121 | O | GLY | A | 13 | 112.312 | 32.184 | 9.531 | 1.00 30.35 |
| ATOM | 122 | N | LEU | A | 14 | 111.952 | 30.817 | 7.779 | 1.00 28.87 |
| ATOM | 124 | CA | LEU | A | 14 | 113.248 | 30.170 | 7.912 | 1.00 28.53 |
| ATOM | 125 | CB | LEU | A | 14 | 113.361 | 28.941 | 7.011 | 1.00 25.60 |
| ATOM | 126 | CG | LEU | A | 14 | 112.564 | 27.698 | 7.419 | 1.00 25.99 |
| ATOM | 127 | CD1 | LEU | A | 14 | 112.959 | 26.547 | 6.531 | 1.00 28.34 |
| ATOM | 128 | CD2 | LEU | A | 14 | 112.829 | 27.330 | 8.855 | 1.00 23.90 |
| ATOM | 129 | C | LEU | A | 14 | 114.359 | 31.155 | 7.613 | 1.00 28.63 |
| ATOM | 130 | O | LEU | A | 14 | 115.346 | 31.207 | 8.335 | 1.00 31.86 |

Page 6-A-2

| ATOM | 131 | N | ASP | A | 15 | 114.176 | 31.972 | 6.582 | 1.00 | 31.30 |
|------|-----|-----|-----|---|----|---------|--------|-------|------|-------|
| ATOM | 133 | CA | ASP | A | 15 | 115.176 | 32.975 | 6.215 | 1.00 | 33.98 |
| ATOM | 134 | CB | ASP | A | 15 | 114.695 | 33.832 | 5.033 | 1.00 | 36.03 |
| ATOM | 135 | CG | ASP | A | 15 | 114.818 | 33.127 | 3.681 | 1.00 | 36.52 |
| ATOM | 136 | OD1 | ASP | A | 15 | 115.662 | 32.209 | 3.515 | 1.00 | 37.01 |
| ATOM | 137 | OD2 | ASP | A | 15 | 114.071 | 33.530 | 2.765 | 1.00 | 36.25 |
| ATOM | 138 | C | ASP | A | 15 | 115.473 | 33.882 | 7.413 | 1.00 | 35.08 |
| ATOM | 139 | O | ASP | A | 15 | 116.626 | 34.246 | 7.654 | 1.00 | 37.07 |
| ATOM | 140 | N | TYR | A | 16 | 114.433 | 34.244 | 8.162 | 1.00 | 34.55 |
| ATOM | 142 | CA | TYR | A | 16 | 114.598 | 35.098 | 9.337 | 1.00 | 34.48 |
| ATOM | 143 | CB | TYR | A | 16 | 113.239 | 35.554 | 9.865 | 1.00 | 34.89 |
| ATOM | 144 | CG | TYR | A | 16 | 113.320 | 36.661 | 10.891 | 1.00 | 35.28 |
| ATOM | 145 | CD1 | TYR | A | 16 | 113.859 | 37.905 | 10.562 | 1.00 | 36.36 |
| ATOM | 146 | CE1 | TYR | A | 16 | 113.921 | 38.936 | 11.496 | 1.00 | 34.26 |
| ATOM | 147 | CD2 | TYR | A | 16 | 112.846 | 36.474 | 12.182 | 1.00 | 33.51 |
| ATOM | 148 | CE2 | TYR | A | 16 | 112.903 | 37.498 | 13.118 | 1.00 | 34.97 |
| ATOM | 149 | CZ | TYR | A | 16 | 113.440 | 38.724 | 12.767 | 1.00 | 34.08 |
| ATOM | 150 | OH | TYR | A | 16 | 113.491 | 39.733 | 13.697 | 1.00 | 37.78 |
| ATOM | 152 | C | TYR | A | 16 | 115.348 | 34.340 | 10.427 | 1.00 | 35.46 |
| ATOM | 153 | O | TYR | A | 16 | 116.240 | 34.883 | 11.074 | 1.00 | 36.90 |
| ATOM | 154 | N | ALA | A | 17 | 114.982 | 33.081 | 10.625 | 1.00 | 36.20 |
| ATOM | 156 | CA | ALA | A | 17 | 115.632 | 32.250 | 11.617 | 1.00 | 35.77 |
| ATOM | 157 | CB | ALA | A | 17 | 115.025 | 30.870 | 11.615 | 1.00 | 33.78 |
| ATOM | 158 | C | ALA | A | 17 | 117.118 | 32.180 | 11.293 | 1.00 | 37.85 |
| ATOM | 159 | O | ALA | A | 17 | 117.957 | 32.330 | 12.178 | 1.00 | 40.31 |
| ATOM | 160 | N | SER | A | 18 | 117.447 | 32.008 | 10.017 | 1.00 | 39.36 |
| ATOM | 162 | CA | SER | A | 18 | 118.846 | 31.927 | 9.612 | 1.00 | 42.40 |
| ATOM | 163 | CB | SER | A | 18 | 118.993 | 31.399 | 8.175 | 1.00 | 43.78 |
| ATOM | 164 | OG | SER | A | 18 | 118.220 | 32.127 | 7.236 | 1.00 | 48.26 |
| ATOM | 166 | C | SER | A | 18 | 119.605 | 33.238 | 9.786 | 1.00 | 42.53 |
| ATOM | 167 | O | SER | A | 18 | 120.768 | 33.228 | 10.178 | 1.00 | 44.52 |
| ATOM | 168 | N | GLN | A | 19 | 118.959 | 34.367 | 9.509 | 1.00 | 42.42 |
| ATOM | 170 | CA | GLN | A | 19 | 119.630 | 35.652 | 9.665 | 1.00 | 42.67 |
| ATOM | 171 | CB | GLN | A | 19 | 118.805 | 36.806 | 9.089 | 1.00 | 47.13 |

| ATOM | 172 | CG | GLN A | 19 | 118.810 | 36.864 | 7.563 | 1.00 | 57.52 |
| ATOM | 173 | CD | GLN A | 19 | 118.457 | 38.238 | 7.012 | 1.00 | 62.74 |
| ATOM | 174 | OE1 | GLN A | 19 | 117.488 | 38.866 | 7.440 | 1.00 | 65.88 |
| ATOM | 175 | NE2 | GLN A | 19 | 119.248 | 38.710 | 6.051 | 1.00 | 64.58 |
| ATOM | 178 | C | GLN A | 19 | 119.943 | 35.906 | 11.126 | 1.00 | 40.97 |
| ATOM | 179 | O | GLN A | 19 | 121.030 | 36.378 | 11.456 | 1.00 | 41.85 |
| ATOM | 180 | N | GLN A | 20 | 119.008 | 35.565 | 12.005 | 1.00 | 39.51 |
| ATOM | 182 | CA | GLN A | 20 | 119.226 | 35.759 | 13.430 | 1.00 | 37.61 |
| ATOM | 183 | CB | GLN A | 20 | 117.944 | 35.507 | 14.228 | 1.00 | 38.26 |
| ATOM | 184 | CG | GLN A | 20 | 116.764 | 36.405 | 13.874 | 1.00 | 38.33 |
| ATOM | 185 | CD | GLN A | 20 | 117.057 | 37.895 | 14.002 | 1.00 | 41.17 |
| ATOM | 186 | OE1 | GLN A | 20 | 116.912 | 38.642 | 13.040 | 1.00 | 43.42 |
| ATOM | 187 | NE2 | GLN A | 20 | 117.441 | 38.335 | 15.192 | 1.00 | 42.94 |
| ATOM | 190 | C | GLN A | 20 | 120.325 | 34.805 | 13.878 | 1.00 | 36.56 |
| ATOM | 191 | O | GLN A | 20 | 121.208 | 35.176 | 14.654 | 1.00 | 38.07 |
| ATOM | 192 | N | GLY A | 21 | 120.285 | 33.587 | 13.348 | 1.00 | 36.41 |
| ATOM | 194 | CA | GLY A | 21 | 121.276 | 32.585 | 13.688 | 1.00 | 33.84 |
| ATOM | 195 | C | GLY A | 21 | 122.665 | 33.023 | 13.289 | 1.00 | 34.61 |
| ATOM | 196 | O | GLY A | 21 | 123.520 | 33.199 | 14.140 | 1.00 | 36.02 |
| ATOM | 197 | N | THR A | 22 | 122.879 | 33.221 | 11.994 | 1.00 | 35.98 |
| ATOM | 199 | CA | THR A | 22 | 124.174 | 33.645 | 11.462 | 1.00 | 39.75 |
| ATOM | 200 | CB | THR A | 22 | 124.036 | 34.109 | 9.983 | 1.00 | 41.34 |
| ATOM | 201 | OG1 | THR A | 22 | 123.400 | 33.082 | 9.212 | 1.00 | 40.97 |
| ATOM | 203 | CG2 | THR A | 22 | 125.397 | 34.408 | 9.377 | 1.00 | 40.54 |
| ATOM | 204 | C | THR A | 22 | 124.780 | 34.785 | 12.285 | 1.00 | 40.46 |
| ATOM | 205 | O | THR A | 22 | 125.954 | 34.741 | 12.667 | 1.00 | 41.11 |
| ATOM | 206 | N | ALA A | 23 | 123.959 | 35.787 | 12.578 | 1.00 | 41.75 |
| ATOM | 208 | CA | ALA A | 23 | 124.387 | 36.944 | 13.351 | 1.00 | 41.89 |
| ATOM | 209 | CB | ALA A | 23 | 123.224 | 37.895 | 13.567 | 1.00 | 40.51 |
| ATOM | 210 | C | ALA A | 23 | 124.919 | 36.461 | 14.678 | 1.00 | 43.71 |
| ATOM | 211 | O | ALA A | 23 | 125.992 | 36.872 | 15.114 | 1.00 | 47.24 |
| ATOM | 212 | N | ALA A | 24 | 124.175 | 35.554 | 15.298 | 1.00 | 43.71 |
| ATOM | 214 | CA | ALA A | 24 | 124.570 | 34.991 | 16.574 | 1.00 | 43.02 |
| ATOM | 215 | CB | ALA A | 24 | 123.413 | 34.238 | 17.185 | 1.00 | 43.37 |

Page 6-A-4

| ATOM | 216 | C | ALA | A | 24 | 125.774 | 34.069 | 16.396 | 1.00 | 42.93 |
| --- | --- | --- | --- | --- | --- | --- | --- | --- | --- | --- |
| ATOM | 217 | O | ALA | A | 24 | 126.549 | 33.868 | 17.328 | 1.00 | 45.41 |
| ATOM | 218 | N | LEU | A | 25 | 125.944 | 33.532 | 15.193 | 1.00 | 41.61 |
| ATOM | 220 | CA | LEU | A | 25 | 127.056 | 32.638 | 14.910 | 1.00 | 40.32 |
| ATOM | 221 | CB | LEU | A | 25 | 126.746 | 31.755 | 13.699 | 1.00 | 36.89 |
| ATOM | 222 | CG | LEU | A | 25 | 127.662 | 30.554 | 13.483 | 1.00 | 34.95 |
| ATOM | 223 | CD1 | LEU | A | 25 | 127.636 | 29.653 | 14.703 | 1.00 | 34.64 |
| ATOM | 224 | CD2 | LEU | A | 25 | 127.218 | 29.797 | 12.262 | 1.00 | 35.16 |
| ATOM | 225 | C | LEU | A | 25 | 128.331 | 33.438 | 14.676 | 1.00 | 40.69 |
| ATOM | 226 | O | LEU | A | 25 | 129.423 | 32.984 | 15.014 | 1.00 | 42.61 |
| ATOM | 227 | N | GLN | A | 26 | 128.194 | 34.644 | 14.138 | 1.00 | 41.51 |
| ATOM | 229 | CA | GLN | A | 26 | 129.352 | 35.494 | 13.878 | 1.00 | 45.29 |
| ATOM | 230 | CB | GLN | A | 26 | 128.920 | 36.850 | 13.317 | 1.00 | 46.09 |
| ATOM | 231 | CG | GLN | A | 26 | 130.087 | 37.811 | 13.108 | 1.00 | 48.70 |
| ATOM | 232 | CD | GLN | A | 26 | 129.650 | 39.240 | 12.861 | 1.00 | 50.15 |
| ATOM | 233 | OE1 | GLN | A | 26 | 129.833 | 40.115 | 13.708 | 1.00 | 51.16 |
| ATOM | 234 | NE2 | GLN | A | 26 | 129.078 | 39.489 | 11.692 | 1.00 | 51.55 |
| ATOM | 237 | C | GLN | A | 26 | 130.175 | 35.728 | 15.145 | 1.00 | 46.79 |
| ATOM | 238 | O | GLN | A | 26 | 131.403 | 35.587 | 15.136 | 1.00 | 46.74 |
| ATOM | 239 | N | LYS | A | 27 | 129.488 | 36.081 | 16.230 | 1.00 | 48.40 |
| ATOM | 241 | CA | LYS | A | 27 | 130.140 | 36.355 | 17.509 | 1.00 | 50.23 |
| ATOM | 242 | CB | LYS | A | 27 | 129.119 | 36.696 | 18.595 | 1.00 | 52.58 |
| ATOM | 243 | CG | LYS | A | 27 | 128.157 | 37.818 | 18.249 | 1.00 | 55.93 |
| ATOM | 244 | CD | LYS | A | 27 | 127.495 | 38.391 | 19.503 | 1.00 | 59.98 |
| ATOM | 245 | CE | LYS | A | 27 | 126.959 | 37.306 | 20.437 | 1.00 | 63.01 |
| ATOM | 246 | NZ | LYS | A | 27 | 125.911 | 36.452 | 19.807 | 1.00 | 66.76 |
| ATOM | 250 | C | LYS | A | 27 | 130.983 | 35.186 | 17.977 | 1.00 | 50.39 |
| ATOM | 251 | O | LYS | A | 27 | 132.121 | 35.369 | 18.398 | 1.00 | 52.00 |
| ATOM | 252 | N | GLU | A | 28 | 130.421 | 33.984 | 17.920 | 1.00 | 50.09 |
| ATOM | 254 | CA | GLU | A | 28 | 131.157 | 32.803 | 18.341 | 1.00 | 48.77 |
| ATOM | 255 | CB | GLU | A | 28 | 130.250 | 31.571 | 18.390 | 1.00 | 48.51 |
| ATOM | 256 | CG | GLU | A | 28 | 129.514 | 31.395 | 19.713 | 1.00 | 50.95 |
| ATOM | 257 | CD | GLU | A | 28 | 130.436 | 30.999 | 20.857 | 1.00 | 52.82 |
| ATOM | 258 | OE1 | GLU | A | 28 | 130.687 | 29.789 | 21.030 | 1.00 | 55.51 |

Page 6-A-5

| | | | | | | | | | |
|---|---|---|---|---|---|---|---|---|---|
| ATOM | 259 | OE2 | GLU | A | 28 | 130.903 | 31.891 | 21.594 | 1.00 54.60 |
| ATOM | 260 | C | GLU | A | 28 | 132.343 | 32.564 | 17.421 | 1.00 46.96 |
| ATOM | 261 | O | GLU | A | 28 | 133.407 | 32.153 | 17.871 | 1.00 49.87 |
| ATOM | 262 | N | LEU | A | 29 | 132.177 | 32.868 | 16.140 | 1.00 43.03 |
| ATOM | 264 | CA | LEU | A | 29 | 133.257 | 32.674 | 15.189 | 1.00 39.75 |
| ATOM | 265 | CB | LEU | A | 29 | 132.740 | 32.817 | 13.763 | 1.00 36.79 |
| ATOM | 266 | CG | LEU | A | 29 | 131.832 | 31.658 | 13.360 | 1.00 33.73 |
| ATOM | 267 | CD1 | LEU | A | 29 | 131.557 | 31.708 | 11.870 | 1.00 34.40 |
| ATOM | 268 | CD2 | LEU | A | 29 | 132.499 | 30.347 | 13.720 | 1.00 31.01 |
| ATOM | 269 | C | LEU | A | 29 | 134.431 | 33.610 | 15.444 | 1.00 38.40 |
| ATOM | 270 | O | LEU | A | 29 | 135.584 | 33.204 | 15.348 | 1.00 38.06 |
| ATOM | 271 | N | LYS | A | 30 | 134.131 | 34.843 | 15.828 | 1.00 38.44 |
| ATOM | 273 | CA | LYS | A | 30 | 135.155 | 35.845 | 16.111 | 1.00 40.67 |
| ATOM | 274 | CB | LYS | A | 30 | 134.495 | 37.225 | 16.210 | 1.00 41.05 |
| ATOM | 275 | CG | LYS | A | 30 | 135.448 | 38.409 | 16.270 | 1.00 43.32 |
| ATOM | 276 | CD | LYS | A | 30 | 134.690 | 39.733 | 16.198 | 1.00 44.53 |
| ATOM | 277 | CE | LYS | A | 30 | 135.633 | 40.926 | 16.343 | 1.00 46.81 |
| ATOM | 278 | NZ | LYS | A | 30 | 134.912 | 42.238 | 16.331 | 1.00 50.27 |
| ATOM | 282 | C | LYS | A | 30 | 135.955 | 35.539 | 17.388 | 1.00 42.29 |
| ATOM | 283 | O | LYS | A | 30 | 136.979 | 36.166 | 17.654 | 1.00 42.94 |
| ATOM | 284 | N | ARG | A | 31 | 135.495 | 34.565 | 18.168 | 1.00 44.02 |
| ATOM | 286 | CA | ARG | A | 31 | 136.162 | 34.190 | 19.411 | 1.00 44.45 |
| ATOM | 287 | CB | ARG | A | 31 | 135.139 | 34.005 | 20.534 | 1.00 46.86 |
| ATOM | 288 | CG | ARG | A | 31 | 134.504 | 35.305 | 20.983 | 1.00 52.93 |
| ATOM | 289 | CD | ARG | A | 31 | 133.479 | 35.095 | 22.078 | 1.00 60.04 |
| ATOM | 290 | NE | ARG | A | 31 | 132.947 | 36.372 | 22.554 | 1.00 67.90 |
| ATOM | 292 | CZ | ARG | A | 31 | 131.839 | 36.505 | 23.279 | 1.00 71.80 |
| ATOM | 293 | NH1 | ARG | A | 31 | 131.128 | 35.437 | 23.621 | 1.00 74.30 |
| ATOM | 296 | NH2 | ARG | A | 31 | 131.444 | 37.710 | 23.672 | 1.00 73.67 |
| ATOM | 299 | C | ARG | A | 31 | 137.008 | 32.937 | 19.276 | 1.00 44.41 |
| ATOM | 300 | O | ARG | A | 31 | 137.339 | 32.293 | 20.273 | 1.00 46.21 |
| ATOM | 301 | N | ILE | A | 32 | 137.343 | 32.581 | 18.041 | 1.00 44.30 |
| ATOM | 303 | CA | ILE | A | 32 | 138.162 | 31.404 | 17.783 | 1.00 42.96 |
| ATOM | 304 | CB | ILE | A | 32 | 138.054 | 30.953 | 16.308 | 1.00 39.50 |

Page 6-A-6

| | | | | | | | | | |
|---|---|---|---|---|---|---|---|---|---|
| ATOM | 305 | CG2 | ILE | A | 32 | 139.146 | 29.950 | 15.973 | 1.00 36.12 |
| ATOM | 306 | CG1 | ILE | A | 32 | 136.674 | 30.351 | 16.052 | 1.00 37.18 |
| ATOM | 307 | CD1 | ILE | A | 32 | 136.431 | 29.975 | 14.624 | 1.00 37.20 |
| ATOM | 308 | C | ILE | A | 32 | 139.613 | 31.707 | 18.103 | 1.00 44.44 |
| ATOM | 309 | O | ILE | A | 32 | 140.109 | 32.794 | 17.798 | 1.00 45.60 |
| ATOM | 310 | N | LYS | A | 33 | 140.288 | 30.747 | 18.725 | 1.00 45.45 |
| ATOM | 312 | CA | LYS | A | 33 | 141.692 | 30.917 | 19.060 | 1.00 46.20 |
| ATOM | 313 | CB | LYS | A | 33 | 141.958 | 30.569 | 20.522 | 1.00 49.33 |
| ATOM | 314 | CG | LYS | A | 33 | 141.336 | 31.546 | 21.492 | 1.00 52.41 |
| ATOM | 315 | CD | LYS | A | 33 | 141.910 | 31.387 | 22.885 | 1.00 56.15 |
| ATOM | 316 | CE | LYS | A | 33 | 143.374 | 31.789 | 22.918 | 1.00 59.63 |
| ATOM | 317 | NZ | LYS | A | 33 | 143.891 | 31.817 | 24.313 | 1.00 63.31 |
| ATOM | 321 | C | LYS | A | 33 | 142.619 | 30.115 | 18.153 | 1.00 44.41 |
| ATOM | 322 | O | LYS | A | 33 | 142.563 | 28.884 | 18.102 | 1.00 42.99 |
| ATOM | 323 | N | ILE | A | 34 | 143.442 | 30.836 | 17.408 | 1.00 43.49 |
| ATOM | 325 | CA | ILE | A | 34 | 144.411 | 30.231 | 16.512 | 1.00 43.47 |
| ATOM | 326 | CB | ILE | A | 34 | 144.452 | 30.958 | 15.159 | 1.00 41.93 |
| ATOM | 327 | CG2 | ILE | A | 34 | 143.322 | 30.464 | 14.280 | 1.00 41.39 |
| ATOM | 328 | CG1 | ILE | A | 34 | 144.347 | 32.470 | 15.363 | 1.00 42.97 |
| ATOM | 329 | CD1 | ILE | A | 34 | 143.967 | 33.234 | 14.108 | 1.00 44.59 |
| ATOM | 330 | C | ILE | A | 34 | 145.761 | 30.288 | 17.216 | 1.00 44.81 |
| ATOM | 331 | O | ILE | A | 34 | 146.142 | 31.319 | 17.778 | 1.00 46.96 |
| ATOM | 332 | N | PRO | A | 35 | 146.464 | 29.151 | 17.267 | 1.00 43.85 |
| ATOM | 333 | CD | PRO | A | 35 | 146.008 | 27.862 | 16.728 | 1.00 44.63 |
| ATOM | 334 | CA | PRO | A | 35 | 147.773 | 29.003 | 17.904 | 1.00 42.65 |
| ATOM | 335 | CB | PRO | A | 35 | 148.109 | 27.534 | 17.650 | 1.00 42.05 |
| ATOM | 336 | CG | PRO | A | 35 | 146.778 | 26.887 | 17.578 | 1.00 44.72 |
| ATOM | 337 | C | PRO | A | 35 | 148.860 | 29.899 | 17.334 | 1.00 43.14 |
| ATOM | 338 | O | PRO | A | 35 | 148.649 | 30.640 | 16.376 | 1.00 44.26 |
| ATOM | 339 | N | ASP | A | 36 | 150.026 | 29.827 | 17.959 | 1.00 42.32 |
| ATOM | 341 | CA | ASP | A | 36 | 151.181 | 30.584 | 17.535 | 1.00 41.85 |
| ATOM | 342 | CB | ASP | A | 36 | 151.933 | 31.125 | 18.745 | 1.00 43.04 |
| ATOM | 343 | CG | ASP | A | 36 | 151.155 | 32.196 | 19.485 | 1.00 45.33 |
| ATOM | 344 | OD1 | ASP | A | 36 | 150.120 | 32.666 | 18.959 | 1.00 49.40 |

| | | | | | | | | | |
|---|---|---|---|---|---|---|---|---|---|
| ATOM | 345 | OD2 | ASP | A | 36 | 151.591 | 32.584 | 20.588 | 1.00 46.99 |
| ATOM | 346 | C | ASP | A | 36 | 152.051 | 29.612 | 16.776 | 1.00 42.29 |
| ATOM | 347 | O | ASP | A | 36 | 152.175 | 28.450 | 17.159 | 1.00 43.32 |
| ATOM | 348 | N | TYR | A | 37 | 152.637 | 30.077 | 15.687 | 1.00 42.04 |
| ATOM | 350 | CA | TYR | A | 37 | 153.476 | 29.228 | 14.877 | 1.00 41.59 |
| ATOM | 351 | CB | TYR | A | 37 | 152.979 | 29.243 | 13.436 | 1.00 42.04 |
| ATOM | 352 | CG | TYR | A | 37 | 151.564 | 28.743 | 13.327 | 1.00 43.15 |
| ATOM | 353 | CD1 | TYR | A | 37 | 151.295 | 27.378 | 13.256 | 1.00 42.32 |
| ATOM | 354 | CE1 | TYR | A | 37 | 149.991 | 26.904 | 13.239 | 1.00 43.09 |
| ATOM | 355 | CD2 | TYR | A | 37 | 150.487 | 29.626 | 13.370 | 1.00 44.59 |
| ATOM | 356 | CE2 | TYR | A | 37 | 149.175 | 29.161 | 13.354 | 1.00 43.64 |
| ATOM | 357 | CZ | TYR | A | 37 | 148.938 | 27.799 | 13.291 | 1.00 42.12 |
| ATOM | 358 | OH | TYR | A | 37 | 147.651 | 27.327 | 13.307 | 1.00 43.31 |
| ATOM | 360 | C | TYR | A | 37 | 154.923 | 29.649 | 14.957 | 1.00 42.22 |
| ATOM | 361 | O | TYR | A | 37 | 155.311 | 30.692 | 14.443 | 1.00 43.15 |
| ATOM | 362 | N | SER | A | 38 | 155.714 | 28.833 | 15.634 | 1.00 44.23 |
| ATOM | 364 | CA | SER | A | 38 | 157.130 | 29.088 | 15.789 | 1.00 47.19 |
| ATOM | 365 | CB | SER | A | 38 | 157.466 | 29.330 | 17.257 | 1.00 47.44 |
| ATOM | 366 | OG | SER | A | 38 | 156.651 | 30.356 | 17.799 | 1.00 54.54 |
| ATOM | 368 | C | SER | A | 38 | 157.887 | 27.878 | 15.285 | 1.00 48.36 |
| ATOM | 369 | O | SER | A | 38 | 157.664 | 26.761 | 15.746 | 1.00 49.57 |
| ATOM | 370 | N | ASP | A | 39 | 158.773 | 28.103 | 14.327 | 1.00 50.18 |
| ATOM | 372 | CA | ASP | A | 39 | 159.569 | 27.030 | 13.763 | 1.00 52.06 |
| ATOM | 373 | CB | ASP | A | 39 | 158.822 | 26.402 | 12.579 | 1.00 53.01 |
| ATOM | 374 | CG | ASP | A | 39 | 159.375 | 25.043 | 12.179 | 1.00 54.91 |
| ATOM | 375 | OD1 | ASP | A | 39 | 159.569 | 24.178 | 13.063 | 1.00 54.67 |
| ATOM | 376 | OD2 | ASP | A | 39 | 159.600 | 24.837 | 10.969 | 1.00 56.72 |
| ATOM | 377 | C | ASP | A | 39 | 160.912 | 27.631 | 13.334 | 1.00 53.93 |
| ATOM | 378 | O | ASP | A | 39 | 161.100 | 28.853 | 13.384 | 1.00 54.67 |
| ATOM | 379 | N | SER | A | 40 | 161.868 | 26.771 | 13.003 | 1.00 54.19 |
| ATOM | 381 | CA | SER | A | 40 | 163.187 | 27.208 | 12.577 | 1.00 52.94 |
| ATOM | 382 | CB | SER | A | 40 | 164.255 | 26.307 | 13.202 | 1.00 52.97 |
| ATOM | 383 | OG | SER | A | 40 | 163.996 | 24.934 | 12.947 | 1.00 53.27 |
| ATOM | 385 | C | SER | A | 40 | 163.283 | 27.163 | 11.057 | 1.00 54.32 |

Page 6-A-8

| | | | | | | | | |
|---|---|---|---|---|---|---|---|---|
| ATOM | 386 | O | SER | A | 40 | 162.394 | 26.623 | 10.386 | 1.00 54.83 |
| ATOM | 387 | N | PHE | A | 41 | 164.358 | 27.730 | 10.516 | 1.00 55.12 |
| ATOM | 389 | CA | PHE | A | 41 | 164.580 | 27.742 | 9.074 | 1.00 55.04 |
| ATOM | 390 | CB | PHE | A | 41 | 163.908 | 28.967 | 8.424 | 1.00 50.91 |
| ATOM | 391 | CG | PHE | A | 41 | 164.564 | 30.285 | 8.756 | 1.00 46.23 |
| ATOM | 392 | CD1 | PHE | A | 41 | 165.720 | 30.695 | 8.092 | 1.00 44.94 |
| ATOM | 393 | CD2 | PHE | A | 41 | 164.019 | 31.124 | 9.719 | 1.00 44.37 |
| ATOM | 394 | CE1 | PHE | A | 41 | 166.321 | 31.918 | 8.386 | 1.00 43.85 |
| ATOM | 395 | CE2 | PHE | A | 41 | 164.614 | 32.350 | 10.018 | 1.00 43.51 |
| ATOM | 396 | CZ | PHE | A | 41 | 165.765 | 32.746 | 9.351 | 1.00 42.57 |
| ATOM | 397 | C | PHE | A | 41 | 166.071 | 27.724 | 8.756 | 1.00 56.75 |
| ATOM | 398 | O | PHE | A | 41 | 166.904 | 27.935 | 9.637 | 1.00 58.20 |
| ATOM | 399 | N | LYS | A | 42 | 166.391 | 27.455 | 7.496 | 1.00 59.71 |
| ATOM | 401 | CA | LYS | A | 42 | 167.768 | 27.427 | 7.010 | 1.00 63.27 |
| ATOM | 402 | CB | LYS | A | 42 | 168.474 | 26.129 | 7.425 | 1.00 64.98 |
| ATOM | 403 | CG | LYS | A | 42 | 169.984 | 26.140 | 7.215 | 1.00 68.46 |
| ATOM | 404 | CD | LYS | A | 42 | 170.706 | 25.591 | 8.449 | 1.00 70.94 |
| ATOM | 405 | CE | LYS | A | 42 | 172.227 | 25.630 | 8.298 | 1.00 71.66 |
| ATOM | 406 | NZ | LYS | A | 42 | 172.928 | 25.300 | 9.582 | 1.00 71.11 |
| ATOM | 410 | C | LYS | A | 42 | 167.706 | 27.552 | 5.487 | 1.00 64.24 |
| ATOM | 411 | O | LYS | A | 42 | 167.585 | 26.555 | 4.773 | 1.00 65.07 |
| ATOM | 412 | N | ILE | A | 43 | 167.725 | 28.792 | 5.003 | 1.00 64.98 |
| ATOM | 414 | CA | ILE | A | 43 | 167.652 | 29.070 | 3.570 | 1.00 64.79 |
| ATOM | 415 | CB | ILE | A | 43 | 166.721 | 30.282 | 3.282 | 1.00 65.08 |
| ATOM | 416 | CG2 | ILE | A | 43 | 166.731 | 30.617 | 1.796 | 1.00 66.08 |
| ATOM | 417 | CG1 | ILE | A | 43 | 165.293 | 29.965 | 3.745 | 1.00 64.11 |
| ATOM | 418 | CD1 | ILE | A | 43 | 164.284 | 31.071 | 3.478 | 1.00 65.50 |
| ATOM | 419 | C | ILE | A | 43 | 169.039 | 29.291 | 2.956 | 1.00 64.78 |
| ATOM | 420 | O | ILE | A | 43 | 169.840 | 30.079 | 3.465 | 1.00 65.23 |
| ATOM | 421 | N | LYS | A | 44 | 169.273 | 28.631 | 1.825 | 1.00 64.51 |
| ATOM | 423 | CA | LYS | A | 44 | 170.539 | 28.672 | 1.093 | 1.00 63.65 |
| ATOM | 424 | CB | LYS | A | 44 | 170.328 | 28.232 | -0.360 | 1.00 63.66 |
| ATOM | 425 | CG | LYS | A | 44 | 170.066 | 26.742 | -0.553 | 1.00 63.81 |
| ATOM | 426 | CD | LYS | A | 44 | 170.064 | 26.396 | -2.035 | 1.00 65.27 |

Page 6-A-9

| | | | | | | | | |
|---|---|---|---|---|---|---|---|---|
| ATOM | 427 | CE | LYS A | 44 | 169.910 | 24.905 | -2.289 | 1.00 65.86 |
| ATOM | 428 | NZ | LYS A | 44 | 169.953 | 24.599 | -3.751 | 1.00 66.87 |
| ATOM | 432 | C | LYS A | 44 | 171.382 | 29.947 | 1.115 | 1.00 63.16 |
| ATOM | 433 | O | LYS A | 44 | 172.600 | 29.876 | 1.274 | 1.00 65.20 |
| ATOM | 434 | N | HIS A | 45 | 170.769 | 31.107 | 0.929 | 1.00 61.08 |
| ATOM | 436 | CA | HIS A | 45 | 171.550 | 32.339 | 0.920 | 1.00 61.08 |
| ATOM | 437 | CB | HIS A | 45 | 171.454 | 33.017 | -0.447 | 1.00 64.62 |
| ATOM | 438 | CG | HIS A | 45 | 172.039 | 32.214 | -1.565 | 1.00 68.00 |
| ATOM | 439 | CD2 | HIS A | 45 | 171.695 | 32.126 | -2.871 | 1.00 68.82 |
| ATOM | 440 | ND1 | HIS A | 45 | 173.124 | 31.380 | -1.397 | 1.00 70.18 |
| ATOM | 442 | CE1 | HIS A | 45 | 173.425 | 30.815 | -2.552 | 1.00 71.24 |
| ATOM | 443 | NE2 | HIS A | 45 | 172.572 | 31.250 | -3.462 | 1.00 70.61 |
| ATOM | 445 | C | HIS A | 45 | 171.167 | 33.337 | 1.994 | 1.00 59.87 |
| ATOM | 446 | O | HIS A | 45 | 171.609 | 34.486 | 1.960 | 1.00 60.80 |
| ATOM | 447 | N | LEU A | 46 | 170.345 | 32.900 | 2.940 | 1.00 57.18 |
| ATOM | 449 | CA | LEU A | 46 | 169.881 | 33.767 | 4.012 | 1.00 53.69 |
| ATOM | 450 | CB | LEU A | 46 | 168.362 | 33.699 | 4.103 | 1.00 53.23 |
| ATOM | 451 | CG | LEU A | 46 | 167.715 | 34.609 | 5.135 | 1.00 51.73 |
| ATOM | 452 | CD1 | LEU A | 46 | 167.712 | 36.039 | 4.628 | 1.00 52.65 |
| ATOM | 453 | CD2 | LEU A | 46 | 166.310 | 34.126 | 5.390 | 1.00 51.01 |
| ATOM | 454 | C | LEU A | 46 | 170.490 | 33.336 | 5.330 | 1.00 52.64 |
| ATOM | 455 | O | LEU A | 46 | 170.908 | 34.168 | 6.136 | 1.00 52.10 |
| ATOM | 456 | N | GLY A | 47 | 170.513 | 32.026 | 5.550 | 1.00 51.88 |
| ATOM | 458 | CA | GLY A | 47 | 171.081 | 31.486 | 6.768 | 1.00 51.77 |
| ATOM | 459 | C | GLY A | 47 | 170.107 | 30.643 | 7.564 | 1.00 51.44 |
| ATOM | 460 | O | GLY A | 47 | 169.059 | 30.235 | 7.065 | 1.00 50.21 |
| ATOM | 461 | N | LYS A | 48 | 170.484 | 30.357 | 8.802 | 1.00 52.15 |
| ATOM | 463 | CA | LYS A | 48 | 169.664 | 29.572 | 9.711 | 1.00 52.12 |
| ATOM | 464 | CB | LYS A | 48 | 170.497 | 28.479 | 10.407 | 1.00 56.73 |
| ATOM | 465 | CG | LYS A | 48 | 171.878 | 28.907 | 10.938 | 1.00 62.50 |
| ATOM | 466 | CD | LYS A | 48 | 172.953 | 28.876 | 9.843 | 1.00 65.46 |
| ATOM | 467 | CE | LYS A | 48 | 174.332 | 29.252 | 10.380 | 1.00 66.23 |
| ATOM | 468 | NZ | LYS A | 48 | 175.380 | 29.178 | 9.318 | 1.00 65.64 |
| ATOM | 472 | C | LYS A | 48 | 169.041 | 30.510 | 10.738 | 1.00 49.63 |

Page 6-A-10

| | | | | | | | | |
|---|---|---|---|---|---|---|---|---|
| ATOM | 473 | O | LYS | A | 48 | 169.632 | 31.533 | 11.101 | 1.00 48.85 |
| ATOM | 474 | N | GLY | A | 49 | 167.846 | 30.174 | 11.200 | 1.00 46.79 |
| ATOM | 476 | CA | GLY | A | 49 | 167.197 | 31.026 | 12.169 | 1.00 47.22 |
| ATOM | 477 | C | GLY | A | 49 | 165.918 | 30.449 | 12.728 | 1.00 47.47 |
| ATOM | 478 | O | GLY | A | 49 | 165.594 | 29.285 | 12.506 | 1.00 46.51 |
| ATOM | 479 | N | HIS | A | 50 | 165.166 | 31.292 | 13.420 | 1.00 47.82 |
| ATOM | 481 | CA | HIS | A | 50 | 163.922 | 30.886 | 14.041 | 1.00 48.80 |
| ATOM | 482 | CB | HIS | A | 50 | 164.126 | 30.793 | 15.554 | 1.00 58.27 |
| ATOM | 483 | CG | HIS | A | 50 | 163.658 | 29.505 | 16.155 | 1.00 68.69 |
| ATOM | 484 | CD2 | HIS | A | 50 | 164.349 | 28.453 | 16.657 | 1.00 72.98 |
| ATOM | 485 | ND1 | HIS | A | 50 | 162.324 | 29.196 | 16.311 | 1.00 73.69 |
| ATOM | 487 | CE1 | HIS | A | 50 | 162.212 | 28.010 | 16.885 | 1.00 76.58 |
| ATOM | 488 | NE2 | HIS | A | 50 | 163.426 | 27.539 | 17.105 | 1.00 77.46 |
| ATOM | 490 | C | HIS | A | 50 | 162.905 | 31.965 | 13.742 | 1.00 45.89 |
| ATOM | 491 | O | HIS | A | 50 | 163.149 | 33.137 | 14.019 | 1.00 41.84 |
| ATOM | 492 | N | TYR | A | 51 | 161.785 | 31.585 | 13.143 | 1.00 46.60 |
| ATOM | 494 | CA | TYR | A | 51 | 160.746 | 32.555 | 12.824 | 1.00 48.52 |
| ATOM | 495 | CB | TYR | A | 51 | 160.308 | 32.420 | 11.354 | 1.00 50.04 |
| ATOM | 496 | CG | TYR | A | 51 | 159.360 | 31.280 | 11.098 | 1.00 51.79 |
| ATOM | 497 | CD1 | TYR | A | 51 | 157.987 | 31.449 | 11.266 | 1.00 53.21 |
| ATOM | 498 | CE1 | TYR | A | 51 | 157.111 | 30.396 | 11.103 | 1.00 56.71 |
| ATOM | 499 | CD2 | TYR | A | 51 | 159.833 | 30.021 | 10.745 | 1.00 52.56 |
| ATOM | 500 | CE2 | TYR | A | 51 | 158.959 | 28.955 | 10.573 | 1.00 56.44 |
| ATOM | 501 | CZ | TYR | A | 51 | 157.597 | 29.149 | 10.761 | 1.00 58.01 |
| ATOM | 502 | OH | TYR | A | 51 | 156.717 | 28.094 | 10.649 | 1.00 60.76 |
| ATOM | 504 | C | TYR | A | 51 | 159.566 | 32.330 | 13.763 | 1.00 47.31 |
| ATOM | 505 | O | TYR | A | 51 | 159.485 | 31.291 | 14.424 | 1.00 47.36 |
| ATOM | 506 | N | SER | A | 52 | 158.648 | 33.288 | 13.812 | 1.00 46.53 |
| ATOM | 508 | CA | SER | A | 52 | 157.480 | 33.163 | 14.669 | 1.00 43.69 |
| ATOM | 509 | CB | SER | A | 52 | 157.862 | 33.449 | 16.123 | 1.00 43.87 |
| ATOM | 510 | OG | SER | A | 52 | 156.759 | 33.233 | 16.986 | 1.00 42.88 |
| ATOM | 512 | C | SER | A | 52 | 156.344 | 34.083 | 14.253 | 1.00 41.60 |
| ATOM | 513 | O | SER | A | 52 | 156.558 | 35.261 | 13.981 | 1.00 42.86 |
| ATOM | 514 | N | PHE | A | 53 | 155.152 | 33.513 | 14.132 | 1.00 39.20 |

Page 6-A-11

| | | | | | | | | | |
|---|---|---|---|---|---|---|---|---|---|
| ATOM | 516 | CA | PHE | A | 53 | 153.944 | 34.260 | 13.796 | 1.00 36.73 |
| ATOM | 517 | CB | PHE | A | 53 | 153.310 | 33.737 | 12.507 | 1.00 33.91 |
| ATOM | 518 | CG | PHE | A | 53 | 154.107 | 34.054 | 11.271 | 1.00 32.26 |
| ATOM | 519 | CD1 | PHE | A | 53 | 154.039 | 35.311 | 10.691 | 1.00 31.58 |
| ATOM | 520 | CD2 | PHE | A | 53 | 154.912 | 33.092 | 10.682 | 1.00 30.53 |
| ATOM | 521 | CE1 | PHE | A | 53 | 154.759 | 35.603 | 9.545 | 1.00 30.85 |
| ATOM | 522 | CE2 | PHE | A | 53 | 155.637 | 33.373 | 9.533 | 1.00 30.45 |
| ATOM | 523 | CZ | PHE | A | 53 | 155.559 | 34.631 | 8.964 | 1.00 30.49 |
| ATOM | 524 | C | PHE | A | 53 | 153.071 | 33.965 | 15.006 | 1.00 35.40 |
| ATOM | 525 | O | PHE | A | 53 | 152.746 | 32.814 | 15.276 | 1.00 34.75 |
| ATOM | 526 | N | TYR | A | 54 | 152.720 | 34.998 | 15.757 | 1.00 34.80 |
| ATOM | 528 | CA | TYR | A | 54 | 151.960 | 34.798 | 16.974 | 1.00 37.29 |
| ATOM | 529 | CB | TYR | A | 54 | 152.947 | 34.533 | 18.103 | 1.00 39.38 |
| ATOM | 530 | CG | TYR | A | 54 | 153.841 | 35.721 | 18.375 | 1.00 42.01 |
| ATOM | 531 | CD1 | TYR | A | 54 | 154.782 | 36.139 | 17.437 | 1.00 42.10 |
| ATOM | 532 | CE1 | TYR | A | 54 | 155.552 | 37.270 | 17.649 | 1.00 40.85 |
| ATOM | 533 | CD2 | TYR | A | 54 | 153.703 | 36.467 | 19.541 | 1.00 43.83 |
| ATOM | 534 | CE2 | TYR | A | 54 | 154.472 | 37.600 | 19.763 | 1.00 43.33 |
| ATOM | 535 | CZ | TYR | A | 54 | 155.391 | 37.995 | 18.811 | 1.00 42.17 |
| ATOM | 536 | OH | TYR | A | 54 | 156.139 | 39.126 | 19.018 | 1.00 46.33 |
| ATOM | 538 | C | TYR | A | 54 | 151.100 | 35.990 | 17.362 | 1.00 38.69 |
| ATOM | 539 | O | TYR | A | 54 | 151.072 | 37.007 | 16.672 | 1.00 41.66 |
| ATOM | 540 | N | SER | A | 55 | 150.430 | 35.858 | 18.505 | 1.00 40.04 |
| ATOM | 542 | CA | SER | A | 55 | 149.562 | 36.894 | 19.056 | 1.00 40.41 |
| ATOM | 543 | CB | SER | A | 55 | 150.407 | 38.091 | 19.499 | 1.00 41.89 |
| ATOM | 544 | OG | SER | A | 55 | 149.708 | 38.923 | 20.409 | 1.00 46.68 |
| ATOM | 546 | C | SER | A | 55 | 148.489 | 37.318 | 18.051 | 1.00 41.35 |
| ATOM | 547 | O | SER | A | 55 | 148.115 | 38.492 | 17.973 | 1.00 40.80 |
| ATOM | 548 | N | MET | A | 56 | 147.984 | 36.346 | 17.299 | 1.00 42.39 |
| ATOM | 550 | CA | MET | A | 56 | 146.968 | 36.606 | 16.292 | 1.00 43.64 |
| ATOM | 551 | CB | MET | A | 56 | 146.996 | 35.513 | 15.225 | 1.00 42.07 |
| ATOM | 552 | CG | MET | A | 56 | 148.310 | 35.414 | 14.475 | 1.00 39.09 |
| ATOM | 553 | SD | MET | A | 56 | 148.335 | 34.056 | 13.289 | 1.00 41.60 |
| ATOM | 554 | CE | MET | A | 56 | 149.266 | 32.847 | 14.209 | 1.00 36.68 |

Page 6-A-12

| ATOM | 555 | C   | MET | A | 56 | 145.580 | 36.708 | 16.910 | 1.00 | 46.06 |
| ATOM | 556 | O   | MET | A | 56 | 145.222 | 35.928 | 17.794 | 1.00 | 48.27 |
| ATOM | 557 | N   | ASP | A | 57 | 144.820 | 37.700 | 16.463 | 1.00 | 47.20 |
| ATOM | 559 | CA  | ASP | A | 57 | 143.466 | 37.930 | 16.941 | 1.00 | 47.94 |
| ATOM | 560 | CB  | ASP | A | 57 | 143.408 | 39.167 | 17.848 | 1.00 | 52.70 |
| ATOM | 561 | CG  | ASP | A | 57 | 143.578 | 38.831 | 19.324 | 1.00 | 58.73 |
| ATOM | 562 | OD1 | ASP | A | 57 | 142.552 | 38.587 | 19.999 | 1.00 | 62.99 |
| ATOM | 563 | OD2 | ASP | A | 57 | 144.729 | 38.835 | 19.818 | 1.00 | 59.77 |
| ATOM | 564 | C   | ASP | A | 57 | 142.566 | 38.151 | 15.736 | 1.00 | 46.86 |
| ATOM | 565 | O   | ASP | A | 57 | 143.001 | 38.684 | 14.712 | 1.00 | 44.98 |
| ATOM | 566 | N   | ILE | A | 58 | 141.324 | 37.699 | 15.843 | 1.00 | 45.46 |
| ATOM | 568 | CA  | ILE | A | 58 | 140.356 | 37.872 | 14.773 | 1.00 | 45.28 |
| ATOM | 569 | CB  | ILE | A | 58 | 139.232 | 36.822 | 14.869 | 1.00 | 42.99 |
| ATOM | 570 | CG2 | ILE | A | 58 | 138.200 | 37.052 | 13.782 | 1.00 | 41.93 |
| ATOM | 571 | CG1 | ILE | A | 58 | 139.825 | 35.415 | 14.744 | 1.00 | 42.15 |
| ATOM | 572 | CD1 | ILE | A | 58 | 138.803 | 34.306 | 14.802 | 1.00 | 41.09 |
| ATOM | 573 | C   | ILE | A | 58 | 139.783 | 39.277 | 14.936 | 1.00 | 47.07 |
| ATOM | 574 | O   | ILE | A | 58 | 139.271 | 39.615 | 15.999 | 1.00 | 48.46 |
| ATOM | 575 | N   | ARG | A | 59 | 139.945 | 40.116 | 13.918 | 1.00 | 49.05 |
| ATOM | 577 | CA  | ARG | A | 59 | 139.441 | 41.486 | 13.973 | 1.00 | 51.28 |
| ATOM | 578 | CB  | ARG | A | 59 | 140.435 | 42.459 | 13.326 | 1.00 | 53.21 |
| ATOM | 579 | CG  | ARG | A | 59 | 141.760 | 42.590 | 14.062 | 1.00 | 55.13 |
| ATOM | 580 | CD  | ARG | A | 59 | 141.578 | 43.175 | 15.453 | 1.00 | 59.25 |
| ATOM | 581 | NE  | ARG | A | 59 | 142.833 | 43.178 | 16.202 | 1.00 | 63.13 |
| ATOM | 583 | CZ  | ARG | A | 59 | 142.981 | 43.681 | 17.424 | 1.00 | 66.00 |
| ATOM | 584 | NH1 | ARG | A | 59 | 141.950 | 44.231 | 18.054 | 1.00 | 68.47 |
| ATOM | 587 | NH2 | ARG | A | 59 | 144.164 | 43.631 | 18.022 | 1.00 | 67.15 |
| ATOM | 590 | C   | ARG | A | 59 | 138.066 | 41.627 | 13.322 | 1.00 | 52.12 |
| ATOM | 591 | O   | ARG | A | 59 | 137.256 | 42.456 | 13.746 | 1.00 | 54.45 |
| ATOM | 592 | N   | GLU | A | 60 | 137.823 | 40.857 | 12.265 | 1.00 | 52.91 |
| ATOM | 594 | CA  | GLU | A | 60 | 136.538 | 40.878 | 11.570 | 1.00 | 52.94 |
| ATOM | 595 | CB  | GLU | A | 60 | 136.492 | 41.944 | 10.476 | 1.00 | 55.28 |
| ATOM | 596 | CG  | GLU | A | 60 | 135.133 | 41.994 | 9.776  | 1.00 | 60.74 |
| ATOM | 597 | CD  | GLU | A | 60 | 135.131 | 42.841 | 8.523  | 1.00 | 64.33 |

Page 6-A-13

| | | | | | | | | | |
|---|---|---|---|---|---|---|---|---|---|
| ATOM | 598 | OE1 | GLU | A | 60 | 135.450 | 44.046 | 8.618 | 1.00 67.37 |
| ATOM | 599 | OE2 | GLU | A | 60 | 134.798 | 42.300 | 7.443 | 1.00 65.16 |
| ATOM | 600 | C | GLU | A | 60 | 136.279 | 39.518 | 10.948 | 1.00 51.42 |
| ATOM | 601 | O | GLU | A | 60 | 137.170 | 38.930 | 10.342 | 1.00 52.44 |
| ATOM | 602 | N | PHE | A | 61 | 135.052 | 39.035 | 11.093 | 1.00 50.66 |
| ATOM | 604 | CA | PHE | A | 61 | 134.646 | 37.741 | 10.558 | 1.00 49.14 |
| ATOM | 605 | CB | PHE | A | 61 | 134.536 | 36.736 | 11.707 | 1.00 44.10 |
| ATOM | 606 | CG | PHE | A | 61 | 134.679 | 35.308 | 11.289 | 1.00 37.41 |
| ATOM | 607 | CD1 | PHE | A | 61 | 133.998 | 34.814 | 10.188 | 1.00 36.68 |
| ATOM | 608 | CD2 | PHE | A | 61 | 135.486 | 34.448 | 12.018 | 1.00 34.73 |
| ATOM | 609 | CE1 | PHE | A | 61 | 134.116 | 33.477 | 9.817 | 1.00 36.53 |
| ATOM | 610 | CE2 | PHE | A | 61 | 135.612 | 33.115 | 11.658 | 1.00 34.86 |
| ATOM | 611 | CZ | PHE | A | 61 | 134.922 | 32.627 | 10.553 | 1.00 35.68 |
| ATOM | 612 | C | PHE | A | 61 | 133.278 | 37.962 | 9.924 | 1.00 50.95 |
| ATOM | 613 | O | PHE | A | 61 | 132.249 | 37.646 | 10.521 | 1.00 52.86 |
| ATOM | 614 | N | GLN | A | 62 | 133.259 | 38.540 | 8.729 | 1.00 51.57 |
| ATOM | 616 | CA | GLN | A | 62 | 131.993 | 38.813 | 8.080 | 1.00 51.07 |
| ATOM | 617 | CB | GLN | A | 62 | 132.097 | 39.993 | 7.120 | 1.00 54.59 |
| ATOM | 618 | CG | GLN | A | 62 | 130.727 | 40.463 | 6.639 | 1.00 62.31 |
| ATOM | 619 | CD | GLN | A | 62 | 130.775 | 41.665 | 5.708 | 1.00 67.35 |
| ATOM | 620 | OE1 | GLN | A | 62 | 129.812 | 41.935 | 4.991 | 1.00 69.86 |
| ATOM | 621 | NE2 | GLN | A | 62 | 131.884 | 42.401 | 5.727 | 1.00 71.01 |
| ATOM | 624 | C | GLN | A | 62 | 131.391 | 37.625 | 7.367 | 1.00 48.52 |
| ATOM | 625 | O | GLN | A | 62 | 132.065 | 36.912 | 6.629 | 1.00 48.13 |
| ATOM | 626 | N | LEU | A | 63 | 130.107 | 37.422 | 7.622 | 1.00 48.11 |
| ATOM | 628 | CA | LEU | A | 63 | 129.324 | 36.358 | 7.017 | 1.00 47.47 |
| ATOM | 629 | CB | LEU | A | 63 | 128.753 | 35.438 | 8.103 | 1.00 44.43 |
| ATOM | 630 | CG | LEU | A | 63 | 129.754 | 34.759 | 9.044 | 1.00 42.13 |
| ATOM | 631 | CD1 | LEU | A | 63 | 129.021 | 34.080 | 10.181 | 1.00 42.20 |
| ATOM | 632 | CD2 | LEU | A | 63 | 130.593 | 33.752 | 8.282 | 1.00 40.96 |
| ATOM | 633 | C | LEU | A | 63 | 128.208 | 37.122 | 6.314 | 1.00 48.35 |
| ATOM | 634 | O | LEU | A | 63 | 127.138 | 37.345 | 6.882 | 1.00 49.30 |
| ATOM | 635 | N | PRO | A | 64 | 128.471 | 37.585 | 5.082 | 1.00 49.75 |
| ATOM | 636 | CD | PRO | A | 64 | 129.686 | 37.302 | 4.297 | 1.00 50.27 |

| ATOM | 637 | CA | PRO A | 64 | 127.508 | 38.347 | 4.283 | 1.00 | 50.73 |
| --- | --- | --- | --- | --- | --- | --- | --- | --- | --- |
| ATOM | 638 | CB | PRO A | 64 | 128.309 | 38.687 | 3.026 | 1.00 | 50.48 |
| ATOM | 639 | CG | PRO A | 64 | 129.210 | 37.513 | 2.878 | 1.00 | 49.49 |
| ATOM | 640 | C | PRO A | 64 | 126.219 | 37.616 | 3.937 | 1.00 | 51.98 |
| ATOM | 641 | O | PRO A | 64 | 125.129 | 38.167 | 4.083 | 1.00 | 54.28 |
| ATOM | 642 | N | SER A | 65 | 126.341 | 36.375 | 3.488 | 1.00 | 51.59 |
| ATOM | 644 | CA | SER A | 65 | 125.177 | 35.607 | 3.101 | 1.00 | 50.95 |
| ATOM | 645 | CB | SER A | 65 | 125.217 | 35.356 | 1.599 | 1.00 | 52.70 |
| ATOM | 646 | OG | SER A | 65 | 126.503 | 34.910 | 1.205 | 1.00 | 55.07 |
| ATOM | 648 | C | SER A | 65 | 125.053 | 34.288 | 3.832 | 1.00 | 50.87 |
| ATOM | 649 | O | SER A | 65 | 126.052 | 33.627 | 4.120 | 1.00 | 52.05 |
| ATOM | 650 | N | SER A | 66 | 123.811 | 33.928 | 4.136 | 1.00 | 50.53 |
| ATOM | 652 | CA | SER A | 66 | 123.477 | 32.680 | 4.805 | 1.00 | 48.85 |
| ATOM | 653 | CB | SER A | 66 | 123.322 | 32.878 | 6.312 | 1.00 | 48.24 |
| ATOM | 654 | OG | SER A | 66 | 122.307 | 33.820 | 6.615 | 1.00 | 49.82 |
| ATOM | 656 | C | SER A | 66 | 122.154 | 32.244 | 4.202 | 1.00 | 49.43 |
| ATOM | 657 | O | SER A | 66 | 121.365 | 33.080 | 3.745 | 1.00 | 48.59 |
| ATOM | 658 | N | GLN A | 67 | 121.925 | 30.940 | 4.165 | 1.00 | 49.88 |
| ATOM | 660 | CA | GLN A | 67 | 120.696 | 30.409 | 3.605 | 1.00 | 49.90 |
| ATOM | 661 | CB | GLN A | 67 | 120.831 | 30.267 | 2.086 | 1.00 | 52.61 |
| ATOM | 662 | CG | GLN A | 67 | 121.928 | 29.308 | 1.632 | 1.00 | 58.79 |
| ATOM | 663 | CD | GLN A | 67 | 121.984 | 29.154 | 0.121 | 1.00 | 62.57 |
| ATOM | 664 | OE1 | GLN A | 67 | 122.550 | 29.997 | -0.576 | 1.00 | 66.32 |
| ATOM | 665 | NE2 | GLN A | 67 | 121.407 | 28.073 | -0.392 | 1.00 | 62.89 |
| ATOM | 668 | C | GLN A | 67 | 120.337 | 29.065 | 4.221 | 1.00 | 48.02 |
| ATOM | 669 | O | GLN A | 67 | 121.215 | 28.306 | 4.635 | 1.00 | 49.44 |
| ATOM | 670 | N | ILE A | 68 | 119.040 | 28.803 | 4.328 | 1.00 | 45.23 |
| ATOM | 672 | CA | ILE A | 68 | 118.551 | 27.544 | 4.864 | 1.00 | 42.63 |
| ATOM | 673 | CB | ILE A | 68 | 117.826 | 27.721 | 6.220 | 1.00 | 44.01 |
| ATOM | 674 | CG2 | ILE A | 68 | 116.977 | 26.499 | 6.546 | 1.00 | 45.24 |
| ATOM | 675 | CG1 | ILE A | 68 | 118.850 | 27.925 | 7.333 | 1.00 | 44.56 |
| ATOM | 676 | CD1 | ILE A | 68 | 118.260 | 27.851 | 8.719 | 1.00 | 47.20 |
| ATOM | 677 | C | ILE A | 68 | 117.613 | 26.935 | 3.835 | 1.00 | 40.01 |
| ATOM | 678 | O | ILE A | 68 | 116.560 | 27.491 | 3.524 | 1.00 | 41.30 |

| | | | | | | | | | |
|---|---|---|---|---|---|---|---|---|---|
| ATOM | 679 | N | SER | A | 69 | 118.051 | 25.833 | 3.250 | 1.00 37.17 |
| ATOM | 681 | CA | SER | A | 69 | 117.264 | 25.140 | 2.258 | 1.00 34.46 |
| ATOM | 682 | CB | SER | A | 69 | 118.165 | 24.600 | 1.147 | 1.00 34.89 |
| ATOM | 683 | OG | SER | A | 69 | 118.890 | 25.640 | 0.511 | 1.00 40.63 |
| ATOM | 685 | C | SER | A | 69 | 116.570 | 23.984 | 2.939 | 1.00 33.71 |
| ATOM | 686 | O | SER | A | 69 | 117.085 | 23.414 | 3.896 | 1.00 34.03 |
| ATOM | 687 | N | MET | A | 70 | 115.405 | 23.625 | 2.430 | 1.00 33.11 |
| ATOM | 689 | CA | MET | A | 70 | 114.659 | 22.519 | 2.981 | 1.00 34.74 |
| ATOM | 690 | CB | MET | A | 70 | 113.166 | 22.841 | 3.012 | 1.00 36.59 |
| ATOM | 691 | CG | MET | A | 70 | 112.794 | 23.880 | 4.051 | 1.00 41.38 |
| ATOM | 692 | SD | MET | A | 70 | 111.050 | 24.288 | 4.028 | 1.00 47.62 |
| ATOM | 693 | CE | MET | A | 70 | 111.101 | 25.834 | 3.173 | 1.00 47.72 |
| ATOM | 694 | C | MET | A | 70 | 114.906 | 21.274 | 2.153 | 1.00 35.74 |
| ATOM | 695 | O | MET | A | 70 | 114.752 | 21.279 | 0.928 | 1.00 37.33 |
| ATOM | 696 | N | VAL | A | 71 | 115.366 | 20.226 | 2.820 | 1.00 35.02 |
| ATOM | 698 | CA | VAL | A | 71 | 115.613 | 18.957 | 2.165 | 1.00 32.82 |
| ATOM | 699 | CB | VAL | A | 71 | 116.938 | 18.343 | 2.637 | 1.00 30.47 |
| ATOM | 700 | CG1 | VAL | A | 71 | 117.206 | 17.049 | 1.905 | 1.00 28.06 |
| ATOM | 701 | CG2 | VAL | A | 71 | 118.069 | 19.324 | 2.404 | 1.00 28.88 |
| ATOM | 702 | C | VAL | A | 71 | 114.438 | 18.072 | 2.571 | 1.00 33.73 |
| ATOM | 703 | O | VAL | A | 71 | 114.430 | 17.505 | 3.664 | 1.00 35.31 |
| ATOM | 704 | N | PRO | A | 72 | 113.411 | 17.975 | 1.708 | 1.00 33.98 |
| ATOM | 705 | CD | PRO | A | 72 | 113.402 | 18.500 | 0.327 | 1.00 33.44 |
| ATOM | 706 | CA | PRO | A | 72 | 112.211 | 17.168 | 1.965 | 1.00 34.72 |
| ATOM | 707 | CB | PRO | A | 72 | 111.660 | 16.936 | 0.562 | 1.00 33.90 |
| ATOM | 708 | CG | PRO | A | 72 | 111.980 | 18.231 | -0.124 | 1.00 32.49 |
| ATOM | 709 | C | PRO | A | 72 | 112.495 | 15.857 | 2.695 | 1.00 36.34 |
| ATOM | 710 | O | PRO | A | 72 | 113.417 | 15.131 | 2.340 | 1.00 39.70 |
| ATOM | 711 | N | ASN | A | 73 | 111.745 | 15.607 | 3.765 | 1.00 38.08 |
| ATOM | 713 | CA | ASN | A | 73 | 111.886 | 14.399 | 4.580 | 1.00 39.44 |
| ATOM | 714 | CB | ASN | A | 73 | 111.553 | 13.146 | 3.768 | 1.00 45.34 |
| ATOM | 715 | CG | ASN | A | 73 | 110.071 | 12.875 | 3.699 | 1.00 50.49 |
| ATOM | 716 | OD1 | ASN | A | 73 | 109.392 | 13.317 | 2.770 | 1.00 53.54 |
| ATOM | 717 | ND2 | ASN | A | 73 | 109.552 | 12.149 | 4.690 | 1.00 53.95 |

Page 6-A-16

| | | | | | | | | | |
|---|---|---|---|---|---|---|---|---|---|
| ATOM | 720 | C | ASN | A | 73 | 113.231 | 14.192 | 5.252 | 1.00 38.00 |
| ATOM | 721 | O | ASN | A | 73 | 113.408 | 13.204 | 5.962 | 1.00 37.89 |
| ATOM | 722 | N | VAL | A | 74 | 114.165 | 15.116 | 5.050 | 1.00 37.67 |
| ATOM | 724 | CA | VAL | A | 74 | 115.498 | 14.995 | 5.632 | 1.00 36.66 |
| ATOM | 725 | CB | VAL | A | 74 | 116.598 | 15.041 | 4.525 | 1.00 37.47 |
| ATOM | 726 | CG1 | VAL | A | 74 | 117.976 | 14.753 | 5.118 | 1.00 35.10 |
| ATOM | 727 | CG2 | VAL | A | 74 | 116.280 | 14.046 | 3.402 | 1.00 33.69 |
| ATOM | 728 | C | VAL | A | 74 | 115.784 | 16.054 | 6.704 | 1.00 37.30 |
| ATOM | 729 | O | VAL | A | 74 | 116.106 | 15.717 | 7.848 | 1.00 39.11 |
| ATOM | 730 | N | GLY | A | 75 | 115.672 | 17.328 | 6.342 | 1.00 35.75 |
| ATOM | 732 | CA | GLY | A | 75 | 115.928 | 18.384 | 7.306 | 1.00 33.77 |
| ATOM | 733 | C | GLY | A | 75 | 116.279 | 19.698 | 6.647 | 1.00 33.37 |
| ATOM | 734 | O | GLY | A | 75 | 115.827 | 19.981 | 5.536 | 1.00 32.85 |
| ATOM | 735 | N | LEU | A | 76 | 117.075 | 20.509 | 7.338 | 1.00 34.22 |
| ATOM | 737 | CA | LEU | A | 76 | 117.504 | 21.811 | 6.828 | 1.00 33.33 |
| ATOM | 738 | CB | LEU | A | 76 | 117.329 | 22.894 | 7.897 | 1.00 30.43 |
| ATOM | 739 | CG | LEU | A | 76 | 115.958 | 23.105 | 8.524 | 1.00 28.67 |
| ATOM | 740 | CD1 | LEU | A | 76 | 116.081 | 24.069 | 9.683 | 1.00 29.06 |
| ATOM | 741 | CD2 | LEU | A | 76 | 114.995 | 23.633 | 7.481 | 1.00 31.34 |
| ATOM | 742 | C | LEU | A | 76 | 118.979 | 21.755 | 6.448 | 1.00 33.33 |
| ATOM | 743 | O | LEU | A | 76 | 119.736 | 20.942 | 6.967 | 1.00 34.06 |
| ATOM | 744 | N | LYS | A | 77 | 119.383 | 22.636 | 5.550 | 1.00 34.34 |
| ATOM | 746 | CA | LYS | A | 77 | 120.766 | 22.711 | 5.131 | 1.00 33.56 |
| ATOM | 747 | CB | LYS | A | 77 | 120.927 | 22.201 | 3.700 | 1.00 35.32 |
| ATOM | 748 | CG | LYS | A | 77 | 122.345 | 22.283 | 3.166 | 1.00 38.99 |
| ATOM | 749 | CD | LYS | A | 77 | 122.450 | 21.670 | 1.782 | 1.00 41.42 |
| ATOM | 750 | CE | LYS | A | 77 | 122.388 | 20.150 | 1.838 | 1.00 41.64 |
| ATOM | 751 | NZ | LYS | A | 77 | 123.630 | 19.565 | 2.421 | 1.00 43.94 |
| ATOM | 755 | C | LYS | A | 77 | 121.131 | 24.175 | 5.228 | 1.00 34.11 |
| ATOM | 756 | O | LYS | A | 77 | 120.556 | 25.013 | 4.538 | 1.00 34.01 |
| ATOM | 757 | N | PHE | A | 78 | 122.009 | 24.478 | 6.173 | 1.00 36.93 |
| ATOM | 759 | CA | PHE | A | 78 | 122.482 | 25.830 | 6.427 | 1.00 37.23 |
| ATOM | 760 | CB | PHE | A | 78 | 122.720 | 25.983 | 7.933 | 1.00 37.11 |
| ATOM | 761 | CG | PHE | A | 78 | 123.233 | 27.329 | 8.340 | 1.00 36.19 |

| | | | | | | | | | |
|---|---|---|---|---|---|---|---|---|---|
| ATOM | 762 | CD1 | PHE | A | 78 | 122.536 | 28.481 | 8.016 | 1.00 35.10 |
| ATOM | 763 | CD2 | PHE | A | 78 | 124.415 | 27.442 | 9.059 | 1.00 36.97 |
| ATOM | 764 | CE1 | PHE | A | 78 | 123.008 | 29.725 | 8.400 | 1.00 33.97 |
| ATOM | 765 | CE2 | PHE | A | 78 | 124.892 | 28.679 | 9.446 | 1.00 36.53 |
| ATOM | 766 | CZ | PHE | A | 78 | 124.185 | 29.824 | 9.115 | 1.00 36.23 |
| ATOM | 767 | C | PHE | A | 78 | 123.780 | 26.063 | 5.646 | 1.00 38.21 |
| ATOM | 768 | O | PHE | A | 78 | 124.706 | 25.256 | 5.731 | 1.00 37.35 |
| ATOM | 769 | N | SER | A | 79 | 123.845 | 27.160 | 4.892 | 1.00 39.48 |
| ATOM | 771 | CA | SER | A | 79 | 125.028 | 27.489 | 4.097 | 1.00 40.20 |
| ATOM | 772 | CB | SER | A | 79 | 124.802 | 27.126 | 2.625 | 1.00 41.51 |
| ATOM | 773 | OG | SER | A | 79 | 124.408 | 25.773 | 2.464 | 1.00 48.40 |
| ATOM | 775 | C | SER | A | 79 | 125.416 | 28.963 | 4.160 | 1.00 40.10 |
| ATOM | 776 | O | SER | A | 79 | 124.557 | 29.842 | 4.112 | 1.00 39.14 |
| ATOM | 777 | N | ILE | A | 80 | 126.713 | 29.219 | 4.297 | 1.00 40.97 |
| ATOM | 779 | CA | ILE | A | 80 | 127.263 | 30.575 | 4.309 | 1.00 41.40 |
| ATOM | 780 | CB | ILE | A | 80 | 128.002 | 30.885 | 5.612 | 1.00 39.45 |
| ATOM | 781 | CG2 | ILE | A | 80 | 128.518 | 32.307 | 5.583 | 1.00 40.67 |
| ATOM | 782 | CG1 | ILE | A | 80 | 127.057 | 30.714 | 6.797 | 1.00 38.41 |
| ATOM | 783 | CD1 | ILE | A | 80 | 127.690 | 31.022 | 8.120 | 1.00 39.45 |
| ATOM | 784 | C | ILE | A | 80 | 128.246 | 30.524 | 3.143 | 1.00 43.93 |
| ATOM | 785 | O | ILE | A | 80 | 128.944 | 29.519 | 2.976 | 1.00 45.50 |
| ATOM | 786 | N | SER | A | 81 | 128.327 | 31.585 | 2.344 | 1.00 47.35 |
| ATOM | 788 | CA | SER | A | 81 | 129.193 | 31.541 | 1.168 | 1.00 49.22 |
| ATOM | 789 | CB | SER | A | 81 | 128.338 | 31.613 | -0.097 | 1.00 49.49 |
| ATOM | 790 | OG | SER | A | 81 | 127.332 | 32.602 | 0.032 | 1.00 52.43 |
| ATOM | 792 | C | SER | A | 81 | 130.412 | 32.432 | 1.004 | 1.00 50.65 |
| ATOM | 793 | O | SER | A | 81 | 131.482 | 31.937 | 0.658 | 1.00 52.88 |
| ATOM | 794 | N | ASN | A | 82 | 130.276 | 33.738 | 1.185 | 1.00 52.50 |
| ATOM | 796 | CA | ASN | A | 82 | 131.442 | 34.599 | 0.995 | 1.00 54.71 |
| ATOM | 797 | CB | ASN | A | 82 | 131.104 | 35.767 | 0.061 | 1.00 58.34 |
| ATOM | 798 | CG | ASN | A | 82 | 132.342 | 36.391 | -0.570 | 1.00 61.43 |
| ATOM | 799 | OD1 | ASN | A | 82 | 132.462 | 37.613 | -0.657 | 1.00 63.94 |
| ATOM | 800 | ND2 | ASN | A | 82 | 133.257 | 35.550 | -1.039 | 1.00 61.92 |
| ATOM | 803 | C | ASN | A | 82 | 132.040 | 35.098 | 2.303 | 1.00 54.00 |

| | | | | | | | | |
|---|---|---|---|---|---|---|---|---|
| ATOM | 804 | O | ASN A | 82 | 132.268 | 36.297 | 2.482 | 1.00 54.15 |
| ATOM | 805 | N | ALA A | 83 | 132.325 | 34.162 | 3.205 | 1.00 53.37 |
| ATOM | 807 | CA | ALA A | 83 | 132.892 | 34.501 | 4.506 | 1.00 52.11 |
| ATOM | 808 | CB | ALA A | 83 | 132.952 | 33.273 | 5.402 | 1.00 51.81 |
| ATOM | 809 | C | ALA A | 83 | 134.272 | 35.131 | 4.359 | 1.00 50.64 |
| ATOM | 810 | O | ALA A | 83 | 135.124 | 34.640 | 3.610 | 1.00 49.58 |
| ATOM | 811 | N | ASN A | 84 | 134.467 | 36.228 | 5.078 | 1.00 48.85 |
| ATOM | 813 | CA | ASN A | 84 | 135.706 | 36.983 | 5.063 | 1.00 47.97 |
| ATOM | 814 | CB | ASN A | 84 | 135.423 | 38.393 | 4.536 | 1.00 51.32 |
| ATOM | 815 | CG | ASN A | 84 | 136.560 | 39.361 | 4.793 | 1.00 56.05 |
| ATOM | 816 | OD1 | ASN A | 84 | 137.470 | 39.499 | 3.978 | 1.00 61.24 |
| ATOM | 817 | ND2 | ASN A | 84 | 136.500 | 40.060 | 5.919 | 1.00 56.91 |
| ATOM | 820 | C | ASN A | 84 | 136.243 | 37.042 | 6.485 | 1.00 45.82 |
| ATOM | 821 | O | ASN A | 84 | 135.601 | 37.606 | 7.368 | 1.00 47.29 |
| ATOM | 822 | N | ILE A | 85 | 137.405 | 36.438 | 6.703 | 1.00 43.85 |
| ATOM | 824 | CA | ILE A | 85 | 138.052 | 36.402 | 8.014 | 1.00 41.41 |
| ATOM | 825 | CB | ILE A | 85 | 138.495 | 34.952 | 8.386 | 1.00 35.61 |
| ATOM | 826 | CG2 | ILE A | 85 | 139.011 | 34.901 | 9.804 | 1.00 32.01 |
| ATOM | 827 | CG1 | ILE A | 85 | 137.342 | 33.965 | 8.222 | 1.00 30.72 |
| ATOM | 828 | CD1 | ILE A | 85 | 137.712 | 32.557 | 8.587 | 1.00 25.79 |
| ATOM | 829 | C | ILE A | 85 | 139.315 | 37.272 | 8.017 | 1.00 43.73 |
| ATOM | 830 | O | ILE A | 85 | 140.343 | 36.873 | 7.471 | 1.00 47.66 |
| ATOM | 831 | N | LYS A | 86 | 139.239 | 38.471 | 8.578 | 1.00 42.83 |
| ATOM | 833 | CA | LYS A | 86 | 140.420 | 39.313 | 8.645 | 1.00 43.65 |
| ATOM | 834 | CB | LYS A | 86 | 140.090 | 40.779 | 8.363 | 1.00 47.39 |
| ATOM | 835 | CG | LYS A | 86 | 139.895 | 41.055 | 6.873 | 1.00 54.31 |
| ATOM | 836 | CD | LYS A | 86 | 140.065 | 42.528 | 6.509 | 1.00 58.05 |
| ATOM | 837 | CE | LYS A | 86 | 138.937 | 43.394 | 7.045 | 1.00 61.18 |
| ATOM | 838 | NZ | LYS A | 86 | 139.107 | 44.820 | 6.642 | 1.00 64.32 |
| ATOM | 842 | C | LYS A | 86 | 141.100 | 39.135 | 9.996 | 1.00 43.61 |
| ATOM | 843 | O | LYS A | 86 | 140.514 | 39.404 | 11.043 | 1.00 42.95 |
| ATOM | 844 | N | ILE A | 87 | 142.327 | 38.627 | 9.961 | 1.00 43.89 |
| ATOM | 846 | CA | ILE A | 87 | 143.104 | 38.373 | 11.165 | 1.00 44.27 |
| ATOM | 847 | CB | ILE A | 87 | 143.568 | 36.895 | 11.206 | 1.00 43.55 |

Page 6-A-19

| ATOM | 848 | CG2 | ILE | A | 87 | 144.365 | 36.609 | 12.473 | 1.00 | 42.71 |
| ATOM | 849 | CG1 | ILE | A | 87 | 142.358 | 35.964 | 11.129 | 1.00 | 41.65 |
| ATOM | 850 | CD1 | ILE | A | 87 | 142.723 | 34.504 | 11.044 | 1.00 | 42.75 |
| ATOM | 851 | C | ILE | A | 87 | 144.327 | 39.291 | 11.212 | 1.00 | 44.82 |
| ATOM | 852 | O | ILE | A | 87 | 144.817 | 39.745 | 10.176 | 1.00 | 46.46 |
| ATOM | 853 | N | SER | A | 88 | 144.805 | 39.568 | 12.417 | 1.00 | 43.43 |
| ATOM | 855 | CA | SER | A | 88 | 145.970 | 40.414 | 12.606 | 1.00 | 44.37 |
| ATOM | 856 | CB | SER | A | 88 | 145.548 | 41.825 | 13.027 | 1.00 | 46.30 |
| ATOM | 857 | OG | SER | A | 88 | 144.757 | 42.451 | 12.029 | 1.00 | 50.16 |
| ATOM | 859 | C | SER | A | 88 | 146.830 | 39.795 | 13.690 | 1.00 | 43.85 |
| ATOM | 860 | O | SER | A | 88 | 146.327 | 39.073 | 14.549 | 1.00 | 43.41 |
| ATOM | 861 | N | GLY | A | 89 | 148.128 | 40.061 | 13.638 | 1.00 | 45.04 |
| ATOM | 863 | CA | GLY | A | 89 | 149.029 | 39.525 | 14.640 | 1.00 | 47.03 |
| ATOM | 864 | C | GLY | A | 89 | 150.415 | 40.123 | 14.532 | 1.00 | 47.50 |
| ATOM | 865 | O | GLY | A | 89 | 150.611 | 41.140 | 13.861 | 1.00 | 47.81 |
| ATOM | 866 | N | LYS | A | 90 | 151.377 | 39.497 | 15.200 | 1.00 | 47.62 |
| ATOM | 868 | CA | LYS | A | 90 | 152.759 | 39.957 | 15.176 | 1.00 | 47.17 |
| ATOM | 869 | CB | LYS | A | 90 | 153.197 | 40.427 | 16.567 | 1.00 | 47.20 |
| ATOM | 870 | CG | LYS | A | 90 | 152.328 | 41.514 | 17.189 | 1.00 | 49.57 |
| ATOM | 871 | CD | LYS | A | 90 | 152.708 | 41.723 | 18.651 | 1.00 | 53.99 |
| ATOM | 872 | CE | LYS | A | 90 | 151.725 | 42.625 | 19.391 | 1.00 | 57.45 |
| ATOM | 873 | NZ | LYS | A | 90 | 152.042 | 42.735 | 20.855 | 1.00 | 59.91 |
| ATOM | 877 | C | LYS | A | 90 | 153.629 | 38.787 | 14.738 | 1.00 | 45.69 |
| ATOM | 878 | O | LYS | A | 90 | 153.171 | 37.644 | 14.697 | 1.00 | 45.87 |
| ATOM | 879 | N | TRP | A | 91 | 154.874 | 39.078 | 14.389 | 1.00 | 44.12 |
| ATOM | 881 | CA | TRP | A | 91 | 155.817 | 38.052 | 13.969 | 1.00 | 43.19 |
| ATOM | 882 | CB | TRP | A | 91 | 155.734 | 37.824 | 12.456 | 1.00 | 39.90 |
| ATOM | 883 | CG | TRP | A | 91 | 156.078 | 39.038 | 11.694 | 1.00 | 37.85 |
| ATOM | 884 | CD2 | TRP | A | 91 | 157.390 | 39.466 | 11.313 | 1.00 | 39.20 |
| ATOM | 885 | CE2 | TRP | A | 91 | 157.251 | 40.722 | 10.682 | 1.00 | 39.17 |
| ATOM | 886 | CE3 | TRP | A | 91 | 158.672 | 38.918 | 11.451 | 1.00 | 36.54 |
| ATOM | 887 | CD1 | TRP | A | 91 | 155.222 | 40.012 | 11.286 | 1.00 | 39.46 |
| ATOM | 888 | NE1 | TRP | A | 91 | 155.916 | 41.032 | 10.681 | 1.00 | 39.30 |
| ATOM | 890 | CZ2 | TRP | A | 91 | 158.344 | 41.437 | 10.188 | 1.00 | 38.03 |

| | | | | | | | | | |
|---|---|---|---|---|---|---|---|---|---|
| ATOM | 891 | CZ3 | TRP | A | 91 | 159.757 | 39.628 | 10.963 | 1.00 35.59 |
| ATOM | 892 | CH2 | TRP | A | 91 | 159.585 | 40.876 | 10.338 | 1.00 36.22 |
| ATOM | 893 | C | TRP | A | 91 | 157.218 | 38.520 | 14.339 | 1.00 43.43 |
| ATOM | 894 | O | TRP | A | 91 | 157.460 | 39.717 | 14.509 | 1.00 44.14 |
| ATOM | 895 | N | LYS | A | 92 | 158.136 | 37.575 | 14.468 | 1.00 44.32 |
| ATOM | 897 | CA | LYS | A | 92 | 159.517 | 37.892 | 14.789 | 1.00 44.34 |
| ATOM | 898 | CB | LYS | A | 92 | 159.717 | 38.076 | 16.302 | 1.00 47.57 |
| ATOM | 899 | CG | LYS | A | 92 | 159.252 | 36.933 | 17.200 | 1.00 53.21 |
| ATOM | 900 | CD | LYS | A | 92 | 159.361 | 37.354 | 18.678 | 1.00 57.24 |
| ATOM | 901 | CE | LYS | A | 92 | 158.844 | 36.283 | 19.650 | 1.00 59.23 |
| ATOM | 902 | NZ | LYS | A | 92 | 158.816 | 36.742 | 21.083 | 1.00 59.30 |
| ATOM | 906 | C | LYS | A | 92 | 160.409 | 36.801 | 14.227 | 1.00 42.18 |
| ATOM | 907 | O | LYS | A | 92 | 160.052 | 35.623 | 14.255 | 1.00 43.11 |
| ATOM | 908 | N | ALA | A | 93 | 161.521 | 37.214 | 13.632 | 1.00 39.24 |
| ATOM | 910 | CA | ALA | A | 93 | 162.471 | 36.294 | 13.033 | 1.00 36.99 |
| ATOM | 911 | CB | ALA | A | 93 | 162.410 | 36.392 | 11.515 | 1.00 36.10 |
| ATOM | 912 | C | ALA | A | 93 | 163.850 | 36.675 | 13.525 | 1.00 37.81 |
| ATOM | 913 | O | ALA | A | 93 | 164.130 | 37.851 | 13.747 | 1.00 39.61 |
| ATOM | 914 | N | GLN | A | 94 | 164.706 | 35.679 | 13.705 | 1.00 39.81 |
| ATOM | 916 | CA | GLN | A | 94 | 166.060 | 35.919 | 14.173 | 1.00 41.70 |
| ATOM | 917 | CB | GLN | A | 94 | 166.184 | 35.541 | 15.647 | 1.00 45.63 |
| ATOM | 918 | CG | GLN | A | 94 | 167.552 | 35.803 | 16.237 | 1.00 55.83 |
| ATOM | 919 | CD | GLN | A | 94 | 167.559 | 35.745 | 17.750 | 1.00 63.01 |
| ATOM | 920 | OE1 | GLN | A | 94 | 168.328 | 36.456 | 18.406 | 1.00 67.41 |
| ATOM | 921 | NE2 | GLN | A | 94 | 166.703 | 34.899 | 18.320 | 1.00 66.99 |
| ATOM | 924 | C | GLN | A | 94 | 167.067 | 35.139 | 13.340 | 1.00 41.13 |
| ATOM | 925 | O | GLN | A | 94 | 166.952 | 33.921 | 13.194 | 1.00 41.48 |
| ATOM | 926 | N | LYS | A | 95 | 168.024 | 35.865 | 12.771 | 1.00 41.51 |
| ATOM | 928 | CA | LYS | A | 95 | 169.084 | 35.302 | 11.938 | 1.00 40.50 |
| ATOM | 929 | CB | LYS | A | 95 | 169.000 | 35.901 | 10.531 | 1.00 40.86 |
| ATOM | 930 | CG | LYS | A | 95 | 170.099 | 35.478 | 9.580 | 1.00 44.00 |
| ATOM | 931 | CD | LYS | A | 95 | 169.849 | 36.030 | 8.175 | 1.00 46.44 |
| ATOM | 932 | CE | LYS | A | 95 | 169.767 | 37.553 | 8.161 | 1.00 48.82 |
| ATOM | 933 | NZ | LYS | A | 95 | 169.529 | 38.117 | 6.799 | 1.00 49.76 |

Page 6-A-21

| | | | | | | | | |
|---|---|---|---|---|---|---|---|---|
| ATOM | 937 | C | LYS | A | 95 | 170.381 | 35.705 | 12.631 | 1.00 | 39.51 |
| ATOM | 938 | O | LYS | A | 95 | 170.781 | 36.869 | 12.594 | 1.00 | 39.68 |
| ATOM | 939 | N | ARG | A | 96 | 171.000 | 34.743 | 13.304 | 1.00 | 39.70 |
| ATOM | 941 | CA | ARG | A | 96 | 172.229 | 34.965 | 14.065 | 1.00 | 38.81 |
| ATOM | 942 | CB | ARG | A | 96 | 173.386 | 35.432 | 13.159 | 1.00 | 38.58 |
| ATOM | 943 | CG | ARG | A | 96 | 174.757 | 35.415 | 13.848 | 1.00 | 36.99 |
| ATOM | 944 | CD | ARG | A | 96 | 175.919 | 35.584 | 12.869 | 1.00 | 35.28 |
| ATOM | 945 | NE | ARG | A | 96 | 177.207 | 35.640 | 13.562 | 1.00 | 37.59 |
| ATOM | 947 | CZ | ARG | A | 96 | 177.887 | 34.582 | 14.004 | 1.00 | 38.32 |
| ATOM | 948 | NH1 | ARG | A | 96 | 177.425 | 33.351 | 13.832 | 1.00 | 41.87 |
| ATOM | 951 | NH2 | ARG | A | 96 | 179.024 | 34.758 | 14.658 | 1.00 | 34.85 |
| ATOM | 954 | C | ARG | A | 96 | 171.909 | 35.972 | 15.183 | 1.00 | 38.25 |
| ATOM | 955 | O | ARG | A | 96 | 171.091 | 35.672 | 16.048 | 1.00 | 38.45 |
| ATOM | 956 | N | PHE | A | 97 | 172.506 | 37.161 | 15.158 | 1.00 | 36.05 |
| ATOM | 958 | CA | PHE | A | 97 | 172.236 | 38.157 | 16.189 | 1.00 | 32.76 |
| ATOM | 959 | CB | PHE | A | 97 | 173.521 | 38.856 | 16.634 | 1.00 | 29.39 |
| ATOM | 960 | CG | PHE | A | 97 | 174.503 | 37.958 | 17.311 | 1.00 | 27.30 |
| ATOM | 961 | CD1 | PHE | A | 97 | 174.214 | 37.392 | 18.538 | 1.00 | 26.91 |
| ATOM | 962 | CD2 | PHE | A | 97 | 175.733 | 37.695 | 16.728 | 1.00 | 29.62 |
| ATOM | 963 | CE1 | PHE | A | 97 | 175.140 | 36.578 | 19.175 | 1.00 | 28.35 |
| ATOM | 964 | CE2 | PHE | A | 97 | 176.661 | 36.886 | 17.358 | 1.00 | 27.60 |
| ATOM | 965 | CZ | PHE | A | 97 | 176.364 | 36.327 | 18.582 | 1.00 | 28.30 |
| ATOM | 966 | C | PHE | A | 97 | 171.261 | 39.208 | 15.693 | 1.00 | 34.25 |
| ATOM | 967 | O | PHE | A | 97 | 171.016 | 40.199 | 16.387 | 1.00 | 33.16 |
| ATOM | 968 | N | LEU | A | 98 | 170.739 | 39.012 | 14.484 | 1.00 | 36.60 |
| ATOM | 970 | CA | LEU | A | 98 | 169.790 | 39.952 | 13.888 | 1.00 | 39.31 |
| ATOM | 971 | CB | LEU | A | 98 | 169.874 | 39.905 | 12.361 | 1.00 | 38.74 |
| ATOM | 972 | CG | LEU | A | 98 | 169.875 | 41.238 | 11.608 | 1.00 | 38.17 |
| ATOM | 973 | CD1 | LEU | A | 98 | 169.883 | 40.951 | 10.128 | 1.00 | 40.67 |
| ATOM | 974 | CD2 | LEU | A | 98 | 168.680 | 42.093 | 11.971 | 1.00 | 38.92 |
| ATOM | 975 | C | LEU | A | 98 | 168.366 | 39.631 | 14.317 | 1.00 | 40.51 |
| ATOM | 976 | O | LEU | A | 98 | 167.854 | 38.554 | 14.016 | 1.00 | 42.93 |
| ATOM | 977 | N | LYS | A | 99 | 167.737 | 40.570 | 15.018 | 1.00 | 41.98 |
| ATOM | 979 | CA | LYS | A | 99 | 166.365 | 40.410 | 15.488 | 1.00 | 42.37 |

| | | | | | | | | |
|---|---|---|---|---|---|---|---|---|
| ATOM | 980 | CB | LYS A | 99 | 166.258 | 40.705 | 16.989 | 1.00 41.90 |
| ATOM | 981 | CG | LYS A | 99 | 166.690 | 39.566 | 17.898 | 1.00 45.06 |
| ATOM | 982 | CD | LYS A | 99 | 166.389 | 39.882 | 19.361 | 1.00 47.68 |
| ATOM | 983 | CE | LYS A | 99 | 166.638 | 38.671 | 20.250 | 1.00 51.09 |
| ATOM | 984 | NZ | LYS A | 99 | 166.251 | 38.895 | 21.674 | 1.00 53.87 |
| ATOM | 988 | C | LYS A | 99 | 165.440 | 41.351 | 14.727 | 1.00 43.86 |
| ATOM | 989 | O | LYS A | 99 | 165.634 | 42.573 | 14.739 | 1.00 45.41 |
| ATOM | 990 | N | MET A | 100 | 164.438 | 40.785 | 14.064 | 1.00 43.74 |
| ATOM | 992 | CA | MET A | 100 | 163.479 | 41.575 | 13.310 | 1.00 43.78 |
| ATOM | 993 | CB | MET A | 100 | 163.576 | 41.234 | 11.826 | 1.00 44.48 |
| ATOM | 994 | CG | MET A | 100 | 164.885 | 41.651 | 11.195 | 1.00 45.32 |
| ATOM | 995 | SD | MET A | 100 | 165.190 | 40.802 | 9.654 | 1.00 49.68 |
| ATOM | 996 | CE | MET A | 100 | 165.736 | 39.168 | 10.290 | 1.00 44.16 |
| ATOM | 997 | C | MET A | 100 | 162.078 | 41.292 | 13.832 | 1.00 44.78 |
| ATOM | 998 | O | MET A | 100 | 161.693 | 40.132 | 13.987 | 1.00 44.97 |
| ATOM | 999 | N | SER A | 101 | 161.335 | 42.352 | 14.140 | 1.00 46.57 |
| ATOM | 1001 | CA | SER A | 101 | 159.971 | 42.221 | 14.650 | 1.00 47.86 |
| ATOM | 1002 | CB | SER A | 101 | 159.934 | 42.469 | 16.162 | 1.00 49.20 |
| ATOM | 1003 | OG | SER A | 101 | 160.560 | 43.693 | 16.509 | 1.00 51.70 |
| ATOM | 1005 | C | SER A | 101 | 159.009 | 43.168 | 13.937 | 1.00 48.68 |
| ATOM | 1006 | O | SER A | 101 | 159.428 | 44.161 | 13.332 | 1.00 48.84 |
| ATOM | 1007 | N | GLY A | 102 | 157.722 | 42.839 | 13.986 | 1.00 49.46 |
| ATOM | 1009 | CA | GLY A | 102 | 156.716 | 43.664 | 13.343 | 1.00 49.50 |
| ATOM | 1010 | C | GLY A | 102 | 155.359 | 42.989 | 13.341 | 1.00 48.98 |
| ATOM | 1011 | O | GLY A | 102 | 155.251 | 41.795 | 13.613 | 1.00 50.09 |
| ATOM | 1012 | N | ASN A | 103 | 154.317 | 43.766 | 13.079 | 1.00 48.68 |
| ATOM | 1014 | CA | ASN A | 103 | 152.957 | 43.243 | 13.042 | 1.00 47.35 |
| ATOM | 1015 | CB | ASN A | 103 | 151.945 | 44.349 | 13.391 | 1.00 49.87 |
| ATOM | 1016 | CG | ASN A | 103 | 152.061 | 44.837 | 14.840 | 1.00 51.69 |
| ATOM | 1017 | OD1 | ASN A | 103 | 153.067 | 45.423 | 15.234 | 1.00 53.03 |
| ATOM | 1018 | ND2 | ASN A | 103 | 151.014 | 44.621 | 15.625 | 1.00 53.17 |
| ATOM | 1021 | C | ASN A | 103 | 152.703 | 42.743 | 11.625 | 1.00 46.11 |
| ATOM | 1022 | O | ASN A | 103 | 153.459 | 43.073 | 10.708 | 1.00 45.99 |
| ATOM | 1023 | N | PHE A | 104 | 151.667 | 41.926 | 11.451 | 1.00 44.40 |

Page 6-A-23

| ATOM | 1025 | CA | PHE | A | 104 | 151.306 | 41.410 | 10.131 | 1.00 | 42.85 |
| --- | --- | --- | --- | --- | --- | --- | --- | --- | --- | --- |
| ATOM | 1026 | CB | PHE | A | 104 | 151.987 | 40.051 | 9.835 | 1.00 | 42.59 |
| ATOM | 1027 | CG | PHE | A | 104 | 151.319 | 38.849 | 10.482 | 1.00 | 41.53 |
| ATOM | 1028 | CD1 | PHE | A | 104 | 151.650 | 38.458 | 11.776 | 1.00 | 39.25 |
| ATOM | 1029 | CD2 | PHE | A | 104 | 150.380 | 38.095 | 9.778 | 1.00 | 39.79 |
| ATOM | 1030 | CE1 | PHE | A | 104 | 151.058 | 37.339 | 12.357 | 1.00 | 37.60 |
| ATOM | 1031 | CE2 | PHE | A | 104 | 149.784 | 36.976 | 10.353 | 1.00 | 36.72 |
| ATOM | 1032 | CZ | PHE | A | 104 | 150.125 | 36.599 | 11.644 | 1.00 | 37.02 |
| ATOM | 1033 | C | PHE | A | 104 | 149.788 | 41.303 | 10.006 | 1.00 | 42.22 |
| ATOM | 1034 | O | PHE | A | 104 | 149.081 | 41.251 | 11.014 | 1.00 | 43.09 |
| ATOM | 1035 | N | ASP | A | 105 | 149.298 | 41.346 | 8.771 | 1.00 | 41.99 |
| ATOM | 1037 | CA | ASP | A | 105 | 147.874 | 41.227 | 8.475 | 1.00 | 41.67 |
| ATOM | 1038 | CB | ASP | A | 105 | 147.352 | 42.455 | 7.724 | 1.00 | 43.33 |
| ATOM | 1039 | CG | ASP | A | 105 | 146.986 | 43.602 | 8.648 | 1.00 | 46.56 |
| ATOM | 1040 | OD1 | ASP | A | 105 | 146.898 | 43.395 | 9.876 | 1.00 | 49.37 |
| ATOM | 1041 | OD2 | ASP | A | 105 | 146.770 | 44.720 | 8.141 | 1.00 | 51.38 |
| ATOM | 1042 | C | ASP | A | 105 | 147.658 | 39.985 | 7.622 | 1.00 | 41.95 |
| ATOM | 1043 | O | ASP | A | 105 | 148.470 | 39.655 | 6.758 | 1.00 | 42.85 |
| ATOM | 1044 | N | LEU | A | 106 | 146.538 | 39.322 | 7.841 | 1.00 | 40.99 |
| ATOM | 1046 | CA | LEU | A | 106 | 146.220 | 38.115 | 7.115 | 1.00 | 39.85 |
| ATOM | 1047 | CB | LEU | A | 106 | 146.424 | 36.934 | 8.058 | 1.00 | 38.87 |
| ATOM | 1048 | CG | LEU | A | 106 | 146.224 | 35.489 | 7.629 | 1.00 | 39.36 |
| ATOM | 1049 | CD1 | LEU | A | 106 | 146.825 | 34.605 | 8.690 | 1.00 | 40.16 |
| ATOM | 1050 | CD2 | LEU | A | 106 | 144.758 | 35.175 | 7.464 | 1.00 | 41.07 |
| ATOM | 1051 | C | LEU | A | 106 | 144.767 | 38.248 | 6.698 | 1.00 | 40.07 |
| ATOM | 1052 | O | LEU | A | 106 | 143.968 | 38.841 | 7.414 | 1.00 | 41.85 |
| ATOM | 1053 | N | SER | A | 107 | 144.427 | 37.748 | 5.523 | 1.00 | 41.19 |
| ATOM | 1055 | CA | SER | A | 107 | 143.054 | 37.830 | 5.061 | 1.00 | 43.48 |
| ATOM | 1056 | CB | SER | A | 107 | 142.911 | 38.907 | 3.979 | 1.00 | 45.09 |
| ATOM | 1057 | OG | SER | A | 107 | 143.440 | 40.155 | 4.402 | 1.00 | 50.35 |
| ATOM | 1059 | C | SER | A | 107 | 142.633 | 36.484 | 4.502 | 1.00 | 43.83 |
| ATOM | 1060 | O | SER | A | 107 | 143.290 | 35.957 | 3.610 | 1.00 | 44.06 |
| ATOM | 1061 | N | ILE | A | 108 | 141.587 | 35.900 | 5.077 | 1.00 | 45.70 |
| ATOM | 1063 | CA | ILE | A | 108 | 141.056 | 34.617 | 4.615 | 1.00 | 47.58 |

Page 6-A-24

| | | | | | | | | |
|---|---|---|---|---|---|---|---|---|
| ATOM | 1064 | CB | ILE A 108 | 140.829 | 33.644 | 5.789 | 1.00 | 46.97 |
| ATOM | 1065 | CG2 | ILE A 108 | 140.174 | 32.368 | 5.296 | 1.00 | 46.17 |
| ATOM | 1066 | CG1 | ILE A 108 | 142.157 | 33.327 | 6.474 | 1.00 | 47.60 |
| ATOM | 1067 | CD1 | ILE A 108 | 142.042 | 32.368 | 7.637 | 1.00 | 49.72 |
| ATOM | 1068 | C | ILE A 108 | 139.716 | 34.922 | 3.959 | 1.00 | 48.97 |
| ATOM | 1069 | O | ILE A 108 | 138.818 | 35.433 | 4.619 | 1.00 | 51.76 |
| ATOM | 1070 | N | GLU A 109 | 139.582 | 34.652 | 2.664 | 1.00 | 50.18 |
| ATOM | 1072 | CA | GLU A 109 | 138.328 | 34.938 | 1.968 | 1.00 | 52.80 |
| ATOM | 1073 | CB | GLU A 109 | 138.506 | 36.067 | 0.956 | 1.00 | 58.29 |
| ATOM | 1074 | CG | GLU A 109 | 138.871 | 37.409 | 1.556 | 1.00 | 67.61 |
| ATOM | 1075 | CD | GLU A 109 | 138.896 | 38.510 | 0.518 | 1.00 | 72.52 |
| ATOM | 1076 | OE1 | GLU A 109 | 139.591 | 38.345 | -0.510 | 1.00 | 76.73 |
| ATOM | 1077 | OE2 | GLU A 109 | 138.212 | 39.536 | 0.725 | 1.00 | 74.66 |
| ATOM | 1078 | C | GLU A 109 | 137.771 | 33.733 | 1.244 | 1.00 | 51.51 |
| ATOM | 1079 | O | GLU A 109 | 138.449 | 32.717 | 1.091 | 1.00 | 51.13 |
| ATOM | 1080 | N | GLY A 110 | 136.539 | 33.867 | 0.767 | 1.00 | 50.94 |
| ATOM | 1082 | CA | GLY A 110 | 135.904 | 32.778 | 0.051 | 1.00 | 49.27 |
| ATOM | 1083 | C | GLY A 110 | 135.714 | 31.551 | 0.920 | 1.00 | 48.08 |
| ATOM | 1084 | O | GLY A 110 | 135.972 | 30.419 | 0.488 | 1.00 | 47.03 |
| ATOM | 1085 | N | MET A 111 | 135.318 | 31.784 | 2.168 | 1.00 | 46.98 |
| ATOM | 1087 | CA | MET A 111 | 135.078 | 30.699 | 3.104 | 1.00 | 44.78 |
| ATOM | 1088 | CB | MET A 111 | 135.376 | 31.143 | 4.536 | 1.00 | 44.81 |
| ATOM | 1089 | CG | MET A 111 | 135.062 | 30.092 | 5.570 | 1.00 | 44.07 |
| ATOM | 1090 | SD | MET A 111 | 135.669 | 30.518 | 7.178 | 1.00 | 49.80 |
| ATOM | 1091 | CE | MET A 111 | 136.833 | 29.192 | 7.434 | 1.00 | 46.06 |
| ATOM | 1092 | C | MET A 111 | 133.630 | 30.242 | 2.970 | 1.00 | 42.64 |
| ATOM | 1093 | O | MET A 111 | 132.712 | 31.061 | 2.960 | 1.00 | 40.20 |
| ATOM | 1094 | N | SER A 112 | 133.446 | 28.935 | 2.846 | 1.00 | 41.52 |
| ATOM | 1096 | CA | SER A 112 | 132.133 | 28.334 | 2.708 | 1.00 | 41.82 |
| ATOM | 1097 | CB | SER A 112 | 132.045 | 27.607 | 1.360 | 1.00 | 43.85 |
| ATOM | 1098 | OG | SER A 112 | 130.997 | 26.648 | 1.321 | 1.00 | 49.86 |
| ATOM | 1100 | C | SER A 112 | 131.908 | 27.363 | 3.861 | 1.00 | 41.93 |
| ATOM | 1101 | O | SER A 112 | 132.725 | 26.467 | 4.097 | 1.00 | 41.84 |
| ATOM | 1102 | N | ILE A 113 | 130.816 | 27.569 | 4.592 | 1.00 | 42.07 |

| | | | | | | | |
|---|---|---|---|---|---|---|---|
| ATOM | 1104 | CA | ILE A 113 | 130.444 | 26.722 | 5.725 | 1.00 40.13 |
| ATOM | 1105 | CB | ILE A 113 | 130.310 | 27.546 | 7.027 | 1.00 39.38 |
| ATOM | 1106 | CG2 | ILE A 113 | 130.227 | 26.620 | 8.231 | 1.00 39.63 |
| ATOM | 1107 | CG1 | ILE A 113 | 131.505 | 28.480 | 7.190 | 1.00 35.78 |
| ATOM | 1108 | CD1 | ILE A 113 | 131.284 | 29.547 | 8.225 | 1.00 38.78 |
| ATOM | 1109 | C | ILE A 113 | 129.083 | 26.105 | 5.405 | 1.00 40.48 |
| ATOM | 1110 | O | ILE A 113 | 128.118 | 26.821 | 5.117 | 1.00 40.10 |
| ATOM | 1111 | N | SER A 114 | 129.016 | 24.780 | 5.414 | 1.00 40.69 |
| ATOM | 1113 | CA | SER A 114 | 127.775 | 24.076 | 5.126 | 1.00 39.86 |
| ATOM | 1114 | CB | SER A 114 | 127.915 | 23.277 | 3.835 | 1.00 39.27 |
| ATOM | 1115 | OG | SER A 114 | 126.695 | 22.645 | 3.486 | 1.00 45.23 |
| ATOM | 1117 | C | SER A 114 | 127.489 | 23.152 | 6.297 | 1.00 40.43 |
| ATOM | 1118 | O | SER A 114 | 128.370 | 22.407 | 6.730 | 1.00 42.01 |
| ATOM | 1119 | N | ALA A 115 | 126.261 | 23.198 | 6.804 | 1.00 40.94 |
| ATOM | 1121 | CA | ALA A 115 | 125.863 | 22.380 | 7.947 | 1.00 40.28 |
| ATOM | 1122 | CB | ALA A 115 | 125.990 | 23.186 | 9.227 | 1.00 41.97 |
| ATOM | 1123 | C | ALA A 115 | 124.446 | 21.856 | 7.814 | 1.00 39.55 |
| ATOM | 1124 | O | ALA A 115 | 123.551 | 22.581 | 7.385 | 1.00 38.65 |
| ATOM | 1125 | N | ASP A 116 | 124.248 | 20.603 | 8.213 | 1.00 39.92 |
| ATOM | 1127 | CA | ASP A 116 | 122.943 | 19.954 | 8.155 | 1.00 40.51 |
| ATOM | 1128 | CB | ASP A 116 | 123.092 | 18.513 | 7.672 | 1.00 44.07 |
| ATOM | 1129 | CG | ASP A 116 | 123.359 | 18.421 | 6.184 | 1.00 48.91 |
| ATOM | 1130 | OD1 | ASP A 116 | 124.455 | 18.829 | 5.741 | 1.00 53.18 |
| ATOM | 1131 | OD2 | ASP A 116 | 122.467 | 17.940 | 5.455 | 1.00 52.27 |
| ATOM | 1132 | C | ASP A 116 | 122.241 | 19.956 | 9.504 | 1.00 39.36 |
| ATOM | 1133 | O | ASP A 116 | 122.804 | 19.501 | 10.495 | 1.00 40.86 |
| ATOM | 1134 | N | LEU A 117 | 121.009 | 20.459 | 9.537 | 1.00 38.66 |
| ATOM | 1136 | CA | LEU A 117 | 120.220 | 20.508 | 10.766 | 1.00 35.83 |
| ATOM | 1137 | CB | LEU A 117 | 119.578 | 21.888 | 10.944 | 1.00 34.68 |
| ATOM | 1138 | CG | LEU A 117 | 120.493 | 23.096 | 11.140 | 1.00 34.59 |
| ATOM | 1139 | CD1 | LEU A 117 | 119.667 | 24.361 | 11.279 | 1.00 35.67 |
| ATOM | 1140 | CD2 | LEU A 117 | 121.346 | 22.895 | 12.370 | 1.00 35.88 |
| ATOM | 1141 | C | LEU A 117 | 119.131 | 19.437 | 10.721 | 1.00 35.13 |
| ATOM | 1142 | O | LEU A 117 | 118.287 | 19.435 | 9.824 | 1.00 35.15 |

Page 6-A-26

| | | | | | | | | |
|---|---|---|---|---|---|---|---|---|
| ATOM | 1143 | N | LYS | A | 118 | 119.155 | 18.531 | 11.691 | 1.00 35.41 |
| ATOM | 1145 | CA | LYS | A | 118 | 118.180 | 17.450 | 11.776 | 1.00 34.03 |
| ATOM | 1146 | CB | LYS | A | 118 | 118.896 | 16.128 | 12.047 | 1.00 36.61 |
| ATOM | 1147 | CG | LYS | A | 118 | 118.027 | 14.904 | 11.907 | 1.00 41.84 |
| ATOM | 1148 | CD | LYS | A | 118 | 118.870 | 13.640 | 11.890 | 1.00 45.83 |
| ATOM | 1149 | CE | LYS | A | 118 | 117.998 | 12.400 | 11.773 | 1.00 49.70 |
| ATOM | 1150 | NZ | LYS | A | 118 | 117.098 | 12.434 | 10.576 | 1.00 52.85 |
| ATOM | 1154 | C | LYS | A | 118 | 117.184 | 17.760 | 12.884 | 1.00 32.08 |
| ATOM | 1155 | O | LYS | A | 118 | 117.572 | 18.045 | 14.014 | 1.00 30.72 |
| ATOM | 1156 | N | LEU | A | 119 | 115.900 | 17.737 | 12.545 | 1.00 34.05 |
| ATOM | 1158 | CA | LEU | A | 119 | 114.838 | 18.036 | 13.503 | 1.00 33.03 |
| ATOM | 1159 | CB | LEU | A | 119 | 113.782 | 18.917 | 12.844 | 1.00 30.64 |
| ATOM | 1160 | CG | LEU | A | 119 | 114.277 | 20.278 | 12.372 | 1.00 26.32 |
| ATOM | 1161 | CD1 | LEU | A | 119 | 113.434 | 20.751 | 11.229 | 1.00 27.43 |
| ATOM | 1162 | CD2 | LEU | A | 119 | 114.230 | 21.258 | 13.511 | 1.00 29.44 |
| ATOM | 1163 | C | LEU | A | 119 | 114.192 | 16.771 | 14.065 | 1.00 33.62 |
| ATOM | 1164 | O | LEU | A | 119 | 113.904 | 15.819 | 13.334 | 1.00 32.69 |
| ATOM | 1165 | N | GLY | A | 120 | 113.952 | 16.776 | 15.368 | 1.00 33.78 |
| ATOM | 1167 | CA | GLY | A | 120 | 113.353 | 15.624 | 16.000 | 1.00 33.21 |
| ATOM | 1168 | C | GLY | A | 120 | 112.431 | 16.059 | 17.109 | 1.00 34.60 |
| ATOM | 1169 | O | GLY | A | 120 | 112.238 | 17.250 | 17.340 | 1.00 34.75 |
| ATOM | 1170 | N | SER | A | 121 | 111.883 | 15.086 | 17.817 | 1.00 37.06 |
| ATOM | 1172 | CA | SER | A | 121 | 110.961 | 15.355 | 18.902 | 1.00 40.83 |
| ATOM | 1173 | CB | SER | A | 121 | 109.541 | 14.982 | 18.464 | 1.00 41.68 |
| ATOM | 1174 | OG | SER | A | 121 | 108.638 | 14.924 | 19.554 | 1.00 44.95 |
| ATOM | 1176 | C | SER | A | 121 | 111.357 | 14.527 | 20.108 | 1.00 43.32 |
| ATOM | 1177 | O | SER | A | 121 | 111.990 | 13.476 | 19.975 | 1.00 44.77 |
| ATOM | 1178 | N | ASN | A | 122 | 111.034 | 15.038 | 21.287 | 1.00 45.49 |
| ATOM | 1180 | CA | ASN | A | 122 | 111.308 | 14.330 | 22.525 | 1.00 48.51 |
| ATOM | 1181 | CB | ASN | A | 122 | 112.014 | 15.244 | 23.523 | 1.00 47.83 |
| ATOM | 1182 | CG | ASN | A | 122 | 112.693 | 14.474 | 24.633 | 1.00 49.31 |
| ATOM | 1183 | OD1 | ASN | A | 122 | 112.445 | 13.283 | 24.827 | 1.00 48.55 |
| ATOM | 1184 | ND2 | ASN | A | 122 | 113.574 | 15.146 | 25.359 | 1.00 52.06 |
| ATOM | 1187 | C | ASN | A | 122 | 109.925 | 13.955 | 23.040 | 1.00 50.18 |

| | | | | | | | | |
|---|---|---|---|---|---|---|---|---|
| ATOM | 1188 | O | ASN | A | 122 | 109.197 | 14.810 | 23.534 | 1.00 51.08 |
| ATOM | 1189 | N | PRO | A | 123 | 109.530 | 12.678 | 22.895 | 1.00 51.66 |
| ATOM | 1190 | CD | PRO | A | 123 | 110.378 | 11.593 | 22.375 | 1.00 51.97 |
| ATOM | 1191 | CA | PRO | A | 123 | 108.229 | 12.152 | 23.323 | 1.00 51.81 |
| ATOM | 1192 | CB | PRO | A | 123 | 108.291 | 10.696 | 22.875 | 1.00 52.33 |
| ATOM | 1193 | CG | PRO | A | 123 | 109.744 | 10.377 | 22.996 | 1.00 52.53 |
| ATOM | 1194 | C | PRO | A | 123 | 107.903 | 12.255 | 24.808 | 1.00 52.83 |
| ATOM | 1195 | O | PRO | A | 123 | 106.777 | 12.593 | 25.171 | 1.00 54.24 |
| ATOM | 1196 | N | THR | A | 124 | 108.879 | 11.969 | 25.664 | 1.00 53.70 |
| ATOM | 1198 | CA | THR | A | 124 | 108.658 | 12.016 | 27.109 | 1.00 55.10 |
| ATOM | 1199 | CB | THR | A | 124 | 109.782 | 11.285 | 27.873 | 1.00 55.63 |
| ATOM | 1200 | OG1 | THR | A | 124 | 111.038 | 11.556 | 27.244 | 1.00 57.26 |
| ATOM | 1202 | CG2 | THR | A | 124 | 109.536 | 9.782 | 27.879 | 1.00 57.40 |
| ATOM | 1203 | C | THR | A | 124 | 108.467 | 13.418 | 27.687 | 1.00 54.39 |
| ATOM | 1204 | O | THR | A | 124 | 108.031 | 13.568 | 28.833 | 1.00 56.00 |
| ATOM | 1205 | N | SER | A | 125 | 108.794 | 14.439 | 26.901 | 1.00 52.41 |
| ATOM | 1207 | CA | SER | A | 125 | 108.647 | 15.824 | 27.345 | 1.00 49.57 |
| ATOM | 1208 | CB | SER | A | 125 | 110.023 | 16.448 | 27.598 | 1.00 49.34 |
| ATOM | 1209 | OG | SER | A | 125 | 110.859 | 16.328 | 26.459 | 1.00 50.88 |
| ATOM | 1211 | C | SER | A | 125 | 107.855 | 16.676 | 26.355 | 1.00 46.68 |
| ATOM | 1212 | O | SER | A | 125 | 107.366 | 17.747 | 26.702 | 1.00 46.69 |
| ATOM | 1213 | N | GLY | A | 126 | 107.734 | 16.191 | 25.123 | 1.00 44.84 |
| ATOM | 1215 | CA | GLY | A | 126 | 107.008 | 16.906 | 24.091 | 1.00 42.00 |
| ATOM | 1216 | C | GLY | A | 126 | 107.739 | 18.113 | 23.537 | 1.00 40.90 |
| ATOM | 1217 | O | GLY | A | 126 | 107.125 | 18.953 | 22.885 | 1.00 41.68 |
| ATOM | 1218 | N | LYS | A | 127 | 109.044 | 18.201 | 23.780 | 1.00 40.27 |
| ATOM | 1220 | CA | LYS | A | 127 | 109.846 | 19.330 | 23.303 | 1.00 38.06 |
| ATOM | 1221 | CB | LYS | A | 127 | 110.914 | 19.708 | 24.340 | 1.00 41.48 |
| ATOM | 1222 | CG | LYS | A | 127 | 110.408 | 20.194 | 25.705 | 1.00 44.59 |
| ATOM | 1223 | CD | LYS | A | 127 | 109.966 | 21.657 | 25.697 | 1.00 48.40 |
| ATOM | 1224 | CE | LYS | A | 127 | 109.668 | 22.142 | 27.118 | 1.00 49.68 |
| ATOM | 1225 | NZ | LYS | A | 127 | 109.045 | 23.498 | 27.151 | 1.00 50.76 |
| ATOM | 1229 | C | LYS | A | 127 | 110.533 | 18.984 | 21.980 | 1.00 36.38 |
| ATOM | 1230 | O | LYS | A | 127 | 110.916 | 17.827 | 21.751 | 1.00 36.93 |

Page 6-A-28

| | | | | | | | | | |
|---|---|---|---|---|---|---|---|---|---|
| ATOM | 1231 | N | PRO | A | 128 | 110.705 | 19.980 | 21.093 | 1.00 33.49 |
| ATOM | 1232 | CD | PRO | A | 128 | 110.310 | 21.395 | 21.226 | 1.00 31.99 |
| ATOM | 1233 | CA | PRO | A | 128 | 111.354 | 19.747 | 19.803 | 1.00 31.41 |
| ATOM | 1234 | CB | PRO | A | 128 | 111.023 | 21.020 | 19.037 | 1.00 31.27 |
| ATOM | 1235 | CG | PRO | A | 128 | 111.085 | 22.056 | 20.109 | 1.00 29.23 |
| ATOM | 1236 | C | PRO | A | 128 | 112.853 | 19.611 | 20.007 | 1.00 31.58 |
| ATOM | 1237 | O | PRO | A | 128 | 113.389 | 20.080 | 21.010 | 1.00 31.45 |
| ATOM | 1238 | N | THR | A | 129 | 113.523 | 18.936 | 19.087 | 1.00 31.21 |
| ATOM | 1240 | CA | THR | A | 129 | 114.960 | 18.779 | 19.181 | 1.00 30.79 |
| ATOM | 1241 | CB | THR | A | 129 | 115.377 | 17.332 | 19.510 | 1.00 29.38 |
| ATOM | 1242 | OG1 | THR | A | 129 | 114.952 | 16.451 | 18.467 | 1.00 30.58 |
| ATOM | 1244 | CG2 | THR | A | 129 | 114.773 | 16.886 | 20.818 | 1.00 27.50 |
| ATOM | 1245 | C | THR | A | 129 | 115.568 | 19.185 | 17.856 | 1.00 32.76 |
| ATOM | 1246 | O | THR | A | 129 | 114.907 | 19.148 | 16.813 | 1.00 32.88 |
| ATOM | 1247 | N | ILE | A | 130 | 116.828 | 19.582 | 17.904 | 1.00 35.82 |
| ATOM | 1249 | CA | ILE | A | 130 | 117.554 | 19.999 | 16.717 | 1.00 37.64 |
| ATOM | 1250 | CB | ILE | A | 130 | 117.302 | 21.506 | 16.401 | 1.00 38.78 |
| ATOM | 1251 | CG2 | ILE | A | 130 | 117.277 | 22.335 | 17.665 | 1.00 40.02 |
| ATOM | 1252 | CG1 | ILE | A | 130 | 118.345 | 22.042 | 15.425 | 1.00 38.94 |
| ATOM | 1253 | CD1 | ILE | A | 130 | 118.138 | 21.591 | 14.014 | 1.00 42.34 |
| ATOM | 1254 | C | ILE | A | 130 | 119.026 | 19.740 | 16.985 | 1.00 38.69 |
| ATOM | 1255 | O | ILE | A | 130 | 119.534 | 20.085 | 18.048 | 1.00 40.22 |
| ATOM | 1256 | N | THR | A | 131 | 119.681 | 19.039 | 16.069 | 1.00 39.62 |
| ATOM | 1258 | CA | THR | A | 131 | 121.098 | 18.748 | 16.217 | 1.00 40.39 |
| ATOM | 1259 | CB | THR | A | 131 | 121.351 | 17.318 | 16.747 | 1.00 40.39 |
| ATOM | 1260 | OG1 | THR | A | 131 | 120.833 | 16.354 | 15.825 | 1.00 40.07 |
| ATOM | 1262 | CG2 | THR | A | 131 | 120.696 | 17.124 | 18.113 | 1.00 43.21 |
| ATOM | 1263 | C | THR | A | 131 | 121.788 | 18.927 | 14.878 | 1.00 41.17 |
| ATOM | 1264 | O | THR | A | 131 | 121.139 | 18.951 | 13.839 | 1.00 41.86 |
| ATOM | 1265 | N | CYS | A | 132 | 123.099 | 19.107 | 14.911 | 1.00 42.72 |
| ATOM | 1267 | CA | CYS | A | 132 | 123.875 | 19.284 | 13.696 | 1.00 42.81 |
| ATOM | 1268 | CB | CYS | A | 132 | 124.963 | 20.326 | 13.932 | 1.00 42.56 |
| ATOM | 1269 | SG | CYS | A | 132 | 126.009 | 20.629 | 12.530 | 1.00 38.05 |
| ATOM | 1270 | C | CYS | A | 132 | 124.494 | 17.940 | 13.333 | 1.00 44.48 |

| | | | | | | | | |
|---|---|---|---|---|---|---|---|---|
| ATOM | 1271 | O | CYS | A 132 | 125.370 | 17.446 | 14.041 | 1.00 46.08 |
| ATOM | 1272 | N | SER | A 133 | 124.019 | 17.344 | 12.244 | 1.00 45.05 |
| ATOM | 1274 | CA | SER | A 133 | 124.508 | 16.045 | 11.794 | 1.00 45.93 |
| ATOM | 1275 | CB | SER | A 133 | 123.410 | 15.315 | 11.015 | 1.00 47.62 |
| ATOM | 1276 | OG | SER | A 133 | 122.962 | 16.082 | 9.908 | 1.00 51.90 |
| ATOM | 1278 | C | SER | A 133 | 125.793 | 16.072 | 10.966 | 1.00 45.39 |
| ATOM | 1279 | O | SER | A 133 | 126.512 | 15.078 | 10.916 | 1.00 46.00 |
| ATOM | 1280 | N | SER | A 134 | 126.056 | 17.182 | 10.282 | 1.00 45.72 |
| ATOM | 1282 | CA | SER | A 134 | 127.257 | 17.322 | 9.453 | 1.00 45.69 |
| ATOM | 1283 | CB | SER | A 134 | 127.048 | 16.672 | 8.073 | 1.00 47.17 |
| ATOM | 1284 | OG | SER | A 134 | 127.221 | 15.263 | 8.110 | 1.00 50.20 |
| ATOM | 1286 | C | SER | A 134 | 127.642 | 18.788 | 9.265 | 1.00 44.02 |
| ATOM | 1287 | O | SER | A 134 | 126.775 | 19.663 | 9.212 | 1.00 45.04 |
| ATOM | 1288 | N | CYS | A 135 | 128.939 | 19.047 | 9.145 | 1.00 42.35 |
| ATOM | 1290 | CA | CYS | A 135 | 129.442 | 20.398 | 8.941 | 1.00 40.67 |
| ATOM | 1291 | C | CYS | A 135 | 130.728 | 20.345 | 8.144 | 1.00 41.67 |
| ATOM | 1292 | O | CYS | A 135 | 131.469 | 19.361 | 8.216 | 1.00 40.71 |
| ATOM | 1293 | CB | CYS | A 135 | 129.718 | 21.084 | 10.274 | 1.00 39.61 |
| ATOM | 1294 | SG | CYS | A 135 | 130.296 | 22.800 | 10.094 | 1.00 34.66 |
| ATOM | 1295 | N | SER | A 136 | 130.975 | 21.383 | 7.354 | 1.00 43.65 |
| ATOM | 1297 | CA | SER | A 136 | 132.192 | 21.451 | 6.562 | 1.00 45.71 |
| ATOM | 1298 | CB | SER | A 136 | 132.131 | 20.504 | 5.357 | 1.00 48.55 |
| ATOM | 1299 | OG | SER | A 136 | 131.231 | 20.961 | 4.363 | 1.00 54.17 |
| ATOM | 1301 | C | SER | A 136 | 132.465 | 22.874 | 6.114 | 1.00 45.23 |
| ATOM | 1302 | O | SER | A 136 | 131.582 | 23.551 | 5.583 | 1.00 44.66 |
| ATOM | 1303 | N | SER | A 137 | 133.673 | 23.339 | 6.411 | 1.00 45.29 |
| ATOM | 1305 | CA | SER | A 137 | 134.110 | 24.671 | 6.040 | 1.00 45.90 |
| ATOM | 1306 | CB | SER | A 137 | 134.896 | 25.302 | 7.186 | 1.00 45.32 |
| ATOM | 1307 | OG | SER | A 137 | 135.302 | 26.620 | 6.867 | 1.00 46.54 |
| ATOM | 1309 | C | SER | A 137 | 134.990 | 24.514 | 4.806 | 1.00 47.49 |
| ATOM | 1310 | O | SER | A 137 | 135.330 | 23.392 | 4.416 | 1.00 48.14 |
| ATOM | 1311 | N | HIS | A 138 | 135.371 | 25.630 | 4.200 | 1.00 48.87 |
| ATOM | 1313 | CA | HIS | A 138 | 136.196 | 25.599 | 3.003 | 1.00 49.64 |
| ATOM | 1314 | CB | HIS | A 138 | 135.338 | 25.149 | 1.811 | 1.00 53.41 |

Page 6-A-30

| | | | | | | | | |
|---|---|---|---|---|---|---|---|---|
| ATOM | 1315 | CG | HIS A 138 | 136.097 | 24.992 | 0.529 | 1.00 | 56.80 |
| ATOM | 1316 | CD2 | HIS A 138 | 136.712 | 23.915 | -0.016 | 1.00 | 58.14 |
| ATOM | 1317 | ND1 | HIS A 138 | 136.268 | 26.025 | -0.368 | 1.00 | 59.15 |
| ATOM | 1319 | CE1 | HIS A 138 | 136.956 | 25.592 | -1.412 | 1.00 | 59.11 |
| ATOM | 1320 | NE2 | HIS A 138 | 137.238 | 24.316 | -1.222 | 1.00 | 59.30 |
| ATOM | 1322 | C | HIS A 138 | 136.779 | 26.983 | 2.742 | 1.00 | 49.79 |
| ATOM | 1323 | O | HIS A 138 | 136.042 | 27.938 | 2.510 | 1.00 | 49.66 |
| ATOM | 1324 | N | ILE A 139 | 138.102 | 27.082 | 2.808 | 1.00 | 50.32 |
| ATOM | 1326 | CA | ILE A 139 | 138.822 | 28.330 | 2.565 | 1.00 | 50.43 |
| ATOM | 1327 | CB | ILE A 139 | 139.937 | 28.519 | 3.606 | 1.00 | 50.04 |
| ATOM | 1328 | CG2 | ILE A 139 | 140.876 | 29.651 | 3.195 | 1.00 | 46.81 |
| ATOM | 1329 | CG1 | ILE A 139 | 139.313 | 28.751 | 4.982 | 1.00 | 49.41 |
| ATOM | 1330 | CD1 | ILE A 139 | 140.310 | 28.816 | 6.105 | 1.00 | 53.48 |
| ATOM | 1331 | C | ILE A 139 | 139.430 | 28.312 | 1.159 | 1.00 | 51.98 |
| ATOM | 1332 | O | ILE A 139 | 140.019 | 27.311 | 0.743 | 1.00 | 51.75 |
| ATOM | 1333 | N | ASN A 140 | 139.267 | 29.409 | 0.425 | 1.00 | 53.16 |
| ATOM | 1335 | CA | ASN A 140 | 139.792 | 29.503 | -0.935 | 1.00 | 54.65 |
| ATOM | 1336 | CB | ASN A 140 | 138.824 | 30.291 | -1.832 | 1.00 | 57.65 |
| ATOM | 1337 | CG | ASN A 140 | 139.311 | 30.400 | -3.276 | 1.00 | 60.64 |
| ATOM | 1338 | OD1 | ASN A 140 | 139.295 | 31.483 | -3.867 | 1.00 | 61.18 |
| ATOM | 1339 | ND2 | ASN A 140 | 139.742 | 29.279 | -3.848 | 1.00 | 62.27 |
| ATOM | 1342 | C | ASN A 140 | 141.203 | 30.092 | -1.024 | 1.00 | 53.67 |
| ATOM | 1343 | O | ASN A 140 | 142.097 | 29.463 | -1.589 | 1.00 | 53.36 |
| ATOM | 1344 | N | SER A 141 | 141.401 | 31.289 | -0.474 | 1.00 | 52.97 |
| ATOM | 1346 | CA | SER A 141 | 142.711 | 31.943 | -0.518 | 1.00 | 52.86 |
| ATOM | 1347 | CB | SER A 141 | 142.728 | 33.051 | -1.585 | 1.00 | 52.81 |
| ATOM | 1348 | OG | SER A 141 | 141.928 | 34.167 | -1.218 | 1.00 | 50.44 |
| ATOM | 1350 | C | SER A 141 | 143.114 | 32.526 | 0.832 | 1.00 | 52.49 |
| ATOM | 1351 | O | SER A 141 | 142.263 | 32.778 | 1.684 | 1.00 | 54.02 |
| ATOM | 1352 | N | VAL A 142 | 144.415 | 32.724 | 1.023 | 1.00 | 52.25 |
| ATOM | 1354 | CA | VAL A 142 | 144.947 | 33.290 | 2.256 | 1.00 | 50.52 |
| ATOM | 1355 | CB | VAL A 142 | 145.583 | 32.203 | 3.152 | 1.00 | 49.93 |
| ATOM | 1356 | CG1 | VAL A 142 | 146.214 | 32.826 | 4.380 | 1.00 | 49.68 |
| ATOM | 1357 | CG2 | VAL A 142 | 144.533 | 31.197 | 3.577 | 1.00 | 50.61 |

Page 6-A-31

| | | | | | | | | |
|---|---|---|---|---|---|---|---|---|
| ATOM | 1358 | C | VAL | A | 142 | 145.990 | 34.335 | 1.880 | 1.00 51.54 |
| ATOM | 1359 | O | VAL | A | 142 | 147.083 | 34.000 | 1.418 | 1.00 50.89 |
| ATOM | 1360 | N | HIS | A | 143 | 145.611 | 35.603 | 2.021 | 1.00 54.44 |
| ATOM | 1362 | CA | HIS | A | 143 | 146.470 | 36.742 | 1.709 | 1.00 57.63 |
| ATOM | 1363 | CB | HIS | A | 143 | 145.639 | 37.904 | 1.154 | 1.00 60.05 |
| ATOM | 1364 | CG | HIS | A | 143 | 145.323 | 37.789 | -0.306 | 1.00 65.61 |
| ATOM | 1365 | CD2 | HIS | A | 143 | 145.600 | 38.615 | -1.343 | 1.00 67.19 |
| ATOM | 1366 | ND1 | HIS | A | 143 | 144.632 | 36.722 | -0.841 | 1.00 67.65 |
| ATOM | 1368 | CE1 | HIS | A | 143 | 144.498 | 36.896 | -2.145 | 1.00 68.08 |
| ATOM | 1369 | NE2 | HIS | A | 143 | 145.078 | 38.037 | -2.473 | 1.00 67.35 |
| ATOM | 1371 | C | HIS | A | 143 | 147.229 | 37.232 | 2.936 | 1.00 58.93 |
| ATOM | 1372 | O | HIS | A | 143 | 146.663 | 37.914 | 3.791 | 1.00 58.93 |
| ATOM | 1373 | N | VAL | A | 144 | 148.510 | 36.893 | 3.012 | 1.00 60.40 |
| ATOM | 1375 | CA | VAL | A | 144 | 149.347 | 37.316 | 4.124 | 1.00 62.35 |
| ATOM | 1376 | CB | VAL | A | 144 | 150.423 | 36.270 | 4.441 | 1.00 61.34 |
| ATOM | 1377 | CG1 | VAL | A | 144 | 151.245 | 36.703 | 5.641 | 1.00 62.08 |
| ATOM | 1378 | CG2 | VAL | A | 144 | 149.771 | 34.938 | 4.709 | 1.00 62.01 |
| ATOM | 1379 | C | VAL | A | 144 | 150.000 | 38.632 | 3.724 | 1.00 64.53 |
| ATOM | 1380 | O | VAL | A | 144 | 150.971 | 38.658 | 2.971 | 1.00 64.35 |
| ATOM | 1381 | N | HIS | A | 145 | 149.440 | 39.729 | 4.214 | 1.00 67.48 |
| ATOM | 1383 | CA | HIS | A | 145 | 149.945 | 41.050 | 3.886 | 1.00 71.08 |
| ATOM | 1384 | CB | HIS | A | 145 | 148.791 | 42.045 | 3.771 | 1.00 72.13 |
| ATOM | 1385 | CG | HIS | A | 145 | 147.860 | 41.751 | 2.642 | 1.00 74.06 |
| ATOM | 1386 | CD2 | HIS | A | 145 | 148.098 | 41.536 | 1.327 | 1.00 74.26 |
| ATOM | 1387 | ND1 | HIS | A | 145 | 146.497 | 41.640 | 2.810 | 1.00 75.07 |
| ATOM | 1389 | CE1 | HIS | A | 145 | 145.934 | 41.370 | 1.646 | 1.00 75.64 |
| ATOM | 1390 | NE2 | HIS | A | 145 | 146.884 | 41.303 | 0.730 | 1.00 75.46 |
| ATOM | 1392 | C | HIS | A | 145 | 150.998 | 41.600 | 4.830 | 1.00 73.50 |
| ATOM | 1393 | O | HIS | A | 145 | 150.742 | 42.560 | 5.553 | 1.00 74.03 |
| ATOM | 1394 | N | ILE | A | 146 | 152.184 | 40.999 | 4.826 | 1.00 76.22 |
| ATOM | 1396 | CA | ILE | A | 146 | 153.277 | 41.497 | 5.660 | 1.00 78.65 |
| ATOM | 1397 | CB | ILE | A | 146 | 154.282 | 40.374 | 6.055 | 1.00 77.20 |
| ATOM | 1398 | CG2 | ILE | A | 146 | 155.320 | 40.905 | 7.037 | 1.00 75.80 |
| ATOM | 1399 | CG1 | ILE | A | 146 | 153.545 | 39.214 | 6.729 | 1.00 76.58 |

Page 6-A-32

| | | | | | | | | |
|---|---|---|---|---|---|---|---|---|
| ATOM | 1400 | CD1 | ILE A 146 | 154.451 | 38.091 | 7.184 | 1.00 | 75.69 |
| ATOM | 1401 | C | ILE A 146 | 153.972 | 42.574 | 4.815 | 1.00 | 81.85 |
| ATOM | 1402 | O | ILE A 146 | 155.107 | 42.970 | 5.082 | 1.00 | 81.33 |
| ATOM | 1403 | N | SER A 147 | 153.273 | 43.023 | 3.774 | 1.00 | 85.84 |
| ATOM | 1405 | CA | SER A 147 | 153.758 | 44.049 | 2.864 | 1.00 | 89.73 |
| ATOM | 1406 | CB | SER A 147 | 152.736 | 44.267 | 1.737 | 1.00 | 89.11 |
| ATOM | 1407 | OG | SER A 147 | 152.396 | 43.046 | 1.097 | 1.00 | 89.21 |
| ATOM | 1409 | C | SER A 147 | 153.983 | 45.354 | 3.637 | 1.00 | 92.25 |
| ATOM | 1410 | O | SER A 147 | 153.080 | 46.188 | 3.753 | 1.00 | 94.01 |
| ATOM | 1411 | N | ALA A 148 | 155.182 | 45.494 | 4.197 | 1.00 | 92.99 |
| ATOM | 1413 | CA | ALA A 148 | 155.568 | 46.675 | 4.967 | 1.00 | 92.04 |
| ATOM | 1414 | CB | ALA A 148 | 155.027 | 46.577 | 6.395 | 1.00 | 92.57 |
| ATOM | 1415 | C | ALA A 148 | 157.092 | 46.778 | 4.982 | 1.00 | 91.03 |
| ATOM | 1416 | O | ALA A 148 | 157.657 | 47.869 | 5.086 | 1.00 | 92.24 |
| ATOM | 1417 | N | ALA A 149 | 157.749 | 45.628 | 4.875 | 1.00 | 88.25 |
| ATOM | 1419 | CA | ALA A 149 | 159.201 | 45.558 | 4.864 | 1.00 | 85.00 |
| ATOM | 1420 | CB | ALA A 149 | 159.720 | 45.237 | 6.263 | 1.00 | 85.37 |
| ATOM | 1421 | C | ALA A 149 | 159.624 | 44.474 | 3.874 | 1.00 | 82.20 |
| ATOM | 1422 | O | ALA A 149 | 158.888 | 43.508 | 3.650 | 1.00 | 83.34 |
| ATOM | 1423 | N | SER A 150 | 160.785 | 44.657 | 3.252 | 1.00 | 77.07 |
| ATOM | 1425 | CA | SER A 150 | 161.304 | 43.690 | 2.293 | 1.00 | 71.37 |
| ATOM | 1426 | CB | SER A 150 | 162.463 | 44.313 | 1.509 | 1.00 | 72.17 |
| ATOM | 1427 | OG | SER A 150 | 162.092 | 45.574 | 0.968 | 1.00 | 72.35 |
| ATOM | 1429 | C | SER A 150 | 161.768 | 42.434 | 3.037 | 1.00 | 66.95 |
| ATOM | 1430 | O | SER A 150 | 162.927 | 42.330 | 3.440 | 1.00 | 66.96 |
| ATOM | 1431 | N | VAL A 151 | 160.847 | 41.496 | 3.240 | 1.00 | 60.88 |
| ATOM | 1433 | CA | VAL A 151 | 161.146 | 40.257 | 3.949 | 1.00 | 54.82 |
| ATOM | 1434 | CB | VAL A 151 | 160.736 | 40.381 | 5.446 | 1.00 | 55.79 |
| ATOM | 1435 | CG1 | VAL A 151 | 159.233 | 40.593 | 5.584 | 1.00 | 55.13 |
| ATOM | 1436 | CG2 | VAL A 151 | 161.206 | 39.176 | 6.242 | 1.00 | 55.16 |
| ATOM | 1437 | C | VAL A 151 | 160.417 | 39.104 | 3.259 | 1.00 | 51.49 |
| ATOM | 1438 | O | VAL A 151 | 159.721 | 38.308 | 3.887 | 1.00 | 51.42 |
| ATOM | 1439 | N | GLY A 152 | 160.639 | 38.992 | 1.957 | 1.00 | 48.87 |
| ATOM | 1441 | CA | GLY A 152 | 159.994 | 37.961 | 1.167 | 1.00 | 45.39 |

| | | | | | | | |
|---|---|---|---|---|---|---|---|
| ATOM | 1442 | C | GLY A 152 | 160.100 | 36.531 | 1.656 | 1.00 42.87 |
| ATOM | 1443 | O | GLY A 152 | 159.144 | 35.766 | 1.543 | 1.00 43.01 |
| ATOM | 1444 | N | TRP A 153 | 161.245 | 36.160 | 2.211 | 1.00 41.58 |
| ATOM | 1446 | CA | TRP A 153 | 161.432 | 34.795 | 2.682 | 1.00 41.92 |
| ATOM | 1447 | CB | TRP A 153 | 162.853 | 34.591 | 3.196 | 1.00 42.78 |
| ATOM | 1448 | CG | TRP A 153 | 163.153 | 35.267 | 4.501 | 1.00 43.10 |
| ATOM | 1449 | CD2 | TRP A 153 | 163.738 | 36.559 | 4.678 | 1.00 43.00 |
| ATOM | 1450 | CE2 | TRP A 153 | 163.953 | 36.738 | 6.064 | 1.00 43.32 |
| ATOM | 1451 | CE3 | TRP A 153 | 164.112 | 37.583 | 3.796 | 1.00 45.47 |
| ATOM | 1452 | CD1 | TRP A 153 | 163.022 | 34.730 | 5.760 | 1.00 42.27 |
| ATOM | 1453 | NE1 | TRP A 153 | 163.508 | 35.607 | 6.700 | 1.00 42.43 |
| ATOM | 1455 | CZ2 | TRP A 153 | 164.528 | 37.897 | 6.587 | 1.00 44.70 |
| ATOM | 1456 | CZ3 | TRP A 153 | 164.686 | 38.738 | 4.317 | 1.00 47.45 |
| ATOM | 1457 | CH2 | TRP A 153 | 164.889 | 38.885 | 5.701 | 1.00 47.30 |
| ATOM | 1458 | C | TRP A 153 | 160.442 | 34.393 | 3.763 | 1.00 41.11 |
| ATOM | 1459 | O | TRP A 153 | 160.053 | 33.236 | 3.852 | 1.00 41.06 |
| ATOM | 1460 | N | LEU A 154 | 160.045 | 35.357 | 4.585 | 1.00 40.39 |
| ATOM | 1462 | CA | LEU A 154 | 159.109 | 35.103 | 5.669 | 1.00 38.88 |
| ATOM | 1463 | CB | LEU A 154 | 159.080 | 36.284 | 6.618 | 1.00 37.14 |
| ATOM | 1464 | CG | LEU A 154 | 158.607 | 35.931 | 8.011 | 1.00 35.27 |
| ATOM | 1465 | CD1 | LEU A 154 | 159.491 | 34.860 | 8.602 | 1.00 35.45 |
| ATOM | 1466 | CD2 | LEU A 154 | 158.655 | 37.166 | 8.838 | 1.00 37.10 |
| ATOM | 1467 | C | LEU A 154 | 157.721 | 34.847 | 5.115 | 1.00 38.87 |
| ATOM | 1468 | O | LEU A 154 | 156.997 | 33.985 | 5.611 | 1.00 39.93 |
| ATOM | 1469 | N | ILE A 155 | 157.357 | 35.596 | 4.079 | 1.00 40.01 |
| ATOM | 1471 | CA | ILE A 155 | 156.062 | 35.435 | 3.430 | 1.00 40.45 |
| ATOM | 1472 | CB | ILE A 155 | 155.765 | 36.579 | 2.454 | 1.00 39.45 |
| ATOM | 1473 | CG2 | ILE A 155 | 154.467 | 36.307 | 1.721 | 1.00 39.70 |
| ATOM | 1474 | CG1 | ILE A 155 | 155.679 | 37.906 | 3.215 | 1.00 39.53 |
| ATOM | 1475 | CD1 | ILE A 155 | 155.426 | 39.114 | 2.337 | 1.00 39.05 |
| ATOM | 1476 | C | ILE A 155 | 156.048 | 34.106 | 2.686 | 1.00 42.61 |
| ATOM | 1477 | O | ILE A 155 | 155.015 | 33.435 | 2.619 | 1.00 44.53 |
| ATOM | 1478 | N | GLN A 156 | 157.187 | 33.745 | 2.100 | 1.00 43.49 |
| ATOM | 1480 | CA | GLN A 156 | 157.323 | 32.475 | 1.398 | 1.00 44.17 |

| | | | | | | | | |
|---|---|---|---|---|---|---|---|---|
| ATOM | 1481 | CB | GLN | A | 156 | 158.708 | 32.368 | 0.760 | 1.00 | 48.67 |
| ATOM | 1482 | CG | GLN | A | 156 | 159.097 | 30.954 | 0.310 | 1.00 | 55.67 |
| ATOM | 1483 | CD | GLN | A | 156 | 160.369 | 30.440 | 0.988 | 1.00 | 59.91 |
| ATOM | 1484 | OE1 | GLN | A | 156 | 160.673 | 30.802 | 2.125 | 1.00 | 61.96 |
| ATOM | 1485 | NE2 | GLN | A | 156 | 161.114 | 29.593 | 0.285 | 1.00 | 60.94 |
| ATOM | 1488 | C | GLN | A | 156 | 157.163 | 31.384 | 2.452 | 1.00 | 43.64 |
| ATOM | 1489 | O | GLN | A | 156 | 156.445 | 30.408 | 2.249 | 1.00 | 43.84 |
| ATOM | 1490 | N | LEU | A | 157 | 157.834 | 31.581 | 3.585 | 1.00 | 43.44 |
| ATOM | 1492 | CA | LEU | A | 157 | 157.794 | 30.653 | 4.704 | 1.00 | 41.27 |
| ATOM | 1493 | CB | LEU | A | 157 | 158.644 | 31.175 | 5.866 | 1.00 | 42.44 |
| ATOM | 1494 | CG | LEU | A | 157 | 160.152 | 30.930 | 5.797 | 1.00 | 42.39 |
| ATOM | 1495 | CD1 | LEU | A | 157 | 160.873 | 31.722 | 6.876 | 1.00 | 41.73 |
| ATOM | 1496 | CD2 | LEU | A | 157 | 160.426 | 29.447 | 5.948 | 1.00 | 42.15 |
| ATOM | 1497 | C | LEU | A | 157 | 156.372 | 30.423 | 5.173 | 1.00 | 40.27 |
| ATOM | 1498 | O | LEU | A | 157 | 155.948 | 29.280 | 5.328 | 1.00 | 41.05 |
| ATOM | 1499 | N | PHE | A | 158 | 155.620 | 31.497 | 5.378 | 1.00 | 39.18 |
| ATOM | 1501 | CA | PHE | A | 158 | 154.246 | 31.341 | 5.821 | 1.00 | 41.38 |
| ATOM | 1502 | CB | PHE | A | 158 | 153.519 | 32.684 | 5.927 | 1.00 | 40.94 |
| ATOM | 1503 | CG | PHE | A | 158 | 152.145 | 32.570 | 6.537 | 1.00 | 43.98 |
| ATOM | 1504 | CD1 | PHE | A | 158 | 151.068 | 32.087 | 5.788 | 1.00 | 44.07 |
| ATOM | 1505 | CD2 | PHE | A | 158 | 151.939 | 32.886 | 7.878 | 1.00 | 43.45 |
| ATOM | 1506 | CE1 | PHE | A | 158 | 149.814 | 31.915 | 6.367 | 1.00 | 42.96 |
| ATOM | 1507 | CE2 | PHE | A | 158 | 150.690 | 32.718 | 8.465 | 1.00 | 41.63 |
| ATOM | 1508 | CZ | PHE | A | 158 | 149.626 | 32.231 | 7.707 | 1.00 | 43.20 |
| ATOM | 1509 | C | PHE | A | 158 | 153.472 | 30.409 | 4.893 | 1.00 | 42.96 |
| ATOM | 1510 | O | PHE | A | 158 | 152.862 | 29.443 | 5.350 | 1.00 | 44.53 |
| ATOM | 1511 | N | HIS | A | 159 | 153.513 | 30.682 | 3.594 | 1.00 | 45.12 |
| ATOM | 1513 | CA | HIS | A | 159 | 152.790 | 29.860 | 2.624 | 1.00 | 46.02 |
| ATOM | 1514 | CB | HIS | A | 159 | 152.808 | 30.507 | 1.230 | 1.00 | 45.21 |
| ATOM | 1515 | CG | HIS | A | 159 | 152.049 | 31.796 | 1.145 | 1.00 | 44.03 |
| ATOM | 1516 | CD2 | HIS | A | 159 | 152.477 | 33.081 | 1.099 | 1.00 | 44.13 |
| ATOM | 1517 | ND1 | HIS | A | 159 | 150.674 | 31.851 | 1.087 | 1.00 | 44.17 |
| ATOM | 1519 | CE1 | HIS | A | 159 | 150.285 | 33.111 | 1.012 | 1.00 | 45.07 |
| ATOM | 1520 | NE2 | HIS | A | 159 | 151.360 | 33.878 | 1.016 | 1.00 | 45.02 |

| ATOM | 1522 | C   | HIS A 159 | 153.314 | 28.426 | 2.524  | 1.00 | 47.97 |
|------|------|-----|-----------|---------|--------|--------|------|-------|
| ATOM | 1523 | O   | HIS A 159 | 152.530 | 27.491 | 2.353  | 1.00 | 48.86 |
| ATOM | 1524 | N   | LYS A 160 | 154.624 | 28.253 | 2.678  | 1.00 | 49.77 |
| ATOM | 1526 | CA  | LYS A 160 | 155.246 | 26.935 | 2.562  | 1.00 | 50.79 |
| ATOM | 1527 | CB  | LYS A 160 | 156.664 | 27.080 | 1.990  | 1.00 | 51.90 |
| ATOM | 1528 | CG  | LYS A 160 | 157.285 | 25.768 | 1.539  | 1.00 | 53.77 |
| ATOM | 1529 | CD  | LYS A 160 | 158.669 | 25.957 | 0.950  | 1.00 | 54.99 |
| ATOM | 1530 | CE  | LYS A 160 | 159.130 | 24.690 | 0.231  | 1.00 | 57.16 |
| ATOM | 1531 | NZ  | LYS A 160 | 158.253 | 24.330 | -0.934 | 1.00 | 55.19 |
| ATOM | 1535 | C   | LYS A 160 | 155.286 | 26.065 | 3.825  | 1.00 | 51.12 |
| ATOM | 1536 | O   | LYS A 160 | 155.537 | 24.862 | 3.736  | 1.00 | 52.93 |
| ATOM | 1537 | N   | LYS A 161 | 155.031 | 26.646 | 4.991  | 1.00 | 49.90 |
| ATOM | 1539 | CA  | LYS A 161 | 155.086 | 25.873 | 6.229  | 1.00 | 48.78 |
| ATOM | 1540 | CB  | LYS A 161 | 156.340 | 26.263 | 7.016  | 1.00 | 51.36 |
| ATOM | 1541 | CG  | LYS A 161 | 157.660 | 25.983 | 6.310  | 1.00 | 55.24 |
| ATOM | 1542 | CD  | LYS A 161 | 158.186 | 24.592 | 6.626  | 1.00 | 59.40 |
| ATOM | 1543 | CE  | LYS A 161 | 158.484 | 24.443 | 8.114  | 1.00 | 61.04 |
| ATOM | 1544 | NZ  | LYS A 161 | 159.015 | 23.095 | 8.464  | 1.00 | 62.60 |
| ATOM | 1548 | C   | LYS A 161 | 153.875 | 26.012 | 7.149  | 1.00 | 47.20 |
| ATOM | 1549 | O   | LYS A 161 | 153.460 | 25.042 | 7.787  | 1.00 | 46.35 |
| ATOM | 1550 | N   | ILE A 162 | 153.311 | 27.214 | 7.209  | 1.00 | 46.07 |
| ATOM | 1552 | CA  | ILE A 162 | 152.186 | 27.506 | 8.094  | 1.00 | 45.42 |
| ATOM | 1553 | CB  | ILE A 162 | 152.421 | 28.854 | 8.806  | 1.00 | 45.05 |
| ATOM | 1554 | CG2 | ILE A 162 | 151.211 | 29.251 | 9.646  | 1.00 | 45.73 |
| ATOM | 1555 | CG1 | ILE A 162 | 153.679 | 28.764 | 9.670  | 1.00 | 43.35 |
| ATOM | 1556 | CD1 | ILE A 162 | 154.015 | 30.042 | 10.353 | 1.00 | 43.37 |
| ATOM | 1557 | C   | ILE A 162 | 150.764 | 27.483 | 7.520  | 1.00 | 45.58 |
| ATOM | 1558 | O   | ILE A 162 | 149.849 | 26.960 | 8.157  | 1.00 | 45.52 |
| ATOM | 1559 | N   | GLU A 163 | 150.570 | 28.036 | 6.329  | 1.00 | 46.35 |
| ATOM | 1561 | CA  | GLU A 163 | 149.239 | 28.093 | 5.731  | 1.00 | 47.82 |
| ATOM | 1562 | CB  | GLU A 163 | 149.310 | 28.624 | 4.302  | 1.00 | 49.25 |
| ATOM | 1563 | CG  | GLU A 163 | 147.956 | 29.028 | 3.735  | 1.00 | 51.68 |
| ATOM | 1564 | CD  | GLU A 163 | 147.965 | 29.204 | 2.224  | 1.00 | 52.54 |
| ATOM | 1565 | OE1 | GLU A 163 | 149.007 | 29.597 | 1.658  | 1.00 | 53.57 |

| ATOM | 1566 | OE2 | GLU A 163 | 146.918 | 28.941 | 1.599 | 1.00 | 53.52 |
| ATOM | 1567 | C | GLU A 163 | 148.470 | 26.775 | 5.746 | 1.00 | 47.94 |
| ATOM | 1568 | O | GLU A 163 | 147.289 | 26.757 | 6.069 | 1.00 | 49.00 |
| ATOM | 1569 | N | SER A 164 | 149.142 | 25.678 | 5.420 | 1.00 | 49.09 |
| ATOM | 1571 | CA | SER A 164 | 148.510 | 24.360 | 5.383 | 1.00 | 49.75 |
| ATOM | 1572 | CB | SER A 164 | 149.486 | 23.327 | 4.818 | 1.00 | 50.94 |
| ATOM | 1573 | OG | SER A 164 | 149.971 | 23.737 | 3.548 | 1.00 | 56.63 |
| ATOM | 1575 | C | SER A 164 | 147.953 | 23.865 | 6.717 | 1.00 | 49.89 |
| ATOM | 1576 | O | SER A 164 | 147.100 | 22.982 | 6.739 | 1.00 | 52.82 |
| ATOM | 1577 | N | ALA A 165 | 148.442 | 24.415 | 7.824 | 1.00 | 48.05 |
| ATOM | 1579 | CA | ALA A 165 | 147.978 | 24.017 | 9.151 | 1.00 | 44.58 |
| ATOM | 1580 | CB | ALA A 165 | 149.153 | 23.920 | 10.109 | 1.00 | 45.11 |
| ATOM | 1581 | C | ALA A 165 | 146.947 | 25.009 | 9.678 | 1.00 | 43.87 |
| ATOM | 1582 | O | ALA A 165 | 145.980 | 24.626 | 10.335 | 1.00 | 43.62 |
| ATOM | 1583 | N | LEU A 166 | 147.169 | 26.287 | 9.391 | 1.00 | 43.88 |
| ATOM | 1585 | CA | LEU A 166 | 146.267 | 27.349 | 9.812 | 1.00 | 44.57 |
| ATOM | 1586 | CB | LEU A 166 | 146.783 | 28.701 | 9.313 | 1.00 | 41.17 |
| ATOM | 1587 | CG | LEU A 166 | 145.977 | 29.957 | 9.655 | 1.00 | 39.43 |
| ATOM | 1588 | CD1 | LEU A 166 | 146.438 | 30.508 | 10.979 | 1.00 | 40.32 |
| ATOM | 1589 | CD2 | LEU A 166 | 146.165 | 31.005 | 8.577 | 1.00 | 39.33 |
| ATOM | 1590 | C | LEU A 166 | 144.870 | 27.094 | 9.246 | 1.00 | 47.80 |
| ATOM | 1591 | O | LEU A 166 | 143.899 | 27.003 | 9.995 | 1.00 | 50.31 |
| ATOM | 1592 | N | ARG A 167 | 144.777 | 26.946 | 7.927 | 1.00 | 49.83 |
| ATOM | 1594 | CA | ARG A 167 | 143.493 | 26.714 | 7.274 | 1.00 | 53.68 |
| ATOM | 1595 | CB | ARG A 167 | 143.659 | 26.564 | 5.753 | 1.00 | 54.31 |
| ATOM | 1596 | CG | ARG A 167 | 144.488 | 25.354 | 5.329 | 1.00 | 57.76 |
| ATOM | 1597 | CD | ARG A 167 | 144.282 | 24.966 | 3.869 | 1.00 | 58.03 |
| ATOM | 1598 | NE | ARG A 167 | 144.657 | 26.032 | 2.948 | 1.00 | 56.39 |
| ATOM | 1600 | CZ | ARG A 167 | 143.786 | 26.753 | 2.256 | 1.00 | 55.99 |
| ATOM | 1601 | NH1 | ARG A 167 | 142.485 | 26.525 | 2.380 | 1.00 | 56.36 |
| ATOM | 1604 | NH2 | ARG A 167 | 144.214 | 27.699 | 1.436 | 1.00 | 55.25 |
| ATOM | 1607 | C | ARG A 167 | 142.774 | 25.495 | 7.836 | 1.00 | 56.26 |
| ATOM | 1608 | O | ARG A 167 | 141.570 | 25.544 | 8.088 | 1.00 | 58.47 |
| ATOM | 1609 | N | ASN A 168 | 143.517 | 24.418 | 8.077 | 1.00 | 59.06 |

Page 6-A-37

| | | | | | | | | |
|---|---|---|---|---|---|---|---|---|
| ATOM | 1611 | CA | ASN A 168 | 142.924 | 23.188 | 8.596 | 1.00 | 60.42 |
| ATOM | 1612 | CB | ASN A 168 | 143.936 | 22.037 | 8.586 | 1.00 | 63.69 |
| ATOM | 1613 | CG | ASN A 168 | 143.264 | 20.670 | 8.594 | 1.00 | 69.44 |
| ATOM | 1614 | OD1 | ASN A 168 | 142.186 | 20.491 | 8.021 | 1.00 | 73.41 |
| ATOM | 1615 | ND2 | ASN A 168 | 143.902 | 19.696 | 9.232 | 1.00 | 71.02 |
| ATOM | 1618 | C | ASN A 168 | 142.358 | 23.378 | 9.995 | 1.00 | 58.54 |
| ATOM | 1619 | O | ASN A 168 | 141.291 | 22.857 | 10.312 | 1.00 | 59.34 |
| ATOM | 1620 | N | LYS A 169 | 143.059 | 24.138 | 10.826 | 1.00 | 56.61 |
| ATOM | 1622 | CA | LYS A 169 | 142.591 | 24.380 | 12.179 | 1.00 | 54.57 |
| ATOM | 1623 | CB | LYS A 169 | 143.732 | 24.882 | 13.065 | 1.00 | 56.85 |
| ATOM | 1624 | CG | LYS A 169 | 143.365 | 25.002 | 14.540 | 1.00 | 60.65 |
| ATOM | 1625 | CD | LYS A 169 | 144.599 | 24.927 | 15.425 | 1.00 | 65.37 |
| ATOM | 1626 | CE | LYS A 169 | 145.276 | 23.560 | 15.329 | 1.00 | 68.82 |
| ATOM | 1627 | NZ | LYS A 169 | 146.576 | 23.504 | 16.062 | 1.00 | 70.63 |
| ATOM | 1631 | C | LYS A 169 | 141.439 | 25.372 | 12.173 | 1.00 | 51.59 |
| ATOM | 1632 | O | LYS A 169 | 140.570 | 25.327 | 13.035 | 1.00 | 51.73 |
| ATOM | 1633 | N | MET A 170 | 141.426 | 26.264 | 11.192 | 1.00 | 49.16 |
| ATOM | 1635 | CA | MET A 170 | 140.362 | 27.251 | 11.090 | 1.00 | 47.96 |
| ATOM | 1636 | CB | MET A 170 | 140.733 | 28.340 | 10.087 | 1.00 | 49.44 |
| ATOM | 1637 | CG | MET A 170 | 139.792 | 29.528 | 10.105 | 1.00 | 52.89 |
| ATOM | 1638 | SD | MET A 170 | 139.730 | 30.289 | 11.734 | 1.00 | 55.23 |
| ATOM | 1639 | CE | MET A 170 | 141.170 | 31.310 | 11.695 | 1.00 | 55.26 |
| ATOM | 1640 | C | MET A 170 | 139.075 | 26.565 | 10.659 | 1.00 | 45.37 |
| ATOM | 1641 | O | MET A 170 | 137.989 | 26.892 | 11.139 | 1.00 | 46.51 |
| ATOM | 1642 | N | ASN A 171 | 139.207 | 25.601 | 9.759 | 1.00 | 42.65 |
| ATOM | 1644 | CA | ASN A 171 | 138.063 | 24.858 | 9.268 | 1.00 | 41.99 |
| ATOM | 1645 | CB | ASN A 171 | 138.448 | 24.034 | 8.039 | 1.00 | 42.92 |
| ATOM | 1646 | CG | ASN A 171 | 138.644 | 24.889 | 6.795 | 1.00 | 43.47 |
| ATOM | 1647 | OD1 | ASN A 171 | 138.041 | 25.957 | 6.658 | 1.00 | 44.24 |
| ATOM | 1648 | ND2 | ASN A 171 | 139.478 | 24.415 | 5.875 | 1.00 | 44.77 |
| ATOM | 1651 | C | ASN A 171 | 137.487 | 23.962 | 10.353 | 1.00 | 42.70 |
| ATOM | 1652 | O | ASN A 171 | 136.284 | 23.701 | 10.374 | 1.00 | 43.68 |
| ATOM | 1653 | N | SER A 172 | 138.341 | 23.502 | 11.263 | 1.00 | 44.20 |
| ATOM | 1655 | CA | SER A 172 | 137.898 | 22.645 | 12.358 | 1.00 | 45.11 |

| ATOM | 1656 | CB | SER A 172 | 139.069 | 21.841 | 12.935 | 1.00 | 46.36 |
|---|---|---|---|---|---|---|---|---|
| ATOM | 1657 | OG | SER A 172 | 140.094 | 22.685 | 13.438 | 1.00 | 49.96 |
| ATOM | 1659 | C | SER A 172 | 137.230 | 23.474 | 13.454 | 1.00 | 44.96 |
| ATOM | 1660 | O | SER A 172 | 136.204 | 23.069 | 14.005 | 1.00 | 47.71 |
| ATOM | 1661 | N | GLN A 173 | 137.811 | 24.635 | 13.759 | 1.00 | 43.91 |
| ATOM | 1663 | CA | GLN A 173 | 137.276 | 25.541 | 14.776 | 1.00 | 40.36 |
| ATOM | 1664 | CB | GLN A 173 | 138.214 | 26.730 | 14.990 | 1.00 | 41.61 |
| ATOM | 1665 | CG | GLN A 173 | 139.444 | 26.421 | 15.816 | 1.00 | 43.62 |
| ATOM | 1666 | CD | GLN A 173 | 139.095 | 25.943 | 17.205 | 1.00 | 46.78 |
| ATOM | 1667 | OE1 | GLN A 173 | 138.657 | 26.722 | 18.052 | 1.00 | 50.29 |
| ATOM | 1668 | NE2 | GLN A 173 | 139.279 | 24.654 | 17.448 | 1.00 | 48.32 |
| ATOM | 1671 | C | GLN A 173 | 135.893 | 26.047 | 14.386 | 1.00 | 38.81 |
| ATOM | 1672 | O | GLN A 173 | 134.990 | 26.098 | 15.218 | 1.00 | 38.42 |
| ATOM | 1673 | N | VAL A 174 | 135.734 | 26.423 | 13.120 | 1.00 | 36.59 |
| ATOM | 1675 | CA | VAL A 174 | 134.456 | 26.912 | 12.621 | 1.00 | 34.47 |
| ATOM | 1676 | CB | VAL A 174 | 134.559 | 27.328 | 11.147 | 1.00 | 32.46 |
| ATOM | 1677 | CG1 | VAL A 174 | 133.183 | 27.559 | 10.564 | 1.00 | 32.42 |
| ATOM | 1678 | CG2 | VAL A 174 | 135.380 | 28.601 | 11.037 | 1.00 | 31.13 |
| ATOM | 1679 | C | VAL A 174 | 133.363 | 25.861 | 12.810 | 1.00 | 34.32 |
| ATOM | 1680 | O | VAL A 174 | 132.350 | 26.130 | 13.445 | 1.00 | 36.14 |
| ATOM | 1681 | N | CYS A 175 | 133.586 | 24.652 | 12.308 | 1.00 | 35.02 |
| ATOM | 1683 | CA | CYS A 175 | 132.601 | 23.591 | 12.460 | 1.00 | 35.40 |
| ATOM | 1684 | C | CYS A 175 | 132.440 | 23.152 | 13.906 | 1.00 | 36.62 |
| ATOM | 1685 | O | CYS A 175 | 131.405 | 22.597 | 14.284 | 1.00 | 37.92 |
| ATOM | 1686 | CB | CYS A 175 | 132.925 | 22.396 | 11.573 | 1.00 | 33.94 |
| ATOM | 1687 | SG | CYS A 175 | 132.302 | 22.595 | 9.876 | 1.00 | 42.37 |
| ATOM | 1688 | N | GLU A 176 | 133.459 | 23.386 | 14.720 | 1.00 | 38.42 |
| ATOM | 1690 | CA | GLU A 176 | 133.365 | 23.034 | 16.123 | 1.00 | 40.14 |
| ATOM | 1691 | CB | GLU A 176 | 134.739 | 23.093 | 16.793 | 1.00 | 43.35 |
| ATOM | 1692 | CG | GLU A 176 | 134.747 | 22.502 | 18.193 | 1.00 | 50.93 |
| ATOM | 1693 | CD | GLU A 176 | 136.132 | 22.385 | 18.783 | 1.00 | 53.93 |
| ATOM | 1694 | OE1 | GLU A 176 | 136.867 | 21.459 | 18.382 | 1.00 | 58.04 |
| ATOM | 1695 | OE2 | GLU A 176 | 136.481 | 23.207 | 19.658 | 1.00 | 57.02 |
| ATOM | 1696 | C | GLU A 176 | 132.386 | 24.024 | 16.772 | 1.00 | 40.43 |

| | | | | | | | | |
|---|---|---|---|---|---|---|---|---|
| ATOM | 1697 | O | GLU | A | 176 | 131.498 | 23.627 | 17.528 | 1.00 41.95 |
| ATOM | 1698 | N | LYS | A | 177 | 132.507 | 25.301 | 16.419 | 1.00 39.36 |
| ATOM | 1700 | CA | LYS | A | 177 | 131.625 | 26.332 | 16.956 | 1.00 38.66 |
| ATOM | 1701 | CB | LYS | A | 177 | 132.074 | 27.729 | 16.510 | 1.00 38.94 |
| ATOM | 1702 | CG | LYS | A | 177 | 133.403 | 28.194 | 17.089 | 1.00 40.75 |
| ATOM | 1703 | CD | LYS | A | 177 | 133.336 | 28.424 | 18.592 | 1.00 40.88 |
| ATOM | 1704 | CE | LYS | A | 177 | 134.694 | 28.852 | 19.152 | 1.00 40.13 |
| ATOM | 1705 | NZ | LYS | A | 177 | 134.688 | 28.995 | 20.637 | 1.00 40.04 |
| ATOM | 1709 | C | LYS | A | 177 | 130.190 | 26.099 | 16.503 | 1.00 37.24 |
| ATOM | 1710 | O | LYS | A | 177 | 129.277 | 26.078 | 17.318 | 1.00 39.39 |
| ATOM | 1711 | N | VAL | A | 178 | 130.002 | 25.901 | 15.204 | 1.00 35.46 |
| ATOM | 1713 | CA | VAL | A | 178 | 128.676 | 25.676 | 14.641 | 1.00 33.61 |
| ATOM | 1714 | CB | VAL | A | 178 | 128.747 | 25.442 | 13.124 | 1.00 31.21 |
| ATOM | 1715 | CG1 | VAL | A | 178 | 127.365 | 25.166 | 12.568 | 1.00 32.70 |
| ATOM | 1716 | CG2 | VAL | A | 178 | 129.346 | 26.652 | 12.446 | 1.00 31.16 |
| ATOM | 1717 | C | VAL | A | 178 | 127.960 | 24.505 | 15.299 | 1.00 34.02 |
| ATOM | 1718 | O | VAL | A | 178 | 126.844 | 24.656 | 15.784 | 1.00 36.09 |
| ATOM | 1719 | N | THR | A | 179 | 128.611 | 23.349 | 15.338 | 1.00 34.04 |
| ATOM | 1721 | CA | THR | A | 179 | 128.018 | 22.167 | 15.947 | 1.00 35.60 |
| ATOM | 1722 | CB | THR | A | 179 | 128.977 | 20.968 | 15.865 | 1.00 32.77 |
| ATOM | 1723 | OG1 | THR | A | 179 | 129.372 | 20.775 | 14.505 | 1.00 32.73 |
| ATOM | 1725 | CG2 | THR | A | 179 | 128.296 | 19.706 | 16.330 | 1.00 35.18 |
| ATOM | 1726 | C | THR | A | 179 | 127.634 | 22.428 | 17.408 | 1.00 39.92 |
| ATOM | 1727 | O | THR | A | 179 | 126.554 | 22.037 | 17.858 | 1.00 42.33 |
| ATOM | 1728 | N | ASN | A | 180 | 128.497 | 23.131 | 18.132 | 1.00 43.69 |
| ATOM | 1730 | CA | ASN | A | 180 | 128.244 | 23.435 | 19.537 | 1.00 44.92 |
| ATOM | 1731 | CB | ASN | A | 180 | 129.496 | 23.991 | 20.213 | 1.00 49.20 |
| ATOM | 1732 | CG | ASN | A | 180 | 130.522 | 22.920 | 20.532 | 1.00 53.34 |
| ATOM | 1733 | OD1 | ASN | A | 180 | 131.550 | 23.213 | 21.140 | 1.00 58.92 |
| ATOM | 1734 | ND2 | ASN | A | 180 | 130.258 | 21.680 | 20.126 | 1.00 53.15 |
| ATOM | 1737 | C | ASN | A | 180 | 127.101 | 24.406 | 19.738 | 1.00 44.35 |
| ATOM | 1738 | O | ASN | A | 180 | 126.252 | 24.194 | 20.593 | 1.00 46.90 |
| ATOM | 1739 | N | SER | A | 181 | 127.095 | 25.487 | 18.972 | 1.00 42.77 |
| ATOM | 1741 | CA | SER | A | 181 | 126.047 | 26.481 | 19.084 | 1.00 42.55 |

Page 6-A-40

| | | | | | | | | |
|---|---|---|---|---|---|---|---|---|
| ATOM | 1742 | CB | SER A 181 | 126.274 | 27.605 | 18.076 | 1.00 | 46.25 |
| ATOM | 1743 | OG | SER A 181 | 127.508 | 28.261 | 18.319 | 1.00 | 51.45 |
| ATOM | 1745 | C | SER A 181 | 124.686 | 25.841 | 18.869 | 1.00 | 41.46 |
| ATOM | 1746 | O | SER A 181 | 123.720 | 26.203 | 19.528 | 1.00 | 43.31 |
| ATOM | 1747 | N | VAL A 182 | 124.610 | 24.870 | 17.969 | 1.00 | 41.03 |
| ATOM | 1749 | CA | VAL A 182 | 123.346 | 24.195 | 17.712 | 1.00 | 40.50 |
| ATOM | 1750 | CB | VAL A 182 | 123.468 | 23.177 | 16.565 | 1.00 | 40.39 |
| ATOM | 1751 | CG1 | VAL A 182 | 122.133 | 22.489 | 16.333 | 1.00 | 41.54 |
| ATOM | 1752 | CG2 | VAL A 182 | 123.918 | 23.874 | 15.295 | 1.00 | 39.67 |
| ATOM | 1753 | C | VAL A 182 | 122.865 | 23.481 | 18.970 | 1.00 | 41.04 |
| ATOM | 1754 | O | VAL A 182 | 121.831 | 23.836 | 19.536 | 1.00 | 41.32 |
| ATOM | 1755 | N | SER A 183 | 123.647 | 22.510 | 19.429 | 1.00 | 42.02 |
| ATOM | 1757 | CA | SER A 183 | 123.311 | 21.735 | 20.616 | 1.00 | 41.82 |
| ATOM | 1758 | CB | SER A 183 | 124.339 | 20.620 | 20.828 | 1.00 | 42.01 |
| ATOM | 1759 | OG | SER A 183 | 124.180 | 19.588 | 19.867 | 1.00 | 47.44 |
| ATOM | 1761 | C | SER A 183 | 123.187 | 22.553 | 21.895 | 1.00 | 41.66 |
| ATOM | 1762 | O | SER A 183 | 122.251 | 22.358 | 22.673 | 1.00 | 43.45 |
| ATOM | 1763 | N | SER A 184 | 124.120 | 23.472 | 22.102 | 1.00 | 40.24 |
| ATOM | 1765 | CA | SER A 184 | 124.143 | 24.293 | 23.305 | 1.00 | 40.26 |
| ATOM | 1766 | CB | SER A 184 | 125.590 | 24.639 | 23.670 | 1.00 | 42.61 |
| ATOM | 1767 | OG | SER A 184 | 126.340 | 23.468 | 23.947 | 1.00 | 47.85 |
| ATOM | 1769 | C | SER A 184 | 123.307 | 25.567 | 23.312 | 1.00 | 39.22 |
| ATOM | 1770 | O | SER A 184 | 122.991 | 26.088 | 24.382 | 1.00 | 40.56 |
| ATOM | 1771 | N | GLU A 185 | 122.942 | 26.078 | 22.145 | 1.00 | 37.87 |
| ATOM | 1773 | CA | GLU A 185 | 122.169 | 27.313 | 22.098 | 1.00 | 37.71 |
| ATOM | 1774 | CB | GLU A 185 | 123.060 | 28.485 | 21.683 | 1.00 | 40.53 |
| ATOM | 1775 | CG | GLU A 185 | 124.010 | 28.960 | 22.768 | 1.00 | 45.79 |
| ATOM | 1776 | CD | GLU A 185 | 124.987 | 30.024 | 22.296 | 1.00 | 50.89 |
| ATOM | 1777 | OE1 | GLU A 185 | 124.887 | 30.490 | 21.138 | 1.00 | 55.20 |
| ATOM | 1778 | OE2 | GLU A 185 | 125.872 | 30.390 | 23.097 | 1.00 | 55.19 |
| ATOM | 1779 | C | GLU A 185 | 120.934 | 27.277 | 21.225 | 1.00 | 35.83 |
| ATOM | 1780 | O | GLU A 185 | 119.921 | 27.861 | 21.584 | 1.00 | 38.77 |
| ATOM | 1781 | N | LEU A 186 | 121.008 | 26.605 | 20.082 | 1.00 | 34.44 |
| ATOM | 1783 | CA | LEU A 186 | 119.864 | 26.533 | 19.187 | 1.00 | 33.39 |

Page 6-A-41

| | | | | | | | | |
|---|---|---|---|---|---|---|---|---|
| ATOM | 1784 | CB | LEU A 186 | 120.269 | 25.978 | 17.818 | 1.00 | 30.92 |
| ATOM | 1785 | CG | LEU A 186 | 119.709 | 26.645 | 16.553 | 1.00 | 26.02 |
| ATOM | 1786 | CD1 | LEU A 186 | 119.228 | 25.581 | 15.601 | 1.00 | 23.97 |
| ATOM | 1787 | CD2 | LEU A 186 | 118.581 | 27.619 | 16.867 | 1.00 | 25.38 |
| ATOM | 1788 | C | LEU A 186 | 118.794 | 25.652 | 19.802 | 1.00 | 34.20 |
| ATOM | 1789 | O | LEU A 186 | 117.655 | 26.083 | 19.963 | 1.00 | 35.35 |
| ATOM | 1790 | N | GLN A 187 | 119.168 | 24.433 | 20.181 | 1.00 | 35.06 |
| ATOM | 1792 | CA | GLN A 187 | 118.218 | 23.500 | 20.778 | 1.00 | 37.32 |
| ATOM | 1793 | CB | GLN A 187 | 118.856 | 22.130 | 21.031 | 1.00 | 38.08 |
| ATOM | 1794 | CG | GLN A 187 | 117.859 | 21.104 | 21.549 | 1.00 | 39.72 |
| ATOM | 1795 | CD | GLN A 187 | 118.388 | 19.696 | 21.506 | 1.00 | 39.64 |
| ATOM | 1796 | OE1 | GLN A 187 | 118.203 | 18.984 | 20.520 | 1.00 | 42.24 |
| ATOM | 1797 | NE2 | GLN A 187 | 119.031 | 19.272 | 22.585 | 1.00 | 43.70 |
| ATOM | 1800 | C | GLN A 187 | 117.548 | 24.041 | 22.041 | 1.00 | 36.63 |
| ATOM | 1801 | O | GLN A 187 | 116.325 | 24.022 | 22.138 | 1.00 | 40.27 |
| ATOM | 1802 | N | PRO A 188 | 118.333 | 24.493 | 23.038 | 1.00 | 36.32 |
| ATOM | 1803 | CD | PRO A 188 | 119.782 | 24.293 | 23.223 | 1.00 | 38.65 |
| ATOM | 1804 | CA | PRO A 188 | 117.748 | 25.033 | 24.268 | 1.00 | 35.72 |
| ATOM | 1805 | CB | PRO A 188 | 118.977 | 25.432 | 25.075 | 1.00 | 34.46 |
| ATOM | 1806 | CG | PRO A 188 | 119.933 | 24.364 | 24.730 | 1.00 | 35.29 |
| ATOM | 1807 | C | PRO A 188 | 116.829 | 26.231 | 24.030 | 1.00 | 36.20 |
| ATOM | 1808 | O | PRO A 188 | 115.933 | 26.490 | 24.835 | 1.00 | 38.62 |
| ATOM | 1809 | N | TYR A 189 | 117.062 | 26.983 | 22.957 | 1.00 | 35.08 |
| ATOM | 1811 | CA | TYR A 189 | 116.203 | 28.122 | 22.667 | 1.00 | 33.10 |
| ATOM | 1812 | CB | TYR A 189 | 116.799 | 29.059 | 21.625 | 1.00 | 30.49 |
| ATOM | 1813 | CG | TYR A 189 | 115.767 | 30.037 | 21.113 | 1.00 | 29.52 |
| ATOM | 1814 | CD1 | TYR A 189 | 115.222 | 30.996 | 21.958 | 1.00 | 28.37 |
| ATOM | 1815 | CE1 | TYR A 189 | 114.211 | 31.842 | 21.523 | 1.00 | 27.60 |
| ATOM | 1816 | CD2 | TYR A 189 | 115.274 | 29.950 | 19.808 | 1.00 | 28.40 |
| ATOM | 1817 | CE2 | TYR A 189 | 114.261 | 30.792 | 19.366 | 1.00 | 26.35 |
| ATOM | 1818 | CZ | TYR A 189 | 113.737 | 31.732 | 20.231 | 1.00 | 25.96 |
| ATOM | 1819 | OH | TYR A 189 | 112.735 | 32.568 | 19.815 | 1.00 | 27.51 |
| ATOM | 1821 | C | TYR A 189 | 114.841 | 27.660 | 22.186 | 1.00 | 34.73 |
| ATOM | 1822 | O | TYR A 189 | 113.824 | 28.113 | 22.694 | 1.00 | 38.35 |

Page 6-A-42

| ATOM | 1823 | N | PHE | A | 190 | 114.811 | 26.771 | 21.197 | 1.00 | 36.21 |
|------|------|-----|-----|---|-----|---------|--------|--------|------|-------|
| ATOM | 1825 | CA | PHE | A | 190 | 113.538 | 26.288 | 20.684 | 1.00 | 37.47 |
| ATOM | 1826 | CB | PHE | A | 190 | 113.697 | 25.649 | 19.302 | 1.00 | 38.76 |
| ATOM | 1827 | CG | PHE | A | 190 | 113.522 | 26.633 | 18.177 | 1.00 | 41.54 |
| ATOM | 1828 | CD1 | PHE | A | 190 | 112.273 | 27.194 | 17.920 | 1.00 | 40.00 |
| ATOM | 1829 | CD2 | PHE | A | 190 | 114.610 | 27.042 | 17.406 | 1.00 | 43.58 |
| ATOM | 1830 | CE1 | PHE | A | 190 | 112.109 | 28.146 | 16.919 | 1.00 | 39.03 |
| ATOM | 1831 | CE2 | PHE | A | 190 | 114.454 | 27.999 | 16.398 | 1.00 | 40.39 |
| ATOM | 1832 | CZ | PHE | A | 190 | 113.201 | 28.550 | 16.159 | 1.00 | 39.28 |
| ATOM | 1833 | C | PHE | A | 190 | 112.768 | 25.408 | 21.662 | 1.00 | 37.92 |
| ATOM | 1834 | O | PHE | A | 190 | 111.655 | 24.960 | 21.380 | 1.00 | 38.40 |
| ATOM | 1835 | N | GLN | A | 191 | 113.351 | 25.193 | 22.835 | 1.00 | 36.94 |
| ATOM | 1837 | CA | GLN | A | 191 | 112.685 | 24.425 | 23.869 | 1.00 | 36.24 |
| ATOM | 1838 | CB | GLN | A | 191 | 113.637 | 23.426 | 24.529 | 1.00 | 36.06 |
| ATOM | 1839 | CG | GLN | A | 191 | 113.987 | 22.259 | 23.609 | 1.00 | 37.66 |
| ATOM | 1840 | CD | GLN | A | 191 | 114.786 | 21.170 | 24.287 | 1.00 | 36.77 |
| ATOM | 1841 | OE1 | GLN | A | 191 | 115.365 | 21.379 | 25.349 | 1.00 | 38.68 |
| ATOM | 1842 | NE2 | GLN | A | 191 | 114.828 | 19.997 | 23.669 | 1.00 | 35.78 |
| ATOM | 1845 | C | GLN | A | 191 | 112.042 | 25.369 | 24.881 | 1.00 | 37.61 |
| ATOM | 1846 | O | GLN | A | 191 | 111.621 | 24.945 | 25.956 | 1.00 | 38.67 |
| ATOM | 1847 | N | THR | A | 192 | 111.992 | 26.659 | 24.541 | 1.00 | 38.44 |
| ATOM | 1849 | CA | THR | A | 192 | 111.338 | 27.650 | 25.392 | 1.00 | 37.16 |
| ATOM | 1850 | CB | THR | A | 192 | 111.946 | 29.055 | 25.263 | 1.00 | 36.82 |
| ATOM | 1851 | OG1 | THR | A | 192 | 111.937 | 29.461 | 23.890 | 1.00 | 37.79 |
| ATOM | 1853 | CG2 | THR | A | 192 | 113.357 | 29.083 | 25.802 | 1.00 | 36.99 |
| ATOM | 1854 | C | THR | A | 192 | 109.894 | 27.702 | 24.913 | 1.00 | 37.14 |
| ATOM | 1855 | O | THR | A | 192 | 109.082 | 28.485 | 25.403 | 1.00 | 38.53 |
| ATOM | 1856 | N | LEU | A | 193 | 109.604 | 26.884 | 23.906 | 1.00 | 38.31 |
| ATOM | 1858 | CA | LEU | A | 193 | 108.273 | 26.765 | 23.339 | 1.00 | 40.73 |
| ATOM | 1859 | CB | LEU | A | 193 | 108.325 | 25.772 | 22.174 | 1.00 | 42.93 |
| ATOM | 1860 | CG | LEU | A | 193 | 107.191 | 25.727 | 21.151 | 1.00 | 44.96 |
| ATOM | 1861 | CD1 | LEU | A | 193 | 107.000 | 27.100 | 20.518 | 1.00 | 45.48 |
| ATOM | 1862 | CD2 | LEU | A | 193 | 107.531 | 24.696 | 20.085 | 1.00 | 44.59 |
| ATOM | 1863 | C | LEU | A | 193 | 107.403 | 26.218 | 24.472 | 1.00 | 40.91 |

Page 6-A-43

| | | | | | | | | |
|---|---|---|---|---|---|---|---|---|
| ATOM | 1864 | O | LEU | A 193 | 107.788 | 25.265 | 25.150 | 1.00 41.30 |
| ATOM | 1865 | N | PRO | A 194 | 106.230 | 26.824 | 24.707 | 1.00 41.79 |
| ATOM | 1866 | CD | PRO | A 194 | 105.632 | 27.950 | 23.974 | 1.00 41.39 |
| ATOM | 1867 | CA | PRO | A 194 | 105.334 | 26.373 | 25.777 | 1.00 41.80 |
| ATOM | 1868 | CB | PRO | A 194 | 104.217 | 27.420 | 25.754 | 1.00 42.00 |
| ATOM | 1869 | CG | PRO | A 194 | 104.823 | 28.603 | 25.045 | 1.00 42.94 |
| ATOM | 1870 | C | PRO | A 194 | 104.755 | 24.985 | 25.522 | 1.00 41.75 |
| ATOM | 1871 | O | PRO | A 194 | 104.174 | 24.734 | 24.469 | 1.00 44.72 |
| ATOM | 1872 | N | VAL | A 195 | 104.930 | 24.080 | 26.476 | 1.00 39.33 |
| ATOM | 1874 | CA | VAL | A 195 | 104.383 | 22.738 | 26.338 | 1.00 37.64 |
| ATOM | 1875 | CB | VAL | A 195 | 105.403 | 21.659 | 26.756 | 1.00 37.05 |
| ATOM | 1876 | CG1 | VAL | A 195 | 104.744 | 20.295 | 26.840 | 1.00 34.56 |
| ATOM | 1877 | CG2 | VAL | A 195 | 106.515 | 21.607 | 25.747 | 1.00 36.43 |
| ATOM | 1878 | C | VAL | A 195 | 103.118 | 22.644 | 27.183 | 1.00 38.20 |
| ATOM | 1879 | O | VAL | A 195 | 102.062 | 22.245 | 26.694 | 1.00 40.04 |
| ATOM | 1880 | N | MET | A 196 | 103.234 | 23.007 | 28.454 | 1.00 38.05 |
| ATOM | 1882 | CA | MET | A 196 | 102.103 | 22.987 | 29.370 | 1.00 37.71 |
| ATOM | 1883 | CB | MET | A 196 | 102.414 | 22.128 | 30.592 | 1.00 40.52 |
| ATOM | 1884 | CG | MET | A 196 | 102.756 | 20.681 | 30.283 | 1.00 43.85 |
| ATOM | 1885 | SD | MET | A 196 | 101.356 | 19.738 | 29.695 | 1.00 42.31 |
| ATOM | 1886 | CE | MET | A 196 | 100.644 | 19.226 | 31.232 | 1.00 41.10 |
| ATOM | 1887 | C | MET | A 196 | 101.924 | 24.428 | 29.796 | 1.00 37.52 |
| ATOM | 1888 | O | MET | A 196 | 102.521 | 24.877 | 30.771 | 1.00 40.72 |
| ATOM | 1889 | N | THR | A 197 | 101.134 | 25.167 | 29.039 | 1.00 36.00 |
| ATOM | 1891 | CA | THR | A 197 | 100.914 | 26.565 | 29.335 | 1.00 34.89 |
| ATOM | 1892 | CB | THR | A 197 | 100.650 | 27.324 | 28.036 | 1.00 37.85 |
| ATOM | 1893 | OG1 | THR | A 197 | 101.329 | 26.660 | 26.963 | 1.00 41.31 |
| ATOM | 1895 | CG2 | THR | A 197 | 101.177 | 28.733 | 28.131 | 1.00 39.84 |
| ATOM | 1896 | C | THR | A 197 | 99.751 | 26.772 | 30.302 | 1.00 32.85 |
| ATOM | 1897 | O | THR | A 197 | 98.594 | 26.571 | 29.939 | 1.00 33.57 |
| ATOM | 1898 | N | LYS | A 198 | 100.061 | 27.122 | 31.545 | 1.00 29.63 |
| ATOM | 1900 | CA | LYS | A 198 | 99.036 | 27.372 | 32.551 | 1.00 27.13 |
| ATOM | 1901 | CB | LYS | A 198 | 99.630 | 27.266 | 33.952 | 1.00 26.01 |
| ATOM | 1902 | CG | LYS | A 198 | 98.609 | 27.379 | 35.047 | 1.00 26.97 |

Page 6-A-44

| | | | | | | | | | |
|---|---|---|---|---|---|---|---|---|---|
| ATOM | 1903 | CD | LYS | A | 198 | 99.269 | 27.457 | 36.389 | 1.00 31.48 |
| ATOM | 1904 | CE | LYS | A | 198 | 98.232 | 27.489 | 37.482 | 1.00 33.31 |
| ATOM | 1905 | NZ | LYS | A | 198 | 97.393 | 26.263 | 37.448 | 1.00 38.94 |
| ATOM | 1909 | C | LYS | A | 198 | 98.555 | 28.789 | 32.307 | 1.00 26.60 |
| ATOM | 1910 | O | LYS | A | 198 | 99.365 | 29.706 | 32.264 | 1.00 27.53 |
| ATOM | 1911 | N | ILE | A | 199 | 97.248 | 28.975 | 32.154 | 1.00 26.62 |
| ATOM | 1913 | CA | ILE | A | 199 | 96.711 | 30.298 | 31.878 | 1.00 23.94 |
| ATOM | 1914 | CB | ILE | A | 199 | 95.817 | 30.283 | 30.613 | 1.00 25.54 |
| ATOM | 1915 | CG2 | ILE | A | 199 | 96.561 | 29.614 | 29.477 | 1.00 26.32 |
| ATOM | 1916 | CG1 | ILE | A | 199 | 94.543 | 29.487 | 30.843 | 1.00 23.67 |
| ATOM | 1917 | CD1 | ILE | A | 199 | 93.795 | 29.189 | 29.564 | 1.00 22.95 |
| ATOM | 1918 | C | ILE | A | 199 | 95.992 | 30.954 | 33.041 | 1.00 25.86 |
| ATOM | 1919 | O | ILE | A | 199 | 95.827 | 32.169 | 33.061 | 1.00 28.61 |
| ATOM | 1920 | N | ASP | A | 200 | 95.561 | 30.148 | 34.007 | 1.00 27.99 |
| ATOM | 1922 | CA | ASP | A | 200 | 94.878 | 30.651 | 35.197 | 1.00 26.92 |
| ATOM | 1923 | CB | ASP | A | 200 | 93.484 | 31.220 | 34.867 | 1.00 26.06 |
| ATOM | 1924 | CG | ASP | A | 200 | 92.582 | 30.234 | 34.151 | 1.00 24.60 |
| ATOM | 1925 | OD1 | ASP | A | 200 | 92.621 | 29.037 | 34.465 | 1.00 26.68 |
| ATOM | 1926 | OD2 | ASP | A | 200 | 91.813 | 30.664 | 33.271 | 1.00 28.99 |
| ATOM | 1927 | C | ASP | A | 200 | 94.805 | 29.589 | 36.289 | 1.00 27.44 |
| ATOM | 1928 | O | ASP | A | 200 | 95.509 | 28.591 | 36.225 | 1.00 29.73 |
| ATOM | 1929 | N | SER | A | 201 | 93.966 | 29.808 | 37.294 | 1.00 28.30 |
| ATOM | 1931 | CA | SER | A | 201 | 93.825 | 28.859 | 38.397 | 1.00 30.40 |
| ATOM | 1932 | CB | SER | A | 201 | 93.032 | 29.507 | 39.531 | 1.00 31.85 |
| ATOM | 1933 | OG | SER | A | 201 | 91.882 | 30.170 | 39.026 | 1.00 39.39 |
| ATOM | 1935 | C | SER | A | 201 | 93.137 | 27.562 | 38.000 | 1.00 29.79 |
| ATOM | 1936 | O | SER | A | 201 | 93.230 | 26.557 | 38.695 | 1.00 31.67 |
| ATOM | 1937 | N | VAL | A | 202 | 92.430 | 27.604 | 36.884 | 1.00 30.29 |
| ATOM | 1939 | CA | VAL | A | 202 | 91.683 | 26.457 | 36.409 | 1.00 29.89 |
| ATOM | 1940 | CB | VAL | A | 202 | 90.284 | 26.911 | 35.932 | 1.00 28.59 |
| ATOM | 1941 | CG1 | VAL | A | 202 | 89.426 | 25.723 | 35.568 | 1.00 30.45 |
| ATOM | 1942 | CG2 | VAL | A | 202 | 89.613 | 27.740 | 36.998 | 1.00 28.22 |
| ATOM | 1943 | C | VAL | A | 202 | 92.346 | 25.667 | 35.282 | 1.00 31.71 |
| ATOM | 1944 | O | VAL | A | 202 | 92.752 | 24.520 | 35.470 | 1.00 33.93 |

Page 6-A-45

| | | | | | | | | |
|---|---|---|---|---|---|---|---|---|
| ATOM | 1945 | N | ALA A 203 | 92.463 | 26.291 | 34.115 | 1.00 | 31.10 |
| ATOM | 1947 | CA | ALA A 203 | 92.997 | 25.621 | 32.944 | 1.00 | 29.58 |
| ATOM | 1948 | CB | ALA A 203 | 92.039 | 25.821 | 31.767 | 1.00 | 29.01 |
| ATOM | 1949 | C | ALA A 203 | 94.416 | 25.908 | 32.497 | 1.00 | 28.91 |
| ATOM | 1950 | O | ALA A 203 | 95.096 | 26.807 | 33.001 | 1.00 | 27.86 |
| ATOM | 1951 | N | GLY A 204 | 94.822 | 25.124 | 31.503 | 1.00 | 26.23 |
| ATOM | 1953 | CA | GLY A 204 | 96.124 | 25.227 | 30.894 | 1.00 | 22.94 |
| ATOM | 1954 | C | GLY A 204 | 95.936 | 24.686 | 29.495 | 1.00 | 22.27 |
| ATOM | 1955 | O | GLY A 204 | 94.900 | 24.098 | 29.206 | 1.00 | 24.27 |
| ATOM | 1956 | N | ILE A 205 | 96.909 | 24.893 | 28.619 | 1.00 | 22.81 |
| ATOM | 1958 | CA | ILE A 205 | 96.817 | 24.402 | 27.250 | 1.00 | 21.62 |
| ATOM | 1959 | CB | ILE A 205 | 96.868 | 25.542 | 26.222 | 1.00 | 17.56 |
| ATOM | 1960 | CG2 | ILE A 205 | 96.458 | 25.020 | 24.870 | 1.00 | 17.14 |
| ATOM | 1961 | CG1 | ILE A 205 | 95.928 | 26.672 | 26.627 | 1.00 | 16.69 |
| ATOM | 1962 | CD1 | ILE A 205 | 96.021 | 27.878 | 25.753 | 1.00 | 10.87 |
| ATOM | 1963 | C | ILE A 205 | 98.010 | 23.492 | 27.008 | 1.00 | 24.34 |
| ATOM | 1964 | O | ILE A 205 | 99.120 | 23.784 | 27.452 | 1.00 | 26.93 |
| ATOM | 1965 | N | ASN A 206 | 97.770 | 22.374 | 26.333 | 1.00 | 24.44 |
| ATOM | 1967 | CA | ASN A 206 | 98.817 | 21.414 | 26.039 | 1.00 | 20.90 |
| ATOM | 1968 | CB | ASN A 206 | 98.280 | 19.989 | 26.217 | 1.00 | 21.75 |
| ATOM | 1969 | CG | ASN A 206 | 99.359 | 18.921 | 26.099 | 1.00 | 22.44 |
| ATOM | 1970 | OD1 | ASN A 206 | 99.077 | 17.727 | 26.218 | 1.00 | 26.27 |
| ATOM | 1971 | ND2 | ASN A 206 | 100.593 | 19.337 | 25.878 | 1.00 | 24.68 |
| ATOM | 1974 | C | ASN A 206 | 99.285 | 21.629 | 24.614 | 1.00 | 22.48 |
| ATOM | 1975 | O | ASN A 206 | 98.579 | 21.296 | 23.664 | 1.00 | 23.50 |
| ATOM | 1976 | N | TYR A 207 | 100.458 | 22.239 | 24.475 | 1.00 | 23.09 |
| ATOM | 1978 | CA | TYR A 207 | 101.065 | 22.517 | 23.179 | 1.00 | 21.41 |
| ATOM | 1979 | CB | TYR A 207 | 101.647 | 23.927 | 23.165 | 1.00 | 17.69 |
| ATOM | 1980 | CG | TYR A 207 | 100.625 | 25.008 | 22.986 | 1.00 | 16.56 |
| ATOM | 1981 | CD1 | TYR A 207 | 99.703 | 24.943 | 21.961 | 1.00 | 19.32 |
| ATOM | 1982 | CE1 | TYR A 207 | 98.795 | 25.963 | 21.757 | 1.00 | 20.24 |
| ATOM | 1983 | CD2 | TYR A 207 | 100.611 | 26.122 | 23.810 | 1.00 | 18.10 |
| ATOM | 1984 | CE2 | TYR A 207 | 99.711 | 27.144 | 23.613 | 1.00 | 18.49 |
| ATOM | 1985 | CZ | TYR A 207 | 98.809 | 27.060 | 22.581 | 1.00 | 18.16 |

Page 6-A-46

| | | | | | | | | |
|---|---|---|---|---|---|---|---|---|
| ATOM | 1986 | OH | TYR A 207 | 97.939 | 28.089 | 22.332 | 1.00 | 21.72 |
| ATOM | 1988 | C | TYR A 207 | 102.181 | 21.532 | 22.868 | 1.00 | 24.14 |
| ATOM | 1989 | O | TYR A 207 | 103.111 | 21.851 | 22.134 | 1.00 | 25.16 |
| ATOM | 1990 | N | GLY A 208 | 102.083 | 20.328 | 23.418 | 1.00 | 28.50 |
| ATOM | 1992 | CA | GLY A 208 | 103.112 | 19.330 | 23.194 | 1.00 | 29.80 |
| ATOM | 1993 | C | GLY A 208 | 103.130 | 18.752 | 21.795 | 1.00 | 32.56 |
| ATOM | 1994 | O | GLY A 208 | 102.067 | 18.467 | 21.231 | 1.00 | 33.45 |
| ATOM | 1995 | N | LEU A 209 | 104.332 | 18.598 | 21.235 | 1.00 | 33.15 |
| ATOM | 1997 | CA | LEU A 209 | 104.512 | 18.038 | 19.899 | 1.00 | 31.79 |
| ATOM | 1998 | CB | LEU A 209 | 105.985 | 18.081 | 19.484 | 1.00 | 29.49 |
| ATOM | 1999 | CG | LEU A 209 | 106.491 | 19.337 | 18.773 | 1.00 | 28.06 |
| ATOM | 2000 | CD1 | LEU A 209 | 106.302 | 20.558 | 19.641 | 1.00 | 24.35 |
| ATOM | 2001 | CD2 | LEU A 209 | 107.953 | 19.158 | 18.416 | 1.00 | 24.06 |
| ATOM | 2002 | C | LEU A 209 | 104.052 | 16.599 | 19.941 | 1.00 | 31.52 |
| ATOM | 2003 | O | LEU A 209 | 104.416 | 15.863 | 20.854 | 1.00 | 33.82 |
| ATOM | 2004 | N | VAL A 210 | 103.254 | 16.199 | 18.961 | 1.00 | 29.87 |
| ATOM | 2006 | CA | VAL A 210 | 102.752 | 14.836 | 18.915 | 1.00 | 29.99 |
| ATOM | 2007 | CB | VAL A 210 | 101.226 | 14.817 | 18.732 | 1.00 | 30.37 |
| ATOM | 2008 | CG1 | VAL A 210 | 100.559 | 15.363 | 19.972 | 1.00 | 31.24 |
| ATOM | 2009 | CG2 | VAL A 210 | 100.824 | 15.642 | 17.522 | 1.00 | 30.83 |
| ATOM | 2010 | C | VAL A 210 | 103.430 | 13.992 | 17.837 | 1.00 | 30.78 |
| ATOM | 2011 | O | VAL A 210 | 103.038 | 12.854 | 17.578 | 1.00 | 32.27 |
| ATOM | 2012 | N | ALA A 211 | 104.460 | 14.552 | 17.221 | 1.00 | 30.97 |
| ATOM | 2014 | CA | ALA A 211 | 105.199 | 13.857 | 16.178 | 1.00 | 32.26 |
| ATOM | 2015 | CB | ALA A 211 | 104.324 | 13.661 | 14.941 | 1.00 | 34.28 |
| ATOM | 2016 | C | ALA A 211 | 106.417 | 14.692 | 15.839 | 1.00 | 31.64 |
| ATOM | 2017 | O | ALA A 211 | 106.463 | 15.884 | 16.145 | 1.00 | 32.86 |
| ATOM | 2018 | N | PRO A 212 | 107.437 | 14.077 | 15.232 | 1.00 | 30.38 |
| ATOM | 2019 | CD | PRO A 212 | 107.550 | 12.667 | 14.820 | 1.00 | 28.87 |
| ATOM | 2020 | CA | PRO A 212 | 108.642 | 14.824 | 14.876 | 1.00 | 30.59 |
| ATOM | 2021 | CB | PRO A 212 | 109.576 | 13.724 | 14.384 | 1.00 | 30.90 |
| ATOM | 2022 | CG | PRO A 212 | 108.628 | 12.731 | 13.785 | 1.00 | 31.64 |
| ATOM | 2023 | C | PRO A 212 | 108.345 | 15.824 | 13.774 | 1.00 | 31.31 |
| ATOM | 2024 | O | PRO A 212 | 107.483 | 15.574 | 12.938 | 1.00 | 33.01 |

Page 6-A-47

| | | | | | | | | |
|---|---|---|---|---|---|---|---|---|
| ATOM | 2025 | N | PRO | A | 213 | 109.005 | 16.996 | 13.802 | 1.00 | 30.25 |
| ATOM | 2026 | CD | PRO | A | 213 | 109.882 | 17.457 | 14.892 | 1.00 | 28.21 |
| ATOM | 2027 | CA | PRO | A | 213 | 108.832 | 18.056 | 12.803 | 1.00 | 29.74 |
| ATOM | 2028 | CB | PRO | A | 213 | 109.889 | 19.076 | 13.220 | 1.00 | 29.54 |
| ATOM | 2029 | CG | PRO | A | 213 | 109.896 | 18.958 | 14.690 | 1.00 | 26.77 |
| ATOM | 2030 | C | PRO | A | 213 | 109.115 | 17.526 | 11.398 | 1.00 | 30.72 |
| ATOM | 2031 | O | PRO | A | 213 | 110.187 | 16.975 | 11.140 | 1.00 | 33.55 |
| ATOM | 2032 | N | ALA | A | 214 | 108.157 | 17.700 | 10.495 | 1.00 | 30.16 |
| ATOM | 2034 | CA | ALA | A | 214 | 108.296 | 17.231 | 9.123 | 1.00 | 29.31 |
| ATOM | 2035 | CB | ALA | A | 214 | 106.964 | 16.701 | 8.609 | 1.00 | 27.36 |
| ATOM | 2036 | C | ALA | A | 214 | 108.771 | 18.336 | 8.212 | 1.00 | 30.52 |
| ATOM | 2037 | O | ALA | A | 214 | 108.229 | 19.440 | 8.235 | 1.00 | 32.72 |
| ATOM | 2038 | N | THR | A | 215 | 109.781 | 18.052 | 7.405 | 1.00 | 30.13 |
| ATOM | 2040 | CA | THR | A | 215 | 110.268 | 19.047 | 6.472 | 1.00 | 31.47 |
| ATOM | 2041 | CB | THR | A | 215 | 111.805 | 19.044 | 6.366 | 1.00 | 32.14 |
| ATOM | 2042 | OG1 | THR | A | 215 | 112.381 | 19.228 | 7.665 | 1.00 | 36.33 |
| ATOM | 2044 | CG2 | THR | A | 215 | 112.268 | 20.177 | 5.474 | 1.00 | 33.34 |
| ATOM | 2045 | C | THR | A | 215 | 109.656 | 18.698 | 5.127 | 1.00 | 32.34 |
| ATOM | 2046 | O | THR | A | 215 | 109.642 | 17.533 | 4.729 | 1.00 | 32.18 |
| ATOM | 2047 | N | THR | A | 216 | 109.103 | 19.692 | 4.451 | 1.00 | 34.34 |
| ATOM | 2049 | CA | THR | A | 216 | 108.489 | 19.463 | 3.154 | 1.00 | 36.27 |
| ATOM | 2050 | CB | THR | A | 216 | 106.996 | 19.862 | 3.167 | 1.00 | 36.83 |
| ATOM | 2051 | OG1 | THR | A | 216 | 106.872 | 21.255 | 3.477 | 1.00 | 37.89 |
| ATOM | 2053 | CG2 | THR | A | 216 | 106.241 | 19.055 | 4.216 | 1.00 | 36.73 |
| ATOM | 2054 | C | THR | A | 216 | 109.247 | 20.254 | 2.092 | 1.00 | 37.93 |
| ATOM | 2055 | O | THR | A | 216 | 110.390 | 20.642 | 2.307 | 1.00 | 36.96 |
| ATOM | 2056 | N | ALA | A | 217 | 108.610 | 20.483 | 0.948 | 1.00 | 40.73 |
| ATOM | 2058 | CA | ALA | A | 217 | 109.228 | 21.215 | -0.151 | 1.00 | 41.25 |
| ATOM | 2059 | CB | ALA | A | 217 | 108.452 | 20.967 | -1.437 | 1.00 | 42.73 |
| ATOM | 2060 | C | ALA | A | 217 | 109.302 | 22.704 | 0.125 | 1.00 | 40.38 |
| ATOM | 2061 | O | ALA | A | 217 | 110.218 | 23.379 | -0.337 | 1.00 | 40.36 |
| ATOM | 2062 | N | GLU | A | 218 | 108.319 | 23.215 | 0.860 | 1.00 | 41.20 |
| ATOM | 2064 | CA | GLU | A | 218 | 108.271 | 24.633 | 1.170 | 1.00 | 40.88 |
| ATOM | 2065 | CB | GLU | A | 218 | 107.443 | 25.372 | 0.113 | 1.00 | 46.00 |

| | | | | | | | | | |
|---|---|---|---|---|---|---|---|---|---|
| ATOM | 2066 | CG | GLU | A | 218 | 108.304 | 26.058 | -0.947 | 1.00 53.45 |
| ATOM | 2067 | CD | GLU | A | 218 | 107.610 | 26.213 | -2.286 | 1.00 57.50 |
| ATOM | 2068 | OE1 | GLU | A | 218 | 106.543 | 25.588 | -2.487 | 1.00 60.01 |
| ATOM | 2069 | OE2 | GLU | A | 218 | 108.149 | 26.945 | -3.146 | 1.00 59.32 |
| ATOM | 2070 | C | GLU | A | 218 | 107.832 | 25.030 | 2.580 | 1.00 39.13 |
| ATOM | 2071 | O | GLU | A | 218 | 107.635 | 26.216 | 2.839 | 1.00 40.54 |
| ATOM | 2072 | N | THR | A | 219 | 107.668 | 24.066 | 3.488 | 1.00 37.20 |
| ATOM | 2074 | CA | THR | A | 219 | 107.295 | 24.388 | 4.875 | 1.00 35.55 |
| ATOM | 2075 | CB | THR | A | 219 | 105.762 | 24.464 | 5.103 | 1.00 32.68 |
| ATOM | 2076 | OG1 | THR | A | 219 | 105.144 | 23.249 | 4.674 | 1.00 35.48 |
| ATOM | 2078 | CG2 | THR | A | 219 | 105.151 | 25.641 | 4.387 | 1.00 33.81 |
| ATOM | 2079 | C | THR | A | 219 | 107.828 | 23.400 | 5.906 | 1.00 34.31 |
| ATOM | 2080 | O | THR | A | 219 | 108.013 | 22.217 | 5.614 | 1.00 34.57 |
| ATOM | 2081 | N | LEU | A | 220 | 108.087 | 23.903 | 7.109 | 1.00 31.67 |
| ATOM | 2083 | CA | LEU | A | 220 | 108.533 | 23.079 | 8.219 | 1.00 29.70 |
| ATOM | 2084 | CB | LEU | A | 220 | 109.587 | 23.834 | 9.033 | 1.00 29.62 |
| ATOM | 2085 | CG | LEU | A | 220 | 110.345 | 23.149 | 10.177 | 1.00 31.10 |
| ATOM | 2086 | CD1 | LEU | A | 220 | 109.511 | 23.047 | 11.435 | 1.00 30.08 |
| ATOM | 2087 | CD2 | LEU | A | 220 | 110.794 | 21.791 | 9.727 | 1.00 30.78 |
| ATOM | 2088 | C | LEU | A | 220 | 107.236 | 22.902 | 9.017 | 1.00 29.78 |
| ATOM | 2089 | O | LEU | A | 220 | 106.693 | 23.878 | 9.545 | 1.00 30.49 |
| ATOM | 2090 | N | ASP | A | 221 | 106.698 | 21.685 | 9.032 | 1.00 29.15 |
| ATOM | 2092 | CA | ASP | A | 221 | 105.441 | 21.397 | 9.728 | 1.00 30.48 |
| ATOM | 2093 | CB | ASP | A | 221 | 104.603 | 20.394 | 8.924 | 1.00 34.57 |
| ATOM | 2094 | CG | ASP | A | 221 | 104.178 | 20.924 | 7.557 | 1.00 37.91 |
| ATOM | 2095 | OD1 | ASP | A | 221 | 104.480 | 22.090 | 7.222 | 1.00 37.84 |
| ATOM | 2096 | OD2 | ASP | A | 221 | 103.534 | 20.158 | 6.811 | 1.00 42.30 |
| ATOM | 2097 | C | ASP | A | 221 | 105.607 | 20.865 | 11.143 | 1.00 30.64 |
| ATOM | 2098 | O | ASP | A | 221 | 106.274 | 19.852 | 11.350 | 1.00 31.22 |
| ATOM | 2099 | N | VAL | A | 222 | 104.950 | 21.519 | 12.100 | 1.00 29.81 |
| ATOM | 2101 | CA | VAL | A | 222 | 104.999 | 21.131 | 13.512 | 1.00 29.49 |
| ATOM | 2102 | CB | VAL | A | 222 | 105.588 | 22.261 | 14.389 | 1.00 29.52 |
| ATOM | 2103 | CG1 | VAL | A | 222 | 105.617 | 21.831 | 15.845 | 1.00 28.17 |
| ATOM | 2104 | CG2 | VAL | A | 222 | 106.988 | 22.632 | 13.914 | 1.00 26.55 |

Page 6-A-49

| | | | | | | | | |
|---|---|---|---|---|---|---|---|---|
| ATOM | 2105 | C | VAL A 222 | 103.586 | 20.791 | 14.016 | 1.00 | 29.65 |
| ATOM | 2106 | O | VAL A 222 | 102.686 | 21.620 | 13.958 | 1.00 | 31.27 |
| ATOM | 2107 | N | GLN A 223 | 103.400 | 19.560 | 14.485 | 1.00 | 29.35 |
| ATOM | 2109 | CA | GLN A 223 | 102.114 | 19.081 | 14.978 | 1.00 | 25.88 |
| ATOM | 2110 | CB | GLN A 223 | 101.870 | 17.649 | 14.488 | 1.00 | 29.16 |
| ATOM | 2111 | CG | GLN A 223 | 101.731 | 17.505 | 12.969 | 1.00 | 30.27 |
| ATOM | 2112 | CD | GLN A 223 | 101.704 | 16.052 | 12.510 | 1.00 | 32.10 |
| ATOM | 2113 | OE1 | GLN A 223 | 100.832 | 15.275 | 12.897 | 1.00 | 31.46 |
| ATOM | 2114 | NE2 | GLN A 223 | 102.668 | 15.681 | 11.686 | 1.00 | 37.75 |
| ATOM | 2117 | C | GLN A 223 | 102.081 | 19.116 | 16.494 | 1.00 | 24.57 |
| ATOM | 2118 | O | GLN A 223 | 102.910 | 18.490 | 17.147 | 1.00 | 23.51 |
| ATOM | 2119 | N | MET A 224 | 101.112 | 19.840 | 17.042 | 1.00 | 22.94 |
| ATOM | 2121 | CA | MET A 224 | 100.959 | 19.984 | 18.480 | 1.00 | 22.16 |
| ATOM | 2122 | CB | MET A 224 | 101.064 | 21.459 | 18.866 | 1.00 | 23.89 |
| ATOM | 2123 | CG | MET A 224 | 102.353 | 22.116 | 18.423 | 1.00 | 22.07 |
| ATOM | 2124 | SD | MET A 224 | 102.393 | 23.853 | 18.797 | 1.00 | 28.37 |
| ATOM | 2125 | CE | MET A 224 | 104.122 | 24.130 | 18.771 | 1.00 | 25.60 |
| ATOM | 2126 | C | MET A 224 | 99.620 | 19.408 | 18.927 | 1.00 | 23.31 |
| ATOM | 2127 | O | MET A 224 | 98.702 | 19.294 | 18.124 | 1.00 | 27.48 |
| ATOM | 2128 | N | LYS A 225 | 99.519 | 19.024 | 20.197 | 1.00 | 25.28 |
| ATOM | 2130 | CA | LYS A 225 | 98.292 | 18.440 | 20.735 | 1.00 | 27.30 |
| ATOM | 2131 | CB | LYS A 225 | 98.522 | 17.889 | 22.140 | 1.00 | 28.45 |
| ATOM | 2132 | CG | LYS A 225 | 97.613 | 16.724 | 22.452 | 1.00 | 30.88 |
| ATOM | 2133 | CD | LYS A 225 | 97.912 | 16.108 | 23.793 | 1.00 | 33.18 |
| ATOM | 2134 | CE | LYS A 225 | 97.153 | 14.802 | 23.938 | 1.00 | 38.68 |
| ATOM | 2135 | NZ | LYS A 225 | 95.741 | 14.928 | 23.460 | 1.00 | 43.39 |
| ATOM | 2139 | C | LYS A 225 | 97.135 | 19.434 | 20.726 | 1.00 | 27.30 |
| ATOM | 2140 | O | LYS A 225 | 96.052 | 19.123 | 20.238 | 1.00 | 29.51 |
| ATOM | 2141 | N | GLY A 226 | 97.364 | 20.617 | 21.286 | 1.00 | 26.18 |
| ATOM | 2143 | CA | GLY A 226 | 96.360 | 21.665 | 21.285 | 1.00 | 21.95 |
| ATOM | 2144 | C | GLY A 226 | 95.015 | 21.379 | 21.903 | 1.00 | 23.48 |
| ATOM | 2145 | O | GLY A 226 | 93.983 | 21.420 | 21.238 | 1.00 | 23.78 |
| ATOM | 2146 | N | GLU A 227 | 95.021 | 21.131 | 23.201 | 1.00 | 26.02 |
| ATOM | 2148 | CA | GLU A 227 | 93.792 | 20.882 | 23.915 | 1.00 | 26.24 |

Page 6-A-50

| | | | | | | | | |
|---|---|---|---|---|---|---|---|---|
| ATOM | 2149 | CB | GLU | A | 227 | 93.547 | 19.384 | 24.068 | 1.00 29.17 |
| ATOM | 2150 | CG | GLU | A | 227 | 94.467 | 18.697 | 25.052 | 1.00 25.81 |
| ATOM | 2151 | CD | GLU | A | 227 | 93.967 | 17.330 | 25.456 | 1.00 29.15 |
| ATOM | 2152 | OE1 | GLU | A | 227 | 93.343 | 16.654 | 24.614 | 1.00 33.43 |
| ATOM | 2153 | OE2 | GLU | A | 227 | 94.199 | 16.928 | 26.615 | 1.00 31.54 |
| ATOM | 2154 | C | GLU | A | 227 | 93.937 | 21.514 | 25.283 | 1.00 27.06 |
| ATOM | 2155 | O | GLU | A | 227 | 95.006 | 21.447 | 25.892 | 1.00 26.79 |
| ATOM | 2156 | N | PHE | A | 228 | 92.904 | 22.219 | 25.722 | 1.00 26.37 |
| ATOM | 2158 | CA | PHE | A | 228 | 92.942 | 22.816 | 27.034 | 1.00 24.07 |
| ATOM | 2159 | CB | PHE | A | 228 | 91.785 | 23.792 | 27.242 | 1.00 24.55 |
| ATOM | 2160 | CG | PHE | A | 228 | 91.987 | 25.134 | 26.592 | 1.00 23.72 |
| ATOM | 2161 | CD1 | PHE | A | 228 | 92.066 | 25.251 | 25.207 | 1.00 21.59 |
| ATOM | 2162 | CD2 | PHE | A | 228 | 92.045 | 26.287 | 27.366 | 1.00 21.39 |
| ATOM | 2163 | CE1 | PHE | A | 228 | 92.193 | 26.498 | 24.607 | 1.00 21.74 |
| ATOM | 2164 | CE2 | PHE | A | 228 | 92.172 | 27.531 | 26.779 | 1.00 21.24 |
| ATOM | 2165 | CZ | PHE | A | 228 | 92.246 | 27.640 | 25.395 | 1.00 24.55 |
| ATOM | 2166 | C | PHE | A | 228 | 92.779 | 21.630 | 27.949 | 1.00 25.56 |
| ATOM | 2167 | O | PHE | A | 228 | 92.069 | 20.680 | 27.624 | 1.00 26.15 |
| ATOM | 2168 | N | TYR | A | 229 | 93.479 | 21.655 | 29.067 | 1.00 29.13 |
| ATOM | 2170 | CA | TYR | A | 229 | 93.400 | 20.573 | 30.025 | 1.00 34.87 |
| ATOM | 2171 | CB | TYR | A | 229 | 94.735 | 19.820 | 30.084 | 1.00 32.93 |
| ATOM | 2172 | CG | TYR | A | 229 | 95.870 | 20.654 | 30.639 | 1.00 33.77 |
| ATOM | 2173 | CD1 | TYR | A | 229 | 96.034 | 20.816 | 32.015 | 1.00 34.08 |
| ATOM | 2174 | CE1 | TYR | A | 229 | 97.021 | 21.637 | 32.530 | 1.00 33.96 |
| ATOM | 2175 | CD2 | TYR | A | 229 | 96.739 | 21.332 | 29.793 | 1.00 34.25 |
| ATOM | 2176 | CE2 | TYR | A | 229 | 97.735 | 22.152 | 30.302 | 1.00 34.53 |
| ATOM | 2177 | CZ | TYR | A | 229 | 97.863 | 22.302 | 31.670 | 1.00 33.54 |
| ATOM | 2178 | OH | TYR | A | 229 | 98.819 | 23.138 | 32.185 | 1.00 38.50 |
| ATOM | 2180 | C | TYR | A | 229 | 93.097 | 21.196 | 31.380 | 1.00 39.53 |
| ATOM | 2181 | O | TYR | A | 229 | 93.192 | 22.414 | 31.545 | 1.00 39.55 |
| ATOM | 2182 | N | SER | A | 230 | 92.738 | 20.355 | 32.341 | 1.00 46.28 |
| ATOM | 2184 | CA | SER | A | 230 | 92.453 | 20.796 | 33.699 | 1.00 53.45 |
| ATOM | 2185 | CB | SER | A | 230 | 90.998 | 20.491 | 34.071 | 1.00 54.47 |
| ATOM | 2186 | OG | SER | A | 230 | 90.720 | 20.820 | 35.424 | 1.00 56.07 |

| | | | | | | | | |
|---|---|---|---|---|---|---|---|---|
| ATOM | 2188 | C | SER | A | 230 | 93.396 | 19.996 | 34.582 | 1.00 | 58.48 |
| ATOM | 2189 | O | SER | A | 230 | 93.659 | 18.826 | 34.301 | 1.00 | 58.09 |
| ATOM | 2190 | N | GLU | A | 231 | 93.946 | 20.632 | 35.611 | 1.00 | 66.92 |
| ATOM | 2192 | CA | GLU | A | 231 | 94.860 | 19.940 | 36.517 | 1.00 | 74.85 |
| ATOM | 2193 | CB | GLU | A | 231 | 95.976 | 20.878 | 36.995 | 1.00 | 77.02 |
| ATOM | 2194 | CG | GLU | A | 231 | 97.377 | 20.450 | 36.548 | 1.00 | 81.62 |
| ATOM | 2195 | CD | GLU | A | 231 | 98.476 | 21.372 | 37.054 | 1.00 | 84.67 |
| ATOM | 2196 | OE1 | GLU | A | 231 | 98.402 | 22.592 | 36.790 | 1.00 | 86.64 |
| ATOM | 2197 | OE2 | GLU | A | 231 | 99.421 | 20.876 | 37.709 | 1.00 | 85.89 |
| ATOM | 2198 | C | GLU | A | 231 | 94.119 | 19.328 | 37.706 | 1.00 | 78.17 |
| ATOM | 2199 | O | GLU | A | 231 | 94.602 | 18.379 | 38.323 | 1.00 | 79.46 |
| ATOM | 2200 | N | ALA | A | 232 | 92.934 | 19.855 | 38.003 | 1.00 | 81.24 |
| ATOM | 2202 | CA | ALA | A | 232 | 92.131 | 19.363 | 39.118 | 1.00 | 84.16 |
| ATOM | 2203 | CB | ALA | A | 232 | 91.111 | 20.417 | 39.544 | 1.00 | 84.14 |
| ATOM | 2204 | C | ALA | A | 232 | 91.426 | 18.053 | 38.777 | 1.00 | 86.04 |
| ATOM | 2205 | O | ALA | A | 232 | 91.078 | 17.279 | 39.671 | 1.00 | 87.55 |
| ATOM | 2206 | N | ALA | A | 233 | 91.203 | 17.819 | 37.487 | 1.00 | 86.79 |
| ATOM | 2208 | CA | ALA | A | 233 | 90.534 | 16.608 | 37.023 | 1.00 | 88.81 |
| ATOM | 2209 | CB | ALA | A | 233 | 89.052 | 16.659 | 37.381 | 1.00 | 89.87 |
| ATOM | 2210 | C | ALA | A | 233 | 90.702 | 16.464 | 35.516 | 1.00 | 90.03 |
| ATOM | 2211 | O | ALA | A | 233 | 90.288 | 17.341 | 34.756 | 1.00 | 90.77 |
| ATOM | 2212 | N | ALA | A | 234 | 91.309 | 15.361 | 35.090 | 1.00 | 91.16 |
| ATOM | 2214 | CA | ALA | A | 234 | 91.536 | 15.106 | 33.670 | 1.00 | 91.66 |
| ATOM | 2215 | CB | ALA | A | 234 | 92.810 | 14.288 | 33.470 | 1.00 | 92.37 |
| ATOM | 2216 | C | ALA | A | 234 | 90.354 | 14.394 | 33.034 | 1.00 | 91.31 |
| ATOM | 2217 | O | ALA | A | 234 | 89.874 | 13.384 | 33.550 | 1.00 | 91.09 |
| ATOM | 2218 | N | ALA | A | 235 | 89.894 | 14.926 | 31.908 | 1.00 | 91.34 |
| ATOM | 2220 | CA | ALA | A | 235 | 88.774 | 14.346 | 31.180 | 1.00 | 90.88 |
| ATOM | 2221 | CB | ALA | A | 235 | 87.457 | 14.975 | 31.627 | 1.00 | 91.57 |
| ATOM | 2222 | C | ALA | A | 235 | 88.993 | 14.572 | 29.691 | 1.00 | 89.83 |
| ATOM | 2223 | O | ALA | A | 235 | 89.205 | 15.706 | 29.247 | 1.00 | 89.77 |
| ATOM | 2224 | N | PRO | A | 236 | 89.032 | 13.480 | 28.912 | 1.00 | 88.56 |
| ATOM | 2225 | CD | PRO | A | 236 | 88.962 | 12.083 | 29.376 | 1.00 | 88.69 |
| ATOM | 2226 | CA | PRO | A | 236 | 89.232 | 13.539 | 27.463 | 1.00 | 85.91 |

Page 6-A-52

| | | | | | | | | |
|---|---|---|---|---|---|---|---|---|
| ATOM | 2227 | CB | PRO | A | 236 | 89.511 | 12.080 | 27.104 | 1.00 86.56 |
| ATOM | 2228 | CG | PRO | A | 236 | 88.680 | 11.334 | 28.099 | 1.00 88.16 |
| ATOM | 2229 | C | PRO | A | 236 | 87.997 | 14.085 | 26.738 | 1.00 82.58 |
| ATOM | 2230 | O | PRO | A | 236 | 86.861 | 13.877 | 27.172 | 1.00 81.75 |
| ATOM | 2231 | N | PRO | A | 237 | 88.217 | 14.829 | 25.644 | 1.00 79.77 |
| ATOM | 2232 | CD | PRO | A | 237 | 89.551 | 15.264 | 25.202 | 1.00 80.44 |
| ATOM | 2233 | CA | PRO | A | 237 | 87.178 | 15.444 | 24.811 | 1.00 77.34 |
| ATOM | 2234 | CB | PRO | A | 237 | 87.985 | 16.332 | 23.863 | 1.00 77.69 |
| ATOM | 2235 | CG | PRO | A | 237 | 89.249 | 16.604 | 24.617 | 1.00 79.85 |
| ATOM | 2236 | C | PRO | A | 237 | 86.366 | 14.426 | 24.015 | 1.00 75.23 |
| ATOM | 2237 | O | PRO | A | 237 | 86.919 | 13.462 | 23.480 | 1.00 75.90 |
| ATOM | 2238 | N | PRO | A | 238 | 85.042 | 14.634 | 23.918 | 1.00 72.71 |
| ATOM | 2239 | CD | PRO | A | 238 | 84.282 | 15.606 | 24.724 | 1.00 72.84 |
| ATOM | 2240 | CA | PRO | A | 238 | 84.131 | 13.750 | 23.182 | 1.00 70.12 |
| ATOM | 2241 | CB | PRO | A | 238 | 82.774 | 14.086 | 23.793 | 1.00 71.89 |
| ATOM | 2242 | CG | PRO | A | 238 | 82.907 | 15.535 | 24.109 | 1.00 72.51 |
| ATOM | 2243 | C | PRO | A | 238 | 84.146 | 14.004 | 21.672 | 1.00 67.49 |
| ATOM | 2244 | O | PRO | A | 238 | 83.099 | 14.016 | 21.017 | 1.00 66.70 |
| ATOM | 2245 | N | PHE | A | 239 | 85.340 | 14.216 | 21.130 | 1.00 64.79 |
| ATOM | 2247 | CA | PHE | A | 239 | 85.521 | 14.472 | 19.706 | 1.00 61.01 |
| ATOM | 2248 | CB | PHE | A | 239 | 84.959 | 15.849 | 19.319 | 1.00 60.29 |
| ATOM | 2249 | CG | PHE | A | 239 | 85.172 | 16.923 | 20.362 | 1.00 57.87 |
| ATOM | 2250 | CD1 | PHE | A | 239 | 86.307 | 17.721 | 20.339 | 1.00 56.42 |
| ATOM | 2251 | CD2 | PHE | A | 239 | 84.216 | 17.159 | 21.343 | 1.00 55.75 |
| ATOM | 2252 | CE1 | PHE | A | 239 | 86.484 | 18.737 | 21.274 | 1.00 53.82 |
| ATOM | 2253 | CE2 | PHE | A | 239 | 84.387 | 18.171 | 22.279 | 1.00 53.85 |
| ATOM | 2254 | CZ | PHE | A | 239 | 85.522 | 18.960 | 22.243 | 1.00 52.72 |
| ATOM | 2255 | C | PHE | A | 239 | 86.989 | 14.355 | 19.307 | 1.00 58.61 |
| ATOM | 2256 | O | PHE | A | 239 | 87.873 | 14.266 | 20.164 | 1.00 58.11 |
| ATOM | 2257 | N | ALA | A | 240 | 87.234 | 14.314 | 18.002 | 1.00 55.15 |
| ATOM | 2259 | CA | ALA | A | 240 | 88.586 | 14.203 | 17.472 | 1.00 51.42 |
| ATOM | 2260 | CB | ALA | A | 240 | 88.716 | 12.936 | 16.631 | 1.00 51.91 |
| ATOM | 2261 | C | ALA | A | 240 | 88.884 | 15.441 | 16.629 | 1.00 49.88 |
| ATOM | 2262 | O | ALA | A | 240 | 87.972 | 16.034 | 16.048 | 1.00 48.56 |

Page 6-A-53

| | | | | | | | | |
|---|---|---|---|---|---|---|---|---|
| ATOM | 2263 | N | PRO | A | 241 | 90.155 | 15.885 | 16.604 | 1.00 | 48.54 |
| ATOM | 2264 | CD | PRO | A | 241 | 91.270 | 15.398 | 17.436 | 1.00 | 47.09 |
| ATOM | 2265 | CA | PRO | A | 241 | 90.567 | 17.064 | 15.830 | 1.00 | 46.53 |
| ATOM | 2266 | CB | PRO | A | 241 | 92.043 | 17.218 | 16.205 | 1.00 | 44.66 |
| ATOM | 2267 | CG | PRO | A | 241 | 92.113 | 16.633 | 17.574 | 1.00 | 45.79 |
| ATOM | 2268 | C | PRO | A | 241 | 90.412 | 16.864 | 14.322 | 1.00 | 46.25 |
| ATOM | 2269 | O | PRO | A | 241 | 90.536 | 15.743 | 13.819 | 1.00 | 47.76 |
| ATOM | 2270 | N | PRO | A | 242 | 90.118 | 17.947 | 13.582 | 1.00 | 45.32 |
| ATOM | 2271 | CD | PRO | A | 242 | 89.818 | 19.314 | 14.050 | 1.00 | 44.47 |
| ATOM | 2272 | CA | PRO | A | 242 | 89.959 | 17.844 | 12.130 | 1.00 | 44.33 |
| ATOM | 2273 | CB | PRO | A | 242 | 89.187 | 19.114 | 11.792 | 1.00 | 43.70 |
| ATOM | 2274 | CG | PRO | A | 242 | 89.769 | 20.107 | 12.755 | 1.00 | 43.85 |
| ATOM | 2275 | C | PRO | A | 242 | 91.325 | 17.835 | 11.442 | 1.00 | 45.10 |
| ATOM | 2276 | O | PRO | A | 242 | 92.331 | 18.261 | 12.019 | 1.00 | 44.03 |
| ATOM | 2277 | N | VAL | A | 243 | 91.370 | 17.302 | 10.228 | 1.00 | 45.79 |
| ATOM | 2279 | CA | VAL | A | 243 | 92.615 | 17.279 | 9.485 | 1.00 | 47.91 |
| ATOM | 2280 | CB | VAL | A | 243 | 92.613 | 16.226 | 8.347 | 1.00 | 48.72 |
| ATOM | 2281 | CG1 | VAL | A | 243 | 92.629 | 14.827 | 8.934 | 1.00 | 50.59 |
| ATOM | 2282 | CG2 | VAL | A | 243 | 91.403 | 16.401 | 7.446 | 1.00 | 51.20 |
| ATOM | 2283 | C | VAL | A | 243 | 92.753 | 18.679 | 8.926 | 1.00 | 48.35 |
| ATOM | 2284 | O | VAL | A | 243 | 91.939 | 19.122 | 8.116 | 1.00 | 48.79 |
| ATOM | 2285 | N | MET | A | 244 | 93.731 | 19.412 | 9.434 | 1.00 | 48.68 |
| ATOM | 2287 | CA | MET | A | 244 | 93.937 | 20.771 | 8.987 | 1.00 | 46.91 |
| ATOM | 2288 | CB | MET | A | 244 | 94.406 | 21.638 | 10.147 | 1.00 | 42.52 |
| ATOM | 2289 | CG | MET | A | 244 | 93.369 | 21.770 | 11.233 | 1.00 | 30.61 |
| ATOM | 2290 | SD | MET | A | 244 | 93.963 | 22.834 | 12.505 | 1.00 | 30.25 |
| ATOM | 2291 | CE | MET | A | 244 | 94.948 | 21.710 | 13.447 | 1.00 | 25.62 |
| ATOM | 2292 | C | MET | A | 244 | 94.884 | 20.877 | 7.811 | 1.00 | 50.14 |
| ATOM | 2293 | O | MET | A | 244 | 96.102 | 20.935 | 7.983 | 1.00 | 50.38 |
| ATOM | 2294 | N | GLU | A | 245 | 94.302 | 20.867 | 6.615 | 1.00 | 53.76 |
| ATOM | 2296 | CA | GLU | A | 245 | 95.046 | 20.985 | 5.367 | 1.00 | 58.60 |
| ATOM | 2297 | CB | GLU | A | 245 | 94.597 | 19.905 | 4.364 | 1.00 | 61.51 |
| ATOM | 2298 | CG | GLU | A | 245 | 93.085 | 19.861 | 4.078 | 1.00 | 67.59 |
| ATOM | 2299 | CD | GLU | A | 245 | 92.692 | 18.811 | 3.041 | 1.00 | 69.79 |

Page 6-A-54

| | | | | | | | | |
|---|---|---|---|---|---|---|---|---|
| ATOM | 2300 | OE1 | GLU A 245 | 92.943 | 19.024 | 1.827 | 1.00 | 72.17 |
| ATOM | 2301 | OE2 | GLU A 245 | 92.104 | 17.778 | 3.439 | 1.00 | 68.95 |
| ATOM | 2302 | C | GLU A 245 | 94.817 | 22.382 | 4.794 | 1.00 | 59.59 |
| ATOM | 2303 | O | GLU A 245 | 93.765 | 22.664 | 4.220 | 1.00 | 60.79 |
| ATOM | 2304 | N | PHE A 246 | 95.773 | 23.278 | 5.010 | 1.00 | 61.44 |
| ATOM | 2306 | CA | PHE A 246 | 95.637 | 24.635 | 4.510 | 1.00 | 63.27 |
| ATOM | 2307 | CB | PHE A 246 | 95.567 | 25.658 | 5.657 | 1.00 | 60.46 |
| ATOM | 2308 | CG | PHE A 246 | 96.689 | 25.567 | 6.663 | 1.00 | 56.43 |
| ATOM | 2309 | CD1 | PHE A 246 | 97.850 | 26.319 | 6.502 | 1.00 | 54.28 |
| ATOM | 2310 | CD2 | PHE A 246 | 96.532 | 24.825 | 7.834 | 1.00 | 53.72 |
| ATOM | 2311 | CE1 | PHE A 246 | 98.829 | 26.342 | 7.497 | 1.00 | 51.24 |
| ATOM | 2312 | CE2 | PHE A 246 | 97.506 | 24.841 | 8.834 | 1.00 | 51.21 |
| ATOM | 2313 | CZ | PHE A 246 | 98.653 | 25.602 | 8.667 | 1.00 | 48.89 |
| ATOM | 2314 | C | PHE A 246 | 96.676 | 25.022 | 3.473 | 1.00 | 67.53 |
| ATOM | 2315 | O | PHE A 246 | 97.723 | 24.382 | 3.357 | 1.00 | 68.37 |
| ATOM | 2316 | N | PRO A 247 | 96.375 | 26.050 | 2.664 | 1.00 | 71.27 |
| ATOM | 2317 | CD | PRO A 247 | 95.153 | 26.874 | 2.673 | 1.00 | 72.37 |
| ATOM | 2318 | CA | PRO A 247 | 97.297 | 26.511 | 1.624 | 1.00 | 74.18 |
| ATOM | 2319 | CB | PRO A 247 | 96.504 | 27.627 | 0.938 | 1.00 | 74.64 |
| ATOM | 2320 | CG | PRO A 247 | 95.626 | 28.147 | 2.038 | 1.00 | 73.71 |
| ATOM | 2321 | C | PRO A 247 | 98.620 | 27.016 | 2.180 | 1.00 | 76.26 |
| ATOM | 2322 | O | PRO A 247 | 98.661 | 28.002 | 2.920 | 1.00 | 76.91 |
| ATOM | 2323 | N | ALA A 248 | 99.691 | 26.299 | 1.858 | 1.00 | 78.37 |
| ATOM | 2325 | CA | ALA A 248 | 101.027 | 26.675 | 2.298 | 1.00 | 80.34 |
| ATOM | 2326 | CB | ALA A 248 | 102.025 | 25.578 | 1.963 | 1.00 | 80.57 |
| ATOM | 2327 | C | ALA A 248 | 101.385 | 27.950 | 1.556 | 1.00 | 81.06 |
| ATOM | 2328 | O | ALA A 248 | 101.463 | 27.962 | 0.325 | 1.00 | 81.92 |
| ATOM | 2329 | N | ALA A 249 | 101.564 | 29.030 | 2.300 | 1.00 | 80.72 |
| ATOM | 2331 | CA | ALA A 249 | 101.902 | 30.303 | 1.694 | 1.00 | 79.65 |
| ATOM | 2332 | CB | ALA A 249 | 100.799 | 31.319 | 1.964 | 1.00 | 80.65 |
| ATOM | 2333 | C | ALA A 249 | 103.232 | 30.799 | 2.234 | 1.00 | 78.22 |
| ATOM | 2334 | O | ALA A 249 | 103.799 | 30.201 | 3.150 | 1.00 | 78.60 |
| ATOM | 2335 | N | ALA A 250 | 103.734 | 31.878 | 1.643 | 1.00 | 76.27 |
| ATOM | 2337 | CA | ALA A 250 | 104.997 | 32.476 | 2.062 | 1.00 | 74.32 |

Page 6-A-55

| | | | | | | | | |
|---|---|---|---|---|---|---|---|---|
| ATOM | 2338 | CB | ALA A 250 | 106.093 | 32.174 | 1.042 | 1.00 | 75.66 |
| ATOM | 2339 | C | ALA A 250 | 104.840 | 33.985 | 2.249 | 1.00 | 71.97 |
| ATOM | 2340 | O | ALA A 250 | 105.815 | 34.732 | 2.160 | 1.00 | 72.98 |
| ATOM | 2341 | N | ASP A 251 | 103.606 | 34.422 | 2.496 | 1.00 | 67.46 |
| ATOM | 2343 | CA | ASP A 251 | 103.302 | 35.836 | 2.708 | 1.00 | 61.94 |
| ATOM | 2344 | CB | ASP A 251 | 101.797 | 36.090 | 2.568 | 1.00 | 66.00 |
| ATOM | 2345 | CG | ASP A 251 | 101.277 | 35.785 | 1.177 | 1.00 | 70.21 |
| ATOM | 2346 | OD1 | ASP A 251 | 101.467 | 34.647 | 0.695 | 1.00 | 71.96 |
| ATOM | 2347 | OD2 | ASP A 251 | 100.668 | 36.687 | 0.566 | 1.00 | 72.84 |
| ATOM | 2348 | C | ASP A 251 | 103.760 | 36.265 | 4.101 | 1.00 | 56.10 |
| ATOM | 2349 | O | ASP A 251 | 104.203 | 37.396 | 4.298 | 1.00 | 56.97 |
| ATOM | 2350 | N | ARG A 252 | 103.611 | 35.364 | 5.067 | 1.00 | 47.53 |
| ATOM | 2352 | CA | ARG A 252 | 104.009 | 35.622 | 6.441 | 1.00 | 39.41 |
| ATOM | 2353 | CB | ARG A 252 | 102.815 | 35.472 | 7.384 | 1.00 | 39.71 |
| ATOM | 2354 | CG | ARG A 252 | 101.668 | 36.426 | 7.129 | 1.00 | 39.66 |
| ATOM | 2355 | CD | ARG A 252 | 101.975 | 37.837 | 7.596 | 1.00 | 41.34 |
| ATOM | 2356 | NE | ARG A 252 | 100.830 | 38.714 | 7.375 | 1.00 | 42.20 |
| ATOM | 2358 | CZ | ARG A 252 | 100.628 | 39.416 | 6.263 | 1.00 | 44.51 |
| ATOM | 2359 | NH1 | ARG A 252 | 101.498 | 39.358 | 5.263 | 1.00 | 45.26 |
| ATOM | 2362 | NH2 | ARG A 252 | 99.542 | 40.163 | 6.141 | 1.00 | 44.83 |
| ATOM | 2365 | C | ARG A 252 | 105.070 | 34.594 | 6.798 | 1.00 | 34.91 |
| ATOM | 2366 | O | ARG A 252 | 105.315 | 33.667 | 6.035 | 1.00 | 31.70 |
| ATOM | 2367 | N | MET A 253 | 105.662 | 34.730 | 7.976 | 1.00 | 32.83 |
| ATOM | 2369 | CA | MET A 253 | 106.697 | 33.809 | 8.417 | 1.00 | 30.84 |
| ATOM | 2370 | CB | MET A 253 | 107.605 | 34.499 | 9.441 | 1.00 | 30.27 |
| ATOM | 2371 | CG | MET A 253 | 108.192 | 35.807 | 8.925 | 1.00 | 31.26 |
| ATOM | 2372 | SD | MET A 253 | 109.366 | 36.637 | 10.009 | 1.00 | 34.11 |
| ATOM | 2373 | CE | MET A 253 | 110.335 | 37.492 | 8.834 | 1.00 | 29.80 |
| ATOM | 2374 | C | MET A 253 | 106.130 | 32.501 | 8.979 | 1.00 | 31.42 |
| ATOM | 2375 | O | MET A 253 | 106.568 | 31.419 | 8.595 | 1.00 | 31.42 |
| ATOM | 2376 | N | VAL A 254 | 105.144 | 32.600 | 9.866 | 1.00 | 31.26 |
| ATOM | 2378 | CA | VAL A 254 | 104.540 | 31.419 | 10.480 | 1.00 | 32.17 |
| ATOM | 2379 | CB | VAL A 254 | 104.781 | 31.376 | 12.015 | 1.00 | 32.83 |
| ATOM | 2380 | CG1 | VAL A 254 | 106.243 | 31.143 | 12.324 | 1.00 | 35.48 |

Page 6-A-56

| ATOM | 2381 | CG2 | VAL A 254 | 104.316 | 32.672 | 12.658 | 1.00 | 33.43 |
|------|------|-----|-----------|---------|--------|--------|------|-------|
| ATOM | 2382 | C   | VAL A 254 | 103.043 | 31.378 | 10.262 | 1.00 | 32.00 |
| ATOM | 2383 | O   | VAL A 254 | 102.412 | 32.410 | 10.059 | 1.00 | 33.43 |
| ATOM | 2384 | N   | TYR A 255 | 102.478 | 30.181 | 10.340 | 1.00 | 33.42 |
| ATOM | 2386 | CA  | TYR A 255 | 101.044 | 29.979 | 10.179 | 1.00 | 32.60 |
| ATOM | 2387 | CB  | TYR A 255 | 100.726 | 29.448 |  8.784 | 1.00 | 32.98 |
| ATOM | 2388 | CG  | TYR A 255 | 100.746 | 30.482 |  7.694 | 1.00 | 32.36 |
| ATOM | 2389 | CD1 | TYR A 255 | 101.913 | 30.756 |  6.987 | 1.00 | 31.99 |
| ATOM | 2390 | CE1 | TYR A 255 | 101.921 | 31.674 |  5.947 | 1.00 | 33.10 |
| ATOM | 2391 | CD2 | TYR A 255 |  99.587 | 31.154 |  7.335 | 1.00 | 31.03 |
| ATOM | 2392 | CE2 | TYR A 255 |  99.583 | 32.072 |  6.298 | 1.00 | 32.21 |
| ATOM | 2393 | CZ  | TYR A 255 | 100.750 | 32.325 |  5.607 | 1.00 | 33.29 |
| ATOM | 2394 | OH  | TYR A 255 | 100.741 | 33.230 |  4.573 | 1.00 | 38.59 |
| ATOM | 2396 | C   | TYR A 255 | 100.559 | 28.955 | 11.195 | 1.00 | 31.73 |
| ATOM | 2397 | O   | TYR A 255 | 101.156 | 27.892 | 11.330 | 1.00 | 32.57 |
| ATOM | 2398 | N   | LEU A 256 |  99.490 | 29.279 | 11.914 | 1.00 | 31.36 |
| ATOM | 2400 | CA  | LEU A 256 |  98.916 | 28.370 | 12.893 | 1.00 | 29.13 |
| ATOM | 2401 | CB  | LEU A 256 |  98.878 | 28.992 | 14.280 | 1.00 | 28.40 |
| ATOM | 2402 | CG  | LEU A 256 | 100.206 | 29.125 | 15.014 | 1.00 | 28.89 |
| ATOM | 2403 | CD1 | LEU A 256 | 101.045 | 30.208 | 14.375 | 1.00 | 32.20 |
| ATOM | 2404 | CD2 | LEU A 256 |  99.938 | 29.462 | 16.471 | 1.00 | 32.12 |
| ATOM | 2405 | C   | LEU A 256 |  97.509 | 27.984 | 12.489 | 1.00 | 30.86 |
| ATOM | 2406 | O   | LEU A 256 |  96.748 | 28.814 | 11.987 | 1.00 | 30.77 |
| ATOM | 2407 | N   | GLY A 257 |  97.203 | 26.701 | 12.652 | 1.00 | 31.62 |
| ATOM | 2409 | CA  | GLY A 257 |  95.888 | 26.180 | 12.345 | 1.00 | 29.36 |
| ATOM | 2410 | C   | GLY A 257 |  95.287 | 25.827 | 13.688 | 1.00 | 29.99 |
| ATOM | 2411 | O   | GLY A 257 |  95.662 | 24.830 | 14.295 | 1.00 | 32.08 |
| ATOM | 2412 | N   | LEU A 258 |  94.402 | 26.686 | 14.177 | 1.00 | 29.99 |
| ATOM | 2414 | CA  | LEU A 258 |  93.742 | 26.507 | 15.463 | 1.00 | 26.58 |
| ATOM | 2415 | CB  | LEU A 258 |  93.562 | 27.871 | 16.101 | 1.00 | 26.90 |
| ATOM | 2416 | CG  | LEU A 258 |  94.866 | 28.668 | 16.049 | 1.00 | 28.57 |
| ATOM | 2417 | CD1 | LEU A 258 |  94.583 | 30.144 | 16.176 | 1.00 | 29.14 |
| ATOM | 2418 | CD2 | LEU A 258 |  95.808 | 28.177 | 17.139 | 1.00 | 29.78 |
| ATOM | 2419 | C   | LEU A 258 |  92.397 | 25.838 | 15.253 | 1.00 | 28.27 |

Page 6-A-57

| | | | | | | | | |
|---|---|---|---|---|---|---|---|---|
| ATOM | 2420 | O | LEU | A | 258 | 91.404 | 26.499 | 14.936 | 1.00 29.90 |
| ATOM | 2421 | N | SER | A | 259 | 92.370 | 24.523 | 15.434 | 1.00 28.81 |
| ATOM | 2423 | CA | SER | A | 259 | 91.164 | 23.726 | 15.229 | 1.00 30.63 |
| ATOM | 2424 | CB | SER | A | 259 | 91.491 | 22.237 | 15.348 | 1.00 31.03 |
| ATOM | 2425 | OG | SER | A | 259 | 91.783 | 21.889 | 16.689 | 1.00 33.43 |
| ATOM | 2427 | C | SER | A | 259 | 90.003 | 24.041 | 16.152 | 1.00 31.95 |
| ATOM | 2428 | O | SER | A | 259 | 90.184 | 24.600 | 17.231 | 1.00 33.18 |
| ATOM | 2429 | N | ASP | A | 260 | 88.808 | 23.637 | 15.729 | 1.00 32.89 |
| ATOM | 2431 | CA | ASP | A | 260 | 87.616 | 23.844 | 16.530 | 1.00 31.93 |
| ATOM | 2432 | CB | ASP | A | 260 | 86.326 | 23.521 | 15.739 | 1.00 33.23 |
| ATOM | 2433 | CG | ASP | A | 260 | 86.327 | 22.127 | 15.080 | 1.00 32.26 |
| ATOM | 2434 | OD1 | ASP | A | 260 | 87.138 | 21.246 | 15.425 | 1.00 33.22 |
| ATOM | 2435 | OD2 | ASP | A | 260 | 85.473 | 21.904 | 14.203 | 1.00 32.09 |
| ATOM | 2436 | C | ASP | A | 260 | 87.725 | 23.015 | 17.807 | 1.00 30.67 |
| ATOM | 2437 | O | ASP | A | 260 | 87.234 | 23.417 | 18.856 | 1.00 34.53 |
| ATOM | 2438 | N | TYR | A | 261 | 88.414 | 21.881 | 17.715 | 1.00 27.04 |
| ATOM | 2440 | CA | TYR | A | 261 | 88.629 | 20.983 | 18.847 | 1.00 26.39 |
| ATOM | 2441 | CB | TYR | A | 261 | 89.490 | 19.789 | 18.382 | 1.00 27.42 |
| ATOM | 2442 | CG | TYR | A | 261 | 90.064 | 18.885 | 19.463 | 1.00 26.82 |
| ATOM | 2443 | CD1 | TYR | A | 261 | 91.304 | 19.157 | 20.038 | 1.00 29.26 |
| ATOM | 2444 | CE1 | TYR | A | 261 | 91.855 | 18.318 | 21.006 | 1.00 30.93 |
| ATOM | 2445 | CD2 | TYR | A | 261 | 89.386 | 17.745 | 19.886 | 1.00 26.82 |
| ATOM | 2446 | CE2 | TYR | A | 261 | 89.927 | 16.898 | 20.853 | 1.00 28.99 |
| ATOM | 2447 | CZ | TYR | A | 261 | 91.163 | 17.194 | 21.408 | 1.00 32.15 |
| ATOM | 2448 | OH | TYR | A | 261 | 91.715 | 16.368 | 22.364 | 1.00 36.84 |
| ATOM | 2450 | C | TYR | A | 261 | 89.345 | 21.796 | 19.917 | 1.00 25.35 |
| ATOM | 2451 | O | TYR | A | 261 | 88.939 | 21.824 | 21.076 | 1.00 31.74 |
| ATOM | 2452 | N | PHE | A | 262 | 90.361 | 22.525 | 19.488 | 1.00 23.54 |
| ATOM | 2454 | CA | PHE | A | 262 | 91.151 | 23.361 | 20.368 | 1.00 21.85 |
| ATOM | 2455 | CB | PHE | A | 262 | 92.141 | 24.158 | 19.514 | 1.00 19.79 |
| ATOM | 2456 | CG | PHE | A | 262 | 92.923 | 25.184 | 20.275 | 1.00 20.92 |
| ATOM | 2457 | CD1 | PHE | A | 262 | 93.830 | 24.806 | 21.253 | 1.00 22.00 |
| ATOM | 2458 | CD2 | PHE | A | 262 | 92.761 | 26.536 | 20.002 | 1.00 20.09 |
| ATOM | 2459 | CE1 | PHE | A | 262 | 94.558 | 25.759 | 21.943 | 1.00 19.37 |

Page 6-A-58

| | | | | | | | | |
|---|---|---|---|---|---|---|---|---|
| ATOM | 2460 | CE2 | PHE A 262 | 93.488 | 27.497 | 20.693 | 1.00 | 18.46 |
| ATOM | 2461 | CZ | PHE A 262 | 94.386 | 27.107 | 21.660 | 1.00 | 18.18 |
| ATOM | 2462 | C | PHE A 262 | 90.244 | 24.290 | 21.165 | 1.00 | 21.70 |
| ATOM | 2463 | O | PHE A 262 | 90.236 | 24.266 | 22.391 | 1.00 | 22.47 |
| ATOM | 2464 | N | PHE A 263 | 89.432 | 25.060 | 20.457 | 1.00 | 24.02 |
| ATOM | 2466 | CA | PHE A 263 | 88.522 | 26.014 | 21.079 | 1.00 | 23.57 |
| ATOM | 2467 | CB | PHE A 263 | 87.843 | 26.845 | 20.005 | 1.00 | 22.46 |
| ATOM | 2468 | CG | PHE A 263 | 88.783 | 27.712 | 19.241 | 1.00 | 21.39 |
| ATOM | 2469 | CD1 | PHE A 263 | 89.462 | 28.740 | 19.870 | 1.00 | 25.06 |
| ATOM | 2470 | CD2 | PHE A 263 | 88.982 | 27.510 | 17.887 | 1.00 | 23.84 |
| ATOM | 2471 | CE1 | PHE A 263 | 90.326 | 29.555 | 19.159 | 1.00 | 26.31 |
| ATOM | 2472 | CE2 | PHE A 263 | 89.843 | 28.319 | 17.169 | 1.00 | 25.34 |
| ATOM | 2473 | CZ | PHE A 263 | 90.514 | 29.345 | 17.804 | 1.00 | 25.18 |
| ATOM | 2474 | C | PHE A 263 | 87.457 | 25.378 | 21.933 | 1.00 | 25.63 |
| ATOM | 2475 | O | PHE A 263 | 87.103 | 25.892 | 22.992 | 1.00 | 29.04 |
| ATOM | 2476 | N | ASN A 264 | 86.926 | 24.264 | 21.463 | 1.00 | 27.70 |
| ATOM | 2478 | CA | ASN A 264 | 85.882 | 23.577 | 22.193 | 1.00 | 26.71 |
| ATOM | 2479 | CB | ASN A 264 | 85.136 | 22.617 | 21.278 | 1.00 | 26.91 |
| ATOM | 2480 | CG | ASN A 264 | 84.183 | 23.338 | 20.345 | 1.00 | 26.18 |
| ATOM | 2481 | OD1 | ASN A 264 | 83.115 | 23.779 | 20.755 | 1.00 | 29.25 |
| ATOM | 2482 | ND2 | ASN A 264 | 84.563 | 23.462 | 19.087 | 1.00 | 30.59 |
| ATOM | 2485 | C | ASN A 264 | 86.359 | 22.898 | 23.470 | 1.00 | 26.40 |
| ATOM | 2486 | O | ASN A 264 | 85.587 | 22.763 | 24.414 | 1.00 | 27.80 |
| ATOM | 2487 | N | THR A 265 | 87.628 | 22.498 | 23.527 | 1.00 | 26.30 |
| ATOM | 2489 | CA | THR A 265 | 88.154 | 21.880 | 24.748 | 1.00 | 24.34 |
| ATOM | 2490 | CB | THR A 265 | 89.572 | 21.298 | 24.559 | 1.00 | 24.55 |
| ATOM | 2491 | OG1 | THR A 265 | 90.453 | 22.296 | 24.033 | 1.00 | 26.59 |
| ATOM | 2493 | CG2 | THR A 265 | 89.532 | 20.129 | 23.619 | 1.00 | 21.96 |
| ATOM | 2494 | C | THR A 265 | 88.175 | 22.924 | 25.865 | 1.00 | 23.53 |
| ATOM | 2495 | O | THR A 265 | 88.045 | 22.602 | 27.041 | 1.00 | 26.65 |
| ATOM | 2496 | N | ALA A 266 | 88.309 | 24.186 | 25.483 | 1.00 | 24.00 |
| ATOM | 2498 | CA | ALA A 266 | 88.315 | 25.276 | 26.437 | 1.00 | 22.35 |
| ATOM | 2499 | CB | ALA A 266 | 88.582 | 26.590 | 25.723 | 1.00 | 21.75 |
| ATOM | 2500 | C | ALA A 266 | 86.956 | 25.310 | 27.113 | 1.00 | 23.18 |

Page 6-A-59

| ATOM | 2501 | O | ALA A 266 | 86.865 | 25.297 | 28.336 | 1.00 | 27.51 |
| ATOM | 2502 | N | GLY A 267 | 85.897 | 25.286 | 26.311 | 1.00 | 24.69 |
| ATOM | 2504 | CA | GLY A 267 | 84.549 | 25.323 | 26.852 | 1.00 | 24.20 |
| ATOM | 2505 | C | GLY A 267 | 84.251 | 24.188 | 27.812 | 1.00 | 27.46 |
| ATOM | 2506 | O | GLY A 267 | 83.637 | 24.381 | 28.869 | 1.00 | 27.80 |
| ATOM | 2507 | N | LEU A 268 | 84.699 | 22.997 | 27.445 | 1.00 | 28.36 |
| ATOM | 2509 | CA | LEU A 268 | 84.493 | 21.816 | 28.262 | 1.00 | 29.18 |
| ATOM | 2510 | CB | LEU A 268 | 84.996 | 20.580 | 27.520 | 1.00 | 32.75 |
| ATOM | 2511 | CG | LEU A 268 | 84.728 | 19.224 | 28.169 | 1.00 | 37.10 |
| ATOM | 2512 | CD1 | LEU A 268 | 83.274 | 18.841 | 27.978 | 1.00 | 38.10 |
| ATOM | 2513 | CD2 | LEU A 268 | 85.633 | 18.180 | 27.544 | 1.00 | 41.14 |
| ATOM | 2514 | C | LEU A 268 | 85.209 | 21.940 | 29.596 | 1.00 | 27.77 |
| ATOM | 2515 | O | LEU A 268 | 84.623 | 21.696 | 30.644 | 1.00 | 31.78 |
| ATOM | 2516 | N | VAL A 269 | 86.469 | 22.344 | 29.558 | 1.00 | 26.94 |
| ATOM | 2518 | CA | VAL A 269 | 87.256 | 22.478 | 30.774 | 1.00 | 26.89 |
| ATOM | 2519 | CB | VAL A 269 | 88.752 | 22.720 | 30.448 | 1.00 | 24.63 |
| ATOM | 2520 | CG1 | VAL A 269 | 89.491 | 23.244 | 31.656 | 1.00 | 22.76 |
| ATOM | 2521 | CG2 | VAL A 269 | 89.382 | 21.416 | 30.007 | 1.00 | 21.59 |
| ATOM | 2522 | C | VAL A 269 | 86.722 | 23.535 | 31.740 | 1.00 | 28.84 |
| ATOM | 2523 | O | VAL A 269 | 86.687 | 23.309 | 32.948 | 1.00 | 29.66 |
| ATOM | 2524 | N | TYR A 270 | 86.298 | 24.681 | 31.219 | 1.00 | 30.57 |
| ATOM | 2526 | CA | TYR A 270 | 85.769 | 25.734 | 32.080 | 1.00 | 28.60 |
| ATOM | 2527 | CB | TYR A 270 | 85.753 | 27.079 | 31.350 | 1.00 | 28.80 |
| ATOM | 2528 | CG | TYR A 270 | 87.111 | 27.734 | 31.265 | 1.00 | 27.47 |
| ATOM | 2529 | CD1 | TYR A 270 | 87.766 | 28.169 | 32.415 | 1.00 | 25.23 |
| ATOM | 2530 | CE1 | TYR A 270 | 89.021 | 28.754 | 32.343 | 1.00 | 26.36 |
| ATOM | 2531 | CD2 | TYR A 270 | 87.750 | 27.906 | 30.038 | 1.00 | 29.53 |
| ATOM | 2532 | CE2 | TYR A 270 | 89.008 | 28.494 | 29.959 | 1.00 | 25.30 |
| ATOM | 2533 | CZ | TYR A 270 | 89.632 | 28.912 | 31.114 | 1.00 | 24.84 |
| ATOM | 2534 | OH | TYR A 270 | 90.877 | 29.492 | 31.047 | 1.00 | 30.89 |
| ATOM | 2536 | C | TYR A 270 | 84.385 | 25.405 | 32.631 | 1.00 | 29.08 |
| ATOM | 2537 | O | TYR A 270 | 84.034 | 25.836 | 33.729 | 1.00 | 28.17 |
| ATOM | 2538 | N | GLN A 271 | 83.609 | 24.628 | 31.882 | 1.00 | 30.32 |
| ATOM | 2540 | CA | GLN A 271 | 82.269 | 24.249 | 32.316 | 1.00 | 29.24 |

| | | | | | | | | |
|---|---|---|---|---|---|---|---|---|
| ATOM | 2541 | CB | GLN | A | 271 | 81.464 | 23.689 | 31.139 | 1.00 27.20 |
| ATOM | 2542 | CG | GLN | A | 271 | 79.957 | 23.680 | 31.357 | 1.00 27.60 |
| ATOM | 2543 | CD | GLN | A | 271 | 79.427 | 22.387 | 31.946 | 1.00 31.03 |
| ATOM | 2544 | OE1 | GLN | A | 271 | 79.982 | 21.306 | 31.724 | 1.00 35.11 |
| ATOM | 2545 | NE2 | GLN | A | 271 | 78.318 | 22.484 | 32.668 | 1.00 28.89 |
| ATOM | 2548 | C | GLN | A | 271 | 82.329 | 23.226 | 33.438 | 1.00 30.41 |
| ATOM | 2549 | O | GLN | A | 271 | 81.839 | 23.473 | 34.539 | 1.00 32.81 |
| ATOM | 2550 | N | GLU | A | 272 | 82.976 | 22.098 | 33.168 | 1.00 33.61 |
| ATOM | 2552 | CA | GLU | A | 272 | 83.096 | 21.011 | 34.133 | 1.00 36.97 |
| ATOM | 2553 | CB | GLU | A | 272 | 83.807 | 19.822 | 33.492 | 1.00 40.58 |
| ATOM | 2554 | CG | GLU | A | 272 | 83.084 | 19.264 | 32.274 | 1.00 48.51 |
| ATOM | 2555 | CD | GLU | A | 272 | 83.781 | 18.051 | 31.674 | 1.00 55.01 |
| ATOM | 2556 | OE1 | GLU | A | 272 | 84.998 | 18.129 | 31.405 | 1.00 59.64 |
| ATOM | 2557 | OE2 | GLU | A | 272 | 83.112 | 17.016 | 31.468 | 1.00 57.25 |
| ATOM | 2558 | C | GLU | A | 272 | 83.761 | 21.376 | 35.460 | 1.00 36.60 |
| ATOM | 2559 | O | GLU | A | 272 | 83.674 | 20.622 | 36.425 | 1.00 40.35 |
| ATOM | 2560 | N | ALA | A | 273 | 84.429 | 22.522 | 35.512 | 1.00 35.77 |
| ATOM | 2562 | CA | ALA | A | 273 | 85.079 | 22.970 | 36.741 | 1.00 34.34 |
| ATOM | 2563 | CB | ALA | A | 273 | 86.316 | 23.798 | 36.418 | 1.00 32.87 |
| ATOM | 2564 | C | ALA | A | 273 | 84.104 | 23.778 | 37.594 | 1.00 34.54 |
| ATOM | 2565 | O | ALA | A | 273 | 84.459 | 24.252 | 38.679 | 1.00 35.72 |
| ATOM | 2566 | N | GLY | A | 274 | 82.879 | 23.930 | 37.086 | 1.00 35.04 |
| ATOM | 2568 | CA | GLY | A | 274 | 81.831 | 24.663 | 37.779 | 1.00 35.01 |
| ATOM | 2569 | C | GLY | A | 274 | 82.092 | 26.147 | 37.930 | 1.00 34.45 |
| ATOM | 2570 | O | GLY | A | 274 | 81.640 | 26.761 | 38.897 | 1.00 36.89 |
| ATOM | 2571 | N | VAL | A | 275 | 82.752 | 26.742 | 36.944 | 1.00 34.05 |
| ATOM | 2573 | CA | VAL | A | 275 | 83.083 | 28.157 | 37.018 | 1.00 34.43 |
| ATOM | 2574 | CB | VAL | A | 275 | 84.600 | 28.381 | 36.778 | 1.00 35.67 |
| ATOM | 2575 | CG1 | VAL | A | 275 | 84.898 | 28.616 | 35.308 | 1.00 37.90 |
| ATOM | 2576 | CG2 | VAL | A | 275 | 85.105 | 29.519 | 37.638 | 1.00 38.34 |
| ATOM | 2577 | C | VAL | A | 275 | 82.236 | 29.078 | 36.135 | 1.00 33.65 |
| ATOM | 2578 | O | VAL | A | 275 | 82.211 | 30.286 | 36.343 | 1.00 35.12 |
| ATOM | 2579 | N | LEU | A | 276 | 81.527 | 28.523 | 35.159 | 1.00 32.82 |
| ATOM | 2581 | CA | LEU | A | 276 | 80.683 | 29.352 | 34.307 | 1.00 29.38 |

Page 6-A-61

```
ATOM   2582  CB   LEU A 276      80.478  28.695  32.936  1.00 27.64
ATOM   2583  CG   LEU A 276      81.739  28.482  32.082  1.00 25.37
ATOM   2584  CD1  LEU A 276      81.370  27.883  30.757  1.00 24.34
ATOM   2585  CD2  LEU A 276      82.459  29.793  31.858  1.00 28.39
ATOM   2586  C    LEU A 276      79.363  29.548  35.049  1.00 29.83
ATOM   2587  O    LEU A 276      78.323  29.007  34.674  1.00 30.32
ATOM   2588  N    LYS A 277      79.443  30.271  36.158  1.00 29.10
ATOM   2590  CA   LYS A 277      78.294  30.546  37.004  1.00 27.79
ATOM   2591  CB   LYS A 277      78.327  29.656  38.246  1.00 29.34
ATOM   2592  CG   LYS A 277      78.211  28.183  37.956  1.00 33.13
ATOM   2593  CD   LYS A 277      78.269  27.369  39.230  1.00 39.28
ATOM   2594  CE   LYS A 277      78.064  25.888  38.930  1.00 44.23
ATOM   2595  NZ   LYS A 277      78.321  25.022  40.119  1.00 46.99
ATOM   2599  C    LYS A 277      78.386  32.002  37.420  1.00 26.55
ATOM   2600  O    LYS A 277      79.474  32.556  37.516  1.00 28.05
ATOM   2601  N    MET A 278      77.251  32.608  37.723  1.00 25.90
ATOM   2603  CA   MET A 278      77.251  33.999  38.111  1.00 26.31
ATOM   2604  CB   MET A 278      77.350  34.854  36.864  1.00 25.28
ATOM   2605  CG   MET A 278      77.496  36.310  37.129  1.00 30.09
ATOM   2606  SD   MET A 278      77.760  37.127  35.586  1.00 37.76
ATOM   2607  CE   MET A 278      77.452  38.822  36.056  1.00 34.82
ATOM   2608  C    MET A 278      75.985  34.338  38.872  1.00 28.79
ATOM   2609  O    MET A 278      74.910  33.858  38.533  1.00 30.81
ATOM   2610  N    THR A 279      76.123  35.134  39.925  1.00 30.03
ATOM   2612  CA   THR A 279      74.987  35.544  40.728  1.00 29.69
ATOM   2613  CB   THR A 279      75.242  35.277  42.211  1.00 29.00
ATOM   2614  OG1  THR A 279      75.286  33.864  42.431  1.00 31.54
ATOM   2616  CG2  THR A 279      74.140  35.863  43.060  1.00 28.67
ATOM   2617  C    THR A 279      74.714  37.025  40.515  1.00 31.93
ATOM   2618  O    THR A 279      75.615  37.856  40.644  1.00 32.91
ATOM   2619  N    LEU A 280      73.482  37.338  40.128  1.00 33.14
ATOM   2621  CA   LEU A 280      73.062  38.715  39.893  1.00 33.77
ATOM   2622  CB   LEU A 280      72.268  38.826  38.581  1.00 34.16
ATOM   2623  CG   LEU A 280      72.930  38.757  37.194  1.00 33.72
```

| ATOM | 2624 | CD1 | LEU | A | 280 | 74.391 | 38.394 | 37.271 | 1.00 | 33.08 |
| ATOM | 2625 | CD2 | LEU | A | 280 | 72.186 | 37.766 | 36.333 | 1.00 | 30.96 |
| ATOM | 2626 | C | LEU | A | 280 | 72.196 | 39.173 | 41.064 | 1.00 | 35.73 |
| ATOM | 2627 | O | LEU | A | 280 | 71.223 | 38.508 | 41.438 | 1.00 | 33.09 |
| ATOM | 2628 | N | ARG | A | 281 | 72.584 | 40.290 | 41.666 | 1.00 | 39.95 |
| ATOM | 2630 | CA | ARG | A | 281 | 71.864 | 40.860 | 42.796 | 1.00 | 42.55 |
| ATOM | 2631 | CB | ARG | A | 281 | 72.823 | 41.091 | 43.975 | 1.00 | 44.48 |
| ATOM | 2632 | CG | ARG | A | 281 | 73.472 | 39.824 | 44.534 | 1.00 | 47.55 |
| ATOM | 2633 | CD | ARG | A | 281 | 74.406 | 40.109 | 45.712 | 1.00 | 50.80 |
| ATOM | 2634 | NE | ARG | A | 281 | 75.660 | 40.757 | 45.321 | 1.00 | 57.47 |
| ATOM | 2636 | CZ | ARG | A | 281 | 76.844 | 40.145 | 45.263 | 1.00 | 61.45 |
| ATOM | 2637 | NH1 | ARG | A | 281 | 76.956 | 38.852 | 45.552 | 1.00 | 62.83 |
| ATOM | 2640 | NH2 | ARG | A | 281 | 77.925 | 40.825 | 44.901 | 1.00 | 62.95 |
| ATOM | 2643 | C | ARG | A | 281 | 71.255 | 42.190 | 42.354 | 1.00 | 44.72 |
| ATOM | 2644 | O | ARG | A | 281 | 71.782 | 42.854 | 41.458 | 1.00 | 46.61 |
| ATOM | 2645 | N | ASP | A | 282 | 70.179 | 42.601 | 43.014 | 1.00 | 46.42 |
| ATOM | 2647 | CA | ASP | A | 282 | 69.491 | 43.849 | 42.702 | 1.00 | 47.87 |
| ATOM | 2648 | CB | ASP | A | 282 | 68.284 | 44.039 | 43.634 | 1.00 | 49.38 |
| ATOM | 2649 | CG | ASP | A | 282 | 67.472 | 45.280 | 43.302 | 1.00 | 51.57 |
| ATOM | 2650 | OD1 | ASP | A | 282 | 66.898 | 45.349 | 42.195 | 1.00 | 54.37 |
| ATOM | 2651 | OD2 | ASP | A | 282 | 67.408 | 46.191 | 44.150 | 1.00 | 54.52 |
| ATOM | 2652 | C | ASP | A | 282 | 70.394 | 45.080 | 42.762 | 1.00 | 48.67 |
| ATOM | 2653 | O | ASP | A | 282 | 70.090 | 46.089 | 42.141 | 1.00 | 51.13 |
| ATOM | 2654 | N | ASP | A | 283 | 71.506 | 44.996 | 43.488 | 1.00 | 49.71 |
| ATOM | 2656 | CA | ASP | A | 283 | 72.427 | 46.128 | 43.608 | 1.00 | 50.78 |
| ATOM | 2657 | CB | ASP | A | 283 | 73.111 | 46.138 | 44.987 | 1.00 | 52.25 |
| ATOM | 2658 | CG | ASP | A | 283 | 73.994 | 44.920 | 45.224 | 1.00 | 55.58 |
| ATOM | 2659 | OD1 | ASP | A | 283 | 75.189 | 44.953 | 44.847 | 1.00 | 58.60 |
| ATOM | 2660 | OD2 | ASP | A | 283 | 73.498 | 43.935 | 45.810 | 1.00 | 58.13 |
| ATOM | 2661 | C | ASP | A | 283 | 73.474 | 46.236 | 42.492 | 1.00 | 51.35 |
| ATOM | 2662 | O | ASP | A | 283 | 74.362 | 47.086 | 42.543 | 1.00 | 52.74 |
| ATOM | 2663 | N | MET | A | 284 | 73.395 | 45.359 | 41.500 | 1.00 | 51.07 |
| ATOM | 2665 | CA | MET | A | 284 | 74.342 | 45.404 | 40.399 | 1.00 | 50.50 |
| ATOM | 2666 | CB | MET | A | 284 | 74.629 | 43.994 | 39.887 | 1.00 | 48.87 |

Page 6-A-63

| ATOM | 2667 | CG | MET | A | 284 | 75.169 | 43.058 | 40.956 | 1.00 | 46.76 |
| --- | --- | --- | --- | --- | --- | --- | --- | --- | --- | --- |
| ATOM | 2668 | SD | MET | A | 284 | 75.494 | 41.398 | 40.353 | 1.00 | 43.76 |
| ATOM | 2669 | CE | MET | A | 284 | 76.804 | 40.895 | 41.457 | 1.00 | 47.06 |
| ATOM | 2670 | C | MET | A | 284 | 73.775 | 46.283 | 39.289 | 1.00 | 53.22 |
| ATOM | 2671 | O | MET | A | 284 | 74.515 | 46.824 | 38.466 | 1.00 | 55.85 |
| ATOM | 2672 | N | ILE | A | 285 | 72.455 | 46.433 | 39.285 | 1.00 | 55.37 |
| ATOM | 2674 | CA | ILE | A | 285 | 71.761 | 47.252 | 38.295 | 1.00 | 57.52 |
| ATOM | 2675 | CB | ILE | A | 285 | 70.287 | 46.792 | 38.141 | 1.00 | 55.38 |
| ATOM | 2676 | CG2 | ILE | A | 285 | 69.583 | 47.611 | 37.070 | 1.00 | 56.70 |
| ATOM | 2677 | CG1 | ILE | A | 285 | 70.235 | 45.303 | 37.783 | 1.00 | 53.28 |
| ATOM | 2678 | CD1 | ILE | A | 285 | 68.838 | 44.723 | 37.732 | 1.00 | 50.41 |
| ATOM | 2679 | C | ILE | A | 285 | 71.787 | 48.707 | 38.776 | 1.00 | 59.50 |
| ATOM | 2680 | O | ILE | A | 285 | 71.358 | 48.998 | 39.889 | 1.00 | 60.66 |
| ATOM | 2681 | N | PRO | A | 286 | 72.304 | 49.635 | 37.951 | 1.00 | 61.05 |
| ATOM | 2682 | CD | PRO | A | 286 | 72.787 | 49.459 | 36.573 | 1.00 | 61.08 |
| ATOM | 2683 | CA | PRO | A | 286 | 72.360 | 51.048 | 38.350 | 1.00 | 62.59 |
| ATOM | 2684 | CB | PRO | A | 286 | 72.862 | 51.748 | 37.083 | 1.00 | 62.24 |
| ATOM | 2685 | CG | PRO | A | 286 | 72.481 | 50.801 | 35.974 | 1.00 | 63.04 |
| ATOM | 2686 | C | PRO | A | 286 | 71.004 | 51.583 | 38.817 | 1.00 | 64.15 |
| ATOM | 2687 | O | PRO | A | 286 | 69.986 | 51.400 | 38.154 | 1.00 | 63.39 |
| ATOM | 2688 | N | LYS | A | 287 | 71.016 | 52.268 | 39.956 | 1.00 | 67.25 |
| ATOM | 2690 | CA | LYS | A | 287 | 69.813 | 52.826 | 40.582 | 1.00 | 69.68 |
| ATOM | 2691 | CB | LYS | A | 287 | 70.204 | 53.622 | 41.838 | 1.00 | 72.51 |
| ATOM | 2692 | CG | LYS | A | 287 | 71.285 | 54.675 | 41.607 | 1.00 | 75.76 |
| ATOM | 2693 | CD | LYS | A | 287 | 71.483 | 55.570 | 42.826 | 1.00 | 78.18 |
| ATOM | 2694 | CE | LYS | A | 287 | 72.474 | 56.697 | 42.534 | 1.00 | 79.24 |
| ATOM | 2695 | NZ | LYS | A | 287 | 72.603 | 57.663 | 43.666 | 1.00 | 79.25 |
| ATOM | 2699 | C | LYS | A | 287 | 68.845 | 53.653 | 39.724 | 1.00 | 69.37 |
| ATOM | 2700 | O | LYS | A | 287 | 67.735 | 53.962 | 40.165 | 1.00 | 69.08 |
| ATOM | 2701 | N | GLU | A | 288 | 69.242 | 53.996 | 38.505 | 1.00 | 68.49 |
| ATOM | 2703 | CA | GLU | A | 288 | 68.386 | 54.792 | 37.635 | 1.00 | 69.17 |
| ATOM | 2704 | CB | GLU | A | 288 | 69.152 | 56.004 | 37.094 | 1.00 | 70.77 |
| ATOM | 2705 | CG | GLU | A | 288 | 69.897 | 56.826 | 38.142 | 1.00 | 73.92 |
| ATOM | 2706 | CD | GLU | A | 288 | 71.290 | 56.292 | 38.461 | 1.00 | 76.03 |

Page 6-A-64

| ATOM | 2707 | OE1 | GLU A 288 | 71.656 | 55.195 | 37.983 | 1.00 | 78.84 |
| --- | --- | --- | --- | --- | --- | --- | --- | --- |
| ATOM | 2708 | OE2 | GLU A 288 | 72.031 | 56.981 | 39.196 | 1.00 | 76.47 |
| ATOM | 2709 | C | GLU A 288 | 67.851 | 53.965 | 36.469 | 1.00 | 68.68 |
| ATOM | 2710 | O | GLU A 288 | 68.012 | 54.345 | 35.310 | 1.00 | 70.05 |
| ATOM | 2711 | N | SER A 289 | 67.194 | 52.852 | 36.772 | 1.00 | 68.09 |
| ATOM | 2713 | CA | SER A 289 | 66.655 | 51.985 | 35.727 | 1.00 | 67.82 |
| ATOM | 2714 | CB | SER A 289 | 67.516 | 50.728 | 35.593 | 1.00 | 69.68 |
| ATOM | 2715 | OG | SER A 289 | 68.868 | 51.064 | 35.327 | 1.00 | 73.68 |
| ATOM | 2717 | C | SER A 289 | 65.202 | 51.590 | 35.977 | 1.00 | 66.67 |
| ATOM | 2718 | O | SER A 289 | 64.695 | 51.730 | 37.090 | 1.00 | 67.98 |
| ATOM | 2719 | N | ALA A 290 | 64.537 | 51.110 | 34.928 | 1.00 | 63.49 |
| ATOM | 2721 | CA | ALA A 290 | 63.144 | 50.691 | 35.027 | 1.00 | 60.33 |
| ATOM | 2722 | CB | ALA A 290 | 62.525 | 50.598 | 33.644 | 1.00 | 60.15 |
| ATOM | 2723 | C | ALA A 290 | 63.026 | 49.353 | 35.744 | 1.00 | 58.83 |
| ATOM | 2724 | O | ALA A 290 | 62.236 | 49.208 | 36.673 | 1.00 | 59.19 |
| ATOM | 2725 | N | PHE A 291 | 63.839 | 48.390 | 35.321 | 1.00 | 57.41 |
| ATOM | 2727 | CA | PHE A 291 | 63.829 | 47.043 | 35.894 | 1.00 | 55.46 |
| ATOM | 2728 | CB | PHE A 291 | 64.441 | 46.044 | 34.902 | 1.00 | 54.51 |
| ATOM | 2729 | CG | PHE A 291 | 63.658 | 45.890 | 33.622 | 1.00 | 52.78 |
| ATOM | 2730 | CD1 | PHE A 291 | 62.493 | 45.130 | 33.588 | 1.00 | 52.76 |
| ATOM | 2731 | CD2 | PHE A 291 | 64.085 | 46.505 | 32.451 | 1.00 | 52.05 |
| ATOM | 2732 | CE1 | PHE A 291 | 61.760 | 44.983 | 32.414 | 1.00 | 51.50 |
| ATOM | 2733 | CE2 | PHE A 291 | 63.360 | 46.364 | 31.270 | 1.00 | 52.10 |
| ATOM | 2734 | CZ | PHE A 291 | 62.194 | 45.601 | 31.255 | 1.00 | 51.58 |
| ATOM | 2735 | C | PHE A 291 | 64.519 | 46.912 | 37.260 | 1.00 | 53.52 |
| ATOM | 2736 | O | PHE A 291 | 65.541 | 47.547 | 37.524 | 1.00 | 53.59 |
| ATOM | 2737 | N | ARG A 292 | 63.966 | 46.046 | 38.104 | 1.00 | 50.17 |
| ATOM | 2739 | CA | ARG A 292 | 64.494 | 45.799 | 39.438 | 1.00 | 46.66 |
| ATOM | 2740 | CB | ARG A 292 | 63.677 | 46.562 | 40.481 | 1.00 | 46.93 |
| ATOM | 2741 | CG | ARG A 292 | 63.793 | 48.065 | 40.434 | 1.00 | 47.97 |
| ATOM | 2742 | CD | ARG A 292 | 64.964 | 48.536 | 41.256 | 1.00 | 49.34 |
| ATOM | 2743 | NE | ARG A 292 | 65.959 | 49.215 | 40.438 | 1.00 | 51.19 |
| ATOM | 2745 | CZ | ARG A 292 | 67.266 | 48.993 | 40.521 | 1.00 | 52.32 |
| ATOM | 2746 | NH1 | ARG A 292 | 67.735 | 48.102 | 41.385 | 1.00 | 52.06 |

Page 6-A-65

| ATOM | 2749 | NH2 | ARG A 292 | 68.106 | 49.674 | 39.750 | 1.00 | 52.32 |
|---|---|---|---|---|---|---|---|---|
| ATOM | 2752 | C | ARG A 292 | 64.317 | 44.322 | 39.715 | 1.00 | 46.15 |
| ATOM | 2753 | O | ARG A 292 | 63.333 | 43.720 | 39.278 | 1.00 | 47.65 |
| ATOM | 2754 | N | LEU A 293 | 65.278 | 43.725 | 40.409 | 1.00 | 44.69 |
| ATOM | 2756 | CA | LEU A 293 | 65.169 | 42.320 | 40.769 | 1.00 | 42.76 |
| ATOM | 2757 | CB | LEU A 293 | 66.546 | 41.648 | 40.819 | 1.00 | 37.95 |
| ATOM | 2758 | CG | LEU A 293 | 67.252 | 41.569 | 39.468 | 1.00 | 34.56 |
| ATOM | 2759 | CD1 | LEU A 293 | 68.649 | 41.034 | 39.630 | 1.00 | 33.82 |
| ATOM | 2760 | CD2 | LEU A 293 | 66.459 | 40.692 | 38.537 | 1.00 | 32.43 |
| ATOM | 2761 | C | LEU A 293 | 64.516 | 42.349 | 42.141 | 1.00 | 44.58 |
| ATOM | 2762 | O | LEU A 293 | 65.169 | 42.154 | 43.164 | 1.00 | 46.89 |
| ATOM | 2763 | N | THR A 294 | 63.239 | 42.716 | 42.150 | 1.00 | 44.93 |
| ATOM | 2765 | CA | THR A 294 | 62.453 | 42.804 | 43.370 | 1.00 | 45.20 |
| ATOM | 2766 | CB | THR A 294 | 62.220 | 44.271 | 43.781 | 1.00 | 44.99 |
| ATOM | 2767 | OG1 | THR A 294 | 61.502 | 44.955 | 42.748 | 1.00 | 45.39 |
| ATOM | 2769 | CG2 | THR A 294 | 63.547 | 44.983 | 44.012 | 1.00 | 46.79 |
| ATOM | 2770 | C | THR A 294 | 61.111 | 42.175 | 43.055 | 1.00 | 46.49 |
| ATOM | 2771 | O | THR A 294 | 60.639 | 42.269 | 41.922 | 1.00 | 48.98 |
| ATOM | 2772 | N | THR A 295 | 60.500 | 41.520 | 44.035 | 1.00 | 47.36 |
| ATOM | 2774 | CA | THR A 295 | 59.204 | 40.892 | 43.812 | 1.00 | 48.40 |
| ATOM | 2775 | CB | THR A 295 | 58.720 | 40.139 | 45.063 | 1.00 | 47.45 |
| ATOM | 2776 | OG1 | THR A 295 | 58.837 | 40.986 | 46.210 | 1.00 | 47.38 |
| ATOM | 2778 | CG2 | THR A 295 | 59.550 | 38.891 | 45.287 | 1.00 | 47.66 |
| ATOM | 2779 | C | THR A 295 | 58.179 | 41.952 | 43.410 | 1.00 | 49.59 |
| ATOM | 2780 | O | THR A 295 | 57.292 | 41.693 | 42.599 | 1.00 | 50.18 |
| ATOM | 2781 | N | SER A 296 | 58.347 | 43.157 | 43.950 | 1.00 | 51.29 |
| ATOM | 2783 | CA | SER A 296 | 57.468 | 44.288 | 43.667 | 1.00 | 52.78 |
| ATOM | 2784 | CB | SER A 296 | 57.978 | 45.538 | 44.390 | 1.00 | 54.54 |
| ATOM | 2785 | OG | SER A 296 | 57.219 | 46.688 | 44.056 | 1.00 | 55.48 |
| ATOM | 2787 | C | SER A 296 | 57.412 | 44.551 | 42.172 | 1.00 | 52.76 |
| ATOM | 2788 | O | SER A 296 | 56.340 | 44.532 | 41.562 | 1.00 | 52.27 |
| ATOM | 2789 | N | PHE A 297 | 58.579 | 44.779 | 41.583 | 1.00 | 52.83 |
| ATOM | 2791 | CA | PHE A 297 | 58.656 | 45.033 | 40.160 | 1.00 | 53.94 |
| ATOM | 2792 | CB | PHE A 297 | 60.093 | 45.286 | 39.730 | 1.00 | 55.28 |

Page 6-A-66

| | | | | | | | | |
|---|---|---|---|---|---|---|---|---|
| ATOM | 2793 | CG | PHE A 297 | 60.217 | 45.651 | 38.293 | 1.00 | 57.93 |
| ATOM | 2794 | CD1 | PHE A 297 | 60.028 | 46.964 | 37.884 | 1.00 | 57.66 |
| ATOM | 2795 | CD2 | PHE A 297 | 60.459 | 44.673 | 37.334 | 1.00 | 59.49 |
| ATOM | 2796 | CE1 | PHE A 297 | 60.072 | 47.299 | 36.539 | 1.00 | 59.28 |
| ATOM | 2797 | CE2 | PHE A 297 | 60.503 | 44.997 | 35.990 | 1.00 | 59.71 |
| ATOM | 2798 | CZ | PHE A 297 | 60.309 | 46.315 | 35.590 | 1.00 | 59.93 |
| ATOM | 2799 | C | PHE A 297 | 58.090 | 43.837 | 39.408 | 1.00 | 54.31 |
| ATOM | 2800 | O | PHE A 297 | 57.245 | 43.990 | 38.530 | 1.00 | 54.87 |
| ATOM | 2801 | N | PHE A 298 | 58.542 | 42.643 | 39.776 | 1.00 | 55.31 |
| ATOM | 2803 | CA | PHE A 298 | 58.058 | 41.420 | 39.149 | 1.00 | 55.92 |
| ATOM | 2804 | CB | PHE A 298 | 58.793 | 40.199 | 39.709 | 1.00 | 52.95 |
| ATOM | 2805 | CG | PHE A 298 | 60.118 | 39.943 | 39.057 | 1.00 | 49.79 |
| ATOM | 2806 | CD1 | PHE A 298 | 61.094 | 40.934 | 39.019 | 1.00 | 46.14 |
| ATOM | 2807 | CD2 | PHE A 298 | 60.384 | 38.716 | 38.463 | 1.00 | 47.97 |
| ATOM | 2808 | CE1 | PHE A 298 | 62.312 | 40.709 | 38.400 | 1.00 | 44.36 |
| ATOM | 2809 | CE2 | PHE A 298 | 61.600 | 38.482 | 37.842 | 1.00 | 46.94 |
| ATOM | 2810 | CZ | PHE A 298 | 62.567 | 39.482 | 37.810 | 1.00 | 45.78 |
| ATOM | 2811 | C | PHE A 298 | 56.556 | 41.274 | 39.364 | 1.00 | 58.12 |
| ATOM | 2812 | O | PHE A 298 | 55.904 | 40.453 | 38.716 | 1.00 | 58.39 |
| ATOM | 2813 | N | GLY A 299 | 56.019 | 42.067 | 40.287 | 1.00 | 60.34 |
| ATOM | 2815 | CA | GLY A 299 | 54.599 | 42.042 | 40.576 | 1.00 | 62.61 |
| ATOM | 2816 | C | GLY A 299 | 53.777 | 42.541 | 39.404 | 1.00 | 64.03 |
| ATOM | 2817 | O | GLY A 299 | 52.622 | 42.156 | 39.236 | 1.00 | 64.07 |
| ATOM | 2818 | N | THR A 300 | 54.377 | 43.379 | 38.571 | 1.00 | 65.39 |
| ATOM | 2820 | CA | THR A 300 | 53.672 | 43.904 | 37.416 | 1.00 | 67.18 |
| ATOM | 2821 | CB | THR A 300 | 54.532 | 44.935 | 36.658 | 1.00 | 66.57 |
| ATOM | 2822 | OG1 | THR A 300 | 55.806 | 44.361 | 36.349 | 1.00 | 67.61 |
| ATOM | 2824 | CG2 | THR A 300 | 54.736 | 46.181 | 37.503 | 1.00 | 67.44 |
| ATOM | 2825 | C | THR A 300 | 53.258 | 42.785 | 36.460 | 1.00 | 69.21 |
| ATOM | 2826 | O | THR A 300 | 52.234 | 42.896 | 35.777 | 1.00 | 72.16 |
| ATOM | 2827 | N | PHE A 301 | 54.055 | 41.774 | 36.384 | 1.00 | 69.34 |
| ATOM | 2829 | CA | PHE A 301 | 53.704 | 40.675 | 35.483 | 1.00 | 69.26 |
| ATOM | 2830 | CB | PHE A 301 | 54.608 | 40.680 | 34.241 | 1.00 | 66.47 |
| ATOM | 2831 | CG | PHE A 301 | 56.070 | 40.882 | 34.532 | 1.00 | 64.06 |

Page 6-A-67

| | | | | | | | | |
|---|---|---|---|---|---|---|---|---|
| ATOM | 2832 | CD1 | PHE | A | 301 | 56.629 | 42.154 | 34.478 | 1.00 62.60 |
| ATOM | 2833 | CD2 | PHE | A | 301 | 56.895 | 39.806 | 34.838 | 1.00 63.14 |
| ATOM | 2834 | CE1 | PHE | A | 301 | 57.983 | 42.354 | 34.716 | 1.00 61.30 |
| ATOM | 2835 | CE2 | PHE | A | 301 | 58.251 | 39.995 | 35.077 | 1.00 61.28 |
| ATOM | 2836 | CZ | PHE | A | 301 | 58.795 | 41.274 | 35.016 | 1.00 61.18 |
| ATOM | 2837 | C | PHE | A | 301 | 53.635 | 39.268 | 36.062 | 1.00 71.49 |
| ATOM | 2838 | O | PHE | A | 301 | 53.032 | 38.380 | 35.458 | 1.00 71.98 |
| ATOM | 2839 | N | LEU | A | 302 | 54.199 | 39.072 | 37.250 | 1.00 74.67 |
| ATOM | 2841 | CA | LEU | A | 302 | 54.198 | 37.748 | 37.866 | 1.00 77.56 |
| ATOM | 2842 | CB | LEU | A | 302 | 55.573 | 37.098 | 37.698 | 1.00 75.96 |
| ATOM | 2843 | CG | LEU | A | 302 | 55.833 | 36.472 | 36.337 | 1.00 75.33 |
| ATOM | 2844 | CD1 | LEU | A | 302 | 57.217 | 35.860 | 36.332 | 1.00 75.78 |
| ATOM | 2845 | CD2 | LEU | A | 302 | 54.767 | 35.425 | 36.070 | 1.00 74.63 |
| ATOM | 2846 | C | LEU | A | 302 | 53.782 | 37.667 | 39.338 | 1.00 80.50 |
| ATOM | 2847 | O | LEU | A | 302 | 54.567 | 37.228 | 40.173 | 1.00 81.63 |
| ATOM | 2848 | N | PRO | A | 303 | 52.551 | 38.075 | 39.678 | 1.00 82.47 |
| ATOM | 2849 | CD | PRO | A | 303 | 51.687 | 39.012 | 38.927 | 1.00 83.87 |
| ATOM | 2850 | CA | PRO | A | 303 | 52.127 | 38.002 | 41.087 | 1.00 82.85 |
| ATOM | 2851 | CB | PRO | A | 303 | 51.725 | 39.440 | 41.359 | 1.00 83.29 |
| ATOM | 2852 | CG | PRO | A | 303 | 50.963 | 39.803 | 40.046 | 1.00 84.24 |
| ATOM | 2853 | C | PRO | A | 303 | 50.924 | 37.070 | 41.346 | 1.00 82.81 |
| ATOM | 2854 | O | PRO | A | 303 | 49.809 | 37.403 | 40.953 | 1.00 84.47 |
| ATOM | 2855 | N | GLU | A | 304 | 51.087 | 35.893 | 41.943 | 1.00 81.68 |
| ATOM | 2857 | CA | GLU | A | 304 | 52.308 | 35.254 | 42.438 | 1.00 80.61 |
| ATOM | 2858 | CB | GLU | A | 304 | 52.767 | 34.203 | 41.437 | 1.00 83.61 |
| ATOM | 2859 | CG | GLU | A | 304 | 51.698 | 33.132 | 41.207 | 1.00 86.52 |
| ATOM | 2860 | CD | GLU | A | 304 | 51.179 | 32.502 | 42.499 | 1.00 88.36 |
| ATOM | 2861 | OE1 | GLU | A | 304 | 50.103 | 32.923 | 42.977 | 1.00 89.84 |
| ATOM | 2862 | OE2 | GLU | A | 304 | 51.847 | 31.594 | 43.036 | 1.00 89.41 |
| ATOM | 2863 | C | GLU | A | 304 | 53.501 | 35.887 | 43.175 | 1.00 78.52 |
| ATOM | 2864 | O | GLU | A | 304 | 53.383 | 36.142 | 44.361 | 1.00 78.12 |
| ATOM | 2865 | N | VAL | A | 305 | 54.817 | 36.106 | 42.616 | 1.00 76.19 |
| ATOM | 2867 | CA | VAL | A | 305 | 55.955 | 36.809 | 43.226 | 1.00 74.85 |
| ATOM | 2868 | CB | VAL | A | 305 | 56.904 | 37.447 | 42.170 | 1.00 74.41 |

| | | | | | | | | |
|---|---|---|---|---|---|---|---|---|
| ATOM | 2869 | CG1 | VAL A 305 | 57.405 | 36.392 | 41.202 | 1.00 | 74.39 |
| ATOM | 2870 | CG2 | VAL A 305 | 56.218 | 38.578 | 41.433 | 1.00 | 75.20 |
| ATOM | 2871 | C | VAL A 305 | 55.622 | 37.833 | 44.316 | 1.00 | 74.68 |
| ATOM | 2872 | O | VAL A 305 | 56.110 | 37.711 | 45.438 | 1.00 | 75.57 |
| ATOM | 2873 | N | ALA A 306 | 54.746 | 38.790 | 44.011 | 1.00 | 73.53 |
| ATOM | 2875 | CA | ALA A 306 | 54.357 | 39.823 | 44.975 | 1.00 | 71.77 |
| ATOM | 2876 | CB | ALA A 306 | 53.893 | 41.068 | 44.248 | 1.00 | 71.20 |
| ATOM | 2877 | C | ALA A 306 | 53.273 | 39.348 | 45.935 | 1.00 | 71.50 |
| ATOM | 2878 | O | ALA A 306 | 53.087 | 39.924 | 47.005 | 1.00 | 70.71 |
| ATOM | 2879 | N | LYS A 307 | 52.563 | 38.300 | 45.529 | 1.00 | 71.78 |
| ATOM | 2881 | CA | LYS A 307 | 51.474 | 37.697 | 46.300 | 1.00 | 71.82 |
| ATOM | 2882 | CB | LYS A 307 | 50.508 | 37.010 | 45.324 | 1.00 | 72.68 |
| ATOM | 2883 | CG | LYS A 307 | 49.332 | 36.270 | 45.944 | 1.00 | 75.23 |
| ATOM | 2884 | CD | LYS A 307 | 48.473 | 35.638 | 44.848 | 1.00 | 76.97 |
| ATOM | 2885 | CE | LYS A 307 | 47.247 | 34.935 | 45.413 | 1.00 | 77.90 |
| ATOM | 2886 | NZ | LYS A 307 | 46.352 | 34.434 | 44.331 | 1.00 | 77.64 |
| ATOM | 2890 | C | LYS A 307 | 51.946 | 36.698 | 47.374 | 1.00 | 71.04 |
| ATOM | 2891 | O | LYS A 307 | 51.393 | 36.651 | 48.473 | 1.00 | 72.05 |
| ATOM | 2892 | N | LYS A 308 | 52.958 | 35.898 | 47.050 | 1.00 | 69.00 |
| ATOM | 2894 | CA | LYS A 308 | 53.480 | 34.903 | 47.979 | 1.00 | 66.59 |
| ATOM | 2895 | CB | LYS A 308 | 53.891 | 33.636 | 47.219 | 1.00 | 70.09 |
| ATOM | 2896 | CG | LYS A 308 | 53.887 | 32.346 | 48.046 | 1.00 | 75.24 |
| ATOM | 2897 | CD | LYS A 308 | 54.920 | 32.351 | 49.172 | 1.00 | 79.31 |
| ATOM | 2898 | CE | LYS A 308 | 54.842 | 31.091 | 50.027 | 1.00 | 81.43 |
| ATOM | 2899 | NZ | LYS A 308 | 55.760 | 31.141 | 51.206 | 1.00 | 82.05 |
| ATOM | 2903 | C | LYS A 308 | 54.680 | 35.467 | 48.722 | 1.00 | 64.17 |
| ATOM | 2904 | O | LYS A 308 | 54.840 | 35.240 | 49.921 | 1.00 | 65.45 |
| ATOM | 2905 | N | PHE A 309 | 55.526 | 36.200 | 48.007 | 1.00 | 60.99 |
| ATOM | 2907 | CA | PHE A 309 | 56.725 | 36.784 | 48.597 | 1.00 | 57.85 |
| ATOM | 2908 | CB | PHE A 309 | 57.974 | 36.274 | 47.853 | 1.00 | 53.07 |
| ATOM | 2909 | CG | PHE A 309 | 58.085 | 34.762 | 47.808 | 1.00 | 45.45 |
| ATOM | 2910 | CD1 | PHE A 309 | 58.551 | 34.050 | 48.906 | 1.00 | 42.52 |
| ATOM | 2911 | CD2 | PHE A 309 | 57.689 | 34.052 | 46.679 | 1.00 | 43.68 |
| ATOM | 2912 | CE1 | PHE A 309 | 58.619 | 32.655 | 48.883 | 1.00 | 38.70 |

Page 6-A-69

| ATOM | 2913 | CE2 | PHE | A | 309 | 57.754 | 32.655 | 46.647 | 1.00 | 42.05 |
| --- | --- | --- | --- | --- | --- | --- | --- | --- | --- | --- |
| ATOM | 2914 | CZ | PHE | A | 309 | 58.219 | 31.959 | 47.753 | 1.00 | 39.93 |
| ATOM | 2915 | C | PHE | A | 309 | 56.616 | 38.312 | 48.553 | 1.00 | 58.92 |
| ATOM | 2916 | O | PHE | A | 309 | 57.266 | 38.978 | 47.743 | 1.00 | 58.89 |
| ATOM | 2917 | N | PRO | A | 310 | 55.822 | 38.885 | 49.472 | 1.00 | 60.26 |
| ATOM | 2918 | CD | PRO | A | 310 | 55.173 | 38.142 | 50.569 | 1.00 | 61.34 |
| ATOM | 2919 | CA | PRO | A | 310 | 55.560 | 40.320 | 49.613 | 1.00 | 61.10 |
| ATOM | 2920 | CB | PRO | A | 310 | 54.522 | 40.358 | 50.736 | 1.00 | 62.64 |
| ATOM | 2921 | CG | PRO | A | 310 | 54.934 | 39.217 | 51.598 | 1.00 | 61.52 |
| ATOM | 2922 | C | PRO | A | 310 | 56.737 | 41.239 | 49.927 | 1.00 | 61.05 |
| ATOM | 2923 | O | PRO | A | 310 | 57.307 | 41.187 | 51.016 | 1.00 | 61.70 |
| ATOM | 2924 | N | ASN | A | 311 | 57.044 | 42.121 | 48.979 | 1.00 | 62.21 |
| ATOM | 2926 | CA | ASN | A | 311 | 58.116 | 43.111 | 49.111 | 1.00 | 63.11 |
| ATOM | 2927 | CB | ASN | A | 311 | 57.667 | 44.247 | 50.037 | 1.00 | 66.59 |
| ATOM | 2928 | CG | ASN | A | 311 | 58.589 | 45.448 | 49.976 | 1.00 | 69.63 |
| ATOM | 2929 | OD1 | ASN | A | 311 | 58.596 | 46.186 | 48.991 | 1.00 | 71.72 |
| ATOM | 2930 | ND2 | ASN | A | 311 | 59.373 | 45.651 | 51.027 | 1.00 | 71.51 |
| ATOM | 2933 | C | ASN | A | 311 | 59.458 | 42.547 | 49.583 | 1.00 | 61.81 |
| ATOM | 2934 | O | ASN | A | 311 | 59.855 | 42.737 | 50.738 | 1.00 | 63.25 |
| ATOM | 2935 | N | MET | A | 312 | 60.155 | 41.870 | 48.673 | 1.00 | 58.63 |
| ATOM | 2937 | CA | MET | A | 312 | 61.459 | 41.266 | 48.950 | 1.00 | 53.64 |
| ATOM | 2938 | CB | MET | A | 312 | 61.316 | 39.768 | 49.269 | 1.00 | 53.53 |
| ATOM | 2939 | CG | MET | A | 312 | 60.599 | 39.405 | 50.570 | 1.00 | 52.28 |
| ATOM | 2940 | SD | MET | A | 312 | 60.259 | 37.617 | 50.633 | 1.00 | 52.18 |
| ATOM | 2941 | CE | MET | A | 312 | 58.896 | 37.534 | 51.788 | 1.00 | 54.70 |
| ATOM | 2942 | C | MET | A | 312 | 62.320 | 41.411 | 47.699 | 1.00 | 49.72 |
| ATOM | 2943 | O | MET | A | 312 | 61.801 | 41.656 | 46.605 | 1.00 | 49.26 |
| ATOM | 2944 | N | LYS | A | 313 | 63.630 | 41.275 | 47.865 | 1.00 | 44.80 |
| ATOM | 2946 | CA | LYS | A | 313 | 64.549 | 41.363 | 46.741 | 1.00 | 41.81 |
| ATOM | 2947 | CB | LYS | A | 313 | 65.952 | 41.707 | 47.230 | 1.00 | 42.38 |
| ATOM | 2948 | CG | LYS | A | 313 | 66.050 | 43.081 | 47.846 | 1.00 | 47.04 |
| ATOM | 2949 | CD | LYS | A | 313 | 65.762 | 44.159 | 46.818 | 1.00 | 49.35 |
| ATOM | 2950 | CE | LYS | A | 313 | 65.599 | 45.515 | 47.481 | 1.00 | 53.10 |
| ATOM | 2951 | NZ | LYS | A | 313 | 66.805 | 45.897 | 48.268 | 1.00 | 56.75 |

| | | | | | | | | |
|---|---|---|---|---|---|---|---|---|
| ATOM | 2955 | C | LYS | A | 313 | 64.562 | 40.018 | 46.026 | 1.00 39.61 |
| ATOM | 2956 | O | LYS | A | 313 | 64.133 | 39.013 | 46.592 | 1.00 38.93 |
| ATOM | 2957 | N | ILE | A | 314 | 65.040 | 40.005 | 44.786 | 1.00 37.30 |
| ATOM | 2959 | CA | ILE | A | 314 | 65.115 | 38.785 | 43.995 | 1.00 34.17 |
| ATOM | 2960 | CB | ILE | A | 314 | 64.224 | 38.865 | 42.716 | 1.00 33.93 |
| ATOM | 2961 | CG2 | ILE | A | 314 | 64.607 | 37.783 | 41.708 | 1.00 32.86 |
| ATOM | 2962 | CG1 | ILE | A | 314 | 62.745 | 38.728 | 43.093 | 1.00 33.03 |
| ATOM | 2963 | CD1 | ILE | A | 314 | 61.824 | 38.459 | 41.920 | 1.00 32.90 |
| ATOM | 2964 | C | ILE | A | 314 | 66.567 | 38.565 | 43.604 | 1.00 33.46 |
| ATOM | 2965 | O | ILE | A | 314 | 67.272 | 39.512 | 43.271 | 1.00 32.77 |
| ATOM | 2966 | N | GLN | A | 315 | 67.024 | 37.321 | 43.698 | 1.00 32.44 |
| ATOM | 2968 | CA | GLN | A | 315 | 68.391 | 36.975 | 43.336 | 1.00 32.66 |
| ATOM | 2969 | CB | GLN | A | 315 | 69.118 | 36.366 | 44.529 | 1.00 34.35 |
| ATOM | 2970 | CG | GLN | A | 315 | 70.624 | 36.305 | 44.376 | 1.00 35.08 |
| ATOM | 2971 | CD | GLN | A | 315 | 71.317 | 35.839 | 45.639 | 1.00 33.95 |
| ATOM | 2972 | OE1 | GLN | A | 315 | 71.579 | 36.620 | 46.548 | 1.00 34.44 |
| ATOM | 2973 | NE2 | GLN | A | 315 | 71.607 | 34.554 | 45.701 | 1.00 37.53 |
| ATOM | 2976 | C | GLN | A | 315 | 68.307 | 35.964 | 42.207 | 1.00 33.04 |
| ATOM | 2977 | O | GLN | A | 315 | 67.520 | 35.024 | 42.271 | 1.00 35.05 |
| ATOM | 2978 | N | ILE | A | 316 | 69.116 | 36.155 | 41.175 | 1.00 34.76 |
| ATOM | 2980 | CA | ILE | A | 316 | 69.106 | 35.268 | 40.018 | 1.00 33.81 |
| ATOM | 2981 | CB | ILE | A | 316 | 68.711 | 36.067 | 38.750 | 1.00 35.72 |
| ATOM | 2982 | CG2 | ILE | A | 316 | 68.944 | 35.247 | 37.498 | 1.00 37.16 |
| ATOM | 2983 | CG1 | ILE | A | 316 | 67.249 | 36.518 | 38.864 | 1.00 36.98 |
| ATOM | 2984 | CD1 | ILE | A | 316 | 66.695 | 37.179 | 37.633 | 1.00 38.34 |
| ATOM | 2985 | C | ILE | A | 316 | 70.445 | 34.548 | 39.823 | 1.00 32.92 |
| ATOM | 2986 | O | ILE | A | 316 | 71.513 | 35.160 | 39.900 | 1.00 33.03 |
| ATOM | 2987 | N | HIS | A | 317 | 70.386 | 33.238 | 39.609 | 1.00 33.55 |
| ATOM | 2989 | CA | HIS | A | 317 | 71.586 | 32.428 | 39.409 | 1.00 32.00 |
| ATOM | 2990 | CB | HIS | A | 317 | 71.532 | 31.162 | 40.264 | 1.00 32.50 |
| ATOM | 2991 | CG | HIS | A | 317 | 71.659 | 31.411 | 41.735 | 1.00 32.14 |
| ATOM | 2992 | CD2 | HIS | A | 317 | 71.889 | 32.548 | 42.435 | 1.00 31.63 |
| ATOM | 2993 | ND1 | HIS | A | 317 | 71.572 | 30.398 | 42.666 | 1.00 32.81 |
| ATOM | 2995 | CE1 | HIS | A | 317 | 71.746 | 30.899 | 43.875 | 1.00 33.94 |

Page 6-A-71

| ATOM | 2996 | NE2 | HIS | A | 317 | 71.941 | 32.201 | 43.761 | 1.00 | 32.58 |
| --- | --- | --- | --- | --- | --- | --- | --- | --- | --- | --- |
| ATOM | 2998 | C | HIS | A | 317 | 71.720 | 32.014 | 37.953 | 1.00 | 33.04 |
| ATOM | 2999 | O | HIS | A | 317 | 70.844 | 31.335 | 37.416 | 1.00 | 33.39 |
| ATOM | 3000 | N | VAL | A | 318 | 72.842 | 32.377 | 37.344 | 1.00 | 33.42 |
| ATOM | 3002 | CA | VAL | A | 318 | 73.129 | 32.059 | 35.952 | 1.00 | 31.61 |
| ATOM | 3003 | CB | VAL | A | 318 | 73.535 | 33.338 | 35.193 | 1.00 | 29.43 |
| ATOM | 3004 | CG1 | VAL | A | 318 | 73.993 | 33.003 | 33.789 | 1.00 | 30.90 |
| ATOM | 3005 | CG2 | VAL | A | 318 | 72.376 | 34.311 | 35.161 | 1.00 | 27.51 |
| ATOM | 3006 | C | VAL | A | 318 | 74.273 | 31.043 | 35.861 | 1.00 | 32.81 |
| ATOM | 3007 | O | VAL | A | 318 | 75.392 | 31.325 | 36.296 | 1.00 | 33.30 |
| ATOM | 3008 | N | SER | A | 319 | 73.990 | 29.858 | 35.329 | 1.00 | 32.14 |
| ATOM | 3010 | CA | SER | A | 319 | 75.021 | 28.836 | 35.175 | 1.00 | 32.12 |
| ATOM | 3011 | CB | SER | A | 319 | 74.919 | 27.778 | 36.271 | 1.00 | 28.41 |
| ATOM | 3012 | OG | SER | A | 319 | 73.723 | 27.039 | 36.158 | 1.00 | 29.90 |
| ATOM | 3014 | C | SER | A | 319 | 74.900 | 28.170 | 33.815 | 1.00 | 33.52 |
| ATOM | 3015 | O | SER | A | 319 | 73.834 | 28.174 | 33.210 | 1.00 | 37.50 |
| ATOM | 3016 | N | ALA | A | 320 | 76.005 | 27.632 | 33.319 | 1.00 | 35.33 |
| ATOM | 3018 | CA | ALA | A | 320 | 76.009 | 26.958 | 32.031 | 1.00 | 35.02 |
| ATOM | 3019 | CB | ALA | A | 320 | 77.417 | 26.914 | 31.461 | 1.00 | 36.41 |
| ATOM | 3020 | C | ALA | A | 320 | 75.466 | 25.547 | 32.210 | 1.00 | 36.23 |
| ATOM | 3021 | O | ALA | A | 320 | 75.955 | 24.786 | 33.047 | 1.00 | 35.14 |
| ATOM | 3022 | N | SER | A | 321 | 74.459 | 25.204 | 31.415 | 1.00 | 38.15 |
| ATOM | 3024 | CA | SER | A | 321 | 73.835 | 23.891 | 31.478 | 1.00 | 38.99 |
| ATOM | 3025 | CB | SER | A | 321 | 72.472 | 23.935 | 30.786 | 1.00 | 38.78 |
| ATOM | 3026 | OG | SER | A | 321 | 72.418 | 24.984 | 29.834 | 1.00 | 40.20 |
| ATOM | 3028 | C | SER | A | 321 | 74.724 | 22.824 | 30.848 | 1.00 | 40.78 |
| ATOM | 3029 | O | SER | A | 321 | 74.942 | 21.760 | 31.430 | 1.00 | 44.24 |
| ATOM | 3030 | N | THR | A | 322 | 75.249 | 23.126 | 29.666 | 1.00 | 39.66 |
| ATOM | 3032 | CA | THR | A | 322 | 76.119 | 22.214 | 28.939 | 1.00 | 36.30 |
| ATOM | 3033 | CB | THR | A | 322 | 75.355 | 21.553 | 27.750 | 1.00 | 39.80 |
| ATOM | 3034 | OG1 | THR | A | 322 | 74.613 | 22.548 | 27.027 | 1.00 | 40.24 |
| ATOM | 3036 | CG2 | THR | A | 322 | 74.398 | 20.473 | 28.253 | 1.00 | 41.99 |
| ATOM | 3037 | C | THR | A | 322 | 77.332 | 22.985 | 28.416 | 1.00 | 33.41 |
| ATOM | 3038 | O | THR | A | 322 | 77.372 | 24.214 | 28.487 | 1.00 | 31.80 |

| | | | | | | | | |
|---|---|---|---|---|---|---|---|---|
| ATOM | 3039 | N | PRO | A | 323 | 78.378 | 22.272 | 27.966 | 1.00 32.97 |
| ATOM | 3040 | CD | PRO | A | 323 | 78.606 | 20.826 | 28.133 | 1.00 31.42 |
| ATOM | 3041 | CA | PRO | A | 323 | 79.581 | 22.925 | 27.439 | 1.00 31.79 |
| ATOM | 3042 | CB | PRO | A | 323 | 80.471 | 21.739 | 27.089 | 1.00 31.21 |
| ATOM | 3043 | CG | PRO | A | 323 | 80.099 | 20.740 | 28.128 | 1.00 31.27 |
| ATOM | 3044 | C | PRO | A | 323 | 79.279 | 23.757 | 26.191 | 1.00 33.72 |
| ATOM | 3045 | O | PRO | A | 323 | 78.727 | 23.237 | 25.218 | 1.00 35.68 |
| ATOM | 3046 | N | PRO | A | 324 | 79.650 | 25.053 | 26.196 | 1.00 34.41 |
| ATOM | 3047 | CD | PRO | A | 324 | 80.303 | 25.799 | 27.286 | 1.00 34.36 |
| ATOM | 3048 | CA | PRO | A | 324 | 79.407 | 25.933 | 25.050 | 1.00 36.18 |
| ATOM | 3049 | CB | PRO | A | 324 | 79.863 | 27.301 | 25.567 | 1.00 34.56 |
| ATOM | 3050 | CG | PRO | A | 324 | 80.913 | 26.963 | 26.551 | 1.00 34.54 |
| ATOM | 3051 | C | PRO | A | 324 | 80.186 | 25.511 | 23.811 | 1.00 39.38 |
| ATOM | 3052 | O | PRO | A | 324 | 81.397 | 25.278 | 23.871 | 1.00 43.04 |
| ATOM | 3053 | N | HIS | A | 325 | 79.468 | 25.364 | 22.704 | 1.00 39.27 |
| ATOM | 3055 | CA | HIS | A | 325 | 80.064 | 24.973 | 21.434 | 1.00 39.40 |
| ATOM | 3056 | CB | HIS | A | 325 | 79.045 | 24.236 | 20.562 | 1.00 44.72 |
| ATOM | 3057 | CG | HIS | A | 325 | 78.817 | 22.813 | 20.955 | 1.00 49.32 |
| ATOM | 3058 | CD2 | HIS | A | 325 | 79.471 | 22.015 | 21.831 | 1.00 51.91 |
| ATOM | 3059 | ND1 | HIS | A | 325 | 77.817 | 22.041 | 20.405 | 1.00 52.21 |
| ATOM | 3061 | CE1 | HIS | A | 325 | 77.864 | 20.827 | 20.924 | 1.00 53.83 |
| ATOM | 3062 | NE2 | HIS | A | 325 | 78.859 | 20.785 | 21.793 | 1.00 54.25 |
| ATOM | 3064 | C | HIS | A | 325 | 80.537 | 26.183 | 20.658 | 1.00 37.89 |
| ATOM | 3065 | O | HIS | A | 325 | 80.011 | 27.285 | 20.825 | 1.00 39.24 |
| ATOM | 3066 | N | LEU | A | 326 | 81.514 | 25.958 | 19.788 | 1.00 36.12 |
| ATOM | 3068 | CA | LEU | A | 326 | 82.056 | 26.993 | 18.928 | 1.00 34.45 |
| ATOM | 3069 | CB | LEU | A | 326 | 83.370 | 27.535 | 19.487 | 1.00 34.16 |
| ATOM | 3070 | CG | LEU | A | 326 | 83.906 | 28.758 | 18.745 | 1.00 34.49 |
| ATOM | 3071 | CD1 | LEU | A | 326 | 82.912 | 29.878 | 18.854 | 1.00 36.18 |
| ATOM | 3072 | CD2 | LEU | A | 326 | 85.220 | 29.194 | 19.321 | 1.00 38.20 |
| ATOM | 3073 | C | LEU | A | 326 | 82.285 | 26.329 | 17.569 | 1.00 34.87 |
| ATOM | 3074 | O | LEU | A | 326 | 82.981 | 25.311 | 17.469 | 1.00 35.31 |
| ATOM | 3075 | N | SER | A | 327 | 81.639 | 26.863 | 16.542 | 1.00 32.90 |
| ATOM | 3077 | CA | SER | A | 327 | 81.755 | 26.323 | 15.202 | 1.00 32.76 |

Page 6-A-73

| ATOM | 3078 | CB | SER | A | 327 | 80.359 | 26.173 | 14.591 | 1.00 | 34.44 |
| ATOM | 3079 | OG | SER | A | 327 | 80.390 | 25.407 | 13.394 | 1.00 | 41.05 |
| ATOM | 3081 | C | SER | A | 327 | 82.607 | 27.247 | 14.343 | 1.00 | 30.57 |
| ATOM | 3082 | O | SER | A | 327 | 82.391 | 28.458 | 14.329 | 1.00 | 31.41 |
| ATOM | 3083 | N | VAL | A | 328 | 83.601 | 26.691 | 13.658 | 1.00 | 29.84 |
| ATOM | 3085 | CA | VAL | A | 328 | 84.452 | 27.502 | 12.795 | 1.00 | 28.60 |
| ATOM | 3086 | CB | VAL | A | 328 | 85.951 | 27.275 | 13.056 | 1.00 | 25.61 |
| ATOM | 3087 | CG1 | VAL | A | 328 | 86.733 | 28.389 | 12.423 | 1.00 | 24.98 |
| ATOM | 3088 | CG2 | VAL | A | 328 | 86.245 | 27.218 | 14.544 | 1.00 | 23.23 |
| ATOM | 3089 | C | VAL | A | 328 | 84.159 | 27.174 | 11.336 | 1.00 | 30.19 |
| ATOM | 3090 | O | VAL | A | 328 | 84.221 | 26.015 | 10.928 | 1.00 | 29.56 |
| ATOM | 3091 | N | GLN | A | 329 | 83.791 | 28.194 | 10.569 | 1.00 | 32.32 |
| ATOM | 3093 | CA | GLN | A | 329 | 83.479 | 28.038 | 9.150 | 1.00 | 34.28 |
| ATOM | 3094 | CB | GLN | A | 329 | 81.956 | 27.972 | 8.939 | 1.00 | 39.33 |
| ATOM | 3095 | CG | GLN | A | 329 | 81.222 | 26.924 | 9.774 | 1.00 | 48.55 |
| ATOM | 3096 | CD | GLN | A | 329 | 80.246 | 27.532 | 10.785 | 1.00 | 53.31 |
| ATOM | 3097 | OE1 | GLN | A | 329 | 79.321 | 26.860 | 11.245 | 1.00 | 57.70 |
| ATOM | 3098 | NE2 | GLN | A | 329 | 80.456 | 28.796 | 11.142 | 1.00 | 53.89 |
| ATOM | 3101 | C | GLN | A | 329 | 84.050 | 29.259 | 8.416 | 1.00 | 32.74 |
| ATOM | 3102 | O | GLN | A | 329 | 84.337 | 30.279 | 9.048 | 1.00 | 34.32 |
| ATOM | 3103 | N | PRO | A | 330 | 84.176 | 29.193 | 7.073 | 1.00 | 30.85 |
| ATOM | 3104 | CD | PRO | A | 330 | 83.896 | 28.019 | 6.226 | 1.00 | 27.63 |
| ATOM | 3105 | CA | PRO | A | 330 | 84.711 | 30.301 | 6.265 | 1.00 | 30.72 |
| ATOM | 3106 | CB | PRO | A | 330 | 84.597 | 29.765 | 4.842 | 1.00 | 27.09 |
| ATOM | 3107 | CG | PRO | A | 330 | 84.754 | 28.286 | 5.026 | 1.00 | 27.10 |
| ATOM | 3108 | C | PRO | A | 330 | 83.968 | 31.635 | 6.416 | 1.00 | 33.05 |
| ATOM | 3109 | O | PRO | A | 330 | 84.501 | 32.695 | 6.084 | 1.00 | 34.38 |
| ATOM | 3110 | N | THR | A | 331 | 82.733 | 31.575 | 6.904 | 1.00 | 36.91 |
| ATOM | 3112 | CA | THR | A | 331 | 81.918 | 32.767 | 7.106 | 1.00 | 39.55 |
| ATOM | 3113 | CB | THR | A | 331 | 80.414 | 32.414 | 7.065 | 1.00 | 41.23 |
| ATOM | 3114 | OG1 | THR | A | 331 | 80.179 | 31.221 | 7.826 | 1.00 | 42.58 |
| ATOM | 3116 | CG2 | THR | A | 331 | 79.959 | 32.180 | 5.630 | 1.00 | 42.18 |
| ATOM | 3117 | C | THR | A | 331 | 82.244 | 33.469 | 8.425 | 1.00 | 41.21 |
| ATOM | 3118 | O | THR | A | 331 | 82.114 | 34.691 | 8.535 | 1.00 | 44.22 |

Page 6-A-74

| | | | | | | | | |
|---|---|---|---|---|---|---|---|---|
| ATOM | 3119 | N | GLY | A | 332 | 82.671 | 32.691 | 9.418 | 1.00 39.90 |
| ATOM | 3121 | CA | GLY | A | 332 | 83.005 | 33.240 | 10.720 | 1.00 36.14 |
| ATOM | 3122 | C | GLY | A | 332 | 82.788 | 32.188 | 11.788 | 1.00 36.29 |
| ATOM | 3123 | O | GLY | A | 332 | 82.399 | 31.058 | 11.472 | 1.00 36.21 |
| ATOM | 3124 | N | LEU | A | 333 | 83.048 | 32.542 | 13.044 | 1.00 35.70 |
| ATOM | 3126 | CA | LEU | A | 333 | 82.875 | 31.606 | 14.153 | 1.00 34.12 |
| ATOM | 3127 | CB | LEU | A | 333 | 84.037 | 31.704 | 15.157 | 1.00 31.15 |
| ATOM | 3128 | CG | LEU | A | 333 | 85.438 | 32.183 | 14.766 | 1.00 30.79 |
| ATOM | 3129 | CD1 | LEU | A | 333 | 86.402 | 31.841 | 15.886 | 1.00 29.93 |
| ATOM | 3130 | CD2 | LEU | A | 333 | 85.908 | 31.539 | 13.492 | 1.00 32.11 |
| ATOM | 3131 | C | LEU | A | 333 | 81.570 | 31.889 | 14.889 | 1.00 34.02 |
| ATOM | 3132 | O | LEU | A | 333 | 81.283 | 33.037 | 15.233 | 1.00 35.28 |
| ATOM | 3133 | N | THR | A | 334 | 80.777 | 30.850 | 15.123 | 1.00 32.89 |
| ATOM | 3135 | CA | THR | A | 334 | 79.521 | 30.997 | 15.842 | 1.00 30.97 |
| ATOM | 3136 | CB | THR | A | 334 | 78.344 | 30.435 | 15.037 | 1.00 30.40 |
| ATOM | 3137 | OG1 | THR | A | 334 | 78.673 | 29.124 | 14.568 | 1.00 36.09 |
| ATOM | 3139 | CG2 | THR | A | 334 | 78.043 | 31.324 | 13.850 | 1.00 27.87 |
| ATOM | 3140 | C | THR | A | 334 | 79.649 | 30.274 | 17.184 | 1.00 30.59 |
| ATOM | 3141 | O | THR | A | 334 | 80.293 | 29.229 | 17.267 | 1.00 31.11 |
| ATOM | 3142 | N | PHE | A | 335 | 79.052 | 30.853 | 18.225 | 1.00 31.55 |
| ATOM | 3144 | CA | PHE | A | 335 | 79.095 | 30.334 | 19.598 | 1.00 30.95 |
| ATOM | 3145 | CB | PHE | A | 335 | 79.579 | 31.465 | 20.530 | 1.00 31.73 |
| ATOM | 3146 | CG | PHE | A | 335 | 80.138 | 31.001 | 21.853 | 1.00 32.43 |
| ATOM | 3147 | CD1 | PHE | A | 335 | 81.224 | 30.134 | 21.907 | 1.00 34.10 |
| ATOM | 3148 | CD2 | PHE | A | 335 | 79.611 | 31.483 | 23.044 | 1.00 33.32 |
| ATOM | 3149 | CE1 | PHE | A | 335 | 81.779 | 29.755 | 23.124 | 1.00 36.27 |
| ATOM | 3150 | CE2 | PHE | A | 335 | 80.156 | 31.113 | 24.267 | 1.00 36.93 |
| ATOM | 3151 | CZ | PHE | A | 335 | 81.243 | 30.248 | 24.308 | 1.00 36.83 |
| ATOM | 3152 | C | PHE | A | 335 | 77.674 | 29.910 | 19.975 | 1.00 29.88 |
| ATOM | 3153 | O | PHE | A | 335 | 76.722 | 30.616 | 19.666 | 1.00 29.27 |
| ATOM | 3154 | N | TYR | A | 336 | 77.533 | 28.779 | 20.658 | 1.00 30.87 |
| ATOM | 3156 | CA | TYR | A | 336 | 76.216 | 28.281 | 21.052 | 1.00 33.87 |
| ATOM | 3157 | CB | TYR | A | 336 | 75.936 | 26.953 | 20.345 | 1.00 35.86 |
| ATOM | 3158 | CG | TYR | A | 336 | 76.081 | 27.036 | 18.844 | 1.00 36.58 |

| | | | | | | | | |
|---|---|---|---|---|---|---|---|---|
| ATOM | 3159 | CD1 | TYR A 336 | 75.107 | 27.665 | 18.072 | 1.00 | 38.45 |
| ATOM | 3160 | CE1 | TYR A 336 | 75.245 | 27.791 | 16.700 | 1.00 | 38.32 |
| ATOM | 3161 | CD2 | TYR A 336 | 77.207 | 26.526 | 18.198 | 1.00 | 34.97 |
| ATOM | 3162 | CE2 | TYR A 336 | 77.357 | 26.647 | 16.819 | 1.00 | 36.42 |
| ATOM | 3163 | CZ | TYR A 336 | 76.369 | 27.285 | 16.078 | 1.00 | 37.51 |
| ATOM | 3164 | OH | TYR A 336 | 76.494 | 27.435 | 14.715 | 1.00 | 41.83 |
| ATOM | 3166 | C | TYR A 336 | 76.104 | 28.096 | 22.565 | 1.00 | 36.66 |
| ATOM | 3167 | O | TYR A 336 | 76.280 | 26.988 | 23.074 | 1.00 | 39.11 |
| ATOM | 3168 | N | PRO A 337 | 75.858 | 29.187 | 23.309 | 1.00 | 36.71 |
| ATOM | 3169 | CD | PRO A 337 | 75.890 | 30.605 | 22.904 | 1.00 | 36.11 |
| ATOM | 3170 | CA | PRO A 337 | 75.740 | 29.069 | 24.761 | 1.00 | 35.26 |
| ATOM | 3171 | CB | PRO A 337 | 76.156 | 30.449 | 25.234 | 1.00 | 35.76 |
| ATOM | 3172 | CG | PRO A 337 | 75.564 | 31.327 | 24.192 | 1.00 | 36.30 |
| ATOM | 3173 | C | PRO A 337 | 74.325 | 28.751 | 25.198 | 1.00 | 36.60 |
| ATOM | 3174 | O | PRO A 337 | 73.358 | 29.231 | 24.604 | 1.00 | 39.83 |
| ATOM | 3175 | N | ALA A 338 | 74.218 | 27.909 | 26.218 | 1.00 | 36.08 |
| ATOM | 3177 | CA | ALA A 338 | 72.944 | 27.512 | 26.802 | 1.00 | 35.56 |
| ATOM | 3178 | CB | ALA A 338 | 72.671 | 26.039 | 26.533 | 1.00 | 36.41 |
| ATOM | 3179 | C | ALA A 338 | 73.116 | 27.752 | 28.294 | 1.00 | 36.55 |
| ATOM | 3180 | O | ALA A 338 | 74.059 | 27.241 | 28.902 | 1.00 | 37.65 |
| ATOM | 3181 | N | VAL A 339 | 72.256 | 28.576 | 28.878 | 1.00 | 36.13 |
| ATOM | 3183 | CA | VAL A 339 | 72.360 | 28.872 | 30.295 | 1.00 | 34.95 |
| ATOM | 3184 | CB | VAL A 339 | 72.771 | 30.346 | 30.538 | 1.00 | 33.81 |
| ATOM | 3185 | CG1 | VAL A 339 | 74.046 | 30.667 | 29.776 | 1.00 | 36.08 |
| ATOM | 3186 | CG2 | VAL A 339 | 71.658 | 31.293 | 30.139 | 1.00 | 33.93 |
| ATOM | 3187 | C | VAL A 339 | 71.071 | 28.578 | 31.043 | 1.00 | 35.50 |
| ATOM | 3188 | O | VAL A 339 | 69.990 | 28.553 | 30.451 | 1.00 | 38.45 |
| ATOM | 3189 | N | ASP A 340 | 71.208 | 28.295 | 32.335 | 1.00 | 33.66 |
| ATOM | 3191 | CA | ASP A 340 | 70.078 | 28.029 | 33.213 | 1.00 | 31.12 |
| ATOM | 3192 | CB | ASP A 340 | 70.318 | 26.785 | 34.067 | 1.00 | 31.54 |
| ATOM | 3193 | CG | ASP A 340 | 69.813 | 25.520 | 33.411 | 1.00 | 33.33 |
| ATOM | 3194 | OD1 | ASP A 340 | 68.895 | 25.606 | 32.569 | 1.00 | 35.59 |
| ATOM | 3195 | OD2 | ASP A 340 | 70.324 | 24.432 | 33.742 | 1.00 | 35.60 |
| ATOM | 3196 | C | ASP A 340 | 70.003 | 29.235 | 34.108 | 1.00 | 29.12 |

Page 6-A-76

| ATOM | 3197 | O   | ASP | A | 340 | 70.968 | 29.555 | 34.794 | 1.00 | 29.84 |
| ---- | ---- | --- | --- | - | --- | ------ | ------ | ------ | ---- | ----- |
| ATOM | 3198 | N   | VAL | A | 341 | 68.890 | 29.948 | 34.040 | 1.00 | 28.41 |
| ATOM | 3200 | CA  | VAL | A | 341 | 68.687 | 31.133 | 34.846 | 1.00 | 28.82 |
| ATOM | 3201 | CB  | VAL | A | 341 | 68.249 | 32.316 | 33.969 | 1.00 | 29.73 |
| ATOM | 3202 | CG1 | VAL | A | 341 | 67.868 | 33.496 | 34.831 | 1.00 | 27.89 |
| ATOM | 3203 | CG2 | VAL | A | 341 | 69.364 | 32.703 | 33.017 | 1.00 | 28.62 |
| ATOM | 3204 | C   | VAL | A | 341 | 67.592 | 30.833 | 35.852 | 1.00 | 30.90 |
| ATOM | 3205 | O   | VAL | A | 341 | 66.456 | 30.596 | 35.459 | 1.00 | 34.21 |
| ATOM | 3206 | N   | GLN | A | 342 | 67.931 | 30.821 | 37.139 | 1.00 | 31.91 |
| ATOM | 3208 | CA  | GLN | A | 342 | 66.948 | 30.546 | 38.191 | 1.00 | 31.19 |
| ATOM | 3209 | CB  | GLN | A | 342 | 67.375 | 29.345 | 39.039 | 1.00 | 31.37 |
| ATOM | 3210 | CG  | GLN | A | 342 | 66.319 | 28.867 | 40.028 | 1.00 | 31.56 |
| ATOM | 3211 | CD  | GLN | A | 342 | 66.706 | 27.570 | 40.706 | 1.00 | 33.87 |
| ATOM | 3212 | OE1 | GLN | A | 342 | 67.841 | 27.111 | 40.590 | 1.00 | 37.83 |
| ATOM | 3213 | NE2 | GLN | A | 342 | 65.770 | 26.979 | 41.431 | 1.00 | 35.30 |
| ATOM | 3216 | C   | GLN | A | 342 | 66.752 | 31.761 | 39.088 | 1.00 | 31.20 |
| ATOM | 3217 | O   | GLN | A | 342 | 67.724 | 32.374 | 39.537 | 1.00 | 31.67 |
| ATOM | 3218 | N   | ALA | A | 343 | 65.494 | 32.114 | 39.327 | 1.00 | 30.96 |
| ATOM | 3220 | CA  | ALA | A | 343 | 65.169 | 33.254 | 40.169 | 1.00 | 28.72 |
| ATOM | 3221 | CB  | ALA | A | 343 | 64.042 | 34.054 | 39.563 | 1.00 | 28.77 |
| ATOM | 3222 | C   | ALA | A | 343 | 64.782 | 32.778 | 41.552 | 1.00 | 28.72 |
| ATOM | 3223 | O   | ALA | A | 343 | 64.011 | 31.826 | 41.700 | 1.00 | 30.49 |
| ATOM | 3224 | N   | PHE | A | 344 | 65.320 | 33.447 | 42.559 | 1.00 | 26.88 |
| ATOM | 3226 | CA  | PHE | A | 344 | 65.040 | 33.125 | 43.945 | 1.00 | 26.71 |
| ATOM | 3227 | CB  | PHE | A | 344 | 66.316 | 32.718 | 44.673 | 1.00 | 21.35 |
| ATOM | 3228 | CG  | PHE | A | 344 | 66.891 | 31.428 | 44.210 | 1.00 | 19.20 |
| ATOM | 3229 | CD1 | PHE | A | 344 | 67.806 | 31.396 | 43.173 | 1.00 | 20.33 |
| ATOM | 3230 | CD2 | PHE | A | 344 | 66.547 | 30.247 | 44.834 | 1.00 | 15.57 |
| ATOM | 3231 | CE1 | PHE | A | 344 | 68.372 | 30.198 | 42.766 | 1.00 | 19.57 |
| ATOM | 3232 | CE2 | PHE | A | 344 | 67.106 | 29.049 | 44.438 | 1.00 | 17.79 |
| ATOM | 3233 | CZ  | PHE | A | 344 | 68.023 | 29.026 | 43.401 | 1.00 | 19.23 |
| ATOM | 3234 | C   | PHE | A | 344 | 64.523 | 34.382 | 44.608 | 1.00 | 29.77 |
| ATOM | 3235 | O   | PHE | A | 344 | 64.847 | 35.495 | 44.189 | 1.00 | 33.20 |
| ATOM | 3236 | N   | ALA | A | 345 | 63.712 | 34.206 | 45.637 | 1.00 | 29.97 |

| | | | | | | | | |
|---|---|---|---|---|---|---|---|---|
| ATOM | 3238 | CA | ALA A 345 | 63.204 | 35.331 | 46.390 | 1.00 | 30.90 |
| ATOM | 3239 | CB | ALA A 345 | 61.720 | 35.147 | 46.685 | 1.00 | 32.55 |
| ATOM | 3240 | C | ALA A 345 | 64.030 | 35.266 | 47.669 | 1.00 | 31.52 |
| ATOM | 3241 | O | ALA A 345 | 64.230 | 34.186 | 48.220 | 1.00 | 32.91 |
| ATOM | 3242 | N | VAL A 346 | 64.588 | 36.395 | 48.082 | 1.00 | 32.21 |
| ATOM | 3244 | CA | VAL A 346 | 65.403 | 36.449 | 49.287 | 1.00 | 33.87 |
| ATOM | 3245 | CB | VAL A 346 | 66.490 | 37.559 | 49.176 | 1.00 | 34.53 |
| ATOM | 3246 | CG1 | VAL A 346 | 67.430 | 37.537 | 50.383 | 1.00 | 32.13 |
| ATOM | 3247 | CG2 | VAL A 346 | 67.276 | 37.394 | 47.892 | 1.00 | 33.38 |
| ATOM | 3248 | C | VAL A 346 | 64.497 | 36.755 | 50.474 | 1.00 | 36.21 |
| ATOM | 3249 | O | VAL A 346 | 63.985 | 37.871 | 50.597 | 1.00 | 38.00 |
| ATOM | 3250 | N | LEU A 347 | 64.278 | 35.759 | 51.327 | 1.00 | 37.36 |
| ATOM | 3252 | CA | LEU A 347 | 63.445 | 35.928 | 52.516 | 1.00 | 39.35 |
| ATOM | 3253 | CB | LEU A 347 | 63.172 | 34.567 | 53.162 | 1.00 | 37.87 |
| ATOM | 3254 | CG | LEU A 347 | 62.664 | 33.460 | 52.238 | 1.00 | 37.83 |
| ATOM | 3255 | CD1 | LEU A 347 | 62.315 | 32.231 | 53.057 | 1.00 | 36.57 |
| ATOM | 3256 | CD2 | LEU A 347 | 61.461 | 33.945 | 51.462 | 1.00 | 39.01 |
| ATOM | 3257 | C | LEU A 347 | 64.157 | 36.847 | 53.519 | 1.00 | 42.26 |
| ATOM | 3258 | O | LEU A 347 | 65.376 | 37.021 | 53.449 | 1.00 | 44.26 |
| ATOM | 3259 | N | PRO A 348 | 63.418 | 37.410 | 54.495 | 1.00 | 43.97 |
| ATOM | 3260 | CD | PRO A 348 | 61.973 | 37.254 | 54.728 | 1.00 | 43.89 |
| ATOM | 3261 | CA | PRO A 348 | 64.002 | 38.309 | 55.505 | 1.00 | 43.61 |
| ATOM | 3262 | CB | PRO A 348 | 62.796 | 38.689 | 56.364 | 1.00 | 44.62 |
| ATOM | 3263 | CG | PRO A 348 | 61.875 | 37.514 | 56.206 | 1.00 | 44.98 |
| ATOM | 3264 | C | PRO A 348 | 65.138 | 37.751 | 56.364 | 1.00 | 42.78 |
| ATOM | 3265 | O | PRO A 348 | 65.685 | 38.471 | 57.195 | 1.00 | 43.70 |
| ATOM | 3266 | N | ASN A 349 | 65.478 | 36.478 | 56.184 | 1.00 | 42.71 |
| ATOM | 3268 | CA | ASN A 349 | 66.556 | 35.849 | 56.947 | 1.00 | 41.55 |
| ATOM | 3269 | CB | ASN A 349 | 66.046 | 34.591 | 57.659 | 1.00 | 41.16 |
| ATOM | 3270 | CG | ASN A 349 | 65.583 | 33.518 | 56.689 | 1.00 | 43.53 |
| ATOM | 3271 | OD1 | ASN A 349 | 65.524 | 33.748 | 55.479 | 1.00 | 44.53 |
| ATOM | 3272 | ND2 | ASN A 349 | 65.256 | 32.339 | 57.210 | 1.00 | 43.58 |
| ATOM | 3275 | C | ASN A 349 | 67.731 | 35.482 | 56.038 | 1.00 | 41.09 |
| ATOM | 3276 | O | ASN A 349 | 68.662 | 34.801 | 56.469 | 1.00 | 41.04 |

| | | | | | | | | |
|---|---|---|---|---|---|---|---|---|
| ATOM | 3277 | N | SER | A 350 | 67.678 | 35.954 | 54.793 | 1.00 40.23 |
| ATOM | 3279 | CA | SER | A 350 | 68.697 | 35.704 | 53.768 | 1.00 39.62 |
| ATOM | 3280 | CB | SER | A 350 | 70.122 | 35.854 | 54.314 | 1.00 40.62 |
| ATOM | 3281 | OG | SER | A 350 | 70.518 | 37.214 | 54.317 | 1.00 46.79 |
| ATOM | 3283 | C | SER | A 350 | 68.561 | 34.364 | 53.067 | 1.00 37.74 |
| ATOM | 3284 | O | SER | A 350 | 69.339 | 34.063 | 52.168 | 1.00 40.17 |
| ATOM | 3285 | N | ALA | A 351 | 67.581 | 33.562 | 53.471 | 1.00 34.00 |
| ATOM | 3287 | CA | ALA | A 351 | 67.373 | 32.266 | 52.846 | 1.00 31.70 |
| ATOM | 3288 | CB | ALA | A 351 | 66.426 | 31.429 | 53.670 | 1.00 31.56 |
| ATOM | 3289 | C | ALA | A 351 | 66.799 | 32.505 | 51.455 | 1.00 32.27 |
| ATOM | 3290 | O | ALA | A 351 | 66.150 | 33.526 | 51.212 | 1.00 34.50 |
| ATOM | 3291 | N | LEU | A 352 | 67.022 | 31.560 | 50.549 | 1.00 30.81 |
| ATOM | 3293 | CA | LEU | A 352 | 66.541 | 31.681 | 49.179 | 1.00 27.71 |
| ATOM | 3294 | CB | LEU | A 352 | 67.678 | 31.358 | 48.203 | 1.00 22.61 |
| ATOM | 3295 | CG | LEU | A 352 | 69.026 | 32.057 | 48.373 | 1.00 14.74 |
| ATOM | 3296 | CD1 | LEU | A 352 | 69.958 | 31.612 | 47.280 | 1.00 13.29 |
| ATOM | 3297 | CD2 | LEU | A 352 | 68.853 | 33.554 | 48.306 | 1.00 14.68 |
| ATOM | 3298 | C | LEU | A 352 | 65.348 | 30.775 | 48.886 | 1.00 29.37 |
| ATOM | 3299 | O | LEU | A 352 | 65.375 | 29.573 | 49.179 | 1.00 30.14 |
| ATOM | 3300 | N | ALA | A 353 | 64.309 | 31.349 | 48.289 | 1.00 31.25 |
| ATOM | 3302 | CA | ALA | A 353 | 63.110 | 30.592 | 47.929 | 1.00 34.26 |
| ATOM | 3303 | CB | ALA | A 353 | 61.882 | 31.226 | 48.554 | 1.00 35.51 |
| ATOM | 3304 | C | ALA | A 353 | 62.982 | 30.555 | 46.403 | 1.00 36.03 |
| ATOM | 3305 | O | ALA | A 353 | 62.793 | 31.587 | 45.764 | 1.00 37.52 |
| ATOM | 3306 | N | SER | A 354 | 63.110 | 29.362 | 45.832 | 1.00 37.41 |
| ATOM | 3308 | CA | SER | A 354 | 63.054 | 29.162 | 44.388 | 1.00 37.85 |
| ATOM | 3309 | CB | SER | A 354 | 63.338 | 27.687 | 44.070 | 1.00 40.08 |
| ATOM | 3310 | OG | SER | A 354 | 63.380 | 27.434 | 42.673 | 1.00 45.78 |
| ATOM | 3312 | C | SER | A 354 | 61.744 | 29.601 | 43.741 | 1.00 37.70 |
| ATOM | 3313 | O | SER | A 354 | 60.684 | 29.060 | 44.043 | 1.00 40.21 |
| ATOM | 3314 | N | LEU | A 355 | 61.830 | 30.572 | 42.840 | 1.00 36.34 |
| ATOM | 3316 | CA | LEU | A 355 | 60.657 | 31.074 | 42.137 | 1.00 35.04 |
| ATOM | 3317 | CB | LEU | A 355 | 60.839 | 32.553 | 41.782 | 1.00 30.99 |
| ATOM | 3318 | CG | LEU | A 355 | 60.830 | 33.547 | 42.939 | 1.00 28.58 |

| | | | | | | | | |
|---|---|---|---|---|---|---|---|---|
| ATOM | 3319 | CD1 | LEU A 355 | 61.028 | 34.955 | 42.423 | 1.00 | 28.81 |
| ATOM | 3320 | CD2 | LEU A 355 | 59.520 | 33.441 | 43.678 | 1.00 | 30.20 |
| ATOM | 3321 | C | LEU A 355 | 60.399 | 30.255 | 40.868 | 1.00 | 36.96 |
| ATOM | 3322 | O | LEU A 355 | 59.363 | 29.592 | 40.745 | 1.00 | 36.42 |
| ATOM | 3323 | N | PHE A 356 | 61.356 | 30.286 | 39.939 | 1.00 | 37.24 |
| ATOM | 3325 | CA | PHE A 356 | 61.251 | 29.556 | 38.673 | 1.00 | 36.22 |
| ATOM | 3326 | CB | PHE A 356 | 60.315 | 30.291 | 37.699 | 1.00 | 33.82 |
| ATOM | 3327 | CG | PHE A 356 | 60.661 | 31.741 | 37.491 | 1.00 | 30.90 |
| ATOM | 3328 | CD1 | PHE A 356 | 61.786 | 32.110 | 36.768 | 1.00 | 29.04 |
| ATOM | 3329 | CD2 | PHE A 356 | 59.859 | 32.739 | 38.027 | 1.00 | 30.48 |
| ATOM | 3330 | CE1 | PHE A 356 | 62.111 | 33.451 | 36.586 | 1.00 | 28.29 |
| ATOM | 3331 | CE2 | PHE A 356 | 60.179 | 34.081 | 37.848 | 1.00 | 30.44 |
| ATOM | 3332 | CZ | PHE A 356 | 61.308 | 34.435 | 37.128 | 1.00 | 25.36 |
| ATOM | 3333 | C | PHE A 356 | 62.611 | 29.356 | 38.011 | 1.00 | 36.47 |
| ATOM | 3334 | O | PHE A 356 | 63.546 | 30.112 | 38.271 | 1.00 | 39.86 |
| ATOM | 3335 | N | LEU A 357 | 62.707 | 28.345 | 37.151 | 1.00 | 36.72 |
| ATOM | 3337 | CA | LEU A 357 | 63.937 | 28.035 | 36.423 | 1.00 | 35.97 |
| ATOM | 3338 | CB | LEU A 357 | 64.358 | 26.585 | 36.670 | 1.00 | 34.25 |
| ATOM | 3339 | CG | LEU A 357 | 65.593 | 26.104 | 35.904 | 1.00 | 32.69 |
| ATOM | 3340 | CD1 | LEU A 357 | 66.828 | 26.854 | 36.354 | 1.00 | 30.30 |
| ATOM | 3341 | CD2 | LEU A 357 | 65.784 | 24.620 | 36.120 | 1.00 | 34.02 |
| ATOM | 3342 | C | LEU A 357 | 63.721 | 28.252 | 34.925 | 1.00 | 36.64 |
| ATOM | 3343 | O | LEU A 357 | 62.805 | 27.678 | 34.333 | 1.00 | 39.03 |
| ATOM | 3344 | N | ILE A 358 | 64.585 | 29.054 | 34.318 | 1.00 | 35.88 |
| ATOM | 3346 | CA | ILE A 358 | 64.508 | 29.367 | 32.899 | 1.00 | 34.57 |
| ATOM | 3347 | CB | ILE A 358 | 64.510 | 30.903 | 32.672 | 1.00 | 33.20 |
| ATOM | 3348 | CG2 | ILE A 358 | 64.653 | 31.239 | 31.208 | 1.00 | 31.65 |
| ATOM | 3349 | CG1 | ILE A 358 | 63.220 | 31.510 | 33.207 | 1.00 | 33.82 |
| ATOM | 3350 | CD1 | ILE A 358 | 61.978 | 30.907 | 32.602 | 1.00 | 34.80 |
| ATOM | 3351 | C | ILE A 358 | 65.677 | 28.748 | 32.143 | 1.00 | 36.24 |
| ATOM | 3352 | O | ILE A 358 | 66.784 | 28.628 | 32.666 | 1.00 | 36.67 |
| ATOM | 3353 | N | GLY A 359 | 65.405 | 28.338 | 30.912 | 1.00 | 38.02 |
| ATOM | 3355 | CA | GLY A 359 | 66.419 | 27.753 | 30.061 | 1.00 | 37.56 |
| ATOM | 3356 | C | GLY A 359 | 66.597 | 28.704 | 28.902 | 1.00 | 38.10 |

| | | | | | | | | | |
|---|---|---|---|---|---|---|---|---|---|
| ATOM | 3357 | O | | GLY | A | 359 | 65.679 | 28.932 | 28.113 | 1.00 | 38.54 |
| ATOM | 3358 | N | | MET | A | 360 | 67.769 | 29.305 | 28.830 | 1.00 | 37.31 |
| ATOM | 3360 | CA | | MET | A | 360 | 68.060 | 30.252 | 27.785 | 1.00 | 36.92 |
| ATOM | 3361 | CB | | MET | A | 360 | 68.515 | 31.560 | 28.405 | 1.00 | 38.52 |
| ATOM | 3362 | CG | | MET | A | 360 | 68.813 | 32.656 | 27.421 | 1.00 | 42.50 |
| ATOM | 3363 | SD | | MET | A | 360 | 69.679 | 33.987 | 28.246 | 1.00 | 49.37 |
| ATOM | 3364 | CE | | MET | A | 360 | 68.747 | 34.125 | 29.725 | 1.00 | 46.11 |
| ATOM | 3365 | C | | MET | A | 360 | 69.154 | 29.686 | 26.907 | 1.00 | 38.15 |
| ATOM | 3366 | O | | MET | A | 360 | 69.986 | 28.899 | 27.347 | 1.00 | 38.64 |
| ATOM | 3367 | N | | HIS | A | 361 | 69.114 | 30.054 | 25.641 | 1.00 | 39.81 |
| ATOM | 3369 | CA | | HIS | A | 361 | 70.095 | 29.612 | 24.667 | 1.00 | 41.81 |
| ATOM | 3370 | CB | | HIS | A | 361 | 69.766 | 28.215 | 24.131 | 1.00 | 45.81 |
| ATOM | 3371 | CG | | HIS | A | 361 | 68.310 | 27.988 | 23.878 | 1.00 | 51.49 |
| ATOM | 3372 | CD2 | HIS | A | 361 | 67.290 | 27.716 | 24.728 | 1.00 | 54.71 |
| ATOM | 3373 | ND1 | HIS | A | 361 | 67.753 | 28.041 | 22.618 | 1.00 | 53.69 |
| ATOM | 3375 | CE1 | HIS | A | 361 | 66.455 | 27.813 | 22.702 | 1.00 | 55.98 |
| ATOM | 3376 | NE2 | HIS | A | 361 | 66.148 | 27.614 | 23.972 | 1.00 | 57.77 |
| ATOM | 3378 | C | | HIS | A | 361 | 70.032 | 30.642 | 23.569 | 1.00 | 41.72 |
| ATOM | 3379 | O | | HIS | A | 361 | 69.003 | 31.295 | 23.387 | 1.00 | 42.60 |
| ATOM | 3380 | N | | THR | A | 362 | 71.132 | 30.816 | 22.858 | 1.00 | 40.54 |
| ATOM | 3382 | CA | | THR | A | 362 | 71.168 | 31.803 | 21.803 | 1.00 | 38.28 |
| ATOM | 3383 | CB | | THR | A | 362 | 71.452 | 33.206 | 22.399 | 1.00 | 38.27 |
| ATOM | 3384 | OG1 | THR | A | 362 | 71.408 | 34.200 | 21.371 | 1.00 | 40.01 |
| ATOM | 3386 | CG2 | THR | A | 362 | 72.799 | 33.241 | 23.082 | 1.00 | 38.36 |
| ATOM | 3387 | C | | THR | A | 362 | 72.244 | 31.391 | 20.818 | 1.00 | 37.84 |
| ATOM | 3388 | O | | THR | A | 362 | 72.692 | 30.245 | 20.829 | 1.00 | 38.47 |
| ATOM | 3389 | N | | THR | A | 363 | 72.620 | 32.315 | 19.948 | 1.00 | 37.83 |
| ATOM | 3391 | CA | | THR | A | 363 | 73.640 | 32.091 | 18.940 | 1.00 | 38.05 |
| ATOM | 3392 | CB | | THR | A | 363 | 73.007 | 31.617 | 17.603 | 1.00 | 38.92 |
| ATOM | 3393 | OG1 | THR | A | 363 | 73.993 | 31.618 | 16.567 | 1.00 | 41.55 |
| ATOM | 3395 | CG2 | THR | A | 363 | 71.855 | 32.515 | 17.193 | 1.00 | 42.85 |
| ATOM | 3396 | C | | THR | A | 363 | 74.333 | 33.436 | 18.773 | 1.00 | 36.99 |
| ATOM | 3397 | O | | THR | A | 363 | 73.668 | 34.467 | 18.705 | 1.00 | 38.50 |
| ATOM | 3398 | N | | GLY | A | 364 | 75.660 | 33.438 | 18.763 | 1.00 | 36.22 |

Page 6-A-81

| | | | | | | | | |
|---|---|---|---|---|---|---|---|---|
| ATOM | 3400 | CA | GLY | A | 364 | 76.377 | 34.692 | 18.626 | 1.00 35.40 |
| ATOM | 3401 | C | GLY | A | 364 | 77.639 | 34.632 | 17.794 | 1.00 35.46 |
| ATOM | 3402 | O | GLY | A | 364 | 78.075 | 33.561 | 17.395 | 1.00 35.68 |
| ATOM | 3403 | N | SER | A | 365 | 78.216 | 35.795 | 17.522 | 1.00 37.37 |
| ATOM | 3405 | CA | SER | A | 365 | 79.434 | 35.884 | 16.738 | 1.00 39.81 |
| ATOM | 3406 | CB | SER | A | 365 | 79.399 | 37.121 | 15.840 | 1.00 41.52 |
| ATOM | 3407 | OG | SER | A | 365 | 78.345 | 37.028 | 14.895 | 1.00 50.49 |
| ATOM | 3409 | C | SER | A | 365 | 80.627 | 35.975 | 17.669 | 1.00 40.48 |
| ATOM | 3410 | O | SER | A | 365 | 80.584 | 36.669 | 18.682 | 1.00 43.48 |
| ATOM | 3411 | N | MET | A | 366 | 81.685 | 35.259 | 17.330 | 1.00 40.04 |
| ATOM | 3413 | CA | MET | A | 366 | 82.898 | 35.271 | 18.118 | 1.00 40.25 |
| ATOM | 3414 | CB | MET | A | 366 | 83.254 | 33.836 | 18.509 | 1.00 41.64 |
| ATOM | 3415 | CG | MET | A | 366 | 84.524 | 33.688 | 19.310 | 1.00 44.41 |
| ATOM | 3416 | SD | MET | A | 366 | 84.378 | 34.496 | 20.881 | 1.00 48.93 |
| ATOM | 3417 | CE | MET | A | 366 | 83.512 | 33.252 | 21.833 | 1.00 49.58 |
| ATOM | 3418 | C | MET | A | 366 | 83.978 | 35.880 | 17.224 | 1.00 41.24 |
| ATOM | 3419 | O | MET | A | 366 | 84.400 | 35.262 | 16.249 | 1.00 43.55 |
| ATOM | 3420 | N | GLU | A | 367 | 84.347 | 37.129 | 17.482 | 1.00 42.13 |
| ATOM | 3422 | CA | GLU | A | 367 | 85.383 | 37.780 | 16.686 | 1.00 43.88 |
| ATOM | 3423 | CB | GLU | A | 367 | 85.148 | 39.288 | 16.608 | 1.00 47.79 |
| ATOM | 3424 | CG | GLU | A | 367 | 84.094 | 39.715 | 15.588 | 1.00 54.26 |
| ATOM | 3425 | CD | GLU | A | 367 | 84.551 | 39.555 | 14.143 | 1.00 57.86 |
| ATOM | 3426 | OE1 | GLU | A | 367 | 85.768 | 39.681 | 13.872 | 1.00 60.11 |
| ATOM | 3427 | OE2 | GLU | A | 367 | 83.683 | 39.315 | 13.273 | 1.00 59.61 |
| ATOM | 3428 | C | GLU | A | 367 | 86.724 | 37.492 | 17.336 | 1.00 43.57 |
| ATOM | 3429 | O | GLU | A | 367 | 86.822 | 37.491 | 18.562 | 1.00 44.51 |
| ATOM | 3430 | N | VAL | A | 368 | 87.752 | 37.256 | 16.526 | 1.00 42.06 |
| ATOM | 3432 | CA | VAL | A | 368 | 89.077 | 36.944 | 17.047 | 1.00 42.38 |
| ATOM | 3433 | CB | VAL | A | 368 | 89.412 | 35.454 | 16.810 | 1.00 42.31 |
| ATOM | 3434 | CG1 | VAL | A | 368 | 90.866 | 35.167 | 17.146 | 1.00 44.40 |
| ATOM | 3435 | CG2 | VAL | A | 368 | 88.509 | 34.581 | 17.660 | 1.00 41.44 |
| ATOM | 3436 | C | VAL | A | 368 | 90.204 | 37.822 | 16.491 | 1.00 43.82 |
| ATOM | 3437 | O | VAL | A | 368 | 90.306 | 38.039 | 15.279 | 1.00 44.42 |
| ATOM | 3438 | N | SER | A | 369 | 91.051 | 38.312 | 17.392 | 1.00 44.15 |

Page 6-A-82

| ATOM | 3440 | CA  | SER | A | 369 | 92.182  | 39.160 | 17.032 | 1.00 | 46.20 |
| ATOM | 3441 | CB  | SER | A | 369 | 91.838  | 40.636 | 17.254 | 1.00 | 48.08 |
| ATOM | 3442 | OG  | SER | A | 369 | 90.692  | 41.011 | 16.508 | 1.00 | 55.65 |
| ATOM | 3444 | C   | SER | A | 369 | 93.376  | 38.773 | 17.896 | 1.00 | 46.39 |
| ATOM | 3445 | O   | SER | A | 369 | 93.269  | 37.897 | 18.757 | 1.00 | 45.59 |
| ATOM | 3446 | N   | ALA | A | 370 | 94.503  | 39.447 | 17.692 | 1.00 | 46.96 |
| ATOM | 3448 | CA  | ALA | A | 370 | 95.705  | 39.151 | 18.455 | 1.00 | 46.86 |
| ATOM | 3449 | CB  | ALA | A | 370 | 96.659  | 38.334 | 17.615 | 1.00 | 48.51 |
| ATOM | 3450 | C   | ALA | A | 370 | 96.401  | 40.399 | 18.961 | 1.00 | 47.76 |
| ATOM | 3451 | O   | ALA | A | 370 | 96.526  | 41.384 | 18.234 | 1.00 | 49.78 |
| ATOM | 3452 | N   | GLU | A | 371 | 96.833  | 40.346 | 20.215 | 1.00 | 49.05 |
| ATOM | 3454 | CA  | GLU | A | 371 | 97.546  | 41.429 | 20.889 | 1.00 | 52.58 |
| ATOM | 3455 | CB  | GLU | A | 371 | 96.670  | 42.035 | 21.999 | 1.00 | 55.47 |
| ATOM | 3456 | CG  | GLU | A | 371 | 97.394  | 42.954 | 23.010 | 1.00 | 61.82 |
| ATOM | 3457 | CD  | GLU | A | 371 | 97.662  | 44.365 | 22.494 | 1.00 | 66.05 |
| ATOM | 3458 | OE1 | GLU | A | 371 | 96.728  | 44.994 | 21.945 | 1.00 | 69.54 |
| ATOM | 3459 | OE2 | GLU | A | 371 | 98.801  | 44.859 | 22.662 | 1.00 | 66.75 |
| ATOM | 3460 | C   | GLU | A | 371 | 98.753  | 40.718 | 21.490 | 1.00 | 53.47 |
| ATOM | 3461 | O   | GLU | A | 371 | 98.617  | 39.613 | 22.015 | 1.00 | 54.95 |
| ATOM | 3462 | N   | SER | A | 372 | 99.926  | 41.337 | 21.418 | 1.00 | 54.76 |
| ATOM | 3464 | CA  | SER | A | 372 | 101.145 | 40.718 | 21.932 | 1.00 | 54.93 |
| ATOM | 3465 | CB  | SER | A | 372 | 101.080 | 40.570 | 23.462 | 1.00 | 56.19 |
| ATOM | 3466 | OG  | SER | A | 372 | 100.788 | 41.803 | 24.098 | 1.00 | 57.76 |
| ATOM | 3468 | C   | SER | A | 372 | 101.267 | 39.347 | 21.245 | 1.00 | 54.65 |
| ATOM | 3469 | O   | SER | A | 372 | 101.364 | 39.275 | 20.017 | 1.00 | 56.14 |
| ATOM | 3470 | N   | ASN | A | 373 | 101.207 | 38.271 | 22.023 | 1.00 | 51.39 |
| ATOM | 3472 | CA  | ASN | A | 373 | 101.292 | 36.922 | 21.480 | 1.00 | 48.43 |
| ATOM | 3473 | CB  | ASN | A | 373 | 102.606 | 36.249 | 21.891 | 1.00 | 49.96 |
| ATOM | 3474 | CG  | ASN | A | 373 | 103.830 | 36.981 | 21.379 | 1.00 | 51.10 |
| ATOM | 3475 | OD1 | ASN | A | 373 | 103.780 | 37.674 | 20.361 | 1.00 | 53.30 |
| ATOM | 3476 | ND2 | ASN | A | 373 | 104.946 | 36.818 | 22.078 | 1.00 | 50.08 |
| ATOM | 3479 | C   | ASN | A | 373 | 100.126 | 36.168 | 22.087 | 1.00 | 46.52 |
| ATOM | 3480 | O   | ASN | A | 373 | 100.267 | 35.027 | 22.529 | 1.00 | 45.55 |
| ATOM | 3481 | N   | ARG | A | 374 | 98.983  | 36.838 | 22.156 | 1.00 | 44.90 |

Page 6-A-83

| ATOM | 3483 | CA | ARG A 374 | 97.780 | 36.255 | 22.730 | 1.00 | 43.78 |
| ATOM | 3484 | CB | ARG A 374 | 97.293 | 37.082 | 23.929 | 1.00 | 45.07 |
| ATOM | 3485 | CG | ARG A 374 | 98.263 | 37.183 | 25.090 | 1.00 | 47.75 |
| ATOM | 3486 | CD | ARG A 374 | 97.653 | 37.976 | 26.235 | 1.00 | 52.92 |
| ATOM | 3487 | NE | ARG A 374 | 97.293 | 39.342 | 25.857 | 1.00 | 58.67 |
| ATOM | 3489 | CZ | ARG A 374 | 97.737 | 40.439 | 26.468 | 1.00 | 62.31 |
| ATOM | 3490 | NH1 | ARG A 374 | 98.568 | 40.347 | 27.500 | 1.00 | 63.80 |
| ATOM | 3493 | NH2 | ARG A 374 | 97.345 | 41.637 | 26.047 | 1.00 | 62.63 |
| ATOM | 3496 | C | ARG A 374 | 96.660 | 36.163 | 21.706 | 1.00 | 41.67 |
| ATOM | 3497 | O | ARG A 374 | 96.660 | 36.866 | 20.698 | 1.00 | 42.40 |
| ATOM | 3498 | N | LEU A 375 | 95.720 | 35.268 | 21.972 | 1.00 | 39.53 |
| ATOM | 3500 | CA | LEU A 375 | 94.568 | 35.063 | 21.119 | 1.00 | 38.25 |
| ATOM | 3501 | CB | LEU A 375 | 94.366 | 33.568 | 20.886 | 1.00 | 40.19 |
| ATOM | 3502 | CG | LEU A 375 | 93.330 | 33.154 | 19.846 | 1.00 | 42.29 |
| ATOM | 3503 | CD1 | LEU A 375 | 93.784 | 33.625 | 18.478 | 1.00 | 42.24 |
| ATOM | 3504 | CD2 | LEU A 375 | 93.158 | 31.646 | 19.866 | 1.00 | 41.82 |
| ATOM | 3505 | C | LEU A 375 | 93.399 | 35.623 | 21.917 | 1.00 | 37.82 |
| ATOM | 3506 | O | LEU A 375 | 93.024 | 35.058 | 22.946 | 1.00 | 38.21 |
| ATOM | 3507 | N | VAL A 376 | 92.871 | 36.764 | 21.491 | 1.00 | 38.16 |
| ATOM | 3509 | CA | VAL A 376 | 91.752 | 37.384 | 22.193 | 1.00 | 38.06 |
| ATOM | 3510 | CB | VAL A 376 | 92.057 | 38.847 | 22.613 | 1.00 | 37.73 |
| ATOM | 3511 | CG1 | VAL A 376 | 93.386 | 38.928 | 23.343 | 1.00 | 36.49 |
| ATOM | 3512 | CG2 | VAL A 376 | 92.054 | 39.762 | 21.409 | 1.00 | 37.89 |
| ATOM | 3513 | C | VAL A 376 | 90.517 | 37.376 | 21.313 | 1.00 | 37.85 |
| ATOM | 3514 | O | VAL A 376 | 90.615 | 37.251 | 20.091 | 1.00 | 37.84 |
| ATOM | 3515 | N | GLY A 377 | 89.358 | 37.542 | 21.935 | 1.00 | 38.79 |
| ATOM | 3517 | CA | GLY A 377 | 88.120 | 37.548 | 21.186 | 1.00 | 38.96 |
| ATOM | 3518 | C | GLY A 377 | 87.034 | 38.334 | 21.880 | 1.00 | 38.86 |
| ATOM | 3519 | O | GLY A 377 | 87.235 | 38.860 | 22.976 | 1.00 | 40.46 |
| ATOM | 3520 | N | GLU A 378 | 85.881 | 38.426 | 21.235 | 1.00 | 39.21 |
| ATOM | 3522 | CA | GLU A 378 | 84.752 | 39.143 | 21.793 | 1.00 | 39.89 |
| ATOM | 3523 | CB | GLU A 378 | 84.762 | 40.601 | 21.335 | 1.00 | 42.06 |
| ATOM | 3524 | CG | GLU A 378 | 83.935 | 41.522 | 22.226 | 1.00 | 47.89 |
| ATOM | 3525 | CD | GLU A 378 | 83.384 | 42.725 | 21.488 | 1.00 | 51.11 |

Page 6-A-84

| ATOM | 3526 | OE1 | GLU | A | 378 | 84.142 | 43.357 | 20.718 | 1.00 | 53.99 |
| ATOM | 3527 | OE2 | GLU | A | 378 | 82.184 | 43.031 | 21.679 | 1.00 | 52.17 |
| ATOM | 3528 | C | GLU | A | 378 | 83.481 | 38.456 | 21.315 | 1.00 | 40.11 |
| ATOM | 3529 | O | GLU | A | 378 | 83.352 | 38.132 | 20.133 | 1.00 | 40.78 |
| ATOM | 3530 | N | LEU | A | 379 | 82.569 | 38.211 | 22.249 | 1.00 | 40.26 |
| ATOM | 3532 | CA | LEU | A | 379 | 81.297 | 37.558 | 21.973 | 1.00 | 41.54 |
| ATOM | 3533 | CB | LEU | A | 379 | 80.935 | 36.651 | 23.155 | 1.00 | 43.08 |
| ATOM | 3534 | CG | LEU | A | 379 | 80.208 | 35.314 | 22.991 | 1.00 | 45.34 |
| ATOM | 3535 | CD1 | LEU | A | 379 | 79.839 | 34.798 | 24.377 | 1.00 | 44.87 |
| ATOM | 3536 | CD2 | LEU | A | 379 | 78.966 | 35.444 | 22.136 | 1.00 | 44.17 |
| ATOM | 3537 | C | LEU | A | 379 | 80.199 | 38.613 | 21.799 | 1.00 | 42.68 |
| ATOM | 3538 | O | LEU | A | 379 | 80.179 | 39.623 | 22.507 | 1.00 | 43.44 |
| ATOM | 3539 | N | LYS | A | 380 | 79.303 | 38.384 | 20.845 | 1.00 | 44.09 |
| ATOM | 3541 | CA | LYS | A | 380 | 78.171 | 39.276 | 20.588 | 1.00 | 46.18 |
| ATOM | 3542 | CB | LYS | A | 380 | 78.438 | 40.165 | 19.373 | 1.00 | 48.46 |
| ATOM | 3543 | CG | LYS | A | 380 | 79.444 | 41.279 | 19.660 | 1.00 | 54.25 |
| ATOM | 3544 | CD | LYS | A | 380 | 79.847 | 42.041 | 18.408 | 1.00 | 58.33 |
| ATOM | 3545 | CE | LYS | A | 380 | 80.817 | 43.172 | 18.734 | 1.00 | 60.62 |
| ATOM | 3546 | NZ | LYS | A | 380 | 81.332 | 43.851 | 17.509 | 1.00 | 63.04 |
| ATOM | 3550 | C | LYS | A | 380 | 76.968 | 38.367 | 20.369 | 1.00 | 46.00 |
| ATOM | 3551 | O | LYS | A | 380 | 77.042 | 37.418 | 19.591 | 1.00 | 45.80 |
| ATOM | 3552 | N | LEU | A | 381 | 75.877 | 38.630 | 21.082 | 1.00 | 46.45 |
| ATOM | 3554 | CA | LEU | A | 381 | 74.690 | 37.784 | 20.996 | 1.00 | 46.82 |
| ATOM | 3555 | CB | LEU | A | 381 | 74.115 | 37.545 | 22.400 | 1.00 | 45.07 |
| ATOM | 3556 | CG | LEU | A | 381 | 75.001 | 36.992 | 23.521 | 1.00 | 41.15 |
| ATOM | 3557 | CD1 | LEU | A | 381 | 74.206 | 36.974 | 24.817 | 1.00 | 39.28 |
| ATOM | 3558 | CD2 | LEU | A | 381 | 75.500 | 35.604 | 23.174 | 1.00 | 40.04 |
| ATOM | 3559 | C | LEU | A | 381 | 73.569 | 38.272 | 20.084 | 1.00 | 48.41 |
| ATOM | 3560 | O | LEU | A | 381 | 73.505 | 39.448 | 19.719 | 1.00 | 48.91 |
| ATOM | 3561 | N | ASP | A | 382 | 72.696 | 37.335 | 19.725 | 1.00 | 50.06 |
| ATOM | 3563 | CA | ASP | A | 382 | 71.527 | 37.591 | 18.894 | 1.00 | 54.68 |
| ATOM | 3564 | CB | ASP | A | 382 | 71.371 | 36.488 | 17.845 | 1.00 | 57.78 |
| ATOM | 3565 | CG | ASP | A | 382 | 71.718 | 36.953 | 16.453 | 1.00 | 61.73 |
| ATOM | 3566 | OD1 | ASP | A | 382 | 72.846 | 37.455 | 16.258 | 1.00 | 65.65 |

| | | | | | | | | |
|---|---|---|---|---|---|---|---|---|
| ATOM | 3567 | OD2 | ASP A 382 | 70.862 | 36.809 | 15.552 | 1.00 | 62.89 |
| ATOM | 3568 | C | ASP A 382 | 70.325 | 37.565 | 19.836 | 1.00 | 56.30 |
| ATOM | 3569 | O | ASP A 382 | 70.465 | 37.827 | 21.030 | 1.00 | 57.37 |
| ATOM | 3570 | N | ARG A 383 | 69.147 | 37.244 | 19.304 | 1.00 | 57.17 |
| ATOM | 3572 | CA | ARG A 383 | 67.932 | 37.169 | 20.116 | 1.00 | 56.86 |
| ATOM | 3573 | CB | ARG A 383 | 66.710 | 36.913 | 19.221 | 1.00 | 61.20 |
| ATOM | 3574 | CG | ARG A 383 | 66.368 | 38.054 | 18.262 | 1.00 | 66.61 |
| ATOM | 3575 | CD | ARG A 383 | 65.158 | 37.721 | 17.389 | 1.00 | 68.98 |
| ATOM | 3576 | NE | ARG A 383 | 64.674 | 38.887 | 16.647 | 1.00 | 73.50 |
| ATOM | 3578 | CZ | ARG A 383 | 64.914 | 39.119 | 15.358 | 1.00 | 76.60 |
| ATOM | 3579 | NH1 | ARG A 383 | 65.639 | 38.269 | 14.636 | 1.00 | 77.94 |
| ATOM | 3582 | NH2 | ARG A 383 | 64.421 | 40.210 | 14.784 | 1.00 | 77.33 |
| ATOM | 3585 | C | ARG A 383 | 68.081 | 36.026 | 21.120 | 1.00 | 54.61 |
| ATOM | 3586 | O | ARG A 383 | 68.689 | 35.001 | 20.801 | 1.00 | 56.02 |
| ATOM | 3587 | N | LEU A 384 | 67.565 | 36.207 | 22.333 | 1.00 | 50.19 |
| ATOM | 3589 | CA | LEU A 384 | 67.654 | 35.163 | 23.353 | 1.00 | 47.21 |
| ATOM | 3590 | CB | LEU A 384 | 67.886 | 35.765 | 24.740 | 1.00 | 45.34 |
| ATOM | 3591 | CG | LEU A 384 | 69.072 | 36.707 | 24.951 | 1.00 | 44.13 |
| ATOM | 3592 | CD1 | LEU A 384 | 69.089 | 37.136 | 26.403 | 1.00 | 48.33 |
| ATOM | 3593 | CD2 | LEU A 384 | 70.386 | 36.036 | 24.587 | 1.00 | 44.37 |
| ATOM | 3594 | C | LEU A 384 | 66.366 | 34.355 | 23.360 | 1.00 | 46.05 |
| ATOM | 3595 | O | LEU A 384 | 65.287 | 34.910 | 23.175 | 1.00 | 46.98 |
| ATOM | 3596 | N | LEU A 385 | 66.477 | 33.044 | 23.536 | 1.00 | 45.63 |
| ATOM | 3598 | CA | LEU A 385 | 65.299 | 32.190 | 23.564 | 1.00 | 44.83 |
| ATOM | 3599 | CB | LEU A 385 | 65.417 | 31.034 | 22.577 | 1.00 | 47.07 |
| ATOM | 3600 | CG | LEU A 385 | 65.424 | 31.305 | 21.075 | 1.00 | 49.68 |
| ATOM | 3601 | CD1 | LEU A 385 | 66.807 | 31.742 | 20.610 | 1.00 | 50.06 |
| ATOM | 3602 | CD2 | LEU A 385 | 65.018 | 30.020 | 20.367 | 1.00 | 53.29 |
| ATOM | 3603 | C | LEU A 385 | 65.093 | 31.624 | 24.948 | 1.00 | 43.70 |
| ATOM | 3604 | O | LEU A 385 | 65.973 | 30.965 | 25.500 | 1.00 | 46.13 |
| ATOM | 3605 | N | LEU A 386 | 63.921 | 31.879 | 25.501 | 1.00 | 41.90 |
| ATOM | 3607 | CA | LEU A 386 | 63.586 | 31.399 | 26.819 | 1.00 | 40.93 |
| ATOM | 3608 | CB | LEU A 386 | 62.804 | 32.467 | 27.576 | 1.00 | 38.95 |
| ATOM | 3609 | CG | LEU A 386 | 63.610 | 33.573 | 28.251 | 1.00 | 38.87 |

| | | | | | | | | |
|---|---|---|---|---|---|---|---|---|
| ATOM | 3610 | CD1 | LEU A 386 | 64.732 | 34.076 | 27.364 | 1.00 | 36.69 |
| ATOM | 3611 | CD2 | LEU A 386 | 62.671 | 34.690 | 28.636 | 1.00 | 38.24 |
| ATOM | 3612 | C | LEU A 386 | 62.754 | 30.140 | 26.711 | 1.00 | 41.89 |
| ATOM | 3613 | O | LEU A 386 | 62.154 | 29.861 | 25.677 | 1.00 | 44.73 |
| ATOM | 3614 | N | GLU A 387 | 62.777 | 29.354 | 27.773 | 1.00 | 42.45 |
| ATOM | 3616 | CA | GLU A 387 | 62.006 | 28.133 | 27.867 | 1.00 | 43.22 |
| ATOM | 3617 | CB | GLU A 387 | 62.773 | 26.932 | 27.306 | 1.00 | 44.48 |
| ATOM | 3618 | CG | GLU A 387 | 61.993 | 25.614 | 27.408 | 1.00 | 46.64 |
| ATOM | 3619 | CD | GLU A 387 | 62.699 | 24.436 | 26.762 | 1.00 | 48.74 |
| ATOM | 3620 | OE1 | GLU A 387 | 62.622 | 24.305 | 25.520 | 1.00 | 53.50 |
| ATOM | 3621 | OE2 | GLU A 387 | 63.311 | 23.629 | 27.495 | 1.00 | 48.42 |
| ATOM | 3622 | C | GLU A 387 | 61.791 | 27.966 | 29.359 | 1.00 | 45.59 |
| ATOM | 3623 | O | GLU A 387 | 62.697 | 28.232 | 30.150 | 1.00 | 47.68 |
| ATOM | 3624 | N | LEU A 388 | 60.574 | 27.618 | 29.750 | 1.00 | 47.18 |
| ATOM | 3626 | CA | LEU A 388 | 60.260 | 27.422 | 31.156 | 1.00 | 48.51 |
| ATOM | 3627 | CB | LEU A 388 | 58.795 | 27.778 | 31.418 | 1.00 | 49.74 |
| ATOM | 3628 | CG | LEU A 388 | 58.298 | 27.776 | 32.865 | 1.00 | 49.97 |
| ATOM | 3629 | CD1 | LEU A 388 | 58.957 | 28.902 | 33.656 | 1.00 | 49.70 |
| ATOM | 3630 | CD2 | LEU A 388 | 56.788 | 27.935 | 32.871 | 1.00 | 51.43 |
| ATOM | 3631 | C | LEU A 388 | 60.513 | 25.953 | 31.468 | 1.00 | 49.89 |
| ATOM | 3632 | O | LEU A 388 | 60.033 | 25.071 | 30.754 | 1.00 | 49.90 |
| ATOM | 3633 | N | LYS A 389 | 61.290 | 25.688 | 32.511 | 1.00 | 53.07 |
| ATOM | 3635 | CA | LYS A 389 | 61.599 | 24.312 | 32.883 | 1.00 | 57.61 |
| ATOM | 3636 | CB | LYS A 389 | 63.109 | 24.152 | 33.105 | 1.00 | 58.15 |
| ATOM | 3637 | CG | LYS A 389 | 63.933 | 24.486 | 31.864 | 1.00 | 58.89 |
| ATOM | 3638 | CD | LYS A 389 | 65.377 | 24.022 | 31.971 | 1.00 | 61.45 |
| ATOM | 3639 | CE | LYS A 389 | 66.104 | 24.202 | 30.640 | 1.00 | 63.53 |
| ATOM | 3640 | NZ | LYS A 389 | 67.507 | 23.692 | 30.664 | 1.00 | 66.07 |
| ATOM | 3644 | C | LYS A 389 | 60.800 | 23.813 | 34.094 | 1.00 | 60.00 |
| ATOM | 3645 | O | LYS A 389 | 60.351 | 22.663 | 34.122 | 1.00 | 61.33 |
| ATOM | 3646 | N | HIS A 390 | 60.622 | 24.679 | 35.086 | 1.00 | 61.51 |
| ATOM | 3648 | CA | HIS A 390 | 59.871 | 24.347 | 36.297 | 1.00 | 63.22 |
| ATOM | 3649 | CB | HIS A 390 | 60.713 | 23.474 | 37.242 | 1.00 | 68.01 |
| ATOM | 3650 | CG | HIS A 390 | 59.939 | 22.880 | 38.386 | 1.00 | 74.01 |

| ATOM | 3651 | CD2 | HIS | A | 390 | 59.403 | 21.647 | 38.553 | 1.00 | 76.41 |
| ATOM | 3652 | ND1 | HIS | A | 390 | 59.682 | 23.568 | 39.554 | 1.00 | 76.75 |
| ATOM | 3654 | CE1 | HIS | A | 390 | 59.023 | 22.785 | 40.391 | 1.00 | 78.97 |
| ATOM | 3655 | NE2 | HIS | A | 390 | 58.843 | 21.613 | 39.807 | 1.00 | 79.75 |
| ATOM | 3657 | C | HIS | A | 390 | 59.551 | 25.669 | 36.969 | 1.00 | 61.81 |
| ATOM | 3658 | O | HIS | A | 390 | 60.348 | 26.604 | 36.912 | 1.00 | 62.27 |
| ATOM | 3659 | N | SER | A | 391 | 58.375 | 25.762 | 37.572 | 1.00 | 60.92 |
| ATOM | 3661 | CA | SER | A | 391 | 57.978 | 26.980 | 38.257 | 1.00 | 59.76 |
| ATOM | 3662 | CB | SER | A | 391 | 57.005 | 27.793 | 37.403 | 1.00 | 58.20 |
| ATOM | 3663 | OG | SER | A | 391 | 56.639 | 28.996 | 38.059 | 1.00 | 55.50 |
| ATOM | 3665 | C | SER | A | 391 | 57.322 | 26.605 | 39.567 | 1.00 | 59.99 |
| ATOM | 3666 | O | SER | A | 391 | 56.486 | 25.699 | 39.618 | 1.00 | 60.83 |
| ATOM | 3667 | N | ASN | A | 392 | 57.753 | 27.260 | 40.636 | 1.00 | 59.65 |
| ATOM | 3669 | CA | ASN | A | 392 | 57.190 | 27.008 | 41.949 | 1.00 | 59.99 |
| ATOM | 3670 | CB | ASN | A | 392 | 58.241 | 27.234 | 43.039 | 1.00 | 58.88 |
| ATOM | 3671 | CG | ASN | A | 392 | 59.314 | 26.152 | 43.054 | 1.00 | 58.15 |
| ATOM | 3672 | OD1 | ASN | A | 392 | 59.424 | 25.344 | 42.126 | 1.00 | 59.13 |
| ATOM | 3673 | ND2 | ASN | A | 392 | 60.117 | 26.137 | 44.108 | 1.00 | 57.91 |
| ATOM | 3676 | C | ASN | A | 392 | 55.976 | 27.914 | 42.145 | 1.00 | 60.50 |
| ATOM | 3677 | O | ASN | A | 392 | 55.149 | 27.678 | 43.023 | 1.00 | 61.62 |
| ATOM | 3678 | N | ILE | A | 393 | 55.851 | 28.926 | 41.288 | 1.00 | 61.07 |
| ATOM | 3680 | CA | ILE | A | 393 | 54.730 | 29.861 | 41.351 | 1.00 | 60.89 |
| ATOM | 3681 | CB | ILE | A | 393 | 55.212 | 31.333 | 41.306 | 1.00 | 58.61 |
| ATOM | 3682 | CG2 | ILE | A | 393 | 56.083 | 31.634 | 42.510 | 1.00 | 58.38 |
| ATOM | 3683 | CG1 | ILE | A | 393 | 55.948 | 31.622 | 39.995 | 1.00 | 57.06 |
| ATOM | 3684 | CD1 | ILE | A | 393 | 56.245 | 33.087 | 39.775 | 1.00 | 56.51 |
| ATOM | 3685 | C | ILE | A | 393 | 53.700 | 29.632 | 40.228 | 1.00 | 63.24 |
| ATOM | 3686 | O | ILE | A | 393 | 53.049 | 30.574 | 39.772 | 1.00 | 64.68 |
| ATOM | 3687 | N | GLY | A | 394 | 53.556 | 28.382 | 39.786 | 1.00 | 64.29 |
| ATOM | 3689 | CA | GLY | A | 394 | 52.603 | 28.061 | 38.731 | 1.00 | 62.76 |
| ATOM | 3690 | C | GLY | A | 394 | 53.046 | 28.426 | 37.323 | 1.00 | 62.37 |
| ATOM | 3691 | O | GLY | A | 394 | 53.985 | 29.202 | 37.147 | 1.00 | 62.54 |
| ATOM | 3692 | N | PRO | A | 395 | 52.412 | 27.848 | 36.291 | 1.00 | 62.40 |
| ATOM | 3693 | CD | PRO | A | 395 | 51.333 | 26.846 | 36.373 | 1.00 | 63.52 |

| | | | | | | | | | |
|---|---|---|---|---|---|---|---|---|---|
| ATOM | 3694 | CA | PRO | A | 395 | 52.758 | 28.130 | 34.894 | 1.00 60.73 |
| ATOM | 3695 | CB | PRO | A | 395 | 51.937 | 27.095 | 34.125 | 1.00 61.59 |
| ATOM | 3696 | CG | PRO | A | 395 | 50.728 | 26.910 | 34.992 | 1.00 63.08 |
| ATOM | 3697 | C | PRO | A | 395 | 52.405 | 29.554 | 34.470 | 1.00 59.25 |
| ATOM | 3698 | O | PRO | A | 395 | 51.353 | 30.081 | 34.834 | 1.00 59.47 |
| ATOM | 3699 | N | PHE | A | 396 | 53.295 | 30.171 | 33.702 | 1.00 57.50 |
| ATOM | 3701 | CA | PHE | A | 396 | 53.087 | 31.530 | 33.220 | 1.00 55.80 |
| ATOM | 3702 | CB | PHE | A | 396 | 53.684 | 32.555 | 34.200 | 1.00 54.39 |
| ATOM | 3703 | CG | PHE | A | 396 | 55.194 | 32.588 | 34.223 | 1.00 51.73 |
| ATOM | 3704 | CD1 | PHE | A | 396 | 55.899 | 33.426 | 33.364 | 1.00 49.07 |
| ATOM | 3705 | CD2 | PHE | A | 396 | 55.909 | 31.796 | 35.115 | 1.00 50.73 |
| ATOM | 3706 | CE1 | PHE | A | 396 | 57.283 | 33.474 | 33.394 | 1.00 47.56 |
| ATOM | 3707 | CE2 | PHE | A | 396 | 57.295 | 31.841 | 35.150 | 1.00 47.47 |
| ATOM | 3708 | CZ | PHE | A | 396 | 57.981 | 32.678 | 34.289 | 1.00 47.02 |
| ATOM | 3709 | C | PHE | A | 396 | 53.720 | 31.674 | 31.839 | 1.00 55.76 |
| ATOM | 3710 | O | PHE | A | 396 | 54.463 | 30.792 | 31.392 | 1.00 56.39 |
| ATOM | 3711 | N | PRO | A | 397 | 53.394 | 32.763 | 31.120 | 1.00 54.61 |
| ATOM | 3712 | CD | PRO | A | 397 | 52.354 | 33.768 | 31.393 | 1.00 54.50 |
| ATOM | 3713 | CA | PRO | A | 397 | 53.966 | 32.967 | 29.787 | 1.00 53.13 |
| ATOM | 3714 | CB | PRO | A | 397 | 53.167 | 34.159 | 29.252 | 1.00 53.76 |
| ATOM | 3715 | CG | PRO | A | 397 | 51.877 | 34.095 | 30.011 | 1.00 53.30 |
| ATOM | 3716 | C | PRO | A | 397 | 55.448 | 33.301 | 29.899 | 1.00 51.99 |
| ATOM | 3717 | O | PRO | A | 397 | 55.810 | 34.434 | 30.219 | 1.00 51.04 |
| ATOM | 3718 | N | VAL | A | 398 | 56.300 | 32.322 | 29.609 | 1.00 50.99 |
| ATOM | 3720 | CA | VAL | A | 398 | 57.747 | 32.506 | 29.686 | 1.00 50.88 |
| ATOM | 3721 | CB | VAL | A | 398 | 58.500 | 31.222 | 29.253 | 1.00 50.94 |
| ATOM | 3722 | CG1 | VAL | A | 398 | 58.260 | 30.926 | 27.785 | 1.00 50.60 |
| ATOM | 3723 | CG2 | VAL | A | 398 | 59.987 | 31.340 | 29.561 | 1.00 49.69 |
| ATOM | 3724 | C | VAL | A | 398 | 58.248 | 33.709 | 28.888 | 1.00 51.53 |
| ATOM | 3725 | O | VAL | A | 398 | 59.383 | 34.144 | 29.053 | 1.00 54.45 |
| ATOM | 3726 | N | GLU | A | 399 | 57.385 | 34.268 | 28.050 | 1.00 52.68 |
| ATOM | 3728 | CA | GLU | A | 399 | 57.741 | 35.427 | 27.236 | 1.00 52.46 |
| ATOM | 3729 | CB | GLU | A | 399 | 56.807 | 35.533 | 26.020 | 1.00 53.50 |
| ATOM | 3730 | CG | GLU | A | 399 | 56.637 | 34.234 | 25.210 | 1.00 53.56 |

Page 6-A-89

| ATOM | 3731 | CD | GLU | A | 399 | 55.420 | 33.405 | 25.629 | 1.00 | 53.53 |
| ATOM | 3732 | OE1 | GLU | A | 399 | 54.313 | 33.979 | 25.741 | 1.00 | 54.16 |
| ATOM | 3733 | OE2 | GLU | A | 399 | 55.562 | 32.176 | 25.821 | 1.00 | 52.27 |
| ATOM | 3734 | C | GLU | A | 399 | 57.737 | 36.750 | 28.025 | 1.00 | 51.41 |
| ATOM | 3735 | O | GLU | A | 399 | 58.233 | 37.762 | 27.539 | 1.00 | 52.41 |
| ATOM | 3736 | N | LEU | A | 400 | 57.186 | 36.747 | 29.235 | 1.00 | 49.79 |
| ATOM | 3738 | CA | LEU | A | 400 | 57.148 | 37.955 | 30.060 | 1.00 | 49.44 |
| ATOM | 3739 | CB | LEU | A | 400 | 56.186 | 37.769 | 31.238 | 1.00 | 50.82 |
| ATOM | 3740 | CG | LEU | A | 400 | 54.683 | 38.030 | 31.086 | 1.00 | 49.58 |
| ATOM | 3741 | CD1 | LEU | A | 400 | 54.427 | 39.510 | 30.867 | 1.00 | 50.78 |
| ATOM | 3742 | CD2 | LEU | A | 400 | 54.114 | 37.220 | 29.954 | 1.00 | 50.81 |
| ATOM | 3743 | C | LEU | A | 400 | 58.539 | 38.330 | 30.589 | 1.00 | 50.26 |
| ATOM | 3744 | O | LEU | A | 400 | 58.800 | 39.487 | 30.931 | 1.00 | 50.71 |
| ATOM | 3745 | N | LEU | A | 401 | 59.428 | 37.344 | 30.656 | 1.00 | 50.41 |
| ATOM | 3747 | CA | LEU | A | 401 | 60.790 | 37.548 | 31.143 | 1.00 | 49.44 |
| ATOM | 3748 | CB | LEU | A | 401 | 61.310 | 36.255 | 31.766 | 1.00 | 48.32 |
| ATOM | 3749 | CG | LEU | A | 401 | 60.598 | 35.840 | 33.049 | 1.00 | 46.40 |
| ATOM | 3750 | CD1 | LEU | A | 401 | 60.738 | 34.361 | 33.262 | 1.00 | 45.30 |
| ATOM | 3751 | CD2 | LEU | A | 401 | 61.168 | 36.620 | 34.218 | 1.00 | 48.02 |
| ATOM | 3752 | C | LEU | A | 401 | 61.762 | 38.013 | 30.066 | 1.00 | 49.89 |
| ATOM | 3753 | O | LEU | A | 401 | 62.919 | 38.303 | 30.360 | 1.00 | 51.08 |
| ATOM | 3754 | N | GLN | A | 402 | 61.288 | 38.091 | 28.826 | 1.00 | 51.14 |
| ATOM | 3756 | CA | GLN | A | 402 | 62.107 | 38.511 | 27.686 | 1.00 | 52.43 |
| ATOM | 3757 | CB | GLN | A | 402 | 61.255 | 38.569 | 26.413 | 1.00 | 53.25 |
| ATOM | 3758 | CG | GLN | A | 402 | 60.908 | 37.211 | 25.810 | 1.00 | 55.42 |
| ATOM | 3759 | CD | GLN | A | 402 | 61.966 | 36.697 | 24.851 | 1.00 | 55.66 |
| ATOM | 3760 | OE1 | GLN | A | 402 | 63.075 | 37.229 | 24.780 | 1.00 | 55.93 |
| ATOM | 3761 | NE2 | GLN | A | 402 | 61.619 | 35.667 | 24.090 | 1.00 | 56.71 |
| ATOM | 3764 | C | GLN | A | 402 | 62.800 | 39.855 | 27.890 | 1.00 | 53.23 |
| ATOM | 3765 | O | GLN | A | 402 | 64.009 | 39.977 | 27.684 | 1.00 | 54.78 |
| ATOM | 3766 | N | ASP | A | 403 | 62.031 | 40.866 | 28.275 | 1.00 | 53.89 |
| ATOM | 3768 | CA | ASP | A | 403 | 62.578 | 42.198 | 28.505 | 1.00 | 54.40 |
| ATOM | 3769 | CB | ASP | A | 403 | 61.441 | 43.183 | 28.797 | 1.00 | 58.20 |
| ATOM | 3770 | CG | ASP | A | 403 | 60.524 | 43.394 | 27.597 | 1.00 | 60.37 |

Page 6-A-90

| ATOM | 3771 | OD1 | ASP | A | 403 | 61.001 | 43.915 | 26.563 | 1.00 | 60.48 |
|------|------|-----|-----|---|-----|--------|--------|--------|------|-------|
| ATOM | 3772 | OD2 | ASP | A | 403 | 59.325 | 43.045 | 27.691 | 1.00 | 61.61 |
| ATOM | 3773 | C   | ASP | A | 403 | 63.615 | 42.204 | 29.638 | 1.00 | 53.27 |
| ATOM | 3774 | O   | ASP | A | 403 | 64.669 | 42.836 | 29.525 | 1.00 | 53.59 |
| ATOM | 3775 | N   | ILE | A | 404 | 63.318 | 41.487 | 30.719 | 1.00 | 51.11 |
| ATOM | 3777 | CA  | ILE | A | 404 | 64.229 | 41.387 | 31.852 | 1.00 | 48.30 |
| ATOM | 3778 | CB  | ILE | A | 404 | 63.545 | 40.668 | 33.055 | 1.00 | 45.31 |
| ATOM | 3779 | CG2 | ILE | A | 404 | 64.352 | 39.468 | 33.530 | 1.00 | 47.52 |
| ATOM | 3780 | CG1 | ILE | A | 404 | 63.337 | 41.654 | 34.203 | 1.00 | 42.01 |
| ATOM | 3781 | CD1 | ILE | A | 404 | 64.620 | 42.234 | 34.752 | 1.00 | 36.04 |
| ATOM | 3782 | C   | ILE | A | 404 | 65.497 | 40.656 | 31.400 | 1.00 | 48.48 |
| ATOM | 3783 | O   | ILE | A | 404 | 66.611 | 41.108 | 31.667 | 1.00 | 51.31 |
| ATOM | 3784 | N   | MET | A | 405 | 65.318 | 39.564 | 30.660 | 1.00 | 47.51 |
| ATOM | 3786 | CA  | MET | A | 405 | 66.433 | 38.768 | 30.151 | 1.00 | 47.38 |
| ATOM | 3787 | CB  | MET | A | 405 | 65.920 | 37.479 | 29.505 | 1.00 | 47.17 |
| ATOM | 3788 | CG  | MET | A | 405 | 66.151 | 36.233 | 30.345 | 1.00 | 48.66 |
| ATOM | 3789 | SD  | MET | A | 405 | 65.913 | 36.487 | 32.115 | 1.00 | 49.07 |
| ATOM | 3790 | CE  | MET | A | 405 | 67.594 | 36.786 | 32.640 | 1.00 | 50.09 |
| ATOM | 3791 | C   | MET | A | 405 | 67.291 | 39.540 | 29.160 | 1.00 | 46.62 |
| ATOM | 3792 | O   | MET | A | 405 | 68.500 | 39.339 | 29.092 | 1.00 | 48.06 |
| ATOM | 3793 | N   | ASN | A | 406 | 66.666 | 40.441 | 28.413 | 1.00 | 46.76 |
| ATOM | 3795 | CA  | ASN | A | 406 | 67.383 | 41.239 | 27.433 | 1.00 | 47.68 |
| ATOM | 3796 | CB  | ASN | A | 406 | 66.467 | 41.675 | 26.295 | 1.00 | 51.33 |
| ATOM | 3797 | CG  | ASN | A | 406 | 66.534 | 40.732 | 25.115 | 1.00 | 54.24 |
| ATOM | 3798 | OD1 | ASN | A | 406 | 67.448 | 40.813 | 24.290 | 1.00 | 55.58 |
| ATOM | 3799 | ND2 | ASN | A | 406 | 65.580 | 39.814 | 25.039 | 1.00 | 54.80 |
| ATOM | 3802 | C   | ASN | A | 406 | 68.134 | 42.430 | 27.999 | 1.00 | 46.60 |
| ATOM | 3803 | O   | ASN | A | 406 | 68.803 | 43.148 | 27.263 | 1.00 | 48.59 |
| ATOM | 3804 | N   | TYR | A | 407 | 67.993 | 42.674 | 29.293 | 1.00 | 45.78 |
| ATOM | 3806 | CA  | TYR | A | 407 | 68.732 | 43.760 | 29.922 | 1.00 | 44.83 |
| ATOM | 3807 | CB  | TYR | A | 407 | 67.825 | 44.613 | 30.829 | 1.00 | 46.29 |
| ATOM | 3808 | CG  | TYR | A | 407 | 68.558 | 45.733 | 31.553 | 1.00 | 45.38 |
| ATOM | 3809 | CD1 | TYR | A | 407 | 68.891 | 46.916 | 30.897 | 1.00 | 45.96 |
| ATOM | 3810 | CE1 | TYR | A | 407 | 69.621 | 47.915 | 31.540 | 1.00 | 47.49 |

Page 6-A-91

| | | | | | | | | |
|---|---|---|---|---|---|---|---|---|
| ATOM | 3811 | CD2 | TYR A 407 | 68.966 | 45.582 | 32.880 | 1.00 | 45.49 |
| ATOM | 3812 | CE2 | TYR A 407 | 69.694 | 46.573 | 33.532 | 1.00 | 44.88 |
| ATOM | 3813 | CZ | TYR A 407 | 70.022 | 47.733 | 32.858 | 1.00 | 47.09 |
| ATOM | 3814 | OH | TYR A 407 | 70.771 | 48.701 | 33.493 | 1.00 | 48.41 |
| ATOM | 3816 | C | TYR A 407 | 69.837 | 43.080 | 30.730 | 1.00 | 43.05 |
| ATOM | 3817 | O | TYR A 407 | 71.024 | 43.262 | 30.462 | 1.00 | 42.68 |
| ATOM | 3818 | N | ILE A 408 | 69.423 | 42.229 | 31.661 | 1.00 | 41.43 |
| ATOM | 3820 | CA | ILE A 408 | 70.332 | 41.490 | 32.523 | 1.00 | 40.32 |
| ATOM | 3821 | CB | ILE A 408 | 69.580 | 40.371 | 33.272 | 1.00 | 40.57 |
| ATOM | 3822 | CG2 | ILE A 408 | 70.550 | 39.445 | 33.978 | 1.00 | 42.21 |
| ATOM | 3823 | CG1 | ILE A 408 | 68.613 | 40.974 | 34.281 | 1.00 | 41.88 |
| ATOM | 3824 | CD1 | ILE A 408 | 67.762 | 39.937 | 34.976 | 1.00 | 46.39 |
| ATOM | 3825 | C | ILE A 408 | 71.480 | 40.861 | 31.746 | 1.00 | 39.97 |
| ATOM | 3826 | O | ILE A 408 | 72.639 | 41.158 | 32.006 | 1.00 | 40.89 |
| ATOM | 3827 | N | VAL A 409 | 71.155 | 40.027 | 30.767 | 1.00 | 39.94 |
| ATOM | 3829 | CA | VAL A 409 | 72.178 | 39.342 | 29.988 | 1.00 | 39.04 |
| ATOM | 3830 | CB | VAL A 409 | 71.560 | 38.354 | 28.961 | 1.00 | 38.16 |
| ATOM | 3831 | CG1 | VAL A 409 | 72.656 | 37.687 | 28.142 | 1.00 | 37.45 |
| ATOM | 3832 | CG2 | VAL A 409 | 70.741 | 37.291 | 29.686 | 1.00 | 36.14 |
| ATOM | 3833 | C | VAL A 409 | 73.252 | 40.227 | 29.343 | 1.00 | 38.82 |
| ATOM | 3834 | O | VAL A 409 | 74.426 | 40.093 | 29.675 | 1.00 | 39.64 |
| ATOM | 3835 | N | PRO A 410 | 72.881 | 41.145 | 28.432 | 1.00 | 38.89 |
| ATOM | 3836 | CD | PRO A 410 | 71.583 | 41.362 | 27.770 | 1.00 | 38.55 |
| ATOM | 3837 | CA | PRO A 410 | 73.917 | 41.984 | 27.818 | 1.00 | 38.75 |
| ATOM | 3838 | CB | PRO A 410 | 73.207 | 42.562 | 26.597 | 1.00 | 38.19 |
| ATOM | 3839 | CG | PRO A 410 | 71.806 | 42.667 | 27.051 | 1.00 | 38.80 |
| ATOM | 3840 | C | PRO A 410 | 74.535 | 43.083 | 28.685 | 1.00 | 40.43 |
| ATOM | 3841 | O | PRO A 410 | 75.607 | 43.593 | 28.359 | 1.00 | 41.27 |
| ATOM | 3842 | N | ILE A 411 | 73.870 | 43.461 | 29.771 | 1.00 | 41.44 |
| ATOM | 3844 | CA | ILE A 411 | 74.404 | 44.503 | 30.649 | 1.00 | 41.02 |
| ATOM | 3845 | CB | ILE A 411 | 73.285 | 45.380 | 31.239 | 1.00 | 40.99 |
| ATOM | 3846 | CG2 | ILE A 411 | 73.890 | 46.497 | 32.086 | 1.00 | 41.83 |
| ATOM | 3847 | CG1 | ILE A 411 | 72.418 | 45.967 | 30.122 | 1.00 | 42.47 |
| ATOM | 3848 | CD1 | ILE A 411 | 73.112 | 47.005 | 29.264 | 1.00 | 45.28 |

Page 6-A-92

| ATOM | 3849 | C   | ILE A 411 | 75.212 | 43.923 | 31.809 | 1.00 | 40.15 |
| ATOM | 3850 | O   | ILE A 411 | 76.254 | 44.460 | 32.186 | 1.00 | 39.92 |
| ATOM | 3851 | N   | LEU A 412 | 74.716 | 42.831 | 32.379 | 1.00 | 39.13 |
| ATOM | 3853 | CA  | LEU A 412 | 75.373 | 42.185 | 33.506 | 1.00 | 39.13 |
| ATOM | 3854 | CB  | LEU A 412 | 74.335 | 41.817 | 34.570 | 1.00 | 39.71 |
| ATOM | 3855 | CG  | LEU A 412 | 73.493 | 42.941 | 35.179 | 1.00 | 38.70 |
| ATOM | 3856 | CD1 | LEU A 412 | 72.548 | 42.362 | 36.220 | 1.00 | 36.24 |
| ATOM | 3857 | CD2 | LEU A 412 | 74.403 | 43.986 | 35.802 | 1.00 | 39.15 |
| ATOM | 3858 | C   | LEU A 412 | 76.209 | 40.945 | 33.175 | 1.00 | 39.67 |
| ATOM | 3859 | O   | LEU A 412 | 77.322 | 40.796 | 33.677 | 1.00 | 41.17 |
| ATOM | 3860 | N   | VAL A 413 | 75.678 | 40.060 | 32.336 | 1.00 | 38.13 |
| ATOM | 3862 | CA  | VAL A 413 | 76.369 | 38.818 | 31.991 | 1.00 | 37.18 |
| ATOM | 3863 | CB  | VAL A 413 | 75.344 | 37.708 | 31.642 | 1.00 | 38.08 |
| ATOM | 3864 | CG1 | VAL A 413 | 76.042 | 36.373 | 31.445 | 1.00 | 39.08 |
| ATOM | 3865 | CG2 | VAL A 413 | 74.303 | 37.591 | 32.753 | 1.00 | 35.49 |
| ATOM | 3866 | C   | VAL A 413 | 77.477 | 38.893 | 30.926 | 1.00 | 36.23 |
| ATOM | 3867 | O   | VAL A 413 | 78.634 | 38.583 | 31.221 | 1.00 | 36.97 |
| ATOM | 3868 | N   | LEU A 414 | 77.134 | 39.296 | 29.702 | 1.00 | 34.70 |
| ATOM | 3870 | CA  | LEU A 414 | 78.108 | 39.394 | 28.610 | 1.00 | 32.37 |
| ATOM | 3871 | CB  | LEU A 414 | 77.500 | 40.081 | 27.390 | 1.00 | 31.45 |
| ATOM | 3872 | CG  | LEU A 414 | 77.451 | 39.326 | 26.062 | 1.00 | 31.86 |
| ATOM | 3873 | CD1 | LEU A 414 | 77.167 | 40.338 | 24.952 | 1.00 | 34.05 |
| ATOM | 3874 | CD2 | LEU A 414 | 78.751 | 38.585 | 25.790 | 1.00 | 30.36 |
| ATOM | 3875 | C   | LEU A 414 | 79.403 | 40.109 | 28.972 | 1.00 | 33.92 |
| ATOM | 3876 | O   | LEU A 414 | 80.485 | 39.643 | 28.619 | 1.00 | 36.82 |
| ATOM | 3877 | N   | PRO A 415 | 79.314 | 41.285 | 29.619 | 1.00 | 34.56 |
| ATOM | 3878 | CD  | PRO A 415 | 78.103 | 42.090 | 29.858 | 1.00 | 34.83 |
| ATOM | 3879 | CA  | PRO A 415 | 80.503 | 42.046 | 30.011 | 1.00 | 35.76 |
| ATOM | 3880 | CB  | PRO A 415 | 79.915 | 43.149 | 30.883 | 1.00 | 35.11 |
| ATOM | 3881 | CG  | PRO A 415 | 78.673 | 43.467 | 30.151 | 1.00 | 35.76 |
| ATOM | 3882 | C   | PRO A 415 | 81.583 | 41.263 | 30.748 | 1.00 | 36.22 |
| ATOM | 3883 | O   | PRO A 415 | 82.760 | 41.387 | 30.418 | 1.00 | 37.32 |
| ATOM | 3884 | N   | ARG A 416 | 81.194 | 40.466 | 31.739 | 1.00 | 39.00 |
| ATOM | 3886 | CA  | ARG A 416 | 82.167 | 39.686 | 32.501 | 1.00 | 41.92 |

| | | | | | | | | |
|---|---|---|---|---|---|---|---|---|
| ATOM | 3887 | CB | ARG A 416 | 81.517 | 39.047 | 33.731 | 1.00 | 46.13 |
| ATOM | 3888 | CG | ARG A 416 | 81.111 | 40.038 | 34.823 | 1.00 | 52.86 |
| ATOM | 3889 | CD | ARG A 416 | 82.299 | 40.830 | 35.366 | 1.00 | 60.47 |
| ATOM | 3890 | NE | ARG A 416 | 83.287 | 39.986 | 36.040 | 1.00 | 69.03 |
| ATOM | 3892 | CZ | ARG A 416 | 83.205 | 39.589 | 37.309 | 1.00 | 73.10 |
| ATOM | 3893 | NH1 | ARG A 416 | 82.174 | 39.955 | 38.062 | 1.00 | 76.24 |
| ATOM | 3896 | NH2 | ARG A 416 | 84.163 | 38.833 | 37.834 | 1.00 | 73.45 |
| ATOM | 3899 | C | ARG A 416 | 82.826 | 38.622 | 31.636 | 1.00 | 42.34 |
| ATOM | 3900 | O | ARG A 416 | 84.031 | 38.405 | 31.717 | 1.00 | 43.31 |
| ATOM | 3901 | N | VAL A 417 | 82.040 | 37.990 | 30.774 | 1.00 | 42.15 |
| ATOM | 3903 | CA | VAL A 417 | 82.554 | 36.955 | 29.886 | 1.00 | 41.06 |
| ATOM | 3904 | CB | VAL A 417 | 81.418 | 36.302 | 29.091 | 1.00 | 43.59 |
| ATOM | 3905 | CG1 | VAL A 417 | 81.976 | 35.261 | 28.127 | 1.00 | 48.62 |
| ATOM | 3906 | CG2 | VAL A 417 | 80.414 | 35.672 | 30.038 | 1.00 | 45.02 |
| ATOM | 3907 | C | VAL A 417 | 83.581 | 37.500 | 28.902 | 1.00 | 38.49 |
| ATOM | 3908 | O | VAL A 417 | 84.658 | 36.929 | 28.729 | 1.00 | 38.46 |
| ATOM | 3909 | N | ASN A 418 | 83.236 | 38.598 | 28.243 | 1.00 | 36.89 |
| ATOM | 3911 | CA | ASN A 418 | 84.130 | 39.206 | 27.273 | 1.00 | 34.67 |
| ATOM | 3912 | CB | ASN A 418 | 83.448 | 40.370 | 26.564 | 1.00 | 36.25 |
| ATOM | 3913 | CG | ASN A 418 | 82.506 | 39.913 | 25.475 | 1.00 | 37.58 |
| ATOM | 3914 | OD1 | ASN A 418 | 82.585 | 38.776 | 25.014 | 1.00 | 39.99 |
| ATOM | 3915 | ND2 | ASN A 418 | 81.613 | 40.796 | 25.055 | 1.00 | 36.92 |
| ATOM | 3918 | C | ASN A 418 | 85.426 | 39.671 | 27.896 | 1.00 | 34.68 |
| ATOM | 3919 | O | ASN A 418 | 86.421 | 39.831 | 27.199 | 1.00 | 35.38 |
| ATOM | 3920 | N | GLU A 419 | 85.426 | 39.895 | 29.206 | 1.00 | 35.06 |
| ATOM | 3922 | CA | GLU A 419 | 86.640 | 40.336 | 29.879 | 1.00 | 37.31 |
| ATOM | 3923 | CB | GLU A 419 | 86.351 | 40.788 | 31.304 | 1.00 | 41.20 |
| ATOM | 3924 | CG | GLU A 419 | 87.557 | 41.433 | 31.972 | 1.00 | 49.99 |
| ATOM | 3925 | CD | GLU A 419 | 87.312 | 41.800 | 33.419 | 1.00 | 54.63 |
| ATOM | 3926 | OE1 | GLU A 419 | 86.182 | 42.226 | 33.751 | 1.00 | 59.06 |
| ATOM | 3927 | OE2 | GLU A 419 | 88.257 | 41.666 | 34.227 | 1.00 | 59.31 |
| ATOM | 3928 | C | GLU A 419 | 87.682 | 39.222 | 29.889 | 1.00 | 37.58 |
| ATOM | 3929 | O | GLU A 419 | 88.882 | 39.486 | 29.785 | 1.00 | 38.06 |
| ATOM | 3930 | N | LYS A 420 | 87.232 | 37.980 | 30.049 | 1.00 | 37.28 |

| ATOM | 3932 | CA  | LYS A 420 | 88.154 | 36.853 | 30.033 | 1.00 | 37.63 |
| ATOM | 3933 | CB  | LYS A 420 | 87.492 | 35.591 | 30.587 | 1.00 | 37.80 |
| ATOM | 3934 | CG  | LYS A 420 | 88.379 | 34.342 | 30.510 | 1.00 | 43.22 |
| ATOM | 3935 | CD  | LYS A 420 | 89.698 | 34.521 | 31.265 | 1.00 | 46.31 |
| ATOM | 3936 | CE  | LYS A 420 | 90.650 | 33.352 | 31.031 | 1.00 | 48.33 |
| ATOM | 3937 | NZ  | LYS A 420 | 91.993 | 33.578 | 31.644 | 1.00 | 48.07 |
| ATOM | 3941 | C   | LYS A 420 | 88.610 | 36.631 | 28.593 | 1.00 | 38.72 |
| ATOM | 3942 | O   | LYS A 420 | 89.802 | 36.479 | 28.329 | 1.00 | 41.62 |
| ATOM | 3943 | N   | LEU A 421 | 87.663 | 36.659 | 27.657 | 1.00 | 38.62 |
| ATOM | 3945 | CA  | LEU A 421 | 87.975 | 36.466 | 26.246 | 1.00 | 38.52 |
| ATOM | 3946 | CB  | LEU A 421 | 86.705 | 36.474 | 25.395 | 1.00 | 36.49 |
| ATOM | 3947 | CG  | LEU A 421 | 85.770 | 35.278 | 25.539 | 1.00 | 34.05 |
| ATOM | 3948 | CD1 | LEU A 421 | 84.533 | 35.489 | 24.703 | 1.00 | 31.56 |
| ATOM | 3949 | CD2 | LEU A 421 | 86.492 | 34.014 | 25.113 | 1.00 | 36.95 |
| ATOM | 3950 | C   | LEU A 421 | 88.941 | 37.525 | 25.744 | 1.00 | 40.94 |
| ATOM | 3951 | O   | LEU A 421 | 89.797 | 37.237 | 24.917 | 1.00 | 43.18 |
| ATOM | 3952 | N   | GLN A 422 | 88.783 | 38.756 | 26.218 | 1.00 | 44.55 |
| ATOM | 3954 | CA  | GLN A 422 | 89.672 | 39.844 | 25.820 | 1.00 | 48.56 |
| ATOM | 3955 | CB  | GLN A 422 | 89.036 | 41.210 | 26.101 | 1.00 | 52.32 |
| ATOM | 3956 | CG  | GLN A 422 | 88.278 | 41.821 | 24.914 | 1.00 | 58.07 |
| ATOM | 3957 | CD  | GLN A 422 | 89.197 | 42.459 | 23.863 | 1.00 | 62.49 |
| ATOM | 3958 | OE1 | GLN A 422 | 90.361 | 42.770 | 24.133 | 1.00 | 63.36 |
| ATOM | 3959 | NE2 | GLN A 422 | 88.661 | 42.673 | 22.665 | 1.00 | 63.04 |
| ATOM | 3962 | C   | GLN A 422 | 91.037 | 39.725 | 26.501 | 1.00 | 49.05 |
| ATOM | 3963 | O   | GLN A 422 | 92.013 | 40.323 | 26.045 | 1.00 | 50.57 |
| ATOM | 3964 | N   | LYS A 423 | 91.096 | 38.996 | 27.615 | 1.00 | 49.71 |
| ATOM | 3966 | CA  | LYS A 423 | 92.366 | 38.777 | 28.305 | 1.00 | 50.46 |
| ATOM | 3967 | CB  | LYS A 423 | 92.151 | 38.125 | 29.670 | 1.00 | 52.85 |
| ATOM | 3968 | CG  | LYS A 423 | 93.442 | 37.862 | 30.434 | 1.00 | 56.39 |
| ATOM | 3969 | CD  | LYS A 423 | 93.156 | 37.388 | 31.845 | 1.00 | 59.26 |
| ATOM | 3970 | CE  | LYS A 423 | 92.354 | 38.432 | 32.611 | 1.00 | 60.80 |
| ATOM | 3971 | NZ  | LYS A 423 | 92.070 | 37.998 | 34.006 | 1.00 | 64.66 |
| ATOM | 3975 | C   | LYS A 423 | 93.108 | 37.827 | 27.378 | 1.00 | 49.36 |
| ATOM | 3976 | O   | LYS A 423 | 94.320 | 37.945 | 27.174 | 1.00 | 51.82 |

| | | | | | | | | |
|---|---|---|---|---|---|---|---|---|
| ATOM | 3977 | N | GLY | A 424 | 92.349 | 36.884 | 26.824 | 1.00 46.45 |
| ATOM | 3979 | CA | GLY | A 424 | 92.883 | 35.939 | 25.868 | 1.00 40.64 |
| ATOM | 3980 | C | GLY | A 424 | 93.484 | 34.658 | 26.377 | 1.00 38.23 |
| ATOM | 3981 | O | GLY | A 424 | 93.364 | 34.303 | 27.552 | 1.00 36.91 |
| ATOM | 3982 | N | PHE | A 425 | 94.111 | 33.950 | 25.445 | 1.00 36.95 |
| ATOM | 3984 | CA | PHE | A 425 | 94.768 | 32.684 | 25.712 | 1.00 34.69 |
| ATOM | 3985 | CB | PHE | A 425 | 93.986 | 31.530 | 25.075 | 1.00 38.25 |
| ATOM | 3986 | CG | PHE | A 425 | 92.570 | 31.402 | 25.571 | 1.00 44.42 |
| ATOM | 3987 | CD1 | PHE | A 425 | 92.294 | 31.343 | 26.937 | 1.00 44.31 |
| ATOM | 3988 | CD2 | PHE | A 425 | 91.508 | 31.345 | 24.671 | 1.00 46.34 |
| ATOM | 3989 | CE1 | PHE | A 425 | 90.986 | 31.235 | 27.399 | 1.00 45.62 |
| ATOM | 3990 | CE2 | PHE | A 425 | 90.192 | 31.236 | 25.125 | 1.00 48.05 |
| ATOM | 3991 | CZ | PHE | A 425 | 89.933 | 31.181 | 26.492 | 1.00 46.50 |
| ATOM | 3992 | C | PHE | A 425 | 96.153 | 32.748 | 25.091 | 1.00 31.44 |
| ATOM | 3993 | O | PHE | A 425 | 96.316 | 33.236 | 23.982 | 1.00 31.46 |
| ATOM | 3994 | N | PRO | A 426 | 97.176 | 32.316 | 25.831 | 1.00 29.84 |
| ATOM | 3995 | CD | PRO | A 426 | 97.076 | 31.978 | 27.259 | 1.00 30.24 |
| ATOM | 3996 | CA | PRO | A 426 | 98.571 | 32.299 | 25.396 | 1.00 30.20 |
| ATOM | 3997 | CB | PRO | A 426 | 99.269 | 31.630 | 26.570 | 1.00 28.60 |
| ATOM | 3998 | CG | PRO | A 426 | 98.494 | 32.133 | 27.725 | 1.00 31.57 |
| ATOM | 3999 | C | PRO | A 426 | 98.777 | 31.489 | 24.123 | 1.00 31.10 |
| ATOM | 4000 | O | PRO | A 426 | 98.258 | 30.377 | 23.998 | 1.00 34.08 |
| ATOM | 4001 | N | LEU | A 427 | 99.570 | 32.033 | 23.203 | 1.00 29.97 |
| ATOM | 4003 | CA | LEU | A 427 | 99.878 | 31.377 | 21.935 | 1.00 29.50 |
| ATOM | 4004 | CB | LEU | A 427 | 99.991 | 32.433 | 20.831 | 1.00 28.79 |
| ATOM | 4005 | CG | LEU | A 427 | 99.106 | 32.365 | 19.576 | 1.00 31.67 |
| ATOM | 4006 | CD1 | LEU | A 427 | 97.713 | 31.822 | 19.854 | 1.00 29.49 |
| ATOM | 4007 | CD2 | LEU | A 427 | 99.020 | 33.753 | 18.977 | 1.00 30.38 |
| ATOM | 4008 | C | LEU | A 427 | 101.189 | 30.602 | 22.095 | 1.00 28.95 |
| ATOM | 4009 | O | LEU | A 427 | 102.012 | 30.939 | 22.943 | 1.00 30.17 |
| ATOM | 4010 | N | PRO | A 428 | 101.396 | 29.548 | 21.293 | 1.00 29.54 |
| ATOM | 4011 | CD | PRO | A 428 | 100.502 | 29.048 | 20.234 | 1.00 29.81 |
| ATOM | 4012 | CA | PRO | A 428 | 102.614 | 28.734 | 21.368 | 1.00 31.77 |
| ATOM | 4013 | CB | PRO | A 428 | 102.218 | 27.492 | 20.584 | 1.00 30.20 |

Page 6-A-96

| | | | | | | | | | |
|---|---|---|---|---|---|---|---|---|---|
| ATOM | 4014 | CG | PRO | A | 428 | 101.382 | 28.073 | 19.490 | 1.00 27.41 |
| ATOM | 4015 | C | PRO | A | 428 | 103.843 | 29.405 | 20.753 | 1.00 35.74 |
| ATOM | 4016 | O | PRO | A | 428 | 104.361 | 28.950 | 19.731 | 1.00 39.47 |
| ATOM | 4017 | N | THR | A | 429 | 104.323 | 30.472 | 21.379 | 1.00 36.82 |
| ATOM | 4019 | CA | THR | A | 429 | 105.486 | 31.189 | 20.866 | 1.00 36.58 |
| ATOM | 4020 | CB | THR | A | 429 | 105.200 | 32.694 | 20.735 | 1.00 38.98 |
| ATOM | 4021 | OG1 | THR | A | 429 | 104.616 | 33.183 | 21.953 | 1.00 37.38 |
| ATOM | 4023 | CG2 | THR | A | 429 | 104.262 | 32.956 | 19.565 | 1.00 41.95 |
| ATOM | 4024 | C | THR | A | 429 | 106.686 | 31.024 | 21.769 | 1.00 35.72 |
| ATOM | 4025 | O | THR | A | 429 | 106.567 | 31.108 | 22.994 | 1.00 35.83 |
| ATOM | 4026 | N | PRO | A | 430 | 107.867 | 30.791 | 21.182 | 1.00 34.72 |
| ATOM | 4027 | CD | PRO | A | 430 | 108.180 | 30.643 | 19.753 | 1.00 36.21 |
| ATOM | 4028 | CA | PRO | A | 430 | 109.069 | 30.629 | 21.995 | 1.00 34.61 |
| ATOM | 4029 | CB | PRO | A | 430 | 110.124 | 30.235 | 20.963 | 1.00 33.90 |
| ATOM | 4030 | CG | PRO | A | 430 | 109.658 | 30.907 | 19.726 | 1.00 33.59 |
| ATOM | 4031 | C | PRO | A | 430 | 109.388 | 31.946 | 22.691 | 1.00 35.01 |
| ATOM | 4032 | O | PRO | A | 430 | 108.648 | 32.924 | 22.553 | 1.00 37.38 |
| ATOM | 4033 | N | ALA | A | 431 | 110.457 | 31.973 | 23.471 | 1.00 34.16 |
| ATOM | 4035 | CA | ALA | A | 431 | 110.824 | 33.190 | 24.173 | 1.00 36.53 |
| ATOM | 4036 | CB | ALA | A | 431 | 111.801 | 32.878 | 25.298 | 1.00 36.36 |
| ATOM | 4037 | C | ALA | A | 431 | 111.416 | 34.241 | 23.243 | 1.00 38.15 |
| ATOM | 4038 | O | ALA | A | 431 | 111.944 | 33.932 | 22.174 | 1.00 39.81 |
| ATOM | 4039 | N | ARG | A | 432 | 111.270 | 35.495 | 23.641 | 1.00 40.43 |
| ATOM | 4041 | CA | ARG | A | 432 | 111.819 | 36.620 | 22.902 | 1.00 41.66 |
| ATOM | 4042 | CB | ARG | A | 432 | 113.349 | 36.537 | 22.887 | 1.00 44.65 |
| ATOM | 4043 | CG | ARG | A | 432 | 113.990 | 36.686 | 24.262 | 1.00 51.96 |
| ATOM | 4044 | CD | ARG | A | 432 | 115.516 | 36.654 | 24.185 | 1.00 59.79 |
| ATOM | 4045 | NE | ARG | A | 432 | 116.029 | 35.372 | 23.700 | 1.00 63.72 |
| ATOM | 4047 | CZ | ARG | A | 432 | 117.302 | 34.993 | 23.777 | 1.00 67.96 |
| ATOM | 4048 | NH1 | ARG | A | 432 | 118.212 | 35.795 | 24.320 | 1.00 70.88 |
| ATOM | 4051 | NH2 | ARG | A | 432 | 117.668 | 33.804 | 23.314 | 1.00 68.07 |
| ATOM | 4054 | C | ARG | A | 432 | 111.293 | 36.898 | 21.499 | 1.00 40.87 |
| ATOM | 4055 | O | ARG | A | 432 | 111.963 | 37.567 | 20.721 | 1.00 42.99 |
| ATOM | 4056 | N | VAL | A | 433 | 110.103 | 36.414 | 21.166 | 1.00 40.50 |

| ATOM | 4058 | CA | VAL | A | 433 | 109.538 | 36.693 | 19.847 | 1.00 | 39.69 |
| ATOM | 4059 | CB | VAL | A | 433 | 109.325 | 35.415 | 18.982 | 1.00 | 39.93 |
| ATOM | 4060 | CG1 | VAL | A | 433 | 110.588 | 34.575 | 18.943 | 1.00 | 39.03 |
| ATOM | 4061 | CG2 | VAL | A | 433 | 108.134 | 34.608 | 19.470 | 1.00 | 39.91 |
| ATOM | 4062 | C | VAL | A | 433 | 108.206 | 37.399 | 20.024 | 1.00 | 41.27 |
| ATOM | 4063 | O | VAL | A | 433 | 107.538 | 37.240 | 21.048 | 1.00 | 43.57 |
| ATOM | 4064 | N | GLN | A | 434 | 107.845 | 38.223 | 19.053 | 1.00 | 41.32 |
| ATOM | 4066 | CA | GLN | A | 434 | 106.583 | 38.939 | 19.104 | 1.00 | 41.91 |
| ATOM | 4067 | CB | GLN | A | 434 | 106.802 | 40.411 | 19.454 | 1.00 | 45.76 |
| ATOM | 4068 | CG | GLN | A | 434 | 105.706 | 41.018 | 20.335 | 1.00 | 52.61 |
| ATOM | 4069 | CD | GLN | A | 434 | 105.850 | 40.687 | 21.829 | 1.00 | 56.74 |
| ATOM | 4070 | OE1 | GLN | A | 434 | 105.372 | 41.436 | 22.681 | 1.00 | 58.13 |
| ATOM | 4071 | NE2 | GLN | A | 434 | 106.512 | 39.579 | 22.149 | 1.00 | 57.45 |
| ATOM | 4074 | C | GLN | A | 434 | 106.005 | 38.804 | 17.716 | 1.00 | 40.30 |
| ATOM | 4075 | O | GLN | A | 434 | 106.745 | 38.821 | 16.732 | 1.00 | 40.86 |
| ATOM | 4076 | N | LEU | A | 435 | 104.695 | 38.614 | 17.642 | 1.00 | 39.20 |
| ATOM | 4078 | CA | LEU | A | 435 | 104.018 | 38.439 | 16.366 | 1.00 | 39.99 |
| ATOM | 4079 | CB | LEU | A | 435 | 102.965 | 37.338 | 16.501 | 1.00 | 38.11 |
| ATOM | 4080 | CG | LEU | A | 435 | 103.347 | 36.088 | 17.309 | 1.00 | 37.55 |
| ATOM | 4081 | CD1 | LEU | A | 435 | 102.118 | 35.238 | 17.538 | 1.00 | 37.75 |
| ATOM | 4082 | CD2 | LEU | A | 435 | 104.426 | 35.281 | 16.613 | 1.00 | 36.46 |
| ATOM | 4083 | C | LEU | A | 435 | 103.358 | 39.739 | 15.916 | 1.00 | 41.18 |
| ATOM | 4084 | O | LEU | A | 435 | 102.660 | 40.387 | 16.695 | 1.00 | 42.90 |
| ATOM | 4085 | N | TYR | A | 436 | 103.590 | 40.125 | 14.665 | 1.00 | 42.57 |
| ATOM | 4087 | CA | TYR | A | 436 | 103.004 | 41.348 | 14.116 | 1.00 | 43.80 |
| ATOM | 4088 | CB | TYR | A | 436 | 104.021 | 42.510 | 14.120 | 1.00 | 43.48 |
| ATOM | 4089 | CG | TYR | A | 436 | 105.232 | 42.328 | 13.224 | 1.00 | 43.66 |
| ATOM | 4090 | CD1 | TYR | A | 436 | 106.259 | 41.452 | 13.573 | 1.00 | 43.96 |
| ATOM | 4091 | CE1 | TYR | A | 436 | 107.364 | 41.271 | 12.743 | 1.00 | 44.63 |
| ATOM | 4092 | CD2 | TYR | A | 436 | 105.345 | 43.028 | 12.020 | 1.00 | 43.04 |
| ATOM | 4093 | CE2 | TYR | A | 436 | 106.448 | 42.852 | 11.181 | 1.00 | 43.53 |
| ATOM | 4094 | CZ | TYR | A | 436 | 107.452 | 41.970 | 11.549 | 1.00 | 44.29 |
| ATOM | 4095 | OH | TYR | A | 436 | 108.528 | 41.757 | 10.711 | 1.00 | 44.66 |
| ATOM | 4097 | C | TYR | A | 436 | 102.457 | 41.090 | 12.712 | 1.00 | 43.77 |

| ATOM | 4098 | O | TYR A 436 | 102.729 | 40.046 | 12.122 | 1.00 | 45.49 |
| --- | --- | --- | --- | --- | --- | --- | --- | --- |
| ATOM | 4099 | N | ASN A 437 | 101.687 | 42.042 | 12.189 | 1.00 | 45.09 |
| ATOM | 4101 | CA | ASN A 437 | 101.069 | 41.932 | 10.865 | 1.00 | 45.97 |
| ATOM | 4102 | CB | ASN A 437 | 102.083 | 42.231 | 9.750 | 1.00 | 51.76 |
| ATOM | 4103 | CG | ASN A 437 | 102.161 | 43.720 | 9.416 | 1.00 | 57.75 |
| ATOM | 4104 | OD1 | ASN A 437 | 102.832 | 44.492 | 10.105 | 1.00 | 59.59 |
| ATOM | 4105 | ND2 | ASN A 437 | 101.450 | 44.131 | 8.370 | 1.00 | 60.25 |
| ATOM | 4108 | C | ASN A 437 | 100.385 | 40.581 | 10.665 | 1.00 | 44.47 |
| ATOM | 4109 | O | ASN A 437 | 100.743 | 39.797 | 9.786 | 1.00 | 44.02 |
| ATOM | 4110 | N | VAL A 438 | 99.360 | 40.344 | 11.475 | 1.00 | 44.00 |
| ATOM | 4112 | CA | VAL A 438 | 98.622 | 39.091 | 11.444 | 1.00 | 43.09 |
| ATOM | 4113 | CB | VAL A 438 | 98.214 | 38.646 | 12.871 | 1.00 | 43.35 |
| ATOM | 4114 | CG1 | VAL A 438 | 99.425 | 38.629 | 13.786 | 1.00 | 43.74 |
| ATOM | 4115 | CG2 | VAL A 438 | 97.143 | 39.562 | 13.433 | 1.00 | 43.99 |
| ATOM | 4116 | C | VAL A 438 | 97.374 | 39.101 | 10.579 | 1.00 | 41.42 |
| ATOM | 4117 | O | VAL A 438 | 96.740 | 40.139 | 10.377 | 1.00 | 39.58 |
| ATOM | 4118 | N | VAL A 439 | 97.018 | 37.912 | 10.110 | 1.00 | 41.86 |
| ATOM | 4120 | CA | VAL A 439 | 95.839 | 37.689 | 9.291 | 1.00 | 43.18 |
| ATOM | 4121 | CB | VAL A 439 | 96.202 | 37.377 | 7.829 | 1.00 | 42.54 |
| ATOM | 4122 | CG1 | VAL A 439 | 96.568 | 38.646 | 7.104 | 1.00 | 46.06 |
| ATOM | 4123 | CG2 | VAL A 439 | 97.351 | 36.391 | 7.770 | 1.00 | 41.82 |
| ATOM | 4124 | C | VAL A 439 | 95.117 | 36.482 | 9.866 | 1.00 | 43.37 |
| ATOM | 4125 | O | VAL A 439 | 95.733 | 35.446 | 10.103 | 1.00 | 45.02 |
| ATOM | 4126 | N | LEU A 440 | 93.829 | 36.631 | 10.141 | 1.00 | 43.45 |
| ATOM | 4128 | CA | LEU A 440 | 93.041 | 35.535 | 10.681 | 1.00 | 42.92 |
| ATOM | 4129 | CB | LEU A 440 | 92.355 | 35.956 | 11.978 | 1.00 | 42.49 |
| ATOM | 4130 | CG | LEU A 440 | 93.220 | 36.062 | 13.234 | 1.00 | 42.93 |
| ATOM | 4131 | CD1 | LEU A 440 | 93.920 | 34.745 | 13.462 | 1.00 | 44.28 |
| ATOM | 4132 | CD2 | LEU A 440 | 94.231 | 37.181 | 13.111 | 1.00 | 45.59 |
| ATOM | 4133 | C | LEU A 440 | 92.008 | 35.132 | 9.643 | 1.00 | 44.03 |
| ATOM | 4134 | O | LEU A 440 | 91.017 | 35.831 | 9.446 | 1.00 | 45.13 |
| ATOM | 4135 | N | GLN A 441 | 92.268 | 34.029 | 8.947 | 1.00 | 44.00 |
| ATOM | 4137 | CA | GLN A 441 | 91.363 | 33.536 | 7.910 | 1.00 | 43.66 |
| ATOM | 4138 | CB | GLN A 441 | 92.148 | 33.058 | 6.678 | 1.00 | 48.64 |

| | | | | | | | |
|---|---|---|---|---|---|---|---|
| ATOM | 4139 | CG | GLN A 441 | 92.881 | 34.113 | 5.860 | 1.00 54.68 |
| ATOM | 4140 | CD | GLN A 441 | 93.556 | 33.515 | 4.627 | 1.00 57.71 |
| ATOM | 4141 | OE1 | GLN A 441 | 93.111 | 32.495 | 4.093 | 1.00 59.57 |
| ATOM | 4142 | NE2 | GLN A 441 | 94.637 | 34.141 | 4.179 | 1.00 60.18 |
| ATOM | 4145 | C | GLN A 441 | 90.528 | 32.355 | 8.390 | 1.00 41.14 |
| ATOM | 4146 | O | GLN A 441 | 91.055 | 31.249 | 8.541 | 1.00 41.88 |
| ATOM | 4147 | N | PRO A 442 | 89.217 | 32.553 | 8.613 | 1.00 38.75 |
| ATOM | 4148 | CD | PRO A 442 | 88.444 | 33.805 | 8.553 | 1.00 39.00 |
| ATOM | 4149 | CA | PRO A 442 | 88.372 | 31.442 | 9.065 | 1.00 35.99 |
| ATOM | 4150 | CB | PRO A 442 | 87.049 | 32.131 | 9.381 | 1.00 36.27 |
| ATOM | 4151 | CG | PRO A 442 | 87.038 | 33.295 | 8.450 | 1.00 38.58 |
| ATOM | 4152 | C | PRO A 442 | 88.234 | 30.403 | 7.952 | 1.00 34.89 |
| ATOM | 4153 | O | PRO A 442 | 88.109 | 30.751 | 6.780 | 1.00 37.34 |
| ATOM | 4154 | N | HIS A 443 | 88.332 | 29.130 | 8.317 | 1.00 32.88 |
| ATOM | 4156 | CA | HIS A 443 | 88.242 | 28.036 | 7.361 | 1.00 30.71 |
| ATOM | 4157 | CB | HIS A 443 | 89.610 | 27.377 | 7.172 | 1.00 31.17 |
| ATOM | 4158 | CG | HIS A 443 | 90.508 | 28.103 | 6.225 | 1.00 29.53 |
| ATOM | 4159 | CD2 | HIS A 443 | 91.098 | 27.702 | 5.076 | 1.00 27.37 |
| ATOM | 4160 | ND1 | HIS A 443 | 90.868 | 29.421 | 6.400 | 1.00 31.12 |
| ATOM | 4162 | CE1 | HIS A 443 | 91.635 | 29.804 | 5.397 | 1.00 30.58 |
| ATOM | 4163 | NE2 | HIS A 443 | 91.790 | 28.779 | 4.580 | 1.00 29.90 |
| ATOM | 4165 | C | HIS A 443 | 87.263 | 27.003 | 7.863 | 1.00 31.31 |
| ATOM | 4166 | O | HIS A 443 | 86.698 | 27.157 | 8.936 | 1.00 36.03 |
| ATOM | 4167 | N | GLN A 444 | 87.058 | 25.948 | 7.086 | 1.00 33.00 |
| ATOM | 4169 | CA | GLN A 444 | 86.136 | 24.896 | 7.481 | 1.00 33.08 |
| ATOM | 4170 | CB | GLN A 444 | 85.802 | 24.000 | 6.282 | 1.00 35.23 |
| ATOM | 4171 | CG | GLN A 444 | 84.829 | 22.860 | 6.570 | 1.00 37.52 |
| ATOM | 4172 | CD | GLN A 444 | 83.436 | 23.337 | 6.954 | 1.00 41.28 |
| ATOM | 4173 | OE1 | GLN A 444 | 83.142 | 24.531 | 6.941 | 1.00 42.98 |
| ATOM | 4174 | NE2 | GLN A 444 | 82.570 | 22.395 | 7.298 | 1.00 44.68 |
| ATOM | 4177 | C | GLN A 444 | 86.735 | 24.069 | 8.613 | 1.00 32.22 |
| ATOM | 4178 | O | GLN A 444 | 87.720 | 23.360 | 8.416 | 1.00 34.24 |
| ATOM | 4179 | N | ASN A 445 | 86.175 | 24.230 | 9.808 | 1.00 29.86 |
| ATOM | 4181 | CA | ASN A 445 | 86.584 | 23.492 | 11.003 | 1.00 28.34 |

| | | | | | | | | |
|---|---|---|---|---|---|---|---|---|
| ATOM | 4182 | CB | ASN | A | 445 | 86.628 | 21.984 | 10.714 | 1.00 27.65 |
| ATOM | 4183 | CG | ASN | A | 445 | 85.272 | 21.427 | 10.319 | 1.00 28.84 |
| ATOM | 4184 | OD1 | ASN | A | 445 | 85.155 | 20.637 | 9.385 | 1.00 33.08 |
| ATOM | 4185 | ND2 | ASN | A | 445 | 84.233 | 21.850 | 11.022 | 1.00 32.64 |
| ATOM | 4188 | C | ASN | A | 445 | 87.863 | 23.950 | 11.709 | 1.00 27.86 |
| ATOM | 4189 | O | ASN | A | 445 | 88.318 | 23.306 | 12.658 | 1.00 30.31 |
| ATOM | 4190 | N | PHE | A | 446 | 88.436 | 25.064 | 11.272 | 1.00 26.55 |
| ATOM | 4192 | CA | PHE | A | 446 | 89.639 | 25.582 | 11.904 | 1.00 25.16 |
| ATOM | 4193 | CB | PHE | A | 446 | 90.858 | 24.688 | 11.626 | 1.00 28.26 |
| ATOM | 4194 | CG | PHE | A | 446 | 91.407 | 24.796 | 10.233 | 1.00 29.75 |
| ATOM | 4195 | CD1 | PHE | A | 446 | 90.953 | 23.956 | 9.223 | 1.00 29.14 |
| ATOM | 4196 | CD2 | PHE | A | 446 | 92.413 | 25.711 | 9.940 | 1.00 32.05 |
| ATOM | 4197 | CE1 | PHE | A | 446 | 91.492 | 24.020 | 7.950 | 1.00 26.24 |
| ATOM | 4198 | CE2 | PHE | A | 446 | 92.961 | 25.784 | 8.662 | 1.00 30.94 |
| ATOM | 4199 | CZ | PHE | A | 446 | 92.500 | 24.936 | 7.667 | 1.00 29.55 |
| ATOM | 4200 | C | PHE | A | 446 | 89.906 | 27.020 | 11.506 | 1.00 25.07 |
| ATOM | 4201 | O | PHE | A | 446 | 89.372 | 27.508 | 10.513 | 1.00 24.16 |
| ATOM | 4202 | N | LEU | A | 447 | 90.718 | 27.697 | 12.306 | 1.00 26.36 |
| ATOM | 4204 | CA | LEU | A | 447 | 91.059 | 29.091 | 12.076 | 1.00 25.79 |
| ATOM | 4205 | CB | LEU | A | 447 | 90.825 | 29.880 | 13.365 | 1.00 27.64 |
| ATOM | 4206 | CG | LEU | A | 447 | 91.097 | 31.384 | 13.422 | 1.00 28.75 |
| ATOM | 4207 | CD1 | LEU | A | 447 | 90.193 | 32.125 | 12.449 | 1.00 27.40 |
| ATOM | 4208 | CD2 | LEU | A | 447 | 90.863 | 31.875 | 14.843 | 1.00 25.78 |
| ATOM | 4209 | C | LEU | A | 447 | 92.508 | 29.221 | 11.635 | 1.00 25.68 |
| ATOM | 4210 | O | LEU | A | 447 | 93.398 | 28.619 | 12.223 | 1.00 26.90 |
| ATOM | 4211 | N | LEU | A | 448 | 92.738 | 30.000 | 10.589 | 1.00 26.87 |
| ATOM | 4213 | CA | LEU | A | 448 | 94.080 | 30.199 | 10.084 | 1.00 26.96 |
| ATOM | 4214 | CB | LEU | A | 448 | 94.074 | 30.247 | 8.559 | 1.00 26.42 |
| ATOM | 4215 | CG | LEU | A | 448 | 95.432 | 30.045 | 7.886 | 1.00 25.05 |
| ATOM | 4216 | CD1 | LEU | A | 448 | 96.040 | 28.738 | 8.331 | 1.00 25.88 |
| ATOM | 4217 | CD2 | LEU | A | 448 | 95.273 | 30.049 | 6.396 | 1.00 29.10 |
| ATOM | 4218 | C | LEU | A | 448 | 94.627 | 31.493 | 10.651 | 1.00 29.88 |
| ATOM | 4219 | O | LEU | A | 448 | 94.005 | 32.552 | 10.530 | 1.00 28.70 |
| ATOM | 4220 | N | PHE | A | 449 | 95.788 | 31.386 | 11.283 | 1.00 32.23 |

Page 6-A-101

| | | | | | | | | |
|---|---|---|---|---|---|---|---|---|
| ATOM | 4222 | CA | PHE | A | 449 | 96.469 | 32.511 | 11.897 | 1.00 32.39 |
| ATOM | 4223 | CB | PHE | A | 449 | 96.655 | 32.234 | 13.394 | 1.00 31.41 |
| ATOM | 4224 | CG | PHE | A | 449 | 97.511 | 33.243 | 14.100 | 1.00 31.44 |
| ATOM | 4225 | CD1 | PHE | A | 449 | 98.897 | 33.160 | 14.046 | 1.00 32.18 |
| ATOM | 4226 | CD2 | PHE | A | 449 | 96.934 | 34.296 | 14.797 | 1.00 35.10 |
| ATOM | 4227 | CE1 | PHE | A | 449 | 99.695 | 34.111 | 14.671 | 1.00 32.81 |
| ATOM | 4228 | CE2 | PHE | A | 449 | 97.725 | 35.257 | 15.429 | 1.00 34.26 |
| ATOM | 4229 | CZ | PHE | A | 449 | 99.106 | 35.162 | 15.363 | 1.00 33.12 |
| ATOM | 4230 | C | PHE | A | 449 | 97.829 | 32.685 | 11.228 | 1.00 34.46 |
| ATOM | 4231 | O | PHE | A | 449 | 98.717 | 31.865 | 11.420 | 1.00 38.92 |
| ATOM | 4232 | N | GLY | A | 450 | 97.990 | 33.738 | 10.439 | 1.00 34.70 |
| ATOM | 4234 | CA | GLY | A | 450 | 99.262 | 33.982 | 9.781 | 1.00 33.42 |
| ATOM | 4235 | C | GLY | A | 450 | 99.901 | 35.207 | 10.397 | 1.00 35.08 |
| ATOM | 4236 | O | GLY | A | 450 | 99.194 | 36.140 | 10.784 | 1.00 36.42 |
| ATOM | 4237 | N | ALA | A | 451 | 101.225 | 35.234 | 10.491 | 1.00 33.89 |
| ATOM | 4239 | CA | ALA | A | 451 | 101.889 | 36.383 | 11.092 | 1.00 33.95 |
| ATOM | 4240 | CB | ALA | A | 451 | 101.649 | 36.384 | 12.587 | 1.00 31.78 |
| ATOM | 4241 | C | ALA | A | 451 | 103.382 | 36.454 | 10.815 | 1.00 34.43 |
| ATOM | 4242 | O | ALA | A | 451 | 103.986 | 35.489 | 10.335 | 1.00 36.02 |
| ATOM | 4243 | N | ASP | A | 452 | 103.954 | 37.628 | 11.055 | 1.00 33.44 |
| ATOM | 4245 | CA | ASP | A | 452 | 105.381 | 37.847 | 10.885 | 1.00 35.01 |
| ATOM | 4246 | CB | ASP | A | 452 | 105.670 | 39.186 | 10.196 | 1.00 37.76 |
| ATOM | 4247 | CG | ASP | A | 452 | 105.437 | 39.144 | 8.696 | 1.00 40.65 |
| ATOM | 4248 | OD1 | ASP | A | 452 | 105.743 | 38.106 | 8.074 | 1.00 42.78 |
| ATOM | 4249 | OD2 | ASP | A | 452 | 104.961 | 40.159 | 8.134 | 1.00 42.90 |
| ATOM | 4250 | C | ASP | A | 452 | 105.913 | 37.875 | 12.306 | 1.00 35.28 |
| ATOM | 4251 | O | ASP | A | 452 | 105.196 | 38.247 | 13.237 | 1.00 33.85 |
| ATOM | 4252 | N | VAL | A | 453 | 107.174 | 37.509 | 12.473 | 1.00 37.44 |
| ATOM | 4254 | CA | VAL | A | 453 | 107.771 | 37.468 | 13.798 | 1.00 38.73 |
| ATOM | 4255 | CB | VAL | A | 453 | 108.253 | 36.034 | 14.138 | 1.00 39.37 |
| ATOM | 4256 | CG1 | VAL | A | 453 | 108.678 | 35.955 | 15.591 | 1.00 40.45 |
| ATOM | 4257 | CG2 | VAL | A | 453 | 107.169 | 35.004 | 13.819 | 1.00 37.45 |
| ATOM | 4258 | C | VAL | A | 453 | 108.970 | 38.398 | 13.899 | 1.00 39.49 |
| ATOM | 4259 | O | VAL | A | 453 | 109.669 | 38.641 | 12.914 | 1.00 40.46 |

| | | | | | | | | |
|---|---|---|---|---|---|---|---|---|
| ATOM | 4260 | N | VAL | A | 454 | 109.190 | 38.929 | 15.092 | 1.00 39.41 |
| ATOM | 4262 | CA | VAL | A | 454 | 110.324 | 39.796 | 15.331 | 1.00 40.55 |
| ATOM | 4263 | CB | VAL | A | 454 | 109.895 | 41.280 | 15.511 | 1.00 41.60 |
| ATOM | 4264 | CG1 | VAL | A | 454 | 108.859 | 41.423 | 16.605 | 1.00 42.90 |
| ATOM | 4265 | CG2 | VAL | A | 454 | 111.105 | 42.149 | 15.798 | 1.00 43.42 |
| ATOM | 4266 | C | VAL | A | 454 | 111.037 | 39.256 | 16.561 | 1.00 41.20 |
| ATOM | 4267 | O | VAL | A | 454 | 110.440 | 39.115 | 17.626 | 1.00 41.61 |
| ATOM | 4268 | N | TYR | A | 455 | 112.284 | 38.851 | 16.376 | 1.00 42.91 |
| ATOM | 4270 | CA | TYR | A | 455 | 113.084 | 38.309 | 17.460 | 1.00 45.62 |
| ATOM | 4271 | CB | TYR | A | 455 | 114.015 | 37.227 | 16.908 | 1.00 44.83 |
| ATOM | 4272 | CG | TYR | A | 455 | 115.038 | 36.684 | 17.881 | 1.00 44.58 |
| ATOM | 4273 | CD1 | TYR | A | 455 | 114.682 | 35.774 | 18.875 | 1.00 43.02 |
| ATOM | 4274 | CE1 | TYR | A | 455 | 115.644 | 35.246 | 19.739 | 1.00 44.27 |
| ATOM | 4275 | CD2 | TYR | A | 455 | 116.377 | 37.053 | 17.778 | 1.00 46.42 |
| ATOM | 4276 | CE2 | TYR | A | 455 | 117.341 | 36.535 | 18.631 | 1.00 46.69 |
| ATOM | 4277 | CZ | TYR | A | 455 | 116.973 | 35.634 | 19.607 | 1.00 46.43 |
| ATOM | 4278 | OH | TYR | A | 455 | 117.944 | 35.141 | 20.445 | 1.00 49.56 |
| ATOM | 4280 | C | TYR | A | 455 | 113.864 | 39.443 | 18.128 | 1.00 49.88 |
| ATOM | 4281 | O | TYR | A | 455 | 114.558 | 40.213 | 17.455 | 1.00 49.95 |
| ATOM | 4282 | N | LYS | A | 456 | 113.694 | 39.552 | 19.444 | 1.00 54.41 |
| ATOM | 4284 | CA | LYS | A | 456 | 114.337 | 40.570 | 20.270 | 1.00 59.38 |
| ATOM | 4285 | CB | LYS | A | 456 | 113.760 | 40.514 | 21.693 | 1.00 61.68 |
| ATOM | 4286 | CG | LYS | A | 456 | 114.401 | 41.475 | 22.692 | 1.00 66.56 |
| ATOM | 4287 | CD | LYS | A | 456 | 114.016 | 41.153 | 24.140 | 1.00 68.38 |
| ATOM | 4288 | CE | LYS | A | 456 | 112.538 | 41.396 | 24.409 | 1.00 70.09 |
| ATOM | 4289 | NZ | LYS | A | 456 | 112.154 | 41.067 | 25.812 | 1.00 71.48 |
| ATOM | 4293 | C | LYS | A | 456 | 115.855 | 40.382 | 20.311 | 1.00 62.37 |
| ATOM | 4294 | OT1 | LYS | A | 456 | 116.324 | 39.430 | 20.976 | 1.00 64.57 |
| ATOM | 4295 | OT2 | LYS | A | 456 | 116.559 | 41.196 | 19.673 | 1.00 66.00 |
| ATOM | 4296 | C1 | PC | A | 777 | 121.817 | 32.468 | 19.343 | 1.00 72.53 |
| ATOM | 4297 | C2 | PC | A | 777 | 121.094 | 31.121 | 19.465 | 1.00 63.82 |
| ATOM | 4298 | C3 | PC | A | 777 | 119.917 | 31.017 | 18.492 | 1.00 59.16 |
| ATOM | 4299 | C4 | PC | A | 777 | 123.302 | 33.354 | 23.035 | 1.00 94.69 |
| ATOM | 4300 | C5 | PC | A | 777 | 124.151 | 34.553 | 23.445 | 1.00 98.10 |

Page 6-A-103

| ATOM | 4301 | C6 | PC | A 777 | 125.683 | 33.126 | 24.652 | 1.00 | 99.68 |
| ATOM | 4302 | C7 | PC | A 777 | 126.361 | 35.328 | 24.003 | 1.00 | 100.00 |
| ATOM | 4303 | C8 | PC | A 777 | 126.086 | 33.627 | 22.335 | 1.00 | 100.00 |
| ATOM | 4304 | C31 | PC | A 777 | 122.736 | 29.776 | 18.047 | 1.00 | 54.84 |
| ATOM | 4305 | C32 | PC | A 777 | 122.337 | 30.654 | 16.869 | 1.00 | 51.64 |
| ATOM | 4306 | C33 | PC | A 777 | 122.254 | 29.878 | 15.549 | 1.00 | 47.76 |
| ATOM | 4307 | C34 | PC | A 777 | 123.590 | 29.237 | 15.169 | 1.00 | 42.03 |
| ATOM | 4308 | C35 | PC | A 777 | 123.429 | 28.173 | 14.085 | 1.00 | 39.41 |
| ATOM | 4309 | C36 | PC | A 777 | 122.582 | 28.674 | 12.916 | 1.00 | 36.18 |
| ATOM | 4310 | C37 | PC | A 777 | 121.581 | 27.622 | 12.463 | 1.00 | 33.16 |
| ATOM | 4311 | C38 | PC | A 777 | 120.679 | 28.158 | 11.377 | 1.00 | 31.40 |
| ATOM | 4312 | C39 | PC | A 777 | 119.610 | 29.062 | 11.951 | 1.00 | 36.47 |
| ATOM | 4313 | C40 | PC | A 777 | 118.543 | 28.263 | 12.682 | 1.00 | 40.19 |
| ATOM | 4314 | C41 | PC | A 777 | 117.191 | 28.383 | 12.004 | 1.00 | 39.41 |
| ATOM | 4315 | C42 | PC | A 777 | 116.468 | 27.050 | 11.956 | 1.00 | 41.86 |
| ATOM | 4316 | C43 | PC | A 777 | 115.409 | 26.958 | 13.041 | 1.00 | 43.49 |
| ATOM | 4317 | C44 | PC | A 777 | 114.326 | 25.951 | 12.669 | 1.00 | 46.22 |
| ATOM | 4318 | C45 | PC | A 777 | 113.126 | 26.048 | 13.604 | 1.00 | 47.77 |
| ATOM | 4319 | C46 | PC | A 777 | 112.271 | 24.786 | 13.561 | 1.00 | 48.67 |
| ATOM | 4320 | C47 | PC | A 777 | 111.948 | 24.277 | 14.964 | 1.00 | 48.62 |
| ATOM | 4321 | C48 | PC | A 777 | 110.492 | 24.449 | 15.368 | 1.00 | 45.72 |
| ATOM | 4322 | C11 | PC | A 777 | 118.509 | 32.389 | 17.081 | 1.00 | 49.62 |
| ATOM | 4323 | C12 | PC | A 777 | 117.647 | 31.121 | 17.072 | 1.00 | 45.91 |
| ATOM | 4324 | C13 | PC | A 777 | 116.542 | 31.091 | 16.014 | 1.00 | 42.05 |
| ATOM | 4325 | C14 | PC | A 777 | 115.753 | 32.392 | 15.973 | 1.00 | 37.88 |
| ATOM | 4326 | C15 | PC | A 777 | 114.269 | 32.149 | 16.004 | 1.00 | 39.34 |
| ATOM | 4327 | C16 | PC | A 777 | 113.573 | 32.877 | 14.874 | 1.00 | 39.38 |
| ATOM | 4328 | C17 | PC | A 777 | 112.066 | 32.688 | 14.951 | 1.00 | 43.09 |
| ATOM | 4329 | C18 | PC | A 777 | 111.446 | 32.535 | 13.566 | 1.00 | 45.42 |
| ATOM | 4330 | C19 | PC | A 777 | 111.500 | 31.093 | 13.082 | 1.00 | 47.16 |
| ATOM | 4331 | C20 | PC | A 777 | 110.158 | 30.413 | 13.236 | 1.00 | 46.62 |
| ATOM | 4332 | C21 | PC | A 777 | 109.917 | 30.004 | 14.673 | 1.00 | 46.65 |
| ATOM | 4333 | C22 | PC | A 777 | 108.444 | 29.836 | 14.942 | 1.00 | 46.97 |
| ATOM | 4334 | C23 | PC | A 777 | 107.922 | 30.916 | 15.868 | 1.00 | 47.30 |

| | | | | | | | | |
|---|---|---|---|---|---|---|---|---|
| ATOM | 4335 | C24 | PC | A 777 | 106.409 | 30.835 | 16.001 | 1.00 50.05 |
| ATOM | 4336 | C25 | PC | A 777 | 105.996 | 29.898 | 17.121 | 1.00 50.59 |
| ATOM | 4337 | C26 | PC | A 777 | 105.783 | 28.490 | 16.612 | 1.00 53.56 |
| ATOM | 4338 | C27 | PC | A 777 | 106.972 | 27.593 | 16.941 | 1.00 56.03 |
| ATOM | 4339 | C28 | PC | A 777 | 107.348 | 26.625 | 15.831 | 1.00 55.75 |
| ATOM | 4340 | O11 | PC | A 777 | 118.194 | 33.427 | 16.467 | 1.00 52.98 |
| ATOM | 4341 | O31 | PC | A 777 | 123.576 | 28.862 | 17.906 | 1.00 56.48 |
| ATOM | 4342 | O2 | PC | A 777 | 122.068 | 30.020 | 19.350 | 1.00 61.36 |
| ATOM | 4343 | O3 | PC | A 777 | 119.731 | 32.307 | 17.866 | 1.00 53.04 |
| ATOM | 4344 | O1P | PC | A 777 | 121.661 | 35.196 | 20.857 | 1.00 89.42 |
| ATOM | 4345 | O2P | PC | A 777 | 120.059 | 33.339 | 21.280 | 1.00 90.46 |
| ATOM | 4346 | O3P | PC | A 777 | 122.419 | 32.815 | 20.622 | 1.00 84.15 |
| ATOM | 4347 | O4P | PC | A 777 | 121.916 | 33.769 | 22.889 | 1.00 91.71 |
| ATOM | 4348 | N | PC | A 777 | 125.571 | 34.153 | 23.607 | 1.00 99.82 |
| ATOM | 4349 | P | PC | A 777 | 121.516 | 33.779 | 21.409 | 1.00 89.00 |
| ATOM | 4350 | C1 | PC | A 778 | 87.797 | 32.791 | 33.686 | 1.00 88.29 |
| ATOM | 4351 | C2 | PC | A 778 | 86.274 | 32.868 | 33.502 | 1.00 83.64 |
| ATOM | 4352 | C3 | PC | A 778 | 85.739 | 31.590 | 32.830 | 1.00 80.89 |
| ATOM | 4353 | C31 | PC | A 778 | 84.282 | 33.619 | 34.787 | 1.00 76.37 |
| ATOM | 4354 | C32 | PC | A 778 | 83.704 | 33.859 | 33.391 | 1.00 70.52 |
| ATOM | 4355 | C33 | PC | A 778 | 82.344 | 33.215 | 33.178 | 1.00 63.44 |
| ATOM | 4356 | C34 | PC | A 778 | 81.311 | 34.250 | 32.803 | 1.00 56.98 |
| ATOM | 4357 | C35 | PC | A 778 | 80.231 | 34.364 | 33.854 | 1.00 51.89 |
| ATOM | 4358 | C36 | PC | A 778 | 79.088 | 33.400 | 33.593 | 1.00 48.39 |
| ATOM | 4359 | C37 | PC | A 778 | 78.611 | 33.453 | 32.155 | 1.00 47.51 |
| ATOM | 4360 | C38 | PC | A 778 | 77.593 | 32.352 | 31.868 | 1.00 47.46 |
| ATOM | 4361 | C39 | PC | A 778 | 78.231 | 31.153 | 31.171 | 1.00 45.28 |
| ATOM | 4362 | C40 | PC | A 778 | 78.154 | 31.261 | 29.654 | 1.00 43.25 |
| ATOM | 4363 | C41 | PC | A 778 | 79.381 | 31.957 | 29.099 | 1.00 40.88 |
| ATOM | 4364 | C42 | PC | A 778 | 79.324 | 32.082 | 27.589 | 1.00 42.02 |
| ATOM | 4365 | C43 | PC | A 778 | 78.064 | 32.803 | 27.130 | 1.00 43.52 |
| ATOM | 4366 | C44 | PC | A 778 | 77.971 | 34.223 | 27.684 | 1.00 42.21 |
| ATOM | 4367 | C45 | PC | A 778 | 76.563 | 34.546 | 28.171 | 1.00 42.30 |
| ATOM | 4368 | C46 | PC | A 778 | 75.523 | 34.335 | 27.077 | 1.00 42.97 |

| | | | | | | | | | |
|---|---|---|---|---|---|---|---|---|---|
| ATOM | 4369 | C47 | PC | A | 778 | 74.121 | 34.185 | 27.662 | 1.00 42.80 |
| ATOM | 4370 | C48 | PC | A | 778 | 73.131 | 33.504 | 26.727 | 1.00 43.31 |
| ATOM | 4371 | C11 | PC | A | 778 | 86.101 | 31.542 | 30.412 | 1.00 71.27 |
| ATOM | 4372 | C12 | PC | A | 778 | 84.804 | 32.359 | 30.441 | 1.00 66.82 |
| ATOM | 4373 | C13 | PC | A | 778 | 83.700 | 31.845 | 29.548 | 1.00 59.12 |
| ATOM | 4374 | C14 | PC | A | 778 | 83.836 | 32.380 | 28.141 | 1.00 55.92 |
| ATOM | 4375 | C15 | PC | A | 778 | 82.896 | 31.671 | 27.184 | 1.00 53.76 |
| ATOM | 4376 | C16 | PC | A | 778 | 82.613 | 30.248 | 27.633 | 1.00 52.97 |
| ATOM | 4377 | C17 | PC | A | 778 | 83.562 | 29.250 | 26.990 | 1.00 50.51 |
| ATOM | 4378 | C18 | PC | A | 778 | 84.990 | 29.415 | 27.480 | 1.00 47.60 |
| ATOM | 4379 | C19 | PC | A | 778 | 85.860 | 30.046 | 26.408 | 1.00 47.69 |
| ATOM | 4380 | C20 | PC | A | 778 | 86.359 | 29.011 | 25.411 | 1.00 44.90 |
| ATOM | 4381 | C21 | PC | A | 778 | 85.271 | 28.598 | 24.439 | 1.00 44.44 |
| ATOM | 4382 | C22 | PC | A | 778 | 85.574 | 29.064 | 23.038 | 1.00 44.15 |
| ATOM | 4383 | C23 | PC | A | 778 | 86.167 | 30.453 | 23.044 | 1.00 43.99 |
| ATOM | 4384 | C24 | PC | A | 778 | 87.670 | 30.411 | 22.853 | 1.00 42.63 |
| ATOM | 4385 | C25 | PC | A | 778 | 88.068 | 31.161 | 21.599 | 1.00 43.28 |
| ATOM | 4386 | C26 | PC | A | 778 | 87.733 | 32.642 | 21.693 | 1.00 41.66 |
| ATOM | 4387 | C27 | PC | A | 778 | 88.852 | 33.492 | 21.119 | 1.00 40.33 |
| ATOM | 4388 | C28 | PC | A | 778 | 90.094 | 33.503 | 21.969 | 1.00 37.09 |
| ATOM | 4389 | O11 | PC | A | 778 | 86.692 | 31.253 | 29.343 | 1.00 72.85 |
| ATOM | 4390 | O31 | PC | A | 778 | 83.619 | 33.857 | 35.833 | 1.00 78.26 |
| ATOM | 4391 | O2 | PC | A | 778 | 85.652 | 33.065 | 34.823 | 1.00 81.22 |
| ATOM | 4392 | O3 | PC | A | 778 | 86.615 | 31.154 | 31.736 | 1.00 75.71 |
| ATOM | 4393 | O1P | PC | A | 778 | 89.401 | 31.823 | 36.960 | 1.00100.00 |
| ATOM | 4394 | O2P | PC | A | 778 | 89.563 | 33.853 | 35.511 | 1.00100.00 |
| ATOM | 4395 | O3P | PC | A | 778 | 88.125 | 31.917 | 34.809 | 1.00 96.24 |
| ATOM | 4396 | O4P | PC | A | 778 | 87.424 | 33.342 | 36.757 | 1.00100.00 |
| ATOM | 4397 | P | PC | A | 778 | 88.628 | 32.739 | 36.008 | 1.00100.00 |
| ATOM | 4398 | OH2 | HOH | A | 901 | 116.815 | 15.747 | 16.799 | 1.00 43.90 |
| ATOM | 4401 | OH2 | HOH | A | 902 | 107.439 | 22.033 | 22.778 | 1.00 44.99 |
| ATOM | 4404 | OH2 | HOH | A | 903 | 115.201 | 26.524 | 27.768 | 1.00 47.84 |
| ATOM | 4407 | OH2 | HOH | A | 904 | 83.653 | 23.737 | 13.286 | 1.00 22.80 |
| ATOM | 4410 | OH2 | HOH | A | 905 | 76.576 | 23.779 | 22.886 | 1.00 55.25 |

Page 6-A-106

| | | | | | | | | |
|---|---|---|---|---|---|---|---|---|
| ATOM | 4413 | OH2 | HOH A | 906 | 101.110 | 43.595 | 19.882 | 1.00 44.52 |
| ATOM | 4416 | OH2 | HOH A | 907 | 80.990 | 19.920 | 23.229 | 1.00 48.61 |
| ATOM | 4419 | OH2 | HOH A | 908 | 141.374 | 35.733 | 18.039 | 1.00 56.87 |
| ATOM | 4422 | OH2 | HOH A | 909 | 81.958 | 22.677 | 23.953 | 1.00 61.10 |
| ATOM | 4425 | OH2 | HOH A | 910 | 152.059 | 36.697 | -0.688 | 1.00 62.06 |
| ATOM | 4428 | OH2 | HOH A | 911 | 139.649 | 24.807 | 2.271 | 1.00 53.67 |
| ATOM | 4431 | OH2 | HOH A | 912 | 124.594 | 31.177 | 0.772 | 1.00 55.59 |
| ATOM | 4434 | OH2 | HOH A | 913 | 121.471 | 25.892 | 1.624 | 1.00 38.62 |
| ATOM | 4437 | OH2 | HOH A | 914 | 114.402 | 25.412 | 0.380 | 1.00 31.16 |
| ATOM | 4440 | OH2 | HOH A | 915 | 147.939 | 35.177 | -2.062 | 1.00 45.61 |
| ATOM | 4443 | OH2 | HOH A | 916 | 74.995 | 34.193 | 14.634 | 1.00 73.76 |
| ATOM | 4446 | OH2 | HOH A | 917 | 105.633 | 17.580 | 14.444 | 1.00 37.72 |
| ATOM | 4449 | OH2 | HOH A | 918 | 71.679 | 28.574 | 37.701 | 1.00 51.80 |
| ATOM | 4452 | OH2 | HOH A | 919 | 104.762 | 14.189 | 10.052 | 1.00 57.21 |
| ATOM | 4455 | OH2 | HOH A | 920 | 80.378 | 28.515 | 41.681 | 1.00 81.97 |
| ATOM | 4458 | OH2 | HOH A | 921 | 80.215 | 25.918 | 35.227 | 1.00 29.12 |
| ATOM | 4461 | OH2 | HOH A | 922 | 79.054 | 35.414 | 40.975 | 1.00 41.95 |
| ATOM | 4464 | OH2 | HOH A | 923 | 65.692 | 27.690 | 51.372 | 1.00 65.22 |
| ATOM | 4467 | OH2 | HOH A | 924 | 88.914 | 24.630 | 4.689 | 1.00 48.96 |
| ATOM | 4470 | OH2 | HOH A | 925 | 100.082 | 22.695 | 34.405 | 1.00 48.58 |
| ATOM | 4473 | OH2 | HOH A | 926 | 76.929 | 19.455 | 31.644 | 1.00 86.93 |
| ATOM | 4476 | OH2 | HOH A | 927 | 171.524 | 31.723 | 13.880 | 1.00 59.94 |
| ATOM | 4479 | OH2 | HOH A | 928 | 108.006 | 35.100 | 24.514 | 1.00 49.31 |
| ATOM | 4482 | OH2 | HOH A | 929 | 141.049 | 21.649 | 5.587 | 1.00 42.12 |
| ATOM | 4485 | OH2 | HOH A | 930 | 110.883 | 40.970 | 11.363 | 1.00 35.61 |
| ATOM | 4488 | OH2 | HOH A | 931 | 74.360 | 34.525 | 47.158 | 1.00 75.14 |
| ATOM | 4491 | OH2 | HOH A | 932 | 68.751 | 40.894 | 44.809 | 1.00 43.22 |
| ATOM | 4494 | OH2 | HOH A | 933 | 59.758 | 29.313 | 23.460 | 1.00 61.69 |
| ATOM | 4497 | OH2 | HOH A | 934 | 95.173 | 16.341 | 20.293 | 1.00 48.05 |
| ATOM | 4500 | OH2 | HOH A | 935 | 111.623 | 41.720 | 8.640 | 1.00 53.02 |
| ATOM | 4503 | OH2 | HOH A | 936 | 105.604 | 16.201 | 11.554 | 1.00 71.57 |
| ATOM | 4506 | OH2 | HOH A | 937 | 97.160 | 30.542 | 3.465 | 1.00 58.62 |
| ATOM | 4509 | OH2 | HOH A | 938 | 108.492 | 10.703 | 6.225 | 1.00 76.16 |
| ATOM | 4512 | OH2 | HOH A | 939 | 135.408 | 44.678 | 13.765 | 1.00 61.58 |

Page 6-A-107

```
ATOM   4515  OH2 HOH A 940      91.469  31.723  41.685  1.00 41.59
ATOM   4518  OH2 HOH A 941     164.580  32.799  18.975  1.00 48.97
ATOM   4521  OH2 HOH A 942     157.888  29.985  20.509  1.00 63.61
ATOM   4524  OH2 HOH A 943     121.776  21.112  25.392  1.00 61.93
ATOM   4527  OH2 HOH A 944      96.503  38.299  34.009  1.00 64.71
ATOM   4530  OH2 HOH A 945      96.403  17.036  28.115  1.00 76.51
ATOM   4533  OH2 HOH A 946      88.114  18.204  31.407  1.00 52.33
ATOM   4536  OH2 HOH A 947      81.217  23.098  12.608  1.00 35.93
ATOM   4539  OH2 HOH A 948     126.713  24.917   0.514  1.00 82.50
TER
END
```

```
REMARK   3
REMARK   3  REFINEMENT.
REMARK   3    PROGRAM     : X-PLOR(online) 3.843
REMARK   3    AUTHORS     : BRUNGER
REMARK   3
REMARK   3  DATA USED IN REFINEMENT.
REMARK   3    RESOLUTION RANGE HIGH (ANGSTROMS) : 2.40
REMARK   3    RESOLUTION RANGE LOW  (ANGSTROMS) :50.00
REMARK   3    DATA CUTOFF            (SIGMA(F)) : 0.0
REMARK   3    DATA CUTOFF HIGH         (ABS(F)) :  100000.00
REMARK   3    DATA CUTOFF LOW          (ABS(F)) :       0.010000
REMARK   3    COMPLETENESS (WORKING+TEST ) (%) : 92.7
REMARK   3    NUMBER OF REFLECTIONS             : 18908
REMARK   3
REMARK   3  FIT TO DATA USED IN REFINEMENT.
REMARK   3    CROSS-VALIDATION METHOD          : THROUGHOUT
REMARK   3    FREE R VALUE TEST SET SELECTION  : RANDOM
REMARK   3    R VALUE            (WORKING SET) : 0.225
REMARK   3    FREE R VALUE                     : 0.295
REMARK   3    FREE R VALUE TEST SET SIZE   (%) : 10.2
REMARK   3    FREE R VALUE TEST SET COUNT      : 1926
REMARK   3    ESTIMATED ERROR OF FREE R VALUE  : 0.007
REMARK   3
REMARK   3  FIT IN THE HIGHEST RESOLUTION BIN.
REMARK   3    TOTAL NUMBER OF BINS USED           :   6
REMARK   3    BIN RESOLUTION RANGE HIGH       (A) : 2.40
REMARK   3    BIN RESOLUTION RANGE LOW        (A) : 2.55
REMARK   3    BIN COMPLETENESS (WORKING+TEST) (%) : 94.1
REMARK   3    REFLECTIONS IN BIN    (WORKING SET) : 2875
REMARK   3    BIN R VALUE           (WORKING SET) : 0.368
REMARK   3    BIN FREE R VALUE                    : 0.455
REMARK   3    BIN FREE R VALUE TEST SET SIZE  (%) : 8.7
REMARK   3    BIN FREE R VALUE TEST SET COUNT     :  275
REMARK   3    ESTIMATED ERROR OF BIN FREE R VALUE : 0.027
REMARK   3
REMARK   3  NUMBER OF NON-HYDROGEN ATOMS USED IN REFINEMENT.
REMARK   3    PROTEIN ATOMS      : 3531
REMARK   3    NUCLEIC ACID ATOMS :    0
REMARK   3    HETEROGEN ATOMS    :  102
REMARK   3    SOLVENT ATOMS      :   48
REMARK   3
REMARK   3  B VALUES.
REMARK   3    FROM WILSON PLOT           (A**2) : 45.0
REMARK   3    MEAN B VALUE      (OVERALL, A**2) : 45.0
REMARK   3    OVERALL ANISOTROPIC B VALUE.
REMARK   3     B11 (A**2) :-11.35
REMARK   3     B22 (A**2) :  6.33
REMARK   3     B33 (A**2) :  5.02
REMARK   3     B12 (A**2) :  0.00
REMARK   3     B13 (A**2) :  7.70
REMARK   3     B23 (A**2) :  0.00
REMARK   3
REMARK   3  ESTIMATED COORDINATE ERROR.
REMARK   3    ESD FROM LUZZATI PLOT        (A) : 0.34
REMARK   3    ESD FROM SIGMAA              (A) : 0.47
REMARK   3    LOW RESOLUTION CUTOFF        (A) : 5.00
REMARK   3
REMARK   3  CROSS-VALIDATED ESTIMATED COORDINATE ERROR.
REMARK   3    ESD FROM C-V LUZZATI PLOT    (A) : 0.45
REMARK   3    ESD FROM C-V SIGMAA          (A) : 0.46
REMARK   3
REMARK   3  RMS DEVIATIONS FROM IDEAL VALUES.
REMARK   3    BOND LENGTHS                 (A) : 0.007
REMARK   3    BOND ANGLES            (DEGREES) : 1.4
REMARK   3    DIHEDRAL ANGLES        (DEGREES) : 26.1
REMARK   3    IMPROPER ANGLES        (DEGREES) : 1.24
REMARK   3
REMARK   3  ISOTROPIC THERMAL MODEL : RESTRAINED
```

Page 6-A-109

```
REMARK   3
REMARK   3   ISOTROPIC THERMAL FACTOR RESTRAINTS.      RMS      SIGMA
REMARK   3     MAIN-CHAIN BOND              (A**2) :  1.77 ;   1.50
REMARK   3     MAIN-CHAIN ANGLE             (A**2) :  3.00 ;   2.00
REMARK   3     SIDE-CHAIN BOND              (A**2) :  2.81 ;   2.00
REMARK   3     SIDE-CHAIN ANGLE             (A**2) :  4.53 ;   2.50
REMARK   3
REMARK   3   NCS MODEL                  : NONE
REMARK   3
REMARK   3   NCS RESTRAINTS.                           RMS    SIGMA/WEIGHT
REMARK   3     GROUP 1    POSITIONAL          (A) :  NULL  ;  NULL
REMARK   3     GROUP 1    B-FACTOR         (A**2) :  NULL  ;  NULL
REMARK   3
REMARK   3   PARAMETER FILE  1 : parhcsdx.pro
REMARK   3   PARAMETER FILE  2 : param11.wat
REMARK   3   TOPOLOGY FILE  1  : tophcsdx.pro
REMARK   3   TOPOLOGY FILE  2  : toph11.wat
REMARK   3
REMARK   3   OTHER REFINEMENT REMARKS: BULK SOLVENT MODEL USED
SEQRES    1 A  507   VAL ASN PRO GLY VAL VAL VAL ARG ILE SER GLN LYS GLY
SEQRES    2 A  507   LEU ASP TYR ALA SER GLN GLN GLY THR ALA ALA LEU GLN
SEQRES    3 A  507   LYS GLU LEU LYS ARG ILE LYS ILE PRO ASP TYR SER ASP
SEQRES    4 A  507   SER PHE LYS ILE LYS HIS LEU GLY LYS GLY HIS TYR SER
SEQRES    5 A  507   PHE TYR SER MET ASP ILE ARG GLU PHE GLN LEU PRO SER
SEQRES    6 A  507   SER GLN ILE SER MET VAL PRO ASN VAL GLY LEU LYS PHE
SEQRES    7 A  507   SER ILE SER ASN ALA ASN ILE LYS ILE SER GLY LYS TRP
SEQRES    8 A  507   LYS ALA GLN LYS ARG PHE LEU LYS MET SER GLY ASN PHE
SEQRES    9 A  507   ASP LEU SER ILE GLU GLY MET SER ILE SER ALA ASP LEU
SEQRES   10 A  507   LYS LEU GLY SER ASN PRO THR SER GLY LYS PRO THR ILE
SEQRES   11 A  507   THR CYS SER SER CYS SER SER HIS ILE ASN SER VAL HIS
SEQRES   12 A  507   VAL HIS ILE SER ALA ALA SER VAL GLY TRP LEU ILE GLN
SEQRES   13 A  507   LEU PHE HIS LYS LYS ILE GLU SER ALA LEU ARG ASN LYS
SEQRES   14 A  507   MET ASN SER GLN VAL CYS GLU LYS VAL THR ASN SER VAL
SEQRES   15 A  507   SER SER GLU LEU GLN PRO TYR PHE GLN THR LEU PRO VAL
SEQRES   16 A  507   MET THR LYS ILE ASP SER VAL ALA GLY ILE ASN TYR GLY
SEQRES   17 A  507   LEU VAL ALA PRO PRO ALA THR THR ALA GLU THR LEU ASP
SEQRES   18 A  507   VAL GLN MET LYS GLY GLU PHE TYR SER GLU ALA ALA ALA
SEQRES   19 A  507   ALA PRO PRO PRO PHE ALA PRO PRO VAL MET GLU PHE PRO
SEQRES   20 A  507   ALA ALA ALA ASP ARG MET VAL TYR LEU GLY LEU SER ASP
SEQRES   21 A  507   TYR PHE PHE ASN THR ALA GLY LEU VAL TYR GLN GLU ALA
SEQRES   22 A  507   GLY VAL LEU LYS MET THR LEU ARG ASP ASP MET ILE PRO
SEQRES   23 A  507   LYS GLU SER ALA PHE ARG LEU THR THR SER PHE PHE GLY
SEQRES   24 A  507   THR PHE LEU PRO GLU VAL ALA LYS LYS PHE PRO ASN MET
SEQRES   25 A  507   LYS ILE GLN ILE HIS VAL SER ALA SER THR PRO PRO HIS
SEQRES   26 A  507   LEU SER VAL GLN PRO THR GLY LEU THR PHE TYR PRO ALA
SEQRES   27 A  507   VAL ASP VAL GLN ALA PHE ALA VAL LEU PRO ASN SER ALA
SEQRES   28 A  507   LEU ALA SER LEU PHE LEU ILE GLY MET HIS THR THR GLY
SEQRES   29 A  507   SER MET GLU VAL SER ALA GLU SER ASN ARG LEU VAL GLY
SEQRES   30 A  507   GLU LEU LYS LEU ASP ARG LEU LEU LEU GLU LEU LYS HIS
SEQRES   31 A  507   SER ASN ILE GLY PRO PHE PRO VAL GLU LEU LEU GLN ASP
SEQRES   32 A  507   ILE MET ASN TYR ILE VAL PRO ILE LEU VAL LEU PRO ARG
SEQRES   33 A  507   VAL ASN GLU LYS LEU GLN LYS GLY PHE PRO LEU PRO THR
SEQRES   34 A  507   PRO ALA ARG VAL GLN LEU TYR ASN VAL VAL LEU GLN PRO
SEQRES   35 A  507   HIS GLN ASN PHE LEU LEU PHE GLY ALA ASP VAL VAL TYR
SEQRES   36 A  507   LYS PC  PC  HOH HOH HOH HOH HOH HOH HOH HOH HOH HOH
SEQRES   37 A  507   HOH HOH HOH HOH HOH HOH HOH HOH HOH HOH HOH HOH HOH
SEQRES   38 A  507   HOH HOH HOH HOH HOH HOH HOH HOH HOH HOH HOH HOH HOH
SEQRES   39 A  507   HOH HOH HOH HOH HOH HOH HOH HOH HOH HOH HOH HOH HOH
SSBOND    1 CYS A  135    CYS A  175
CRYST1  185.600   33.000   85.200  90.00 101.60  90.00 C 2         4
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.005388  0.000000  0.001106        0.00000
SCALE2      0.000000  0.030303  0.000000        0.00000
SCALE3      0.000000  0.000000  0.011982        0.00000
```

Page 6-A-110

| N-TERMINAL POCKET - residues contributing to interior | | | | | |
|---|---|---|---|---|---|
| Residue[1] | ΔSA[2] | Within 4Å[3] | Conservation[4] | Alternatives[5] | Mutations[6] |
| Val 7 | ✓ | ✓ | 2/7 | A,T | |
| Ile 9 | ✓ | ✓ | All | | W |
| Gly 13 | ✓ | ✓ | All | | |
| Leu 14 | ✓ | | All | | |
| Tyr 16 | ✓ | | All | | |
| Ala 17 | ✓ | ✓ | All | | F |
| Ser 18 | ✓ | ✓ | 1/7 | C,A | |
| Gly 21 | ✓ | ✓ | All | | F |
| Ala 24 | ✓ | ✓ | 4/7 | V,T,S | Y,H |
| Leu 25 | ✓ | | All | | |
| Ile 68 | ✓ | ✓ | 3/7 | L | |
| Leu 76 | ✓ | ✓ | All | | |
| Phe 78 | ✓ | ✓ | 1/7 | V,L | |
| Leu 117 | ✓ | ✓ | All | | |
| Leu 119 | ✓ | | All | | |
| Pro 128 | ✓ | | 5/7 | A,S | |
| Ile 130 | ✓ | | 1/7 | V | |

Figure 8

| | | | | | |
|---|---|---|---|---|---|
| Val 178 | ✓ | | 2/7 | L,I | |
| Val 182 | ✓ | | All | | |
| Glu 185 | ✓ | ✓ | 1/7 (allele) | K,D,H | |
| Leu 186 | ✓ | ✓ | All | | W |
| Tyr 189 | ✓ | ✓ | All | | |
| Phe 190 | ✓ | ✓ | 2/7 | V,L | |
| Leu 193 | ✓ | ✓ | All | | |
| Leu 220 | ✓ | ✓ | All | | |
| Val 222 | ✓ | | 5/7 | M,W | |
| Val 254 | ✓ | ✓ | 6/7 | I | |
| Leu 256 | ✓ | | 3/7 | F | |
| Pro 428 | ✓ | ✓ | All | | |
| Thr 429 | ✓ | ✓ | 1/7 | M,L | |
| Pro 430 | ✓ | ✓ | 5/7 | L | |
| Val 433 | ✓ | | 3/7 | I | |
| Leu 435 | ✓ | | All | | |
| Val 453 | ✓ | | 6/7 | I | |

Figure 8A

| ENTRY ONLY | | | | | |
|---|---|---|---|---|---|
| Gln 20 | ✓ | ✓ | 3/7 | E | |
| Lys 27 | ✓ | ✓ | 3/7 | R,S | |
| Glu 28 | ✓ | | 6/7 | K | |
| Arg 31 | ✓ | | 2/7 | K,E | |
| Ser 181 | ✓ | ✓ | 5/7 | T,A | |
| Arg 432 | ✓ | ✓ | 3/7 | K,Y,H | |
| Tyr 455 | ✓ | ✓ | 6/7 | H | |
| C-TERMINAL POCKET - residues contributing to interior | | | | | |
| Phe 263 | ✓ | ✓ | All | | |
| Asn 264 | ✓ | | All | | |
| Ala 266 | ✓ | ✓ | All | | F |
| Gly 267 | ✓ | ✓ | 2/7 | A,S,T, | |
| Val 275 | ✓ | ✓ | 1/7 | A,Y | |
| Leu 276 | ✓ | ✓ | 5/7 | F,W | F,W |
| Lys 277 | ✓ | | 1/7 | G,N | |
| Met 278 | ✓ | ✓ | 1/7 | L,F | |
| Val 318 | ✓ | | 1/7 | L,I,G | |
| Ala 320 | ✓ | | 2/7 | V | |

Figure 8B

| | | | | | |
|---|---|---|---|---|---|
| Pro 324 | ✓ | ✓ | 6/7 | Q | |
| Leu 326 | ✓ | ✓ | 6/7 | V | |
| Phe 335 | ✓ | ✓ | 1/7 | L,V,E | |
| Pro 337 | ✓ | ✓ | 5/7 | A,F | |
| Val 339 | ✓ | | 2/7 | L,M | |
| Met 360 | ✓ | ✓ | 2/7 | L,V | |
| Thr 362 | ✓ | ✓ | 5/7 | L | |
| Val 368 | ✓ | ✓ | 2/7 | I,L | |
| Leu 375 | ✓ | ✓ | 3/7 | I,V | |
| Val 376 | ✓ | ✓ | 2/7 | I,T | |
| Gly 377 | ✓ | | All | | |
| Leu 379 | ✓ | ✓ | All | | |
| Leu 381 | ✓ | ✓ | 3/7 | P | |
| Val 409 | ✓ | ✓ | 1/7 | L,M,I | |
| Val 413 | ✓ | ✓ | 1/7 | F,L | F |
| Val 417 | ✓ | ✓ | 3/7 | I,F | W |
| Lys 420 | ✓ | ✓ | 5/7 | E | Y,H |
| Leu 421 | ✓ | ✓ | 5/7 | I,F | |
| Phe 425 | ✓ | ✓ | 6/7 | L | |

Figure 8C

| ENTRY ONLY | | | | | |
|---|---|---|---|---|---|
| Asp 200 | ✓ | | All | | |
| Ser 201 | ✓ | ✓ | 4/7 | K,T,N | |
| Val 202 | ✓ | | 4/7 | F,I | |
| Tyr 270 | ✓ | ✓ | All | | |
| Arg 416 | ✓ | ✓ | 1/7 | K,V,D | |
| Lys 423 | ✓ | | 3/7 | R,E,Q | |

Figure 8D

THREE-DIMENSIONAL STRUCTURE OF BACTERICIDAL/PERMEABILITY-INCREASING PROTEIN (BPI)

The present invention generally pertains to the fields of molecular biology, protein purification, protein crystallization, x-ray diffraction analysis, three-dimensional structural determination, rational drug design and molecular modeling of related proteins. The present invention provides crystallization methods and crystallized bactericidal/permeability-increasing protein (BPI). The crystallized BPI is physically analyzed by x-ray diffraction techniques. The resulting x-ray diffraction patterns are of sufficiently high resolution to be useful for determining the three-dimensional structure of BPI [yielding atomic coordinates], molecular modeling of related proteins and rational drug design (RDD) of mimetics and ligands for BPI and related proteins.

Part of the work performed during development of this invention utilized U.S. Government funds. The U.S. Government has certain rights in this invention.

BACKGROUND OF THE INVENTION

Bactericidal/permeability-increasing protein (BPI) is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 2 hereto. U.S. Pat. No. 5,198,541 and WO89/10486 (PCT/US88/02700) disclose recombinant genes encoding and methods for expression of BPI proteins, including BPI holoprotein and fragments of BPI.

BPI is a member of a gene/protein family of lipopolysaccharide (LPS) binding and lipid transfer proteins whose other currently known members include lipopolysaccharide binding protein (LBP), cholesteryl ester transfer protein (CETP) and phospholipid transfer protein (PLTP).

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).]

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on lipopolysaccharide (LPS). In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. Bacterial LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

A variety of BPI protein products as described herein have been discovered and produced, including naturally and recombinantly produced BPI holoprotein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides.

BPI protein products are also capable of neutralizing the endotoxic properties of bacteria and their LPS to which these products bind. Because of the gram-negative bactericidal properties and the ability to bind to, clear and neutralize bacterial LPS, BPI protein products can be utilized for the treatment of mammals suffering from diseases caused by gram-negative bacteria, including sepsis, bacteremia, and bacterial endotoxemia. In addition BPI was discovered to have killing and/or inhibitory activities alone, or in combination with other agents, against gram-positive bacteria, mycobacteria, chlamydia, protozoans and fungi. These multiple anti-infective properties make BPI protein products particularly useful and advantageous for anti-infective therapeutic administration.

One BPI amino-terminal fragment, comprising approximately the first 199 amino acid residues of the human BPI holoprotein and referred to as "rBPI$_{23}$" (see Gazzano-Santoro et al., 1992, *Infect. Immun.* 60: 4754–4761) has been produced by recombinant means as an approximately 23 kD protein. rBPI$_{23}$ retains the antibacterial activity against gram-negative organisms and also the LPS-binding/neutralizing activity of BPI. A modified N-terminal fragment, engineered for increased stability and homogeneity has been designated rBPI$_{21}$Δcys or rBPI$_{21}$, and is the expression product of DNA encoding from about amino acid 1 to about 193 or 199 of the N-terminal amino acids of BPI holoprotein, but wherein the cysteine at residue number 132 is substituted with alanine.

Three separate functional domains within the N-terminal region of BPI have been discovered [see, e.g., WO94/20532 (PCT/US94/02465); WO95/19372 (PCT/US94/10427); Little et al., *J. Biol. Chem.* 269:1865 (1994), hereby incorporated by reference]. These BPI functional domains comprise specified subregions of the amino acid sequence of BPI that contribute to the total biological activity of the protein. Proteolytic cleavage fragments, overlapping 15-mer peptides and other synthetic peptides have been prepared and analyzed. Domain I is defined as comprising the amino acid sequence of BPI from about amino acid 17 to about amino acid 45. Domain II is defined as comprising the amino acid sequence from about amino acid 65 to about amino acid 99. Domain III is defined as comprising the amino acid sequence of BPI from about amino acid 142 to about amino acid 169. The biological activities of functional domain BPI-derived peptides may include LPS-binding, LPS-neutralization, heparin binding, heparin neutralization or antimicrobial activity, including antibacterial and antifungal activities. These peptides, particularly Domain III-derived peptides possess antifungal activity [see also, e.g., WO96/08509 (PCT/US95/09622) and WO 97/04008 (PCT/US96/03845).

Several BPI protein products (i.e., rBPI$_{23}$, rBPI$_{21}$ which is a BPI analog protein) have been introduced into human clinical trials. Proinflammatory responses to injected endotoxin were significantly ameliorated when rBPI$_{23}$ was administered to human volunteers. Thus, humans with endotoxin in circulation may be effectively treated with BPI protein products as described in U.S. patent application Ser. No. 08/291,112 and WO95/19784 (PCT/US95/01151). rBPI$_2$, is currently in multiple clinical trials for the treatment of severe pediatric meningococcemia, infections complications of hemorrhage due to trauma, infectious complications of liver surgery, severe intra-abdominal infections and antibiotic resistant infections in cystic fibrosis.

A number of other important biological activities of BPI protein products have been discovered. For example, BPI protein products have been shown to have heparin binding and heparin neutralization activities in WO94/20128 (PCT/US94/02401), U.S. Pat. Nos. 5,348,942 and 5,639,727, and U.S. patent application Ser. No. 08/466,624, the disclosures of which are incorporated by reference herein. These heparin binding and neutralization activities of BPI protein products are significant due to the importance of current clinical uses of heparin. Heparin is commonly administered in doses of up to 400 U/kg during surgical procedures such as cardiopulmonary bypass, cardiac catherization and hemodialysis procedures in order to prevent blood coagulation during such procedures. When heparin is administered for anticoagulant effects during surgery, it is an important aspect of post-surgical therapy that the effects of heparin are promptly neutralized so that normal coagulation function can be restored. Currently, protamine is used to neutralize heparin. Protamines are a class of simple, arginine-rich, strongly basic, low molecular weight proteins. Administered alone, protamines (usually in the form of protamine sulfate) have anti-coagulant effects. When administered in the presence of heparin, a stable complex is formed and the anticoagulant activity of both drugs is lost. However, significant hypotensive and anaphylactoid effects of protamine have limited its clinical utility. Thus, due to its heparin binding and neutralization activities, BPI protein products have utility as a substitute for protamine in heparin neutralization in a clinical context without the deleterious side-effects which have limited the usefulness of the protamines (see, e.g., WO94/20128 (PCT/US94/02401) and U.S. Pat. No. 5,348,942). rBPI$_{23}$ has been shown to neutralize the anticoagulant effects of administered heparin in human volunteers. The additional anti-infective properties, including antibacterial and anti-endotoxin effects, of BPI protein products are also useful and advantageous in post-surgical heparin neutralization compared with protamine.

Additionally, BPI protein products are useful in inhibiting angiogenesis due in part to their heparin binding and neutralization activities (see, e.g., WO94/20128 (PCT/US94/02401) and U.S. patent application Ser. No. 08/466,624). In adults, angiogenic growth factors are released as a result of vascular trauma (wound healing), immune stimuli (autoimmune disease), inflammatory mediators (prostaglandins) or from tumor cells. These factors induce proliferation of endothelial cells (which is necessary for angiogenesis) via a heparin-dependent receptor binding mechanism (see Yayon et al., 1991, Cell 64: 841–848). Angiogenesis is also associated with a number of other pathological conditions, including the growth, proliferation, and metastasis of various tumors; diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's sarcoma. Thus, it would be desirable to inhibit angiogenesis in these and other instances, and the heparin binding and neutralization activities of BPI are useful to that end.

Another utility of BPI protein products involve pathological conditions associated with chronic inflammatory disease states, which are usually accompanied by angiogenesis (see, e.g., WO94/20128 (PCT/US94/02401) and U.S. Pat. No. 5,639,727). One example of a human chronic inflammatory disease state is arthritis, which involves inflammation of peripheral joints. In rheumatoid arthritis, the inflammation is immune-driven, while in reactive arthritis, inflammation is associated with infection of the synovial tissue with pyogenic bacteria or other infectious agents. Folkman et al., 1992, supra, have also noted that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease or an epiphenomenon, there is significant evidence that angiogenesis is necessary for the maintenance of synovitis in rheumatoid arthritis. While nonsteroidal anti-inflammatory drugs, corticosteroids and other therapies have provided treatment improvements for relief of arthritis, there remains a need for more effective therapies, such as treatment with BPI protein products, for arthritis and other chronic inflammatory disease states.

BPI is also known to possess biological activity useful for the treatment of thrombotic disorders. BPI protein products reduce the adverse effects of thrombotic disorders by activites that include slowing or delaying clot formation (i.e., anticoagulant activity) and/or by enhancing, accelerating or increasing clot dissolution (i.e., thrombolytic activity). Thus, BPI protein products are useful in methods for the treatment of thrombotic disorders, for dissolving or lysing clots in thrombotic patients, for delaying or inhibiting hard clot formation or supplementing thrombolytic therapy in the patients (see, e.g., U.S. patent application Ser. No. 08/644,290 and PCT/US97/08017, hereby incorporated by reference).

A need continues to exist for new products and methods for use as anti-infective products, including antimicrobial agents (e.g., gram-negative bacteria [U.S. Pat. Nos. 5,198,541 and 5,523,288; WO95/08344 (PCT/US94/11225)] and gram-positive bacteria [U.S. Pat. No. 5,578,572; WO95/19180 (PCT/US95/00656)], fungi [U.S. Pat. No. 5,627,153; WO95/19179 (PCT/US95/00498)], mycobacteria [WO94/20129 (PCT/US94/02463)] and chlamydia [WO96/01647 (PCT/US95/08624)] and endotoxin binding/neutralizing agents [WO95/019784 (PCT/US95/01151)], and as heparin binding/neutralizing products [U.S. Pat. Nos. 5,348,942 and 5,639,727; WO94/20128 (PCT/US94/02401], including for the neutralization of exogeneously administered heparin, inhibition of angiogenesis (normal or pathological) for the treatment of chronic inflammatory disease states, and anti-coagulant and thrombolytic agents for the treatment of thrombotic disorders [PCT/US97/08017]. All of the above-listed references regarding biological activities of BPI are hereby incorporated by reference. One avenue of investigation towards fulfilling this need is the determination of the crystal structure of BPI. Advantageous therapeutic embodiments would therefore comprise therapeutic and/or diagnostic agents based on or derived from the three-dimensional crystal structure of BPI that have one or more than one of the functional activities of BPI. Additional therapeutic embodiments would comprise therapeutic and/or diagnostic agents based on or derived from molecular modeling of other members of the BPI protein family, such as LBP, CETP and PLTP, using three-dimensional crystal structure of BPI.

SUMMARY OF THE INVENTION

The present invention provides methods of expressing, purifying and crystallizing bactericidal/permeability-increasing protein (BPI) products. Also provided is crystallized BPI. The crystallized BPI can be analyzed to provide x-ray diffraction patterns of sufficiently high resolution to be useful for determining the three-dimensional protein structure.

The x-ray diffraction patterns can be either analyzed directly to provide the three-dimensional structure (if of sufficiently high resolution), or atomic coordinates for the crystallized BPI, as provided herein, can be used for structure determination. The x-ray diffraction patterns obtained by methods of the present invention, and provided on computer readable media, are used to provide electron density maps. The amino acid sequence is also useful for three-dimensional structure determination. The data is then used in combination with phase determination (e.g. using multiple isomorphous replacement (MIR) molecular replacement techniques) to generate electron density maps of BPI, using a suitable computer system.

The electron density maps, provided by analysis of either the x-ray diffraction patterns or working backwards from the atomic coordinates, provided herein, are then fitted using suitable computer algorithms to generate secondary, tertiary and/or quaternary structures and/or domains of BPI, which structures and/or domains are then used to provide an overall three-dimensional structure, as well as binding and/or active sites of BPI.

Three-dimensional modeling of BPI and other members of the BPI protein family is provided by the present invention using the coordinates from the x-ray diffraction patterns. The x-ray diffraction coordinates and amino acid sequences are entered into one or more computer programs for molecular modeling. Such molecular modeling programs generate atomic coordinates that reflect the secondary, tertiary and/or quaternary structures of the protein which contribute to its overall three-dimensional structure and provide information related to binding and/or active sites of the protein.

Similar molecular modeling is also provided by the present invention for rational drug design (RDD) of mimetics and ligands of BPI and other members of the BPI protein family. The drug design paradigm uses computer modeling programs to determine potential mimetics and ligands which are expected to interact with sites on the protein. The potential mimetics or ligands are then screened for activity and/or binding. For BPI-related mimetics or ligands, screening methods can be selected from assays for at least one biological activity of BPI, e.g., anti-microbial, LPS-binding/neutralizing, heparin binding/neutralizing, and/or anti-thrombotic activities, according to known method steps. Similarly for LBP-, CETP- or PLTP-related mimetics or ligands, such screening methods can be selected from assays for at least one biological activity of LBP, CETP or PLTP, according to known method steps.

The resulting mimetics or ligands are then provided by methods of the present invention and are useful for treating, inhibiting or preventing BPI-modulated diseases (or LBP-, CETP- and PLTP-modulated) in animals, including humans.

One embodiment of this invention envisions use of atomic coordinates of bactericidal/permeability-increasing ("BPI") protein, or fragment, analog or variant thereof, to model a BPI protein or a BPI-related lipid transfer protein. Preferably, the BPI-related transfer protein is lipopolysaccharide-binding protein (LBP), cholesteryl ester transferase protein (CETP) or phospholipid transfer protein (PLTP), or a fragment, analog or variant thereof.

Preferred embodiments of the aforementioned uses are those wherein the BPI protein comprises a binding site characterized by amino acid residues of at least one binding pocket as defined in Table 3; those wherein the BPI protein comprises a binding site characterized by at least one amino acid sequence, or variant of the sequence, selected from positions about 17 to about 45, positions about 65 to about 99 or positions about 142 to about 169 of BPI; and those wherein the BPI protein comprises a binding site characterized by amino acid residues of at least one binding pocket as defined in Table 3 and a binding site characterized by at least one amino acid sequence, or variant of the sequence, selected from positions about 17 to about 45, positions about 65 to about 99 or positions about 142 to about 169 of BPI.

In another embodiment, this invention envisions use of atomic coordinates of bactericidal/permeability-increasing ("BPI") protein to computationally design a chemical compound for mimicking BPI protein, or fragment, analog or variant thereof; or to computationally design a chemical compound for mimicking a BPI-related lipid transfer protein, or fragment, analog or variant thereof. Preferably, the BPI-related lipid transfer protein is lipopolysaccharide-binding protein (LBP), cholesteryl ester transferase protein (CETP) or phospholipid transfer protein (PLTP).

In another embodiment, this invention envisions use of atomic coordinates of bactericidal/permeability-increasing ("BPI") protein, to design a chemical compound capable of associating with a BPI-related lipid binding protein, or fragment, analog or variant thereof. Preferably, the BPI-related lipid binding protein is lipopolysaccharide-binding protein (LBP), cholesteryl ester transferase protein (CETP) or phospholipid transfer protein (PLTP), or a fragment, analog or variant thereof.

In another embodiment, this invention envisions use of atomic coordinates of bactericidal/permeability-increasing ("BPI") protein to design a model of ligands in an active site of a lipid binding protein. Preferably, the lipid binding protein is bactericidal/permeability-increasing protein (BPI), lipopolysaccharide-binding protein (LBP), cholesteryl ester transferase protein (CETP) or phospholipid transfer protein (PLTP), or a fragment, analog or variant thereof.

In another embodiment, this invention envisions use of atomic coordinates of bactericidal/permeability-increasing ("BPI") protein to design compounds with at least one activity selected from the group consisting of antibacterial, antifungal, antimycobacterial, antichlamydial, antiprotozoan, heparin-binding, endotoxin-binding, heparin-neutralizing, endotoxin-neutralizing, inhibition of tumor and endothelial cell proliferation, inhibition of angiogenesis, anti-inflammatory, anticoagulant and antithrombolytic.

In each of the aforementioned uses of atomic coordinates of BPI, the coordinates according to FIG. 6 are preferred.

In an alternate embodiment, this invention envisions a method of three-dimensional modeling of a bactericidal/permeability-increasing ("BPI") protein or a BPI-related lipid transfer protein, comprising the steps of:

(a) providing three-dimensional atomic coordinates derived from X-ray diffraction measurements of a BPI protein in a computer readable format;

(b) inputting the data from step (a) into a computer with appropriate software programs; and (c) generating a three-dimensional structural representation of the BPI protein suitable for visualization and further computational manipulation.

Preferred embodiments of the aforementioned methods are those methods wherein the BPI protein comprises a binding site characterized by amino acid residues of at least one binding pocket as defined in Table 3; those methods wherein the BPI protein comprises a binding site characterized by at least one amino acid sequence, or variant of the sequence, selected from positions about 17 to about 45, positions about 65 to about 99 or positions about 142 to about 169 of BPI; and those methods wherein the BPI protein comprises a binding site characterized by amino acid residues of at least one binding pocket as defined in Table 3 and a binding site characterized by at least one amino acid sequence, or variant of the sequence, selected from positions about 17 to about 45, positions about 65 to about 99 or positions about 142 to about 169 of BPI.

Other objects of the invention will be apparent to one of ordinary skill in the art from the following detailed description and examples relating to the present invention.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 6 Atomic coordinates of a BPI protein determined as described herein (FIG. 6.1–6.110) and refinement statistics (FIG. 6.111–6.112).

FIG. 8 is a reproduction of Table 3 showing residues of an N-terminal and a C-terminal binding pocket (FIGS. 8.1–8.5). "Residue[1]" shows residue name and number in SEQ ID NO:2; "ΔSA[2]" shows checked residues, which residues show a change in solvent accessible surface area with lipid binding; "Within 4 Å[3]" shows checked residues that have some atom within 4 Å of a lipid atom (if the contact is to the head group of the lipid, the residues are listed at the end, under ENTRY ONLY); "Conservation[4]" shows conservation in 3 BPI and 4 LBP sequences, e.g., for Ile 68, in 3 of the 7 sequences, the residue is similarly Ile; for the other 4 sequences, the residue is Leu (see note 5);

Figure 1:
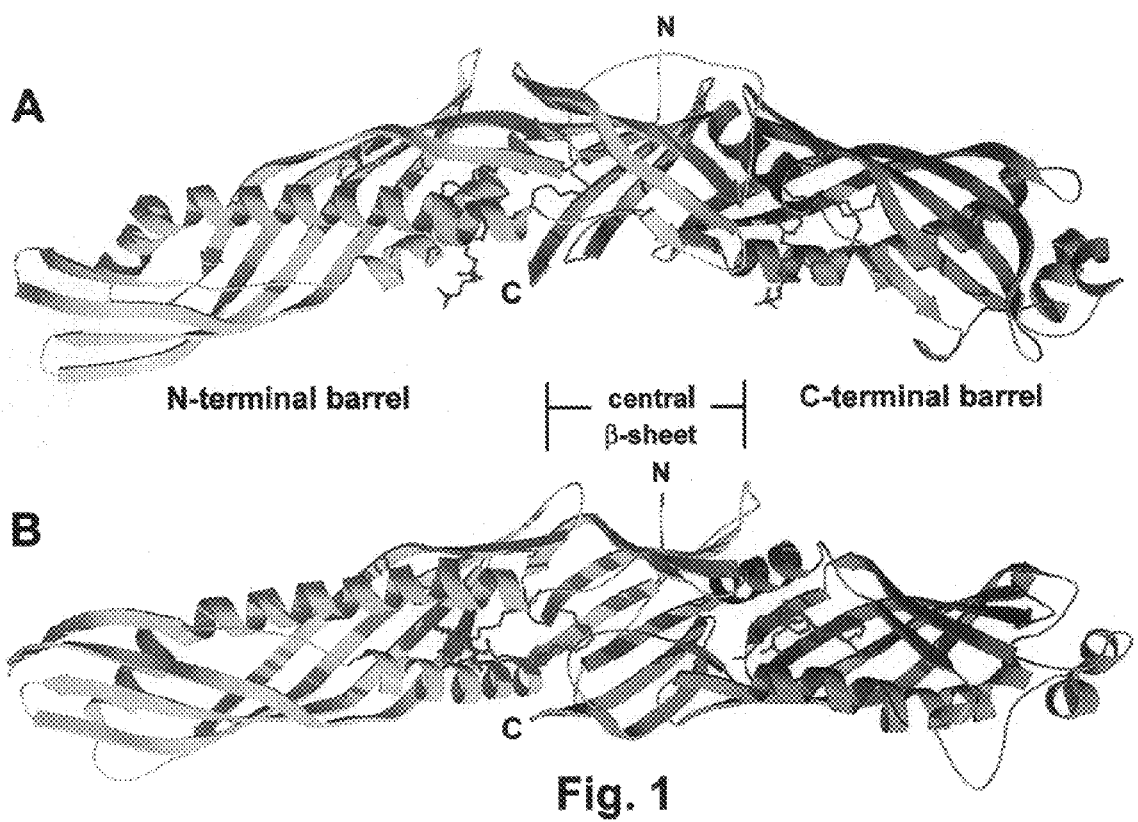
FIG. 1 (A) A ribbon diagram of residues 1–456 of BPI illustrating its boomerang shape. The $NH_2$-terminal domain is shown in green, the COOH-terminal domain in blue, and the two phosphatidylcholine molecules in red. The linker is yellow, and the disulfide bond is shown as a ball-and-stick model. (B) View after rotating (A) 70° about the long axis of the molecule. Figure produced with MOLSCRIPT [P. Krauliz, *J. Appl. Cryst.*, 24:926 (1991)] and RASTER3D [E. A. Merrit and M. E. P. Murphy, *Acta Crystallogr.*, D50:889 (1994); D. J. Bacon and W. F. Anderson, *J. Mo. Graphics*, 6:219 (1988)].

"Alternatives⁵" indicates alternative residues which occur in BPI or LBP at that position for the 7 BPI and LBP sequences analyzed; and "Mutations⁶" indicates residues for mutations to block the pockets using residues selected to be well-conserved (especially in the N-terminal domain) and relatively small. The suggested mutations are all to large sidechains in order to decrease the size of the pocket by as much as possible.

DETAILED DESCRIPTION

The present invention provides methods for crystallizing a BPI protein product where the crystals diffract x-rays with sufficiently high resolution to allow determination of the three-dimensional structure of the BPI protein product, including atomic coordinates. The three-dimensional structure (.e.g, as provided on computer readable media as described herein) is useful for rational drug design of BPI-related (and LBP-, CETP-, PLTP-related) mimetics and/or ligands. Specifically provided is a method for crystallizing a recombinant non-glycosylated human BPI analog holoprotein comprising a 456 amino acid sequence wherein the amino acid serine at position 351 has been changed to alanine. The three-dimensional structure is useful for modeling and/or synthesizing BPI-related mimetics or ligands. Such BPI-related mimetics or ligands are useful for treating, inhibiting or preventing BPI-modulated diseases.

The present invention thus includes methods of expressing, purifying and crystallizing a BPI protein product from suitable sources, such as eukaryotic cells or tissues. The present invention also provides crystallized BPI protein products by these methods. The crystallized BPI is analyzed by x-ray diffraction techniques to obtain high resolution diffraction patterns and atomic coordinates that are suitable for molecular modeling.

As used herein, "BPI protein product" or "BPI protein" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products for therapeutic or diagnostic uses may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI (also referred to as $rBPI_{55}$ or simply $rBPI_{50}$) and recombinant fragments of BPI. U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NO: 2) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in U.S. Pat. No. 5,447,913, and corresponding PCT Application No. PCT/US95/03125, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in U.S. patent application Ser. No. 07/885, 911, and a continuation-in-part application thereof, which matured to U.S. Pat. No. 5,643,570 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Similarly configured hybrid fusion proteins involving part or all Lipopolysaccharide Binding Protein (LBP) are also contemplated for use in the present invention.

Biologically active analogs of BPI (BPI analogs) include but are not limited to BPI protein products wherein one or more amino acid residues have been replaced by a different amino acid. For example, U.S. Pat. No. 5,420,019 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. U.S. Pat. No. 5,447,913 and corresponding PCT Application No. PCT/US95/03125, the disclosures of which are incorporated herein by reference.

Other BPI protein products useful according to the methods of the invention are peptides derived from or based on BPI produced by recombinant or synthetic means (BPI-derived peptides), such as those described in U.S. patent application Ser. No. 08/504,841 filed Jul. 20, 1995 and in PCT Application No. PCT/US94/10427 filed Sep. 15, 1994, which corresponds to U.S. patent application Ser. No. 08/306,473 filed Sep. 15, 1994 now U.S. Pat. No. 5,652,332, and PCT Application No. US94/02465 filed Mar. 11, 1994, which corresponds to U.S. patent application Ser. No. 08/209,762, filed Mar. 11, 1994 now U.S. Pat. No. 5,733,872, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993 now U.S. Pat. No. 5,348,942, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. One pharmaceutical composition containing BPI protein products (e.g., $rBPI_{50}$, $rRBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another pharmaceutical composition containing BPI protein products (e.g., $rBPI_{21}$) comprises the BPI protein product at a concentration of 2 mg/mL in 5 mM citrate, 150 mM NaCl, 0.2% poloxamer 188 and 0.002% polysorbate 80. Such combinations are described in PCT Application No. US94/01239 filed Feb. 2, 1994, which corresponds to U.S. patent application Ser. No. 08/190,869 filed Feb. 2, 1994 now U.S. Pat. No. 5,488,034, and U.S. patent application Ser. No. 08/012,360 filed Feb. 2, 1993, the disclosures of all of which are incorporated herein by reference. Additional formulations are provided in U.S. patent application Ser. Nos. 08/372,104, 08/530,599, and 08/586,133 U.S. Pat. No. 5,912,228, and corresponding WO96/21436 (PCT/US96/01095).

The x-ray diffraction patterns of the invention are now discovered to be of sufficiently high resolution to be useful for three-dimensional modeling of a BPI. Preferably the resolution is in the range of 1.5 to 3.5 Å, preferably 1.5–3.0 Å and more preferably $\leq 2.6$ Å.

Three-dimensional modeling is performed using the diffraction coordinates from these x-ray diffraction patterns. The coordinates are entered into one or more computer programs for molecular modeling, as known in the art. Such molecular modeling can utilize known x-ray diffraction molecular modeling algorithms or molecular modeling software to generate atomic coordinates corresponding to the three-dimensional structure of at least one BPI or a fragment thereof.

The entry of the coordinates of the x-ray diffraction patterns and the amino acid sequence into such programs results in the calculation of most probable secondary, tertiary and quaternary structures of the protein, including overall atomic coordinates of a BPI or a fragment thereof. These structures are combined and refined by additional calculations using such programs to determine the probable or actual three-dimensional structure of the BPI, including potential or actual active or binding sites of the protein.

Such molecular modeling (and related) programs useful for rational drug design of ligands or mimetics, are also provided by the present invention. The drug design uses computer modeling programs which calculate how different molecules interact with the various sites of the BPI. This procedure determines potential ligands or mimetics of a BPI or at least one fragment thereof. The actual BPI-ligand complexes or mimetics are crystallized and analyzed using x-ray diffraction. The diffraction pattern coordinates are similarly used to calculate the three-dimensional interaction of a ligand and the BPI or a mimetic, in order to confirm that the ligand binds to, or changes the conformation of, a particular site on the BPI, or where the mimetic has a similar three-dimensional structure to that of a BPI or a fragment thereof.

The potential ligands or mimetics are then screened for activity relating to a BPI. Such screening methods are selected from assays for at least one biological activity of the native BPI.

The resulting ligands or mimetics, provided by methods of the present invention, are useful for treating, screening or preventing bacterial infections in animals, such as mammals (including humans) and birds. Mimetics or ligands of a particular BPI will similarly react with other BPIs from other species, subgenera or genera of the BPI source organism.

Also provided are biologically active BPI proteins. A BPI protein is also provided as a crystallized protein suitable for x-ray diffraction analysis. The x-ray diffraction patterns obtained by the x-ray analysis are of moderately high to high resolution, e.g., 1.5–3.5 Å. The coordinates from these diffraction patterns are suitable and useful for three-dimensional modeling of the crystallized protein.

During the three-dimensional modeling of the BPI, these coordinates are entered with the BPI amino acid sequence into computer modeling programs to generate secondary, tertiary and quaternary structures of the BPI, as atomic coordinates. These structures together provide the three-dimensional structure of the BPI. The calculated and confirmed three-dimensional structure is then used for rational drug design of ligands or mimetics of the BPI or a fragment thereof.

The determination of the three-dimensional structure of a BPI protein thus has a broad-based utility. Significant sequence identity and conservation of important structural elements is expected to exist among the BPI proteins of a particular species, subgenus, genus, or family. Therefore, the three-dimensional structure from one or a few BPI proteins can be used to identify therapeutics with one or more of the biological activities of BPI (and/or those of related proteins such as LBP, CETP and PLTP).

Determination of Protein Structures

Different techniques give different and complementary information about protein structure. The primary structure is obtained by biochemical methods, either by direct determination of the amino acid sequence from the protein, or from the nucleotide sequence of the corresponding gene or cDNA. The quaternary structure of large proteins or aggregates can also be determined by electron microscopy. To obtain the secondary and tertiary structure, which requires detailed information about the arrangement of atoms within a protein, x-ray crystallography is preferred.

The first prerequisite for solving the three-dimensional structure of a protein by x-ray crystallography is a well-ordered crystal that will diffract x-rays strongly. The crystallographic method directs a beam of x-rays onto a regular, repeating array of many identical molecules so that the x-rays are diffracted from it in a pattern from which the structure of an individual molecule can be retrieved. Well-ordered crystals of globular protein molecules are large, spherical, or ellipsoidal objects with irregular surfaces, and crystals thereof contain large holes or channels that are formed between the individual molecules. These channels, which usually occupy more than half the volume of the crystal, are filled with disordered solvent molecules. The protein molecules are in contact with each other at only a few small regions. This is one reason why structures of proteins determined by x-ray crystallography are generally the same as those for the proteins in solution.

The formation of crystals is dependent on a number of different parameters, including pH, temperature, protein, concentration, the nature of the solvent and precipitant, as well as the presence of added ions or ligands to the protein. Many routine crystallization experiments may be needed to screen all these parameters for the few combinations that might give crystal suitable for x-ray diffraction analysis. Crystallization robots can automate and speed up the work of reproducibly setting up large number of crystallization experiments.

A pure and homogeneous protein sample is important for successful crystallization. Proteins obtained from cloned genes in efficient expression vectors can be purified quickly to homogeneity in large quantities in a few purification steps. A protein to be crystallized is preferably at least 93–99% pure according to standard criteria of homogeneity. Crystals form when molecules are precipitated very slowly from supersaturated solutions. The most frequently used procedure for making protein crystals is the hanging-drop method, in which a drop of protein solution is brought very gradually to supersaturation by loss of water from the droplet to the larger reservoir that contains salt or polyethylene glycol solution.

Different crystal forms can be more or less well-ordered and hence give diffraction patterns of different quality. As a general rule, the more closely the protein molecules pack, and consequently the less water the crystals contain, the better is the diffraction pattern because the molecules are better ordered in the crystal.

X-rays are electromagnetic radiation at short wavelengths, emitted when electrons jump from a higher to a lower energy state. In conventional sources in the laboratory, x-rays are produced by high-voltage tubes in which a metal plate, the anode, is bombarded with accelerating electrons and thereby caused to emit x-rays of a specific wavelength, so-called monochromatic x-rays. The high voltage rapidly heats up the metal plate, which therefore has to be cooled. Efficient cooling is achieved by so-called rotating anode x-ray generators, where the metal plate revolves during the experiment so that different parts are heated up.

More powerful x-ray beams can be produced in synchrotron storage rings where electrons (or positrons) travel close to the speed of light. These particles emit very strong radiation at all wavelengths from short gamma rays to visible light. When used as an x-ray source, only radiation within a window of suitable wavelengths is channeled from the storage ring. Polychromatic x-ray beams are produced by having a broad window that allows through x-ray radiation with wavelengths of 0.2–3.5 Å.

In diffraction experiments a narrow and parallel beam of x-rays is taken out from the x-ray source and directed onto the crystal to produce diffracted beams. The incident primary beam causes damage to both protein and solvent molecules. The crystal is, therefore, usually cooled to prolong its lifetime (e.g., −220 to −50° C.). The primary beam must strike the crystal from many different directions to produce all possible diffraction spots, and so the crystal is rotated in the beam during the experiment.

The diffracted spots are recorded either on a film, the classical method, or by an electronic detector. The exposed film has to be measured and digitized by a scanning device, whereas electronic detectors feed the signals they detect directly in a digitized form into a computer. Electronic area detectors (an electronic film) significantly reduce the time required to collect and measure diffraction data.

When the primary beam from an x-ray source strikes the crystal, some of the x-rays interact with the electrons on each atom and cause them to oscillate. The oscillating electrons serve as a new source of x-rays, which are emitted in almost all directions, referred to as scattering. When atoms (and hence their electrons) are arranged in a regular three-dimensional array, as in a crystal, the x-rays emitted from the oscillating electrons interfere with one another. In most cases, these x-rays, colliding from different directions, cancel each other out; those from certain directions, however, will add together to produce diffracted beams of radiation that can be recorded as a pattern on a photographic plate or detector.

The diffraction pattern obtained in an x-ray experiment is related to the crystal that caused the diffraction. X-rays that are reflected from adjacent planes travel different distances, and diffraction only occurs when the difference in distance is equal to the wavelength of the x-ray beam. This distance is dependent on the reflection angle, which is equal to the angle between the primary beam and the planes.

The relationship between the reflection angle ($\theta$), the distance between the planes (d), and the wavelength ($\lambda$) is given by Bragg's law: $2d \sin \theta = \lambda$. This relation can be used to determine the size of the unit cell in the crystal. Briefly, the position on the film of the diffraction data relates each spot to a specific set of planes through the crystal. By using Bragg's law, these positions can be used to determine the size of the unit call.

Each atom in a crystal scatters x-rays in all directions, and only those that positively interfere with one another, according to Bragg's law, give rise to diffracted beams that can be recorded as a distinct diffraction spot above background. Each diffraction spot is the result of interference of all x-rays with the same diffraction angle emerging from all atoms. For example, for the protein crystal of myoglobin, each of the about 20,000 diffracted beams that have been measured contain scattered x-rays from each of the around 1500 atoms in the molecule. To extract information about individual atoms from such a system requires considerable computation. The mathematical tool that is used to handle such problems is called the Fourier transform.

Each diffracted beam, which is recorded as a spot on the film, is defined by three properties: the amplitude, which we can measure from the intensity of the spot; the wavelength, which is set by the x-ray source; and the phase, which is lost in x-ray experiments. All three properties are needed for all of the diffracted beams, in order to determine the position of the atoms giving rise to the diffracted beams.

For larger molecules, protein crystallographers have determined the phases in many cases using a method called multiple isomorphous replacement (MIR) (including heavy metal scattering), which requires the introduction of new x-ray scatterers into the unit cell of the crystal. These additions are usually heavy atoms (so that they make a significant contribution to the diffraction pattern), such that there should not be too many of them (so that their positions can be located); and they should not change the structure of the molecule or of the crystal cell, i.e., the crystals should be isomorphous. Isomorphous replacement is usually done by diffusing different heavy-metal complexes into the channels of the preformed protein crystals. The protein molecules expose side chains (such as SH groups) into these solvent channels that are able to bind heavy metals. It is also possible to replace endogenous light metals in metalloproteins with heavier ones, e.g., zinc by mercury, or calcium by samarium.

Since such heavy metals contain many more electrons than the light atoms (H,N,C,O and S) of the protein, they scatter x-rays more strongly. All diffracted beams would therefore increase in intensity after heavy-metal substitution if all interference were positive. In fact, however, some interference is negative; consequently, following heavy-metal substitution, some spots measurably increase in intensity, others decrease, and many show no detectable difference.

Phase differences between diffracted spots can be determined from intensity changes following heavy-metal substitution. First, the intensity differences are used to deduce the positions of the heavy atoms in the crystal unit cell. Fourier summations of these intensity differences give maps of the vectors between the heavy atoms, the so-called Patterson maps. From these vector maps the atomic arrangement of the heavy atoms is deduced. From the positions of the heavy metals in the unit cell, one can calculate the amplitudes and phases of their contribution to the diffracted beams of protein crystals containing heavy metals.

This knowledge is then used to find the phase of the contribution from the protein in the absence of the heavy-metal atoms. As both the phase and amplitude of the heavy metals and the amplitude of the protein alone is known, as well as the amplitude of the protein plus heavy metals (i.e., protein heavy-metal complex), one phase and three amplitudes are known. From this, the interference of the x-rays scattered by the heavy metals and protein can be calculated to see if it is constructive or destructive. The extent of positive or negative interference, with knowledge of the phase of the heavy metal, given an estimate of the phase of the protein. Because two different phase angles are determined and are equally good solutions, a second heavy-metal complex can be used which also gives two possible phase angles. Only one of these will have the same value as one of the two previous phase angles; it therefore represents the correct phase angle. In practice, more than two different heavy-metal complexes are usually made in order to give a reasonably good phase determination for all reflections. Each individual phase estimate contains experimental errors arising from errors in the measured amplitudes. Furthermore, for many reflections, the intensity differences are too small to measure after one particular isomorphous replacement, and others can be tried.

The amplitudes and the phases of the diffraction data from the protein crystals are used to calculate an electron-density map of the repeating unit of the crystal. This map then has to be interpreted as a polypeptide chain with a particular amino acid sequence. The interpretation of the electron-density map is made more complex by several limitations of the data. First of all, the map itself contains errors, mainly due to errors in the phase angles. In addition, the quality of the map depends on the resolution of the diffraction data, which in turn depends on how well-ordered the crystals are. This directly influences the image that can be produced. The resolution is measured in Å units; the smaller this number is, the higher the resolution and therefore the greater the amount of detail that can be seen.

Building the initial model is a trial-and-error process. First, one has to decide how the polypeptide chain weaves its way through the electron-density map. The resulting chain trace constitutes a hypothesis, by which one tries to match the density of the side chains to the known sequence of the polypeptide. When a reasonable chain trace has finally been obtained, an initial model is built to give the best fit of the atoms to the electron density. Computer graphics are used both for chain tracing and for model building to present the data and manipulated the models.

The initial model will contain some errors. Provided the protein crystals diffract to high enough resolution (e.g., better than 3.5 Å), most or substantially all of the errors can be removed by crystallographic refinement of the model using computer algorithms. In this process, the model is changed to minimize the difference between the experimentally observed diffraction amplitudes and those calculated for a hypothetical crystal containing the model (instead of the real molecule). This difference is expressed as an R factor (residual disagreement) which is 0.0 for exact agreement and about 0.59 for total disagreement.

In general, the R factor is preferably between 0.15 and 0.35 (such as less than about 0.24–0.28) for a well-determined protein structure. The residual difference is a consequence of errors and imperfections in the data. These derive from various sources, including slight variations in the conformation of the protein molecules, as well as inaccurate corrections both for the presence of solvent and for differences in the orientation of the microcrystals from which the crystal is built. This means that the final model represents an average of molecules that are slightly different both in conformation and orientation.

In refined structures at high resolution, there are usually no major errors in the orientation of individual residues, and the estimated errors in atomic positions are usually around 0.1–0.2 Å, provided the amino acid sequence is known. Hydrogen bonds, both within the protein and to bound ligands, can be identified with a high degree of confidence.

Most x-ray structures are determined to a resolution between 1.7 Å and 3.5 Å. Electron-density maps with this resolution range are preferably interpreted by fitting the known amino acid sequences into regions of electron density in which individual atoms are not resolved.

An amino acid sequence is preferred for accurate x-ray structure determination. Thus, recombinant DNA techniques have had a double impact on x-ray structural work. When a protein is cloned and overexpressed for structural studies, the amino acid sequence, necessary for the x-ray work, is also quickly obtained via the nucleotide sequence. Recombinant DNA techniques give us not only abundant supplies of rare proteins, but also their amino acid sequence as a bonus.

Overview of BPI Purification and Crystallization Methods

In general, a BPI protein is purified as described in Example 1. The resulting BPI is in sufficient purity and concentration for crystallization. The BPI is then isolated and assayed for biological activity and for lack of aggregation (which interferes with crystallization). The purified BPI preferably runs as a single band under reducing or nonreducing polyacrylamide gel electrophoresis (PAGE) (nonreducing is used to evaluate the presence of cysteine bridges).

The purified BPI is preferably crystallized using the hanging drop method under varying conditions of at least one of the following: pH, buffer type, buffer concentration, salt type, polymer type, polymer concentration, other precipitating agents and concentration of purified and cleaved BPI. See, e.g., the methods provided in a commercial kit, such as CRYSTAL SCREEN (Hampton Research, Riverside, Calif.). Differently sized and shaped crystals are tested for suitability for x-ray diffraction. Generally, larger crystals provide better crystallography than smaller crystals, and thicker crystals provide better diffraction than thinner crystals.

Purified BPIs

The results of the purification are optionally analyzed by polyacrylamide gel electrophoresis (PAGE) under reducing or non-reducing conditions. A single band is preferably obtained. With disulfide-containing BPIs, it is preferred that the analysis of the cleaved BPI be under non-reducing conditions to indicate whether the cleaved protein formed disulfide linked dimers. The amino acid sequence can also be determined according to known methods, or otherwise obtained, as this sequence is important in determining the three-dimensional structure of the cleaved protein (in combination with crystallographic analysis), as described herein, using molecular modeling techniques.

Before crystallization, the purified protein is tested for one or more of the known biological activities of a BPI protein.

It is preferred that the biological activity exceed the activity of the native protein. The preferred result indicates that the BPI protein retains its native structure, which is important for determining the three-dimensional crystal structure of the biologically active molecule. To identify the protease cleavage site, the purified and cleaved protein can be sequenced using known techniques. See, e.g., Murti et al., *Proc. Natl. Acad. Sci. USA* 90:1523–1525 (1993); Takimoto et al. (1992), infra, entirely incorporated herein by reference.

Protein Crystallization Methods

The hanging drop method is preferably used to crystallize the purified protein. See, e.g., Taylor et al., *J. Mol. Biol.* 226:1287–1290 (1992); Takimoto et al. (1992), infra; CRYSTAL SCREEN, Hampton Research.

A mixture of the purified protein and precipitant can include the following:

pH (e.g., 4–9);

buffer type (e.g., phosphate, cacodylate, acetates, imidazole, Tris HCl, sodium HEPES);

buffer concentration (e.g., 10–200 mM);

salt type (e.g., calcium chloride, sodium citrate, magnesium chloride, ammonium acetate, ammonium sulfate, potassium phosphate, magnesium acetate, zinc acetate; calcium acetate)

polymer type and concentration: (e.g., polyethylene glycol (PEG) 1–50%, average molecular weight 200–10,000);

other precipitating agents (salts: K, Na tartrate, $NH_4SO_4$, NaAc, $LiSO_4$, NaFormate, NaCitrate, MgFormate, $NaPO_4$, $KPO_4$ $NH_4PO_4$; organics: 2-propanol; nonvolatile: 2-methyl-2,4-pentanediol); and concentration of purified BPI (e.g., 1.0–100 mg/ml).

See, e.g., CRYSTAL SCREEN, Hampton Research.

A non-limiting example of such crystalization conditions is the following:

purified protein (e.g., approximately 3–4 mg/ml);

$H_2O$;

precipitant 10–14% Polyethylene glycol (PEG) 8000 buffered with 100 mM cacodylate buffer and 200 mM of Mg acetate;

at an overall pH of about 3.5–8.5.

The above mixtures are used and screened by varying at least one of pH, buffer type; buffer concentration, precipitating salt type or concentration, PEG type, PEG concentration, and protein concentration. Crystals ranging in size from 0.2–0.7 mm are formed in 1–7 days. These crystals diffract x-rays to at least 3.5 Å resolution, such as 1.5–3.5 Å, or any range of value therein, such as 1.5, 1.6, 1.7, 1.8, 1.9, 2.0, 2.1, 2.2, 2.3, 2.4, 2.5, 2.6, 2.7, 2.8, 2.9, or 3.0, with 3.0 Å or less being preferred.

Protein Crystals

Crystals appear after 1–4 days and grow to maximal size within a week. From one to ten crystals are observed in one drop and crystal forms can occur, such as, but not limited to, bipyramidal, rhomboid, and cubic. Initial x-ray analyses indicate that such crystals diffract at moderately high to high resolution. When fewer crystals are produced in a drop, they can be much larger size, e.g., 0.4–0.9 mm.

X-ray Crystallography Methods and Molecular Modeling

The crystals so produced for BPI are x-ray analyzed using a suitable x-ray source. Diffraction patterns are obtained. Crystals are preferably stable for at least 10 hrs in the x-ray beam. Frozen crystals (e.g., −220 to −50° C.) could also be used for longer x-ray exposures (e.g., 24–72 hrs), the crystals being relatively more stable to the x-rays in the frozen state. To collect the maximum number of useful reflections, multiple frames are optionally collected as the crystal is rotated in the x-ray beam, e.g., for 24–72 hrs. Larger crystals (>0.2 mm) are preferred, to increase the resolution of the x-ray diffraction. Alternatively, crystals may be analyzed using a synchrotron high energy x-ray source. Using frozen crystals, x-ray diffraction data is collected on crystals that diffract to a relatively high resolution of 3.5 Å or less, sufficient to solve the three-dimensional structure of BPI in considerable detail, as presented herein.

Native and/or derivative x-ray diffraction data with medium resolution is collected on area detectors mounted on rotating anode x-ray sources. The alternative program DENZO is preferably used for data processing and reduction (Sawyer et al., eds., *Proceedings of CCP4 Study Weekend*, pp. 56–62, SERC Darsbary Lab., UK (1993)).

The resolution is optionally improved using larger crystals, e.g., 0.2 mm, making data collection more efficient, particularly for the determination of suitable heavy metal derivatives, such as Hg, Pt, Pb, Ba, Cd, and/or La derivatives.

The heavy metal derivatives are used to determine the phase, e.g., by the isomorphous replacement method. Heavy atom isomorphous derivatives of BPI are used for x-ray crystallography, where the structure is solved using one or several derivatives, which, (when combined) improves the overall figure of merit. Derivatives are identified through Patterson maps and/or cross-phase difference Fourier maps, e.g., using the CCP4 package (SERC Collaborative Computing Project No. 4, Daresbury Laboratory, UK, 1979).

Phases were also obtained or improved by optimization of the anomalous dispersion component of the x-ray scattering which can break the phase ambiguity which a single heavy atom derivative gives. In certain cases phase information may be obtained without the need of a native set of data, through the use of multiple wavelength with anomalous dispersion phasing (MAD phasing). The wavelength of the x-rays used may be selected at a synchrotron source to optimize this anomalous scattering. In this case data from a derivatised crystal or crystals is collected at typically three wavelengths, two of which are very close to the absorption edge of the heavy atom scatterer. One way of obtaining a suitable heavy atom derivatised crystal is to derivatise a known ligand of the protein.

The program MLPHARE (Wolf et al., eds., *Isomorphous Replacement and Anomalous Scattering: Proceedings of CCP4 Study Weekend*, pp. 80–86, SERC Daresbury Lab., UK (1991)) is optionally used for refinement of the heavy atom parameters and the phases derived from them by comparing at least one of completeness (%), resolution (Å), $R^r$ (%), heavy atom concentration (mM), soaking time, heavy atom sites, phasing power (acentric, centric) (See Table 1 as an analogous example from The Crystal Structure of diphtheria toxin, Choe et al., *Nature* 357: 216–222 (1992). Addition of heavy atom derivatives produce an MIR map with recognizable features.

The initial phases are calculated to 3.2 Å, and then improved and extended to a higher resolution of 2.8 Å (e.g., $\leq 3.0$ Å) using solvent flattening, histogram matching and/or Sayre's equation in the program DM (Cowtan and Main, *Acta Crystallogr*. D 49:148–157 (1993)). The skeletonization of DM procedure is optionally used to improve connectivity in the bulk of the protein envelope. Both the MIR and density modified maps are optionally used in subsequent stages, to provide sufficient resolution and/or modeling of surface structures.

Skeletonized representations of electron density maps are then computed. These maps are automatically or manually edited using suitable software, e.g., the graphics package FRODO (Jones et al. (1991), infra) to give a continuous Cα trace. The BPI sequence is then aligned to the trace. Initially pieces of idealized polypeptide backbone were placed into regions of the electron density map with obvious secondary structures (e.g., α-helix, β-sheet). After a polyalanine model was constructed for the protein, amino acid sidechains were added where density was present in the maps. The amino acid sequence of BPI was then examined for regions with distinct sidechain patterns (e.g., three consecutive aromatic rings). When a pattern in the sequence was found to match an area of the map, the correct sidechains were built onto the existing model. Eventually fragments containing recognizable sequence motifs were connected into a single chain, completing the tracing of the amino acid sequence into the maps.

X-ray diffraction data (e.g., to $\leq 3.0$ Å) was collected on an RAXIS 11C area detector (e.g., a Mar imaging plate) mounted on a RIGAKU rotating anode or alternatively a synchrotron x-ray source, and processed using a suitable oscillation data reduction program (DENZO, Sawyer et al. eds., *Proceedings of CCP4 Study Weekend*, pp. 56–62, SERC Darsbary Lab., UK (1993). Cycles of simulated annealing against these data were refined using the program X-PLOR for molecular dynamics for R-factor refinement (X-PLOR, Brünger et al., *J. Mol. Biol.* 203:803–816 (1987)). This refinement was followed by manual rebuilding with FRODO using experimental and $2F_o-F_c$ maps. The model can be optionally further refined using a least-squares refinement program, such as TNT (Tronrud et al., *Acta Crystallogr*. A 43:489–501 (1987)).

One or more of the above modeling steps is performed to provide a molecular 3-D model of BPI. It is preferred that the BPI model has no residues in disallowed regions of the Ramachandran plot, and gives a positive 3D-1D profile (Luthy et al., *Nature* 356:83–85 (1992)), suggesting that all the residues are in acceptable environments (Kraulis (1991), infra).

Multiple isomorphous replacement phase determination was used for solving the three-dimensional structure of BPI. This structure is then used for rational drug design of BPI ligands or mimetics of at least one BPI bactericidal activity, or other biological activity important in inactivating bacterial toxicity, replication and/or infection.

Computer Related Embodiments

An amino acid sequence of a BPI protein (or related protein such as LBP, CETP or PLTP) and/or x-ray diffraction data, useful for computer molecular modeling of BPI protein (or related protein such as LBP, CETP or PLTP) or a portion thereof, can be "provided" in a variety of mediums to facilitate use thereof. As used herein, provided refers to a manufacture, which contains, for example, a BPI amino acid sequence and/or atomic coordinate/x-ray diffraction data of the present invention, e.g., an amino acid sequence provided in FIG. 5, a representative fragment thereof, or an amino acid sequence having at least 80–100% overall identity to an amino acid fragment of an amino acid sequence of FIG. 5 or a variant thereof. Such a method provides the amino acid sequence and/or x-ray diffraction data in a form which allows a skilled artisan to analyze and molecular model the three-dimensional structure of a BPI-related protein, including a subdomain thereof.

In one application of this embodiment, BPI (or related protein such as LBP, CETP or PLTP), or at least one subdomain thereof, amino acid sequence and/or x-ray diffraction data of the present invention is recorded on computer readable medium. As used herein, "computer readable medium" refers to any medium which can be read and accessed directly by a computer. Such media include, but are not limited to: magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon an amino acid sequence and/or x-ray diffraction data of the present invention.

As used herein, "recorded" refers to a process for storing information on computer readable medium. A skilled artisan can readily adopt any of the presently know methods for recording information on computer readable medium to generate manufactures comprising an amino acid sequence and/or atomic coordinate/x-ray diffraction data information of the present invention.

A variety of data storage structures are available to a skilled artisan for creating a computer readable medium having recorded thereon an amino acid sequence and/or atomic coordinate/x-ray diffraction data of the present invention. The choice of the data storage structure will generally be based on the means chosen to access the stored information. In addition, a variety of data processor programs and formats can be used to store the sequence and x-ray data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the information of the present invention.

By providing computer readable medium having stored thereon a BPI or related sequence protein and/or atomic coordinates based on x-ray diffraction data, a skilled artisan can routinely access the sequence and atomic coordinate or x-ray diffraction data to model a BPI or related protein, a subdomain thereof, mimetic, or a ligand thereof. Computer algorithms are publicly and commercially available which allow a skilled artisan to access this data provided in a computer readable medium and analyze it for molecular modeling and/or RDD. See, e.g., Biotechnology Software Directory, MaryAnn Liebert Publ., New York (1995).

The present invention further provides systems, particularly computer-based systems, which contain the sequence and/or diffraction data described herein. Such systems are designed to do structure determination and RDD for a BPI or related protein or at least one subdomain thereof. Non-limiting examples are microcomputer workstations available from Silicon Graphics Incorporated and Sun Microsystems running UNIX based, Windows NT or IBM OS/2 operating systems.

As used herein, "a computer-based system" refers to the hardware means, software means, and data storage means used to analyze the sequence and/or x-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein a BPI or related protein or fragment sequence and/or atomic coordinate/x-ray diffraction data of the present invention and the necessary hardware means and software means for supporting and implementing an analysis means. As used herein, "data storage means" refers to memory which can store sequence or atomic coordinate/x-ray diffraction data of the present invention, or a memory access means which can access manufactures having recorded thereon the sequence or x-ray data of the present invention.

As used herein, "search means" or "analysis means" refers to one or more programs which are implemented on the computer-based system to compare a target sequence or target structural motif with the sequence or x-ray data stored within the data storage means. Search means are used to identify fragments or regions of a BPI or related protein which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, "a target structural motif," or "target motif," refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymic active sites, structural subdomains, epitopes, functional domains and signal sequences. A variety of structural formats for the input and output means can be used to input and output the information in the computer-based systems of the present invention.

A variety of comparing means can be used to compare a target sequence or target motif with the data storage means to identify structural motifs or electron density maps derived in part from the atomic coordinate/x-ray diffraction data. A skilled artisan can readily recognize that any one of the publicly available computer modeling programs can be used as the search means for the computer-based systems of the present invention.

Figure 7:
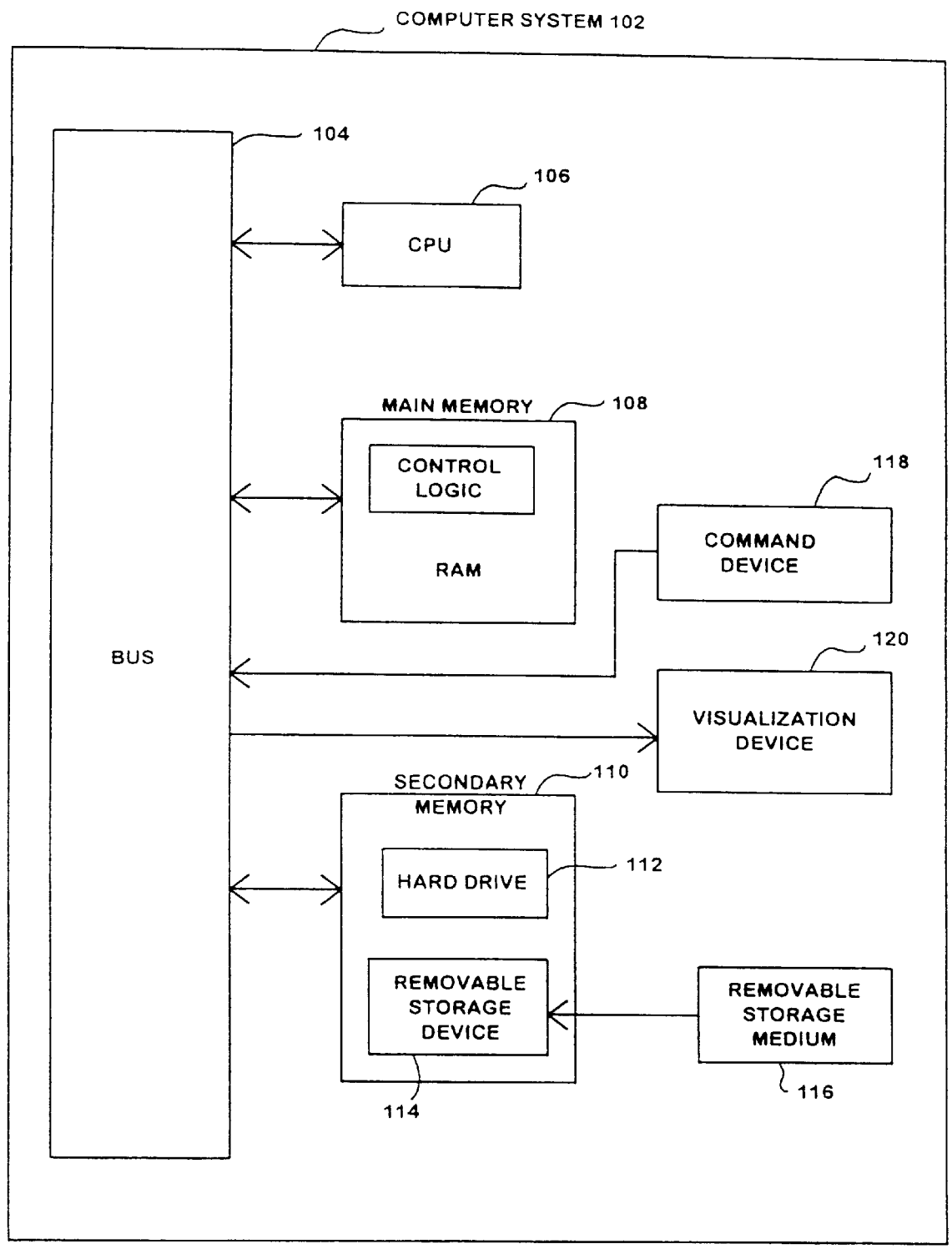
FIG. 7 Block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage memory 110, such as a hard drive 112, a removable medium storage device 114, a command device 118, and a visualization device, 120. Also included is a removable storage medium 116.

One application of this embodiment is provided in FIG. 7. FIG. 7 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage memory 110 such as a hard drive 112, a removable medium storage device 114, a command device 118, and a visualization device, 120. Also included is a removable storage medium 116. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable storage device 114. The computer system 102 includes appropriate software for reading the control logic and/or the data from the removable storage medium 116 once inserted in the removable medium storage device 114.

Amino acid, encoding nucleotide or other sequence and/or atomic coordinate/x-ray diffraction data of the present invention may be stored in a well known manner in the main memory 108, or any of the secondary storage devices 110, and/or a removable storage medium 116. Software for accessing and processing the amino acid sequence and/or atomic coordinate/x-ray diffraction data (such as search tools, comparing tools, etc.) reside in main memory 108 during execution. User commands are implemented through a command device 118, such as a keyboard. The visualization device 120 is optionally used to visualize the structure data.

Structure Determination

Figure 5A:
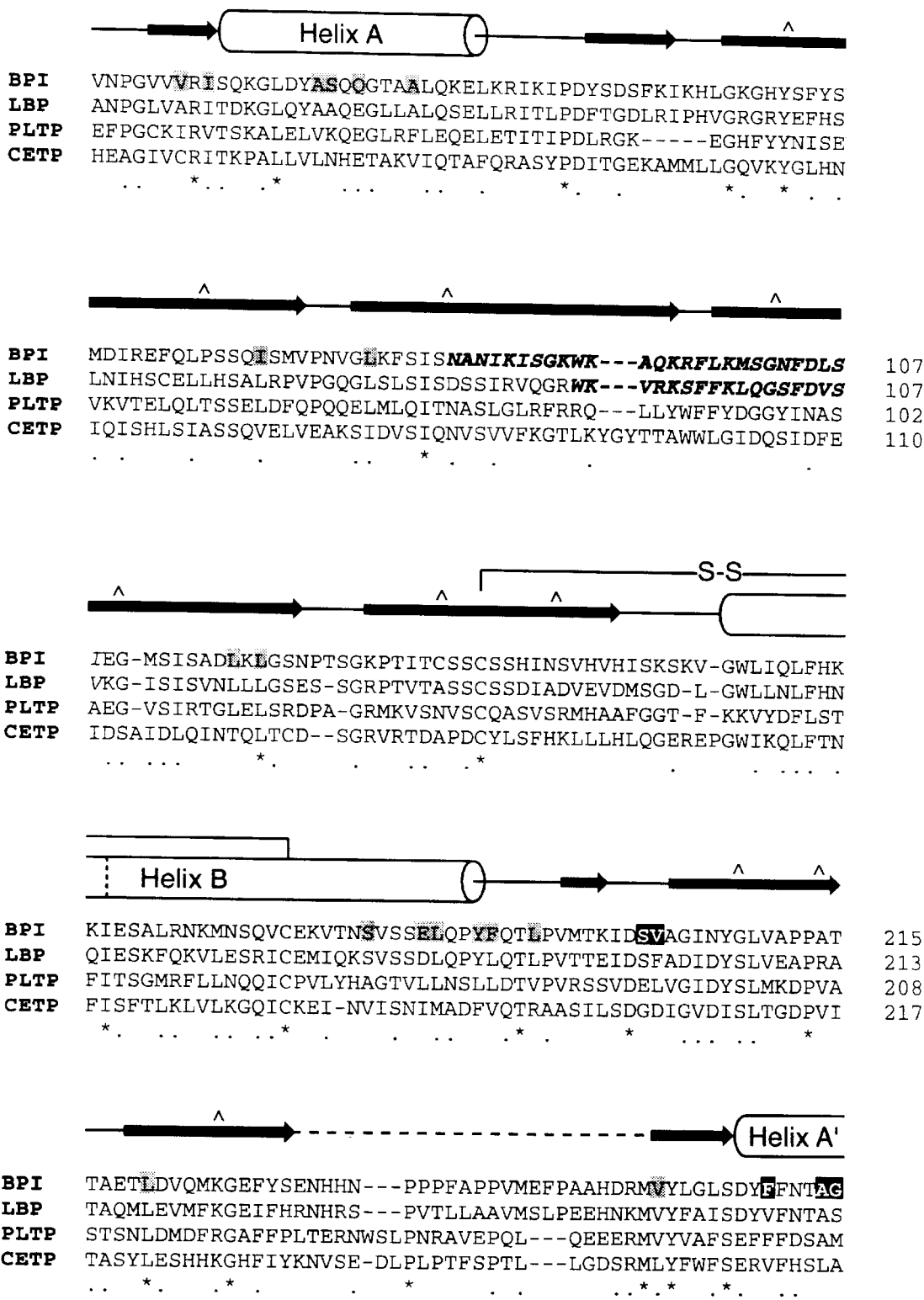
FIG. 5 The amino acid sequences of human BPI (SEQ ID NO:11), LBP (SEQ ID NO:12), PLTP (SEQ ID NO:13), and CETP (SEQ ID NO:14). The alignment was performed with CLUSTAL [D. G. Higgins and P. M. Sharp, *Gene,* 73:237 (1989)] using all eleven known protein sequences from mammals [R. R. Schuman, et al., *Science,* 249:1429 (1990); D. Drayna et al., *Nature,* 327:632 (1987); R. Day et al., *J. Biol. Chem.,* 269:9388 (1994); S. R. Leong and T. Camerato, *Nucleic Acids Res.,* 18:3052 (1990); M. Nagashima, J. W. McLean, R. M. Lawn, *J. Lipid Res.,* 29:1643 (1988); M. E. Pape, E. F. Rehber, K. R. Marotti, G. W. Melchior, *Artheriosclerosis* 11:1759 (1991); G. Su et al., *J. Immunol.,* 153:743 (1994); P. W. Gray et al., *J. Biol. Chem.* 264: 9505 (1989); Albers et al., *Biochem. Biophys. Acta,* 1258:27 (1995); X. C. Jiang et al., *Biochemistry,* 34:7258 (1995); L. B. Agellon et al., *Biochemistry,* 29:1372 (1990); X. C. Jiang et al., *J. Biol. Chem.,* 266:4631 (1991)] but only the four human sequences are shown. Residues that are completely conserved in all proteins are indicated below the sequence *; those which are highly conserved are indicated by •. The secondary structure of BPI is indicated above the sequences. The β strands are indicated by arrows; strands which make up the central β sheet are shown with gray arrows. Because of the β bulges and pronounced twisting, some of the β strands have one or more residues that do not show classical H-bonding patterns or Φψ angles; these breaks are indicated by ^ above the strands. The a helices are shown as cylinders, and one-residue breaks in helices B and B' are indicated with a vertical dashed line. The horizontal dashed line indicates the linker region. Peptides from BPI and LBP with the highest LPS-binding activity (Little, et al., *J. Biol. Chem.* 268: 1865 (1994); Taylor et al., *J. Biol. Chem.* 270: 17934 (1995)) are in bold italics. The disulfide bond is indicated by S-S. Residues with atoms within 4 Å of the $NH_2$-terminal lipid are highlighted with gray shading; residues within 4 Å of the COOH-terminal lipid are shown with white letters in black boxes.

One or more computational steps, computer programs and/or computer algorithms are used to provide a molecular 3-D model of BPI or related protein, using amino acid sequence data from FIG. 5 (or fragments or variants thereof) and/or atomic coordinate/x-ray diffraction data. In x-ray crystallography, x-ray diffraction data and phases are combined to produce electron density maps in which the three-dimensional structure of a BPI protein is then built or modeled. MIR Phase determination was used for solving the three-dimensional structure of BPI. This structure can then be used for RDD of mimetics or ligands of a BPI or related protein and its associated biological activity, which is relevant to a protein modulated disease.

Density Modification and Map Interpretation

Electron density maps were calculated by X-PLOR or alternatively using such programs as those from the CCP4 computing package (SERC (UK) Collaborative Computing Project 4, Daresbury Laboratory, UK, 1979). If non-crystalographic symmetry axes are present, cycles of symmetry averaging can further be used, such as with the program RAVE (Kleywegt & Jones, Bailey et al., eds., *First Map to Final Model*, SERC Daresbury Laboratory, UK, pp 59–66 (1994)) and gradual model expansion. For map visualization and model building the program FRODO was used or alternatively, a program such as "O" (Jones (1991), infra) can be used.

Refinement and Model Validation

Rigid body and positional refinement can be carried out using a program such as X-PLOR (Brünger (1992), infra), e.g., with the stereochemical parameters of Engh and Huber (*Acta Cryst*. A47:392–400 (1991)). If the model at this stage in the averaged maps is still missing residues (e.g., at least 5–10 per subunit), some or all of the missing residues can be incorporated in the model during additional cycles of positional refinement and model building. The refinement procedure can start using data from lower resolution (e.g., 25–10 Å to 10–3.0 Å and then be gradually extended to include higher resolution data from 12–6 Å to 3.0–1.5 Å). B-values (also termed temperature factors) for individual atoms were refined once data between 2.9 and 1.5 Å has been added. Subsequently waters were gradually added by manual inspection of electron density maps. Alternatively, a program such as ARP (Lamzin and Wilson, *Acta Cryst.* D49:129–147 (1993)) can be used to add crystallographic waters and as a tool to check for bad areas in the model. The programs PROCHECK (Lackowski et al., *J. Appl. Cryst.* 26:283–291 (1993)), WHATIF (Vriend, *J. Mol. Graph.* 8:52–56 (1990)), PROFILE 3D (Lüthy et al., *Nature* 356:83–85 (1992)), and ERRAT (Colovos & Yeates *Protein Science,* 2:1511–19 (1993)) as well as the geometrical analysis generated by X-PLOR were used to check the structure for errors. Anisotropic scaling between $F_{obs}$ and $F_{calc}$ was applied after careful assessment of the quality and completeness of the data.

The program DSSP was used to assign the secondary structure elements (Kabsch and Sander, *Biopolymers,* 22:2577–2637 (1983)). A program such as SUPPOS (from the BIOMOL crystallographic computing package) can be used for some or all of the least-squares superpositions of various models and parts of models. The program ALIGN (Cohen *J. Mol. Biol.,* 190: 593–604 (1986)) was used to superimpose N- and C-terminal domains of BPI. Solvent accessible surfaces and electrostatic potentials can be calculated using such programs as GRASP (Nicholls et al. (1991), infra).

The structure of BPI from different organisms and the related proteins LBP, CETP and PLTP can thus be solved with the molecular replacement procedure such as by using X-PLOR (Brunger (1992), infra). A partial search model for a portion or all of these proteins can be constructed using the structures of BPI. The rotation and translation function can be used to yield orientations and positions for these models. Symmetry averaging can also be done using the RAVE program and model expansion can also be used to add missing residues resulting in a model with 95–99.9% of the total number of residues. The model can be refined in a program such as X-PLOR (Brünger (1992), supra), to a suitable crystallographic $R_{factor}$. The model data is then saved on computer readable medium for use in further analysis, such as rational drug design.

Rational Design of Mimetics or Ligands

The determination of the crystal structure of a BPI protein, as described herein, provides a basis for the design of new and specific agents, including proteins or organic compounds.

Several approaches can be taken for the use of the crystal structure of a BPI in the rational design of protein or organic analogs having a relevant activity similar to that of a BPI or related protein. A computer-assisted, manual examination of a BPI potential binding site structure is optionally done. The use of software such as GRID—Goodford, *J. Med. Chem.* 28:849–857 (1985) a program that determines probable interaction sites between probes with various functional group characteristics and the protein surface—is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels.

A diagnostic or therapeutic BPI or related protein modulating ligand of the present invention can be, but is not limited to, at least one selected from a lipid, a nucleic acid, a compound, a protein, an element, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radiosotope or radioactive compounds or elements, fluorescent compounds or metals, chemiluminescent compounds and bioluminescent compounds. Alternatively, any other known diagnostic or therapeutic agent can be used in a method of the invention. Suitable compounds are then tested for activities of a BPI protein or BPI mimetic.

The program DOCK (Kuntz et al. *J. Mol. Biol.,* 161:269–288 (1982)) may be used to analyze an active site or ligand binding site and suggest ligands with complementary steric properties. Several methodologies for searching three-dimensional databases to test pharmacophore hypotheses and select compounds for screening are available. These include the program CAVEAT (Bacon et al. *J. Mol. Biol.,* 225: 849–858 (1992)) which uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. The program LUDI (Bohm et al. *J. Comput.-Aid. Mol. Des.,* 6:61–78 (1992)) can determine a list of interactions sites into which to place both hydrogen bonding and hydrophobic fragments. LUDI then uses a library of approx. 600 linkers to connect up to four different interaction sites into fragments. Then smaller "bridging" groups such as —CH2— and —COO— are used to connect these fragments. For example, for the enzyme DHFR, the placements of key functional groups in the well-known inhibitor methotrexate were reproduced by LUDI. See also, Rotstein and Murcko, *J. Med. Chem.,* 36:1700–1710 (1992)).

After preliminary experiments are done to determine the $K_i$ of a ligand (e.g., a lipid ligand) by BPI (or related) protein to a BPI (or related) protein, mimetic or fragment, the time-dependent nature of the inhibition by the BPI or related protein (e.g., by the method of Henderson (*Biochem. J.* 127:321–333 (1972)) is determined.

For example, a lipid ligand and a BPI mimetic are pre-incubated in buffer. Reactions are initiated by the addition of detecting substrate. Aliquots are removed over a suitable time course and each quenched by addition into the aliquots of suitable quenching solution. The concentration of product are determined by known methods of detection. Plots of activity against time can be close to linear over the assay period, and are used to obtain values for the initial velocity in the presence ($V_i$) or absence ($V_o$) of, for example, a BPI mimetic. Error is present in both axes in a Henderson plot, making it inappropriate for standard regression analysis (Leatherbarrow, *Trends Biochem. Sci.* 15:455–458 (1990)). Therefore, $K_i$ values are obtained from the data by fitting to a modified version of the Henderson equation for competitive inhibition:

$$Qr^2 + (E_t - Q - I_t)r - E_t = 0$$

where (using the notation of Henderson (*Biochem. J.* 127:321–333 (1972)):

$$Q = K_i \left( \frac{A_t + K_a}{K_a} \right)$$

and $$r = \frac{V_o}{V_i}$$

This equation is solved for the positive root with the constraint that $Q = K_i((A_t + K_a)/K_a)$ using PROCNLIN from SAS (SAS Institute Inc., Cary, N.C., USA) which performs nonlinear regression using least-square techniques. The iterative method used is optionally the multivariate secant method, similar to the Gauss-Newton method, except that the derivatives in the Taylor series are estimated from the histogram of iterations rather than supplied analytically. A suitable convergence criterion is optionally used, e.g., where there is a change in loss function of less than $10^{-8}$.

Once modulating compounds are found, crystallographic studies of, for example, BPI mimetics complexed to a ligand are performed. As a non-limiting example, BPI crystals are soaked for 2 days in 0.01–100 mM inhibitor compound and x-ray diffraction data are collected on an area detector and/or an image plate detector (e.g., a Mar image plate detector) using a rotating anode x-ray source. Data are collected to as high a resolution as possible, e.g., $\leq 3.0$ Å, and merged with a suitable R-factor on intensities. An atomic model of the mimetic is built into the difference Fourier map ($F_{inhibitor\ complex} - F_{native}$). The model can be refined to convergence in a cycle of simulated annealing (Brünger (1987), infra) involving 10–100 cycles of energy refinement, 100–10,000 1-fs steps of room temperature dynamics and/or 10–100 more cycles of energy refinement. Harmonic restraints may be used for the atom refinement, except for atoms within a 10–15 Å radius of the inhibitor. An R-factor is calculated for the model as well as an r.m.s. deviation from the ideal bond lengths and angles.

Direct measurements of activity provide further confirmation that the modeled mimetic compounds are high-affinity inhibitors for the lipid ligands. Other suitable assays for biological activity known for BPI or related proteins may be used.

Preferably, little or no change in the structure of the BPI or mimetic occurs in the electron density map described above. $K_j$ values are determined by a previously described method (Henderson (1972), infra) to evaluate mimetic proteins or organic compounds.

Atomic coordinates of BPI proteins are useful in the generation of molecular models of related proteins and of BPI mimetics. Utilizing CLUSTAL (a multiple sequence alignment program in PC-Gene) and the Homology module (a structure-based homology modeling program in InsightII on a Silicon Graphics Incorporated workstation, molecular models (and the corresponding three-dimensional coordinates files) of lipopolysaccharide binding protein (LBP), cholesteryl ester transfer protein (CETP) and phospholipid transfer protein (PLTP) are generated. With these files, existing mutants are mapped and new ones designed.

The results described herein demonstrate that tight-binding mimetics of a BPI or related protein, based on the crystal structure of BPI, are provided by the present invention. Demonstration of clinically relevant levels of a biological activity of the mimetic is also useful.

In evaluating mimetics for biological activity in animal models (e.g., mouse, rat, rabbit, baboon) various oral and parenteral routes of administration are evaluated. Using this approach, it is expected that a biological activity occurs in suitable animal models, e.g., using the mimetics discovered by structure determination and x-ray crystallography.

Having now generally described the invention, the same will be more readily understood through reference to the following examples which are provided by way of illustration, and are not intended to be limiting of the present invention.

EXAMPLE 1

Preparation and Purification for Crystallization
Construction of Plasmids Containing BPI (S351A)

BPI contains a single N-linked glycosylation site at the asparagine at position 349 which was eliminated by genetic engineering of the DNA sequence of BPI as follows. For glycosylation to occur at this position, the asparagine must occur within the sequence Asn-X-Ser/Thr where X can be any amino acid, except proline. N-linked glycosylation can be eliminated by either changing the Asn to another amino acid such as glutamine or by changing the serine or threonine to an alternate amino acid. The latter strategy was used to construct vectors containing BPI with an alanine at position 351 instead of serine.

Construction of Plasmids for BPI Expression

The plasmid pIC108 containing a cDNA encoding BPI cloned in a T3T7 plasmid (Clontech, Palo Alto, Calif.) served as the starting point for the construction of a vector for expression of nonglycosylated rBPI in mammalian cells.

To allow insertion of BPI into an optimized mammalian expression vector, a unique XhoI site was first added to the 3' end of the BPI gene in pIC108. Two oligonucleotides were synthesized for this purpose: BPI-53 (5' ACT GGT TCC ATG GAG GTC AGC GCC 3', SEQ ID NO:3) encoding amino acids 361–370 of BPI and BPI-54 (5' GAC AGA TCT CTC GAG TCA TTT ATA GAC AA 3', SEQ ID NO:4) encoding the the last four amino acids of coding sequence, the stop codon (TGA), and incorporating an XhoI site immediately downstream of the stop codon. These oligonucleotides were used to PCR amplify a 280 bp fragment of the C-terminus of BPI and incorporate the XhoI site at the 3' end of the gene. The amplified fragment was digested with NcoI and BglII and ligated to a ~4100 bp NcoI-BamHI fragment from pIC108 to generate the plasmid pSS101.

Construction of Plasmid with BPI (S351A)

The glycosylation site was next removed by replacing the region from a unique XcmI site to a unique SphI site within the BPI gene in pSS101 with an annealed oligonucleotide that contained the codon (TCC) for the serine at amino acid position 351 changed to the codon (GCC) for alanine as shown below.

```
Wild type
    XcmI                                              SphI
...CCC AAC TCC TCC CTG GCT TCC CTC TTC CTG ATT GGC ATG CAC  (SEQ ID NO:5)
...GGG TTC AGG AGG GAC CGA AGG GAG AAG GAC TAA CCG TAC GTG  (SEQ ID NO:6)
    Pro Asn Ser Ser Leu Ala Ser Leu Phe Leu Ile Gly Met His (SEQ ID NO:7)
                351

Nonglycosylated
    XcmI                                              SphI
...CCC AAC TCC GCC CTG GCT TCC CTC TTC CTG ATT GGC ATG CAC  (SEQ ID NO:8)
...GGG TTC AGG CGG GAC CGA AGG GAG AAG GAC TAA CCG TAC GTG  (SEQ ID NO:9)
    Pro Asn Ser Ala Leu Ala Ser Leu Phe Leu Ile Gly Met His (SEQ ID NO:10)
                351
```

This step generated the plasmid pSS102.

To construct the vector, pING4322, for the expression of full length nonglycosylated holo BPI in mammalian cells, pSS102 was digested with BstBI and XhoI and a 596 bp fragment, which included the modified BPI sequence, was purified and ligated to the large BstBI-XhoI fragment from pING4147 which contains the gpt gene encoding resistance to mycophenolic acid, the human Ig enhancer, the human cytomegalovirus promoter (CMV) and the mouse light chain 3' untranslated region and is identical to the vector, pING4144 as described in U.S. Pat. No. 5,420,019 and WO94/18323 (PCT/US94/01235) hereby incorporated by reference, except that it contains the codon for the native cysteine instead of an alanine at amino acid position 132 of the BPI gene.

Stable Transfection of Mammalian Cells for Expression of Nonglycosylated BPI

Mammalian cells are preferred hosts for production of rBPI protein analogs as described herein. Such cells permit proper secretion, folding, and post-translational modification of expressed proteins. Presently preferred mammalian host cells for production of BPI proteins include cells of fibroblast origin, such as CHO-K1 cells (ATCC CCL61), CHO-DG44 cells (a dihydrofolate reductase [DHFR] minus mutant of CHO Toronto obtained from Dr. Lawrence Chasin, Columbia University), CHO-DXB-11 (a DHFR⁻ mutant of CHO-K1 obtained from Dr. Lawrence Chasin), Vero Cells (ATCC CRL81) and Baby Hamster Kidney (BHK) cells (ATCC CRL6281) and cells of lymphoid origin, such as the hybridoma Sp2/O-Ag14 (ATCC CRL1581) or the myeloma, NSO (ECACC No. 85110503).

Transfection of mammalian cells can be accomplished by a variety of methods. Two of the most common approaches involve calcium phosphate precipitation of the expression vector DNA which is subsequently taken by the cells and electroporation, which causes the cells to take up the DNA through membrane pores created by the generation of a strong electric field. Selection for transfected cells is facilitated by the incorporation in the expression vector of a gene whose product allows the transfected cells to survive and grow under selective conditions. A number of such genes have been identified including, among others, the bacterial Tn5 neo gene, which encodes resistance to the antibiotic G418 and the *Escherichia coli* guanine phosphoribosyl transferase (gpt) gene, which encodes resistance to mycophenolic acid (MPA) in the presence of xanthine (Mulligan and Berg, *Proc. Natl. Acad. Sci.* 78:2072–2076 (1981)), the dihydrofolate reductase (DHFR) gene, which allows for growth of DHFR⁻ cells in the absence of nucleosides and gene amplification in the presence of increasing concentrations of methotrexate, the glutamine synthetase gene, which allows for growth of glutamine auxotrophs without glutamine and gene amplification in the presence of methionine sulfoximine and the *Salmonella typhimurium* hisD gene and the *E. coli* trpB gene (Hartman and Mulligan, *Proc. Natl. Acad. Sci.* 85: 8047–8051 (1988)), which allow growth in the presence of histidinol or without tryptophan (in the presence of indole), respectively. The availability of these selective markers provide significant flexibility for the generation of mammalian cell lines that express recombinant products, since they can be used either alone or in various combinations to provide cell lines with the highest possible productivity.

Transfection of CHO-K1 Cells with pING4322

The CHO-K1 cell line was maintained in Ham's F12 medium plus 10% fetal bovine serum (FBS). Media were supplemented with glutamine/penicillin/streptomycin (Irvine Scientific, Irvine, Calif.).

CHO-K1 cells were transfected by electroporation with 40 μg of pING4322 DNA that was first digested with PvuI, phenol-chloroform extracted and ethanol precipitated. Following the electroporation, the cells were allowed to recover for 24 hours in non-selective Ham's F12 medium. The cells were then trypsinized, resuspended at a concentration of $\sim 5 \times 10^4$ cells/ml in Ham's F12 medium supplemented with MPA (25 μg/mL) and xanthine (250 μg/mL) and plated at $\sim 10^4$ cells/well in 96 well plates. Untransfected CHO-K1 cells are unable to grow in this medium due to the inhibition of pyrimidine synthesis by the MPA. At ~2 weeks, colonies consisting of transfected cells were observed in the 96 well plates. Supernatants from wells containing single colonies were analyzed for the presence of BPI-reactive protein by anti-BPI ELISA using $BPI_{23}$ as a standard. In this assay, Immulon-II 96 well plates (Dynatech) were pre-coated with affinity purified rabbit anti-$BPI_{23}$ antiserum, followed by supernatant samples and detection was with affinity purified, biotinylated rabbit anti-$BPI_{23}$ antiserum followed by peroxidase-labeled aviden. A total of 100 colonies were screened in this manner. The top isolates were transferred to 24 well plates and productivity was assessed as follows. Cells were grown to confluence in a 24 well plate in Ham's F12 medium supplemented with 10% FBS. Once the cells reached confluence, the Ham's F12 medium was removed and 2 ml of HB-CHO serum free medium (Irvine Scientific) plus 40 μL of S-Sepharose beads (Pharmacia) were added. The cells were incubated for 7 days after which the S-Sepharose beads were removed and washed with 0.1 M NaCl in 10 mM Tris buffer (pH 7.5). BPI was eluted from the beads by addition of 1.0 M NaCl in Tris buffer. The top producers, designated Clones 37 and 91, secreted ~17 and 14 μg/ml, respectively in this assay and were frozen as Research Cell Bank numbers C2020 and C2021, respectively. Purified protein was prepared for crystallization studies as follows.

Production and Purification of Nonglycosylated rBPI

The host cells used to prepare protein for crystallization studies were CHO-K1 cells transformed with the DNA vector pING4322 which includes DNA encoding the 456 amino acids of human BPI preceded by its endogenous 31 residue secretory signal as described above. During post-translational secretory processing, the signal sequence residues were removed by the host cell. The desired expression product, nonglycosylated rBPI, was a biologically active variant of the human BPI molecule in which the amino acid serine at position 351 in the human BPI protein has been replaced with an alanine.

Forty roller bottles were prepared which contained the transfected CHO-K1 host cells at $1.3 \times 10^7$ cells per bottle in DME/F12 media supplemented with 5% fetal bovine serum (FBS). The cells were grown for three days, at which time 500 ml of fresh media, DME/F12 with 2.5% FBS was added along with a 10 ml slurry (approximately 8 gr.) of sterilized S-Sepharose (Pharmacia, fast flow #17-0511-01, Uppsula, Sweden) and 1 ml of a 1 M solution of sodium butyrate. After two days, the old media plus the S-Sepharose was removed and fresh media, S-Sepharose and sodium butyrate were added to each roller bottle. This process of harvesting the expressed protein product with S-Sepharose was repeated for a total of three harvests, and the S-Sepharose removed during each harvest was pooled. The use of S-Sepharose beads to capture recombinant BPI protein products has been described in U.S. Pat. No. 5,439,807 and WO93/23540 (PCT/US93/04752).

The expressed nonglycosylated rBPI protein was purified from the pooled S-Sepharose by first removing it from the S-Sepharose resin followed by further purification and concentration on a series of Q-Sepharose (Pharmacia, fast flow #17-0510-01) and CM-Spherodex (Sepracor, #273431, Villeneuve la Garenne, France) columns. Following purification, the protein was buffer exchanged utilizing a Sephacryl S-100 (Pharmacia, high resolution #17-0612-01) column.

Specifically, the pooled S-Sepharose resin from each harvest was allowed to settle for approximately 15 minutes. The media was removed by decanting and the settled resin was washed three times with approximately 400 ml of 20 mM MES, pH 6.8, 150 mM NaCl. For each wash, the buffer was added, the mixture was stirred gently and the resin was allowed to resettle for approximately 15 minutes. Each buffer wash was removed by decanting. The beads were then washed with 400 mL of 20 mM sodium acetate/acetic acid, 150 mM NaCl, pH 4.0 (acetate buffer), and then poured into a 2.5×50 cm liquid chromatography column (BIORAD, Econocolumn, Richmond, Calif.). The column was washed extensively with approximately 2 liters of 400 mM NaCl-acetate buffer, pH 4.0 until the A280 absorbance reading of the column eluate was equal to that of the buffer alone. The column was additionally washed with approximately 600 ml of 600 mM NaCl-acetate buffer until the A280 absorbance of the eluate was again equal to that of buffer alone. The protein was then eluted from the S-Sepharose in approximately 500 ml of 1.0 M NaCl-acetate buffer.

The S-Sepharose eluates from each harvest were pooled and diluted to a NaCl concentration of 300 mM. The diluted material was then loaded on to a two column, serial arrangement of a 100 ml Q-Sepharose column connected to a 12 ml CM-Spherodex column. Both columns were constructed using new, sterile resin and were pre-equilibrated with 20 mM MES, pH 5.5, 200 mM NaCl. The Q-Sepharose column served to remove any nucleic acid in the sample material, and the protein did not bind to this resin. After the approximate 3 liters of protein containing material had been loaded, the Q-Sepharose column was disconnected and the CM-Spherodex column was washed with buffer until the A280 absorbance of the eluate was the same as buffer alone. The protein was eluted from the column in 20 mM MES, 400 mM NaCl, pH 5.5 in a volume of approximately 180 ml. This eluted fraction was then reloaded on to a smaller (2 ml) CM-Spherodex column for protein concentration, and the bound protein removed in a single step of 20 mM MES, 1.2 M NaCl, pH 5.5 in a volume of approximately 12 mL. The protein was then loaded directly on to a 150 ml pyrogen-free Sephacryl S-100 column pre-equilibrated with 20 mM sodium citrate, 150 mM NaCl, pH 5.0 buffer. Column fractions were analyzed by Coommassie-stained (0.5% Coommassie Brilliant Blue-R, 25% isopropanol, 10% methanol, 10% acetic acid) SDS-PAGE and Western analysis. Western analysis was performed using a 1:1000 dilution of a rabbit anti-human BPI antisera. Fractions which contained the nonglycosylated rBPI protein were pooled and resulted in a final lot which was greater than 95% pure as analyzed by Coommassie-stained SDS-PAGE.

The protein samples thus prepared and purified were filtered and/or concentrated for crystallization studies of the purified nonglycosylated rBPI protein. Protein samples were optionally filtered using a 0.2 μm syringe filter (Millipore Corp., Bedford, Mass.) or a 0.2 μm Nalgene filter (Nalge Corp., Rochester, N.Y.) to remove precipitate. Protein samples were concentrated in a Centricon 10 (Amicon Corp., Beverly, Mass.) or a Centriprep 10 (Amicon Corp., Beverly, Mass.). For the Centricon 10 concentrators, a JA 20 rotor (Beckman, Fullerton, Calif.) in a J2-21 Beckman centrifuge was used at 6000 rpm for 60 minutes. For the Centriprep 10 concentrators, a swinging bucket rotor in a J-6B Beckman centrifuge was used at 3000 rpm for 60 minutes. Final volumes for various protein samples prepared for crystallization studies described herein ranged from about 0.1 to 1 mL, and the protein concentrations were generally between about 10 and 20 mg/mL. Protein solutions may be diluted or concentrated for crystallization studies.

EXAMPLE 2

Structure Determination of a Crystallized BPI Protein

Presented herein is the crystal structure of BPI and two bound phospholipids at 2.4 Å resolution. Our model provides the first structural information on the LPS-binding and lipid transport protein family and suggests a common mode of lipid binding for its members.

Purified, full-length, non-glycosylated, recombinant human BPI expressed in CHO cells was crystallized by hanging-drop vapor diffusion at room temperature. The protein concentration was 8.5 mg/ml and the crystallization buffer contained 12% (w/v) PEG 8000, 200 mM magnesium acetate, and 100 mM sodium cacodylate, pH 6.8. Two crystal forms with slightly different cell dimensions grew under the same conditions in space group $C_2$, with one molecule per asymmetric unit. Form 1 crystals were reproducible and had cell dimensions of a=185.0, b=37.2, c=84.3 Å, and β=101.3°. Form 2 crystals appeared rarely and had cell dimensions of a=185.6, b=33.0, c=85.2 Å, and β=101.6°.

Figure 3:
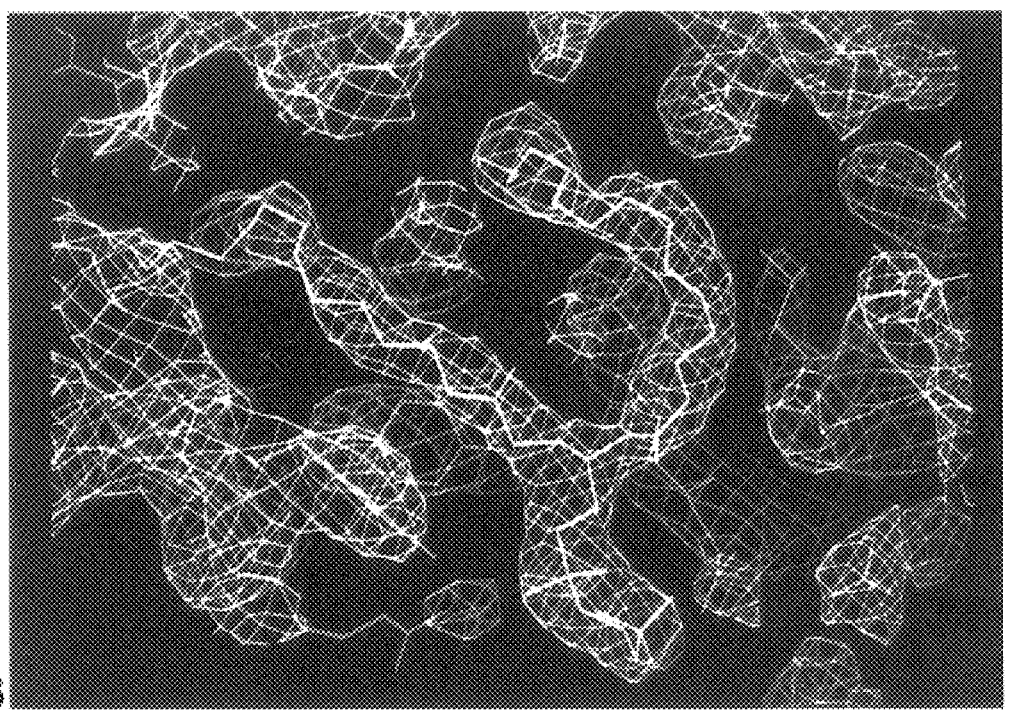
FIG. 3 Electron density (purple) of the final 2.8 Å MIR map contoured at 1.0 σ and superimposed on the refined model. The area shown is in the lipid binding pocket of the $NH_2$-terminal domain of BPI. The phosphatidylcholine is yellow and the surrounding protein atoms are green.

For Table 1, x-ray diffraction data were collected at room temperature with the R-AXIS IIC imaging plate area detector mounted on a Rigaku RU200 rotating anode x-ray generator. Data were processed with DENZO and SCALEPACK [Z. Otwinski, in *Proceedings of CCP4 Study Weekend: Data Collection and Processing*, L. Sawyer, N. Isaacs, S. Baileys, Eds. (SERC Daresbury Laboratory, Warrington, UK, 1993), pp. 56]. For form 1 crystals, a native data set to 2.8 Å was collected from a single crystal, which was 92.4% complete overall (84.9% complete with an average I/σ(I)=2.3 in the outermost resolution shell). A native data set to 2.4 Å for form 2 was collected from two crystals and was 92.7% complete overall (94.6% complete with an average I/σ(I)=2.6 in the outermost shell). Because they could be reliably reproduced, form 1 crystals were used for all heavy atom soaks. The structure was solved by multiple isomorphous replacement (MIR) with anomalous scattering. Heavy atom sites were identified by difference-Patterson and difference-Fourier maps. Phase refinement was performed with [Collaborative Computational Project No. 4, *Acta Crystallogr.*, D50:760 (1994)] producing a mean figure of merit (FOM) of 0.57. The MIR map (FIG. 3) was improved by density modification including solvent flattening, histogram matching, and phase extension using DM [Collaborative Computational Project No. 4, supra]. After a partial model was obtained with FRODO [T. A. Jones, *J. Appl. Crystallogr.*, 11:268 (1978)], phase combination was performed with SIGMAA [Collaborative Computational Project No. 4, supra] (final FOM=0.89). CMNP is chloro-Hg-nitrophenol; DMM is dimethyl mercury; PCMBS is parachloromercury-benzene sulfonate; TELA is triethyl lead acetate.

(1993)], VERIFY [R. Lüthy, J. U. Bowie, D. Eisenberg, *Nature*, 356:83 (1992)], and ERRAT [C. Colovos and T. Yeates, *Protein Sci.*, 2:1511 (1993)].

TABLE 2

REFINEMENT STATISTICS FOR FORM 2 CRYSTALS

| Data | |
|---|---|
| Resolution (Å) | 2.4 |
| Unique reflections (N) | 18,898 |
| Completeness (%) | 92.7 |
| Atoms in model | |
| Protein (non-hydrogen) | 3532 |
| Phosphatidylcholine | 102 |

TABLE 1

X-RAY DIFFRACTION DATA

| Item | Resolution (Å) | Data Completeness | Rsym* (%) | Sites (N) | RCullis† | Phasing Power | Mid‡ |
|---|---|---|---|---|---|---|---|
| Native 1 | 2.8 | 92.4 | 8.6 | | | | |
| Native 2 | 2.4 | 92.7 | 7.2 | | | | |
| CMNP§ | 3.2 | 84.8 | 6.1 | 1 | 66.0 | 2.04 | 0.15 |
| DMM‖ | 3.5 | 72.8 | 9.8 | 11 | 65.0 | 1.49 | 0.26 |
| PCMBS¶ | 3.1 | 66.4 | 9.4 | 3 | 77.0 | 1.27 | 0.38 |
| HgCl$_2$ | 3.0 | 86.5 | 6.9 | 1 | 49.0 | 2.13 | 0.18 |
| K$_2$PtCl$_4$ | 3.2 | 93.3 | 8.2 | 3 | 90.0 | 0.68 | 0.13 |
| K$_2$PtBr$_6$ | 3.1 | 94.8 | 5.8 | 3 | 73.0 | 0.88 | 0.14 |
| TELA# | 3.3 | 94.0 | 11.3 | 2 | 86.0 | 0.80 | 0.15 |
| TELA-HgCl$_2$ | 3.3 | 91.4 | 9.6 | 3 | 63.0 | 1.90 | 0.18 |
| Xenon | 3.4 | 98.2 | 18.9 | 5 | 87.0 | 0.69 | 0.18 |
| K$_3$UO$_2$F$_5$ | 3.0 | 75.0 | 8.6 | 2 | 65.0 | 1.40 | 0.16 |

*Rsym = 100 ($\Sigma_h$ | |$_h$ - <|> |)/($\Sigma$h |h) where <|> is the mean intensity of all symmetry-related reflections |h.
†R$_{Cullis}$ = ($\Sigma$|F$_{PH}$ +/- F$_P$| - F$_{H(calc)}$)/($\Sigma$|F$_{PH}$ +/- F$_P$|) for centric reflections, Phasing power = [$\Sigma$|F$_{H(calc)}$|$^2$]/($\Sigma$|F$_{PH(obs)}$ - F$_{PH(calc)}$|$^2$)½.
‡MID (mean isomorphous difference) = $\Sigma$|F$_{PH}$ - F$_P$|/$\Sigma$ F$_P$, where F$_{PH}$ is the derivative structure factor and F$_P$ is the native structure factor and the sum is over all reflections common to both data sets.
§CMNP, chloro-Hg-nitrophenol; ‖DMM, dimethyl mercury; ¶PCMBS, parachloromercurybenzene sulfonate; #TELA, triethyl lead acetate Table 2 relates to model refinement and statistics. The model was refined at 2.8 Å through iterative cycles of simulated-annealing with X-PLOR [A. T. Brünger and A. Krukowski, *Acta Crystallogr.*, A46:585 (1990)] and manual rebuilding. 10% of the data were set aside before refinement began for R$_{free}$ [A. T. Brünger *Nature*, 355:472 (1992)] calculations. When the model had been refined to an R-factor* of 20.4% (R$_{free}$=32.6%) with the 2.8 Å data, rigid-body minimization was performed against the 2.4 Å data set (R=29.8% to 3.5 Å after minimization). Additional cycles of simulated annealing, positional refinement, correlated individual temperature factor refinement, and manual rebuilding reduced the R-factor to 22.7% and R$_{free}$=31.3% (no intensity cutoff). An overall anisotropic temperature factor and bulk solvent correction were applied to the observed reflections when R$_{free}$ showed improvement. The model was confirmed by calculating simulated-annealing omit-maps for every part of the structure. The final model contains all 456 residues of the protein, 48 well-ordered waters, and 2 molecules of phosphatidylcholine. Regions of the backbone with poor electron density include residues 148, 232–236, 258–260, and parts of the loop between residues 281–311. Sidechains with poorly defined density were truncated to alanine. The model was examined by the programs PROCHECK [R. A. Laskowski, M. W. McArthur, D. S. Moss, J. M. Thornton, *J. Appl. Crystallogr.* 26:283

TABLE 2-continued

REFINEMENT STATISTICS FOR FORM 2 CRYSTALS

| Water | 48 |
|---|---|
| Refinement parameters | |
| Resolution range (Å) | 50.0–2.4 |
| R-factor* (%) | 22.7 |
| R$_{free}$(%) | 31.3 |
| Avg. atomic B factors | |
| Protein | 36.9 |
| Lipid N, C | 49.4, 51.0† |
| Waters | 44.6 |
| rms‡ deviation from ideality | |
| Bonds (Å) | 0.006 |
| Angles (deg) | 1.4 |
| Dihedrals (deg) | 26.0 |
| Impropers (deg) | 1.2 |

*R = 100 ($\Sigma$ | F$_{obs}$-F$_c$ |)/($\Sigma$ F$_{obs}$) where F$_{obs}$ and F$_c$ are the observed and calculated structure factors, respectively.
†B factors for the lipids bound in the NH$_2$— and COOH-terminal domains.
‡rms = root mean square BPI is a boomerang-shaped molecule with approximate dimensions of 135 by 35 by 35 Å (FIG. 1, A and B). It consists of two domains of similar size ($NH_2$- and COOH-terminal) that are connected by a proline-rich linker of 21 residues (positions 230 to 250). The two domains form three structural units; barrels are found at each end of the protein, and a central β sheet forms an interface between the barrels. The secondary structure and topology of the two domains are similar, giving the protein pseudo-twofold symmetry.

Figure 2:
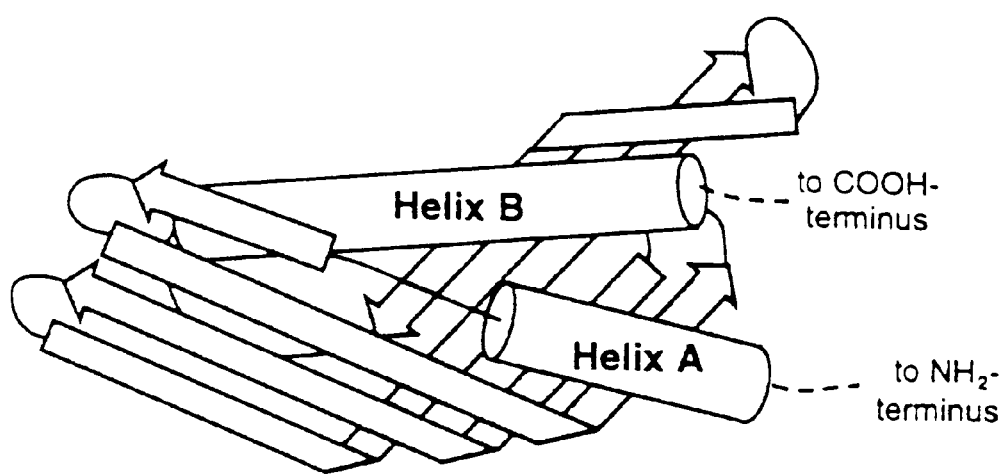
FIG. 2 (A) Schematic drawing of the novel BPI domain fold, shown in same orientation as the $NH_2$-terminal domain in FIG. 1B (B) Superposition of the $NH_2$- and COOH-terminal domains of BPI showing the overall topological similarity. Residues 1 to 230 are green, and 250 to 456 are blue. The $NH_2$-terminal domain is in the same orientation as FIG. 1A.
Figure 2:
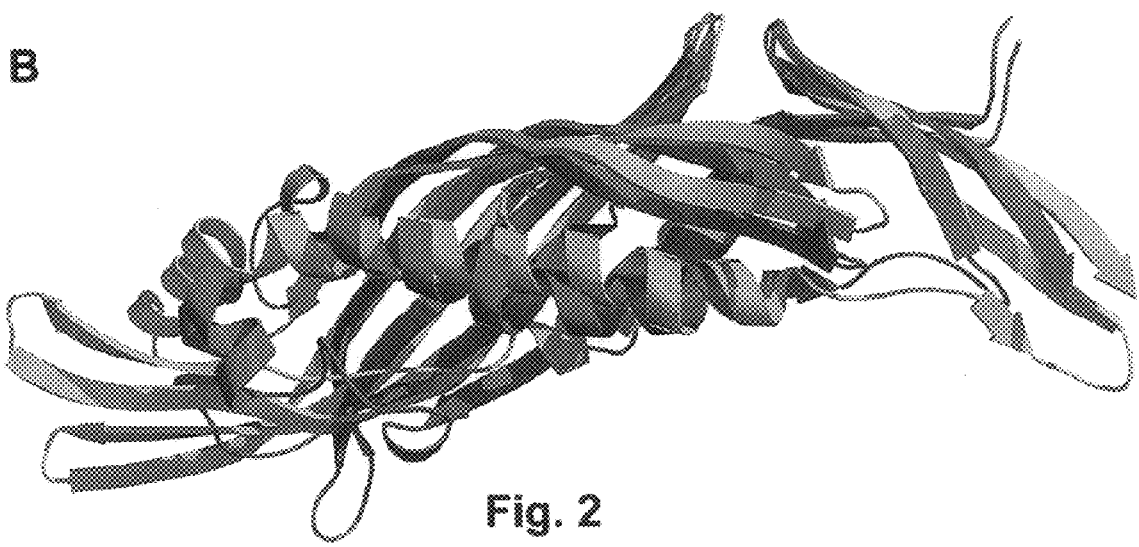

Each barrel (residues 10 to 193 and 260 to 421) contains three common structural elements: a short a helix, a five-stranded antiparallel β sheet, and a long helix (FIG. 2A), in that order. We call these elements helix A, sheet N and helix B in the $NH_2$-terminal domain, and helix A', sheet C and helix B' in the COOH-terminal domain. Sheets N and C have a series of β bulges that change the direction of their strands and cause a pronounced curve in the sheets. In each domain, the long helix lies along the concave face of the sheet, with the helical axis at ~60° to the strands of the β sheet. A single disulfide bond between $Cys^{135}$ and $Cys^{175}$ anchors helix B to the final strand of sheet N. Situated between the $NH_2$- and COOH-terminal barrels is a twisted, seven-stranded antiparallel β sheet composed of four strands from the $NH_2$-terminal domain and three strands from the COOH-terminal domain. This central sheet forms an interface between the two domains and is thus reminiscent of several dimer interfaces stabilized by hydrogen bonds between strands of a β sheet [M. Leeson, B. Henderson, J. Gillig, J. Schwab and J. Smith, *Structure*, 4:253 (1996); D. Ohlendorf, W. F. Anderson, M. Lewis, C. O. Pabo, B. W. Matthews, *J. Mol. Biol.*, 169:757 (1983); G. N. Reeke, J. W. Becker, G. M. Edelman, *J. Biol. Chem.*, 250:1525 (1975)].

The structural similarity of the two domains of BPI is shown by the superposition [G. H. Cohen, *J. Mol. Biol.*, 190:593 (1986)] in FIG. 2B; they are related by a rotation of 173° and have a root mean square deviation (rmsd) of 3.0 Å on the basis of superposition of 169 Cα pairs. The structure shared by these two domains does not resemble other protein folds; several structural alignment programs [N. N. Alexandrov and D. Fischer, *Proteins*, 25:354 (1996); D. Fischer, C. J. Tsai, R. Nussinov, *Protein Eng.*, 8:981 (1995); L. Holm, C. Sander, *Nucl. Acids Res.*, 22:3600 (1996)] failed to reveal a significant match to any known folds. Significant differences between the superimposed domains are found in two loop regions containing residues 45 and 96 in the $NH_2$-terminal domain and residues 280 and 348 in the COOH-terminal domain. These differences may be functionally important because the loops around residues 45 and 96 in the $NH_2$-terminal domain have been implicated in LPS binding and bactericidal activity (see below). This structural similarity of the two domains was unexpected, not only because of their lack of significant sequence identity (<20%), but also because of their functional differences. The $NH_2$-terminal domain of BPI is cationic and retains the bactericidal, LPS-binding, and LPS-neutralization activities of the intact protein [A. H. Horwitz, et al., *Protein Expr. and Purif.*, 8:28 (1996); C. E. Ooi, J. Weiss, P. Elsbach, B. Frangione and B. Mannion, *J. Biol. Chem.*, 262:14891–14894 (1987); C. E. Ooi, J. Weiss, M. E. Doerfier and P. Elsbach, *J. Exp. Med.*, 174:649 (1991)]. The COOH-terminal domain is essentially neutral and shows limited LPS-neutralization activity [S. L. Abrahamson et al., *J. Biol. Chem.*, 272:2149 (1997)]. However, the structural similarity of the two domains may reflect a previously undetected functional similarity: each domain contains a binding pocket for a phospholipid.

After the amino acid sequence had been traced in the electron density maps, two regions of extended electron density remained that could not be accounted for by protein atoms. This density, found in the interior of both domains, was present in the multiple isomorphous replacement (MIR) maps (FIG. 3) at an intensity similar to that of the protein density, and it became the predominant feature in $F_{obs}-F_{calc}$ maps after sequence fitting (both form 1 and form 2 crystals). Electrospray mass spectrometry of the sample used for crystallization revealed two molecules, with relative molecular masses of 522 and 787, in approximately equal amounts. Tandem mass spectrometric analysis was consistent with the two species being phosphoglycerides containing a phosphatidylcholine head group and either one or two 18-carbon acyl chains with one double bond. Phosphatidylcholine (FIG. 4A) is abundant in eukaryotic cells and is presumably bound by BPI in the cells from which the protein is isolated.

Figure 4:
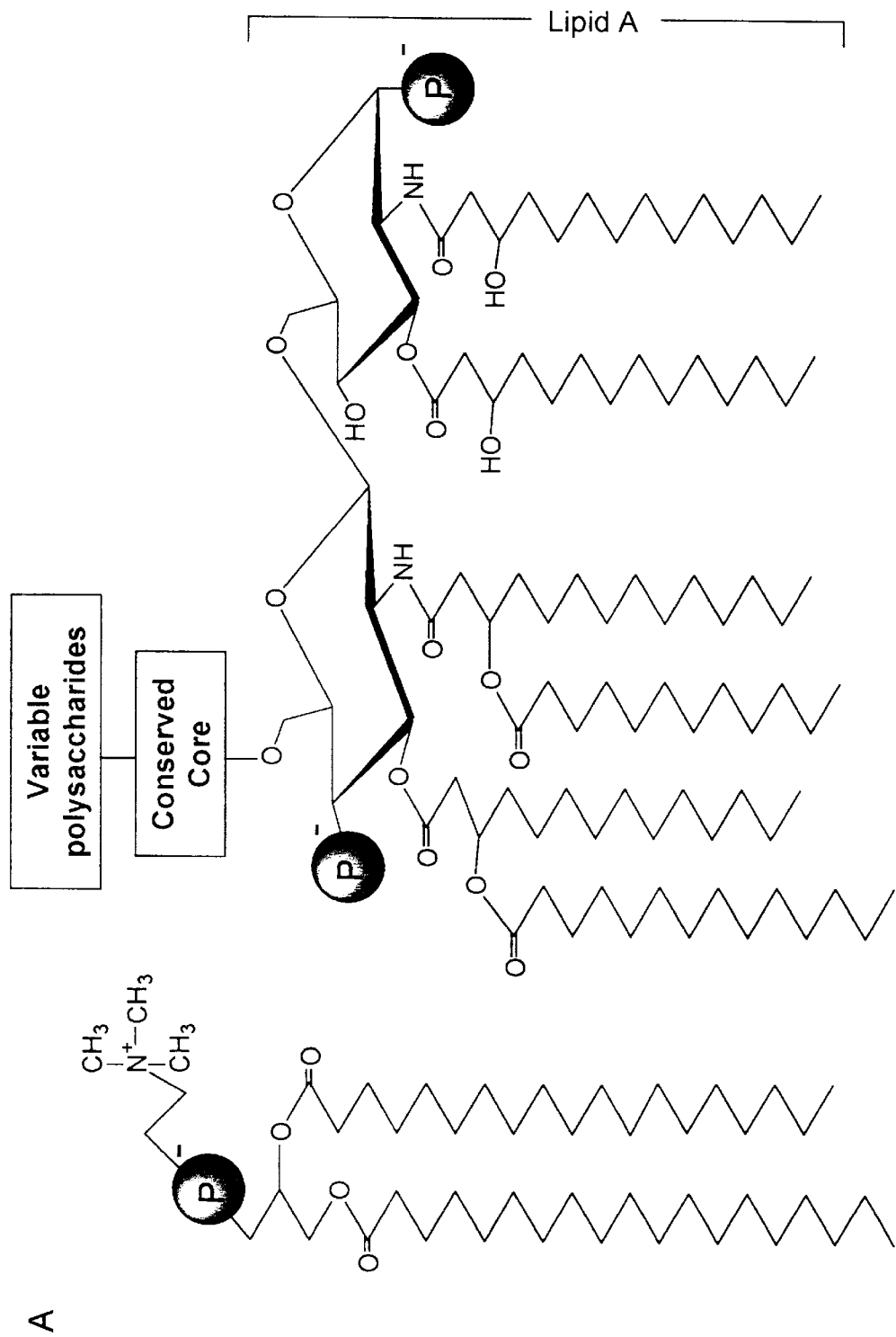
FIG. 4 (A) The covalent structure of phosphatidylcholine and the lipid A region of LPS from *E. coli* and *S. typhimurium*. Phosphate groups are indicated by P. Adapted with changes from [C. R. H. Raetz, *Annu. Rev. Biochem,* 59:129 (1990)]. (B) Slice through the interior of BPI showing the lipid binding pocket in the $NH_2$-terminal domain. The solvent accessible surface of the protein was calculated without lipid present and is shown in white, the interior of the protein is green, and the phosphatidylcholine is purple. Protein residues are shown as ball-and-stick in yellow. Figure produced with MSP [M. L. Connolly, *Science,* 221:709 (1983); M. L. Connolly, *J. Am. Chem. Soc.,* 107:1118 (1985)].
Figure 4:
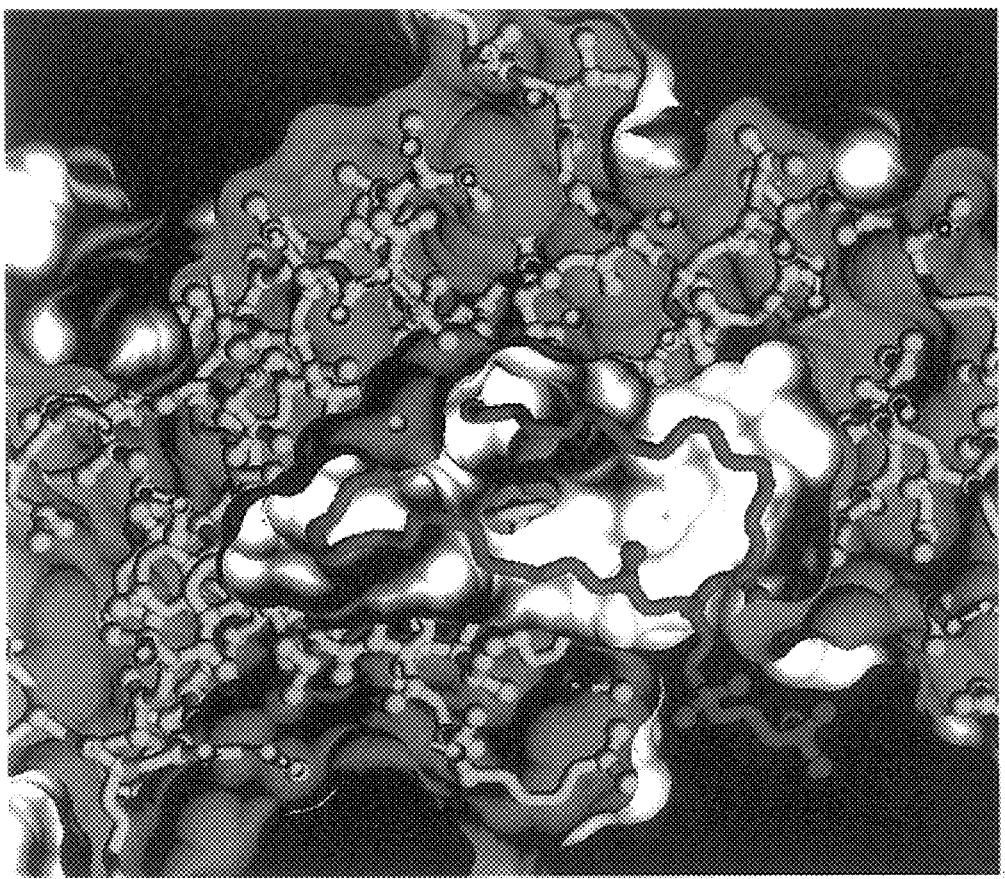

The two lipids are bound in extensive apolar pockets on the concave surface of the boomerang, situated between the $NH_2$-terminal and COOH-terminal barrels and the central β sheet. In the $NH_2$-terminal domain, the entrance to the pocket is formed by helices A and B. The back and sides are formed by sheet N and the central sheet. The two acyl chains insert ~15 Å into the interior of the protein and are surrounded by apolar side chains (FIG. 4B). The head group lies at the entrance of the pocket and is exposed to solvent. The pocket in the COOH-terminal domain, which has a slightly larger opening, is formed by the analogous secondary structures. Both basic and acidic side chains found near the entrances of the pockets are available for electrostatic interactions with the zwitterionic head group. When the lipids are removed from the model, the pocket in $NH_2$-terminal domain has a solvent accessible surface area [M. L. Connolly, *Science*, 221:709 (1983); M. L. Connolly, *J. Am. Chem. Soc.*, 107:1118 (1985)] of 557 $Å^2$, and the pocket in the COOH-terminal domain has an area of 413 $Å^2$, for a total of 970 $Å^2$. The intensity of the electron density for the two acyl chains in both pockets is similar and does not indicate whether the single acyl chain species is found predominantly in either pocket.

The discovery of bound phospholipid in our structure suggests a possible site of interaction between BPI and LPS. As seen in FIG. 4A, phosphatidylcholine and LPS share some structural similarity, including negatively charged phosphate groups and, most notably, acyl chains. Since BPI's function is to bind a lipid, LPS, and since lipid is bound in pockets of BPI, it seems reasonable that the acyl chains of LPS bind in the apolar pockets. The following observations support his hypothesis: i) the acyl chains of lipid A are known to be essential for binding by BPI [H. Gazzano-Santoro et al., *Infection and Immunity*, 63:2201 (1995)]; ii) the binding pockets of BPI are reminiscent of cavities in other lipid-binding proteins [L. Banaszak et al., *Adv. Protein Chem.*, 45:89 (1994)]; and iii) BPI has a significant sequence similarity to two lipid transfer proteins (see below).

Our proposed site of interaction between BPI and the acyl chains of LPS differs from that suggested by previous work focusing on the $NH_2$-terminal domain. Fragments containing the $NH_2$-terminal domain of BPI have been identified with equivalent or greater bactericidal and LPS-binding activities relative to the full-length protein [A. H. Horwitz, et al., *Protein Expression and Purification*, 8:28 (1996); C. E. Ooi, J. Weiss, M. E. Doerfler and P. Elsbach, *J. Exp. Med.*, 174:649 (1991)]. The activity of one $NH_2$-terminal fragment was reduced when residues past positions 12 or between positions 169 and 199 were deleted [C. Capodici and J. Weiss, *J. Immunol.*, 156:4789 (1996)]. The structure shows that these deletions affect elements of the barrel (at the beginning of helix A and from the middle to the end of helix B) and could significantly alter its structure. While the barrel seems to be the minimal structural unit with full activity, three smaller regions of this domain retain significant LPS-binding, LPS-neutralization, and bactericidal activity [R. G. Little, D. N. Kelner, E. Lim, D. J. Burke and P. J. Conlon, *J. Biol. Chem.*, 268:1865 (1994)]: residues 17–45 (most of helix A and the first β strand of sheet N), residues 82–108 (a β hairpin [residues 82 to 106 of BPI show limited sequence similarity with residues 32 to 51 of the limulus anti-LPS factor (LALF), and have been predicted to form an amphipathic β hairpin similar to that seen in the LALF structure [A. Hoess, S. Watson, G. R. Silber and R. Liddington, *EMBO* 12:3351 (1993)]. Although this region of BPI does form a β hairpin, the strict amphipathic character of the loop seen in LALF is not maintained, and a structural superposition shows that the sequence of BPI must be shifted by one residue relative to the proposed sequence alignment] between strands 3 and 4 of sheet N), and residues 142–169 (a segment preceding and including part of helix B). These three regions include 18 basic residues (and only 4 acidic residues) and form a positively charged tip on the $NH_2$-terminal domain (on the left of FIG. 1) which may make favorable electrostatic interactions with negatively charged groups of LPS. Further studies are necessary to determine the relative importance of the apolar pockets and positively charged $NH_2$-terminal tip to BPI's LPS-binding and bactericidal activities.

BPI is the first member of the mammalian LPS-binding and lipid transfer family to have its three-dimensional structure determined. BPI and LBP are related to two lipid transfer proteins, cholesteryl ester transfer protein (CETP) and phospholipid transfer protein (PLTP) [A. Tall, *Annu. Rev. Biochem.*, 64:235 (1995)]. Alignment of the amino acid sequences of human BPI, LBP, CETP, and PLTP with BPI's secondary structure (FIG. 5) shows that structurally important residues are conserved in the four proteins. The two cysteines that form the single disulfide bond and are critical to the function of BPI [A. H. Horwitz, et al., *Protein Expression and Purification*, 8:28 (1996)] are completely conserved. Also, the pattern of hydrophobic/hydrophilic residues in the β strands indicates that the β bulges responsible for the extensive sheet twisting are preserved. The conserved sequences strongly suggest that members of the LPS-binding and lipid transfer family share BPI's two-domain structure and that the two domains are similar in topology.

It is likely that the lipid transfer proteins will also share the apolar binding pockets found in BPI. Striking parallels are found between our BPI-phosphatidylcholine structure and previous work showing that CETP copurifies with an equimolar amount of phosphatidylcholine [A. Tall, *Annu. Rev. Biochem.*, 64:235 (1995)] and has two distinct binding sites [S. Wang, L. Deng, R. W. Milne and A. R. Tall, *J. Biol. Chem.*, 267:17487 (1992)]—one for neutral lipids and another for phospholipids. The known ligands of CETP and PLTP (cholesteryl esters, triglycerides, retinyl esters and phospholipids) all contain at least one acyl chain which could bind in apolar pockets similar to those in BPI, suggesting a common mode of ligand binding in this family. Sequestration of these hydrophobic chains in interior pockets may be critical to the function of the lipid transfer proteins: transfer of apolar ligands in an aqueous environment. Thus, the structure of BPI illuminates the action of the plasma lipid transfer proteins, as well as offering possibilities for how BPI and LBP interact with LPS.

EXAMPLE 3

Molecular Modeling of BPI Ligands and Mimetics

We have used the information derived from the X-ray crystal structure of BPI presented herein, along with the teachings of the art, including, for example, WO94/20532 (PCT/US94/02465) to design various BPI-related proteins and peptides. These constructs may be divided into categories as illustrated below, including peptides and proteins, including fragments, analogs and variants of the protein, since they best describe the different ways in which different domains and portions may be assembled to achieve new molecules.

1. Individual Peptide Domains

The overlapping BPI peptide data indicated that the N-terminal domain of BPI contains at least three independent functional domains that have one or more of the biological activities of BPI, including, for example, antibacterial, antifungal, anti-heparin and anti-angiogenic activities. Domain I is a region of amino acid residues from about 17 to about 45; Domain II is a region of amino acid residues from about 65 to about 99; and Domain III is a region of amino acid residues from about 142 to about 169. Hundreds of peptide sequences derived from these domains have been synthesized, including addition, deletion and substitution variants of the domain-derived sequences. Through further refinements, smaller "core" regions within these domains have been identified that still retain high levels of activity; for example, within Domain II residues 90–99 and within Domain III residues 148–161.

These peptides have included linear molecules that may or may not assume a conformation that maximally express activity. From the X-ray structure data, segments of BPI are designed that should preserve the three-dimensional structure of these domains when constructed outside the context of the intact protein. For example, both Domains I and II contain hairpin loop structures that are positioned adjacent to one another in space on the proximal tip of the molecule. In contrast, although Domain III is a helix+turn and not a loop, extensions from both ends of the domain are positioned near enough to each other to consider linking them together. As a result, peptides can be designed that reflect these structures by replacing selected residues in synthetic or recombinant peptides with cysteines, so as to create disulfide-stablized domain mimetics. Since this approach is based upon the actual structure of BPI, it differs from those of other groups that are based upon putative alignments between BPI and the structure of proteins such as the Limulus amoebocyte lysate factor (LALF). As examples of these embodiments, listed below are a series of exemplary peptides that, with cysteines added to the N- and C-terminus could assume structures similar to those seen in the intact protein: from Domain I: residues 36–54; from Domain II: residues 84–109, 85–108, 86–107, 87–106, 88–105, 89–104, or 90–103; and from Domain III: residues 142–164.

2. Peptide Domain Hybrids

It has also been demonstrated that certain peptide domain hybrids, which include repeats of the same sequence from a single domain or inter-domain comnination of sequences, have enhanced activities. For example, linking Domain II- and III-derived peptides (such as XMP.29: 85–99::148–161) has enhanced biological activity. Interestingly, these domains in the crystal structure are closely associated in space, and peptide XMP.29 may represent a Domain II::III hybrid that actually shares some structural similarity to the intact protein. Based upon the X-ray structure, a Domain II-III peptide that consists of approximately residues 90–103::146–162 is contructed. Such a peptide may even more closely mimic what is seen in the protein.

3. BPI "Tip" Mimetics

As discussed above, portions of all three peptide domains discovered and described in WO94/20532 come together on the proximal tip of the N-terminal fragment. As a result, a BPI "tip" mimetic is designed that essentially "slices" off the most extreme tip of the molecule but preserves the critical domain elements. Such a slice would lack the hydrophobic pockets found in the intact protein, but may exhibit activities beyond those of the individual segments. The following segments represent such a "slice" of the three peptide domains. However, to best preserve the geometry between the domains, it would be desirable to insert "linker" sequences between them so as to ensure proper positioning. By fixing these segments in space, programs such as InsightII (Molecular Simulations, Inc.) can identify possible linker sequences by i) searching protein databases for similar structures or ii) de novo designing appropriate linkers. In this regard it may be desirable to utilize residues that are not readily susceptible to proteolysis (Ala, Ser, Gly, etc.), or to utilize amino acids like Pro that impose additional spatial constraints on peptide structure. An exemplary peptide consists of Domain I-II-III-derived elements: 37–54:90–104:144–162.

Similarly, by analogy with the above-described cyclic domain structures, the fact that residues 37 and 162 are positioned near each other in the protein suggests that a cyclic tip mimetic could be created by replacing these residues with cysteines, for example, Cys::38–54:90–104:144–161::Cys.

4. Extended N-terminal Domains of BPI

The three dimensional structure of BPI indicates that the molecule, which forms N- and C-terminal domains, can be divided into three structural units as described in Example 2. Two of these units represent the N- and C-terminal "barrels" that are formed by residues 10–193 and 260–421, respectively, whereas the third element is a central β sheet structure that forms the interface between the two barrels. Of interest is the fact that the two bound phospholipids in BPI occupy spaces between the two barrel structures and the central β sheet. As a result, the recombinant BPI protein product rBPI$_{21}$, which essentially contains residues 1–193 lacks some of the structural components necessary to form a complete hydrophobic pocket. A new molecule is constructed that encodes residues 1 to approximately 260 which would contain most of the residues necessary to form a complete hydrophobic pocket.

5. Mutants for Immobilizing rBPI$_{21}$

One application for BPI protein products is their use as affinity removal ligands for endotoxin in solution. For example, immobilizing a BPI protein on a column or membrane matrix would allow removal of endotoxin from endotoxin-contaminated solutions by simply passing those solutions over the immobilized BPI protein. Some of the cysteine-mutated peptides described above may be useful for this purpose, as well as rBPI$_{23}$. Alternatively, in order to selectively couple a stable, readily produced protein like rBPI$_{21}$ to a column or membrane, a cysteine could be added to the N- or C-terminus, thus allowing site-specific conjugation and selective orientation of the binding "tip" away from the solid support. Such a construct is alternatively constructed by adding a short linker segment (such as Gly-Gly-Gly-Ser) to the C-terminal residue of the BPI protein product, for example, residue 193 of rBPI(1–193), followed by a cysteine residue. Such a construct would have a high probability of folding correctly, given the domain nature of residues 1–193, and be readily conjugatable. Similarly, a series of new conjugates between rBPI(1–193)C and other thiol-containing proteins or molecules is created for the purposes of evaluating new molecules.

6. New N-terminal Dimeric Molecules

As an extension of the above analysis, a new series of N-terminal dimeric molecules can be constructed that take better advantage of the hydrophobic pockets. For example, by replacing the C-terminal barrel with another copy of the N-terminal barrel, an analog of BPI would be created that contains two functional barrels and possibly two functional hydrophobic pockets. One such dimer could be constructed by replacing residues 260–456 with residues 1–193. Alternatively, other more central locations may be identified within the β sheet structure where symmetry would dictate additional and even better points for duplication.

7. C-terminal Fusion Proteins

The C-terminal domains of LBP and CETP appear to mediate interactions with CD14 and lipoproteins. Similarly, the C-terminal domain of BPI has LPS binding and neutralization activities. As a consequence, the C-terminal barrel of BPI (or other family members) could be fused to barrels or domains of other family members and/or to other proteins to alter/modify/enhance their action.

8. Homology Modeling of BPI Family Members

The BPI coordinates have been useful in the generation of molecular models of other members of the BPI protein family. Utilizing CLUSTAL (a multiple sequence alignment program in PC-Gene) and the Homology module (a structure-based homology modeling program in InsightII on the SGI), molecular models (and the corresponding three-dimensional coordinates files) of lipopolysaccharide binding protein (LBP), cholesteryl ester transfer protein (CETP) and phospholipid transfer protein (PLTP) have been generated. With these files, existing mutants are mapped and new ones designed. Published data [Wang et al., *Biochemistry* 30:3484–3490, (1991)] indicate that insertional alterations in three locations of CETP severely impaired cholesteryl ester transfer activity: residues 48–53, residue 165, and residues 373–379. Since residues 48–53 and residue 165 of CETP coincide structurally with Domains I and III of BPI respectively, the functional domain structure of BPI extends to the other protein family members. Similarly, by virtue of the symmetry between the N- and C-terminal domains, it is likely that the corresponding residues on the C-terminal tip of BPI are involved in recognizing receptors and/or interacting with lipoproteins.

9. Lipid Pocket Mutants

A detailed compilation of the residues in BPI which form the pockets is described in Table 3 as follows. Column 1 of Table 3 indicates the residue name and number. Column 2 shows checked residues which indicate the residues that show a change in solvent accessible surface area with lipid binding. Column 3 shows checked residues that indicate the residues that have some atom within 4 Å of a lipid atom. If the contact is to the head-group of the lipid, the residues are listed at the end, under ENTRY ONLY. Column 4 indicates conservation in 3 BPI and 4 LBP sequences, e.g., for Ile 68, in 3 of the 7 sequences, the residue is similarly Ile; for the other 4 sequences, the residue is Leu (see also column 5). Column 5 indicates alternative residues which occur in BPI or LBP at that position for the 7 BPI and LBP sequences analyzed. Column 6 indicates residues for mutations to block the pockets, using residues selected to be well-conserved (especially in the N-terminal domain) and relatively small. The suggested mutations are all to large sidechains in order to decrease the size of the pocket by as much as possible.

TABLE 3

| Residue[1] | ΔSA[2] | Within 4Å[3] | Conservation[4] | Alternatives[5] | Mutations[6] |
|---|---|---|---|---|---|
| N-TERMINAL POCKET - residues contributing to interior | | | | | |
| Val 7 | √ | √ | 2/7 | A,T | |
| Ile 9 | √ | √ | All | | W |
| Gly 13 | √ | √ | All | | |
| Leu 14 | √ | | All | | |
| Tyr 16 | √ | | All | | |
| Ala 17 | √ | √ | All | | F |
| Ser 18 | √ | √ | 1/7 | C,A | |
| Gly 21 | √ | √ | All | | F |
| Ala 24 | √ | √ | 4/7 | V,T,S | Y,H |
| Leu 25 | √ | | All | | |
| Ile 68 | √ | √ | 3/7 | L | |
| Leu 76 | √ | √ | All | | |
| Phe 78 | √ | √ | 1/7 | V,L | |
| Leu 117 | √ | √ | All | | |
| Leu 119 | √ | | All | | |
| Pro 128 | √ | | 5/7 | A,S | |
| Ile 130 | √ | | 1/7 | V | |
| Val 178 | √ | | 2/7 | L,I | |
| Val 182 | √ | | All | | |
| Glu 185 | √ | √ | 1/7 (allele) | K,D,H | |
| Leu 186 | √ | √ | All | | W |
| Tyr 189 | √ | | All | | |
| Phe 190 | √ | √ | 2/7 | V,L | |
| Leu 193 | √ | √ | All | | |
| Leu 220 | √ | √ | All | | |
| Val 222 | √ | | 5/7 | M,W | |
| Val 254 | √ | √ | 6/7 | I | |
| Leu 256 | √ | | 3/7 | F | |
| Pro 428 | √ | √ | All | | |
| Thr 429 | √ | √ | 1/7 | M,L | |
| Pro 430 | √ | √ | 5/7 | L | |
| Val 433 | √ | | 3/7 | I | |
| Leu 435 | √ | | All | | |
| Val 453 | √ | | 6/7 | I | |
| ENTRY ONLY | | | | | |
| Gln 20 | √ | √ | 3/7 | E | |
| Lys 27 | √ | √ | 3/7 | R,S | |
| Glu 28 | √ | | 6/7 | K | |
| Arg 31 | √ | | 2/7 | K,E | |
| Ser 181 | √ | √ | 5/7 | T,A | |
| Arg 432 | √ | √ | 3/7 | K,Y,H | |
| Tyr 455 | √ | √ | 6/7 | H | |
| C-TERMINAL POCKET - residues contributing to interior | | | | | |
| Phe 263 | √ | √ | All | | |
| Asn 264 | √ | | All | | |
| Ala 266 | √ | √ | All | | F |
| Gly 267 | √ | √ | 2/7 | A,S,T, | |
| Val 275 | √ | √ | 1/7 | A,Y | |
| Leu 276 | √ | √ | 5/7 | F,W | F,W |
| Lys 277 | √ | | 1/7 | G,N | |
| Met 278 | √ | √ | 1/7 | L,F | |
| Val 318 | √ | | 1/7 | L,I,G | |
| Ala 320 | √ | | 2/7 | V | |
| Pro 324 | √ | | 6/7 | Q | |
| Leu 326 | √ | √ | 6/7 | V | |
| Phe 335 | √ | √ | 1/7 | L,V,E | |
| Pro 337 | √ | √ | 5/7 | A,F | |
| Val 339 | √ | | 2/7 | L,M | |
| Met 360 | √ | √ | 2/7 | L,V | |
| Thr 362 | √ | | 5/7 | L | |
| Val 368 | √ | √ | 2/7 | I,L | |
| Leu 375 | √ | √ | 3/7 | I,V | |
| Val 376 | √ | √ | 2/7 | I,T | |
| Gly 377 | √ | | All | | |
| Leu 379 | √ | √ | All | | |
| Leu 381 | √ | √ | 3/7 | P | |
| Val 409 | √ | √ | 1/7 | L,M,I | |
| Val 413 | √ | √ | 1/7 | F,L | F |
| Val 417 | √ | √ | 3/7 | I,F | W |
| Lys 420 | √ | √ | 5/7 | E | Y,H |
| Leu 421 | √ | √ | 5/7 | I,F | |
| Phe 425 | √ | √ | 6/7 | L | |
| ENTRY ONLY | | | | | |
| Asp 200 | √ | | All | | |
| Ser 201 | √ | √ | 4/7 | K,T,N | |
| Val 202 | √ | | 4/7 | F,I | |
| Tyr 270 | √ | √ | All | | |
| Arg 416 | √ | √ | 1/7 | K,V,D | |
| Lys 423 | √ | | 3/7 | R,E,Q | |

[1]Residue name and number.
[2]Checked residues show a change in solvent accessible surface area with lipid binding.
[3]Checked residues have some atom within 4 Å of a lipid atom (if the contact is to the head group of the lipid, the residues are listed at the end, under ENTRY ONLY).
[4]Conservation in 3 BPI and 4 LBP sequences, e.g., for Ile 68, in 3 of the 7 sequences, the residue is similarly Ile; for the other 4 sequences, the residue is Leu (see note 5).
[5]Indicates alternative residues which occur in BPI or LBP at that position for the 7 BPI and LBP sequences analyzed.
[6]Indicates residues for mutations to block the pockets using residues selected to be well-conserved (especially in the N-terminal domain) and relatively small. The suggested mutations are all to large sidechains in order to decrease the size of the pocket by as much as possible.

10. Organomimetics

Molecular modelling of BPI as described herein is useful for the preparation of organomimetics such as "surface" mimetics. As one example, organomimetics are prepared based on "tip" mimetics in which the three-dimensional coordinates of the tip, as described above, are used to create a "surface" (or complementary pocket) into which a computer program builds an organic molecule with similar characteristics.

Numerous modifications and variations in the practice of the invention are expected to occur to those skilled in the art upon consideration of the foregoing description and the presently preferred embodiments thereof. Consequently, the scope of the present invention is to be defined by the appended claims.

What is claimed is:

1. A method for identifying a mutant of a bactericidal/permeability-increasing (BPI) protein with modified activity, wherein the activity is selected from the group consisting of antibacterial, heparin-binding and endotoxin-binding, said method comprising:
   a. constructing a three-dimensional structure of the BPI protein defined by the atomic coordinates shown in FIG. 6;
   b. employing said three-dimensional structure and modeling methods to identify a mutation site that contributes to said activity of said mutant;
   c. producing said mutant;
   d. assaying said mutant to determine said modified activity of said mutant, wherein the activity is selected from the group consisting of antibacterial, heparin-binding, and endotoxin-binding.

2. The method according to claim 1, wherein said mutation site is located in a binding site.

3. The method according to claim 2, wherein said mutation site is selected from one or more of the amino acid residues of a binding pocket defined in column 1 of FIG. 8.

4. The method according to claim 2, wherein said mutation site is selected from one or more amino acid residues selected from positions about 17 to about 45, positions about 65 to about 99, or positions about 142 to about 169 of BPI of SEQ ID NO: 2.

5. The method according to claim 2, wherein said mutation site is selected from one or more amino acid residues selected from column 1 of FIG. 8 and selected from positions about 17 to about 45, positions about 65 to about 99, or positions about 142 to about 169 of BPI of SEQ ID NO: 2.

6. A method for identifying a mutant of bactericidal/permeability-increasing (BPI) protein with modified endotoxin-binding or heparin-binding activity, said method comprising:
   a. constructing a three-dimensional structure of the BPI protein defined by the atomic coordinates shown in FIG. 6;
   b. employing said three-dimensional structure and modeling methods to identify a mutation site that contributes to said activity of said mutant, and wherein said mutation site is selected from one or more amino acid residues of a binding pocket defined in column 1 of FIG. 8 or selected from positions about 17 to about 45, positions about 65 to about 99, or positions about 142 to about 169 of BPI of SEQ ID NO: 2;
   c. producing said mutant;
   d. contacting said mutant with said endotoxin or heparin to determine said modified binding activity.

* * * * *

SEQUENCE LISTING

<160> NUMBER OF SEQ ID NOS: 14

<210> SEQ ID NO 1
<211> LENGTH: 1813
<212> TYPE: DNA
<213> ORGANISM: Human

```
<220> FEATURE:
<221> NAME/KEY: CDS
<222> LOCATION: (31)..(1491)
<220> FEATURE:
<221> NAME/KEY: mat_peptide
<222> LOCATION: (124)..(1491)
<220> FEATURE:
<223> OTHER INFORMATION: "rBPI"

<400> SEQUENCE: 1
```

| | | |
|---|---|---|
| caggccttga ggttttggca gctctggagg atg aga gag aac atg gcc agg ggc<br>                                         Met Arg Glu Asn Met Ala Arg Gly<br>                                             -30                 -25 | 54 | |
| cct tgc aac gcg ccg aga tgg gtg tcc ctg atg gtg ctc gtc gcc ata<br>Pro Cys Asn Ala Pro Arg Trp Val Ser Leu Met Val Leu Val Ala Ile<br>        -20                 -15                 -10 | 102 | |
| ggc acc gcc gtg aca gcg gcc gtc aac cct ggc gtc gtg gtc agg atc<br>Gly Thr Ala Val Thr Ala Ala Val Asn Pro Gly Val Val Val Arg Ile<br>    -5                  -1   1               5 | 150 | |
| tcc cag aag ggc ctg gac tac gcc agc cag cag ggg acg gcc gct ctg<br>Ser Gln Lys Gly Leu Asp Tyr Ala Ser Gln Gln Gly Thr Ala Ala Leu<br>    10                  15                  20                  25 | 198 | |
| cag aag gag ctg aag agg atc aag att cct gac tac tca gac agc ttt<br>Gln Lys Glu Leu Lys Arg Ile Lys Ile Pro Asp Tyr Ser Asp Ser Phe<br>                30                  35                  40 | 246 | |
| aag atc aag cat ctt ggg aag ggg cat tat agc ttc tac agc atg gac<br>Lys Ile Lys His Leu Gly Lys Gly His Tyr Ser Phe Tyr Ser Met Asp<br>            45                  50                  55 | 294 | |
| atc cgt gaa ttc cag ctt ccc agt tcc cag ata agc atg gtg ccc aat<br>Ile Arg Glu Phe Gln Leu Pro Ser Ser Gln Ile Ser Met Val Pro Asn<br>        60                  65                  70 | 342 | |
| gtg ggc ctt aag ttc tcc atc agc aac gcc aat atc aag atc agc ggg<br>Val Gly Leu Lys Phe Ser Ile Ser Asn Ala Asn Ile Lys Ile Ser Gly<br>    75                  80                  85 | 390 | |
| aaa tgg aag gca caa aag aga ttc tta aaa atg agc ggc aat ttt gac<br>Lys Trp Lys Ala Gln Lys Arg Phe Leu Lys Met Ser Gly Asn Phe Asp<br>90                  95                  100                 105 | 438 | |
| ctg agc ata gaa ggc atg tcc att tcg gct gat ctg aag ctg ggc agt<br>Leu Ser Ile Glu Gly Met Ser Ile Ser Ala Asp Leu Lys Leu Gly Ser<br>                110                 115                 120 | 486 | |
| aac ccc acg tca ggc aag ccc acc atc acc tgc tcc agc tgc agc agc<br>Asn Pro Thr Ser Gly Lys Pro Thr Ile Thr Cys Ser Ser Cys Ser Ser<br>            125                 130                 135 | 534 | |
| cac atc aac agt gtc cac gtg cac atc tca aag agc aaa gtc ggg tgg<br>His Ile Asn Ser Val His Val His Ile Ser Lys Ser Lys Val Gly Trp<br>        140                 145                 150 | 582 | |
| ctg atc caa ctc ttc cac aaa aaa att gag tct gcg ctt cga aac aag<br>Leu Ile Gln Leu Phe His Lys Lys Ile Glu Ser Ala Leu Arg Asn Lys<br>    155                 160                 165 | 630 | |
| atg aac agc cag gtc tgc gag aaa gtg acc aat tct gta tcc tcc aag<br>Met Asn Ser Gln Val Cys Glu Lys Val Thr Asn Ser Val Ser Ser Lys<br>170                 175                 180                 185 | 678 | |
| ctg caa cct tat ttc cag act ctg cca gta atg acc aaa ata gat tct<br>Leu Gln Pro Tyr Phe Gln Thr Leu Pro Val Met Thr Lys Ile Asp Ser<br>                190                 195                 200 | 726 | |
| gtg gct gga atc aac tat ggt ctg gtg gca cct cca gca acc acg gct<br>Val Ala Gly Ile Asn Tyr Gly Leu Val Ala Pro Pro Ala Thr Thr Ala<br>            205                 210                 215 | 774 | |
| gag acc ctg gat gta cag atg aag ggg gag ttt tac agt gag aac cac<br>Glu Thr Leu Asp Val Gln Met Lys Gly Glu Phe Tyr Ser Glu Asn His<br>        220                 225                 230 | 822 | |

|  |  |  |  |  |  |  |  |  |  |  |  |  |  |  |  |
|---|---|---|---|---|---|---|---|---|---|---|---|---|---|---|---|
| cac | aat | cca | cct | ccc | ttt | gct | cca | cca | gtg | atg | gag | ttt | ccc | gct | gcc | 870
| His | Asn | Pro | Pro | Pro | Phe | Ala | Pro | Pro | Val | Met | Glu | Phe | Pro | Ala | Ala |
|     |     | 235 |     |     |     |     | 240 |     |     |     |     | 245 |     |     |     |

```
cac aat cca cct ccc ttt gct cca cca gtg atg gag ttt ccc gct gcc      870
His Asn Pro Pro Pro Phe Ala Pro Pro Val Met Glu Phe Pro Ala Ala
        235                 240                 245 cat gac cgc atg gta tac ctg ggc ctc tca gac tac ttc ttc aac aca      918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga      966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc     1014
Asp Asp Met Ile Pro Lys Glu Ser Lys Phe Arg Leu Thr Thr Lys Phe
            285                 290                 295 ttt gga acc ttc cta cct gag gtg gcc aag aag ttt ccc aac atg aag     1062
Phe Gly Thr Phe Leu Pro Glu Val Ala Lys Lys Phe Pro Asn Met Lys
        300                 305                 310 ata cag atc cat gtc tca gcc tcc acc ccg cca cac ctg tct gtg cag     1110
Ile Gln Ile His Val Ser Ala Ser Thr Pro Pro His Leu Ser Val Gln
    315                 320                 325 ccc acc ggc ctt acc ttc tac cct gcc gtg gat gtc cag gcc ttt gcc     1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac     1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga     1254
Thr Thr Gly Ser Met Glu Val Ser Ala Glu Ser Asn Arg Leu Val Gly
            365                 370                 375 gag ctc aag ctg gat agg ctg ctc ctg gaa ctg aag cac tca aat att     1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta     1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc     1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag     1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa         1491
Pro His Gln Asn Phe Leu Leu Phe Gly Ala Asp Val Val Tyr Lys
            445                 450                 455 tgaaggcacc agggtgccg gggctgtca gccgcacctg ttcctgatgg gctgtggggc    1551
accggctgcc tttccccagg gaatcctctc cagatcttaa ccaagagccc cttgcaaact    1611
tcttcgactc agattcagaa atgatctaaa cacgaggaaa cattattcat tggaaaagtg    1671
catggtgtgt attttaggga ttatgagctt ctttcaaggg ctaaggctgc agagatattt    1731
cctccaggaa tcgtgtttca attgtaacca agaaatttcc atttgtgctt catgaaaaaa    1791
aacttctggt ttttttcatg tg                                              1813

<210> SEQ ID NO 2
<211> LENGTH: 487
<212> TYPE: PRT
<213> ORGANISM: Human

<400> SEQUENCE: 2

Met Arg Glu Asn Met Ala Arg Gly Pro Cys Asn Ala Pro Arg Trp Val
    -30                 -25                 -20
```

-continued

```
Ser Leu Met Val Leu Val Ala Ile Gly Thr Ala Val Thr Ala Ala Val
-15              -10                  -5                  -1   1

Asn Pro Gly Val Val Arg Ile Ser Gln Lys Gly Leu Asp Tyr Ala
            5                   10                  15

Ser Gln Gly Thr Ala Ala Leu Gln Lys Glu Leu Lys Arg Ile Lys
        20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
               100                 105                 110

Ser Ala Asp Leu Lys Leu Gly Ser Asn Pro Thr Ser Gly Lys Pro Thr
           115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
```

-continued

```
                 405                 410                 415
Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
    435                 440                 445

Gly Ala Asp Val Val Tyr Lys
450                 455

<210> SEQ ID NO 3
<211> LENGTH: 24
<212> TYPE: DNA
<213> ORGANISM: Human
<220> FEATURE:
<223> OTHER INFORMATION: BPI-53

<400> SEQUENCE: 3
actggttcca tggaggtcag cgcc                                              24

<210> SEQ ID NO 4
<211> LENGTH: 29
<212> TYPE: DNA
<213> ORGANISM: Human
<220> FEATURE:
<223> OTHER INFORMATION: BPI-54

<400> SEQUENCE: 4
gacagatctc tcgagtcatt tatagacaa                                         29

<210> SEQ ID NO 5
<211> LENGTH: 42
<212> TYPE: DNA
<213> ORGANISM: Human
<220> FEATURE:
<223> OTHER INFORMATION: oligonucleotide from XcmI site to SphI site
      within BPI gene (encoding residues 348-361) containing
      the codon TCC for the serine at amino acid
      position 351

<400> SEQUENCE: 5
cccaactcct ccctggcttc cctcttcctg attggcatgc ac                          42

<210> SEQ ID NO 6
<211> LENGTH: 42
<212> TYPE: DNA
<213> ORGANISM: Human
<220> FEATURE:
<223> OTHER INFORMATION: Oligonucleotide complementary to SEQ ID NO:5

<400> SEQUENCE: 6
gggttcagga gggaccgaag ggagaaggac taaccgtacg tg                          42

<210> SEQ ID NO 7
<211> LENGTH: 14
<212> TYPE: PRT
<213> ORGANISM: Human
<220> FEATURE:
<223> OTHER INFORMATION: "wild type" amino acid sequence of residues
      348-361 in BPI

<400> SEQUENCE: 7

Pro Asn Ser Ser Leu Ala Ser Leu Phe Leu Ile Gly Met His
  1               5                  10

<210> SEQ ID NO 8
<211> LENGTH: 42
```

```
<212> TYPE: DNA
<213> ORGANISM: Human
<220> FEATURE:
<223> OTHER INFORMATION: oligonucleotide from XcmI site to SphI site
      within the BPI gene (encoding residues 348-361)
      containing the codon GCC for alanine at amino acid
      position 351

<400> SEQUENCE: 8
cccaactccg ccctggcttc cctcttcctg attggcatgc ac                         42

<210> SEQ ID NO 9
<211> LENGTH: 42
<212> TYPE: DNA
<213> ORGANISM: Human
<220> FEATURE:
<223> OTHER INFORMATION: Oligonucleotide complementary to SEQ ID NO:8

<400> SEQUENCE: 9
gggttcaggc gggaccgaag ggagaaggac taaccgtacg tg                         42

<210> SEQ ID NO 10
<211> LENGTH: 14
<212> TYPE: PRT
<213> ORGANISM: Human
<220> FEATURE:
<223> OTHER INFORMATION: "nonglycosylated" amino acid sequence of
      residues 348-361 in BPI

<400> SEQUENCE: 10

Pro Asn Ser Ala Leu Ala Ser Leu Phe Leu Ile Gly Met His
 1               5                  10

<210> SEQ ID NO 11
<211> LENGTH: 456
<212> TYPE: PRT
<213> ORGANISM: Human
<220> FEATURE:
<223> OTHER INFORMATION: bactericidal/permeability-increasing protein
      (BPI) (Figure 5)

<400> SEQUENCE: 11

Val Asn Pro Gly Val Val Val Arg Ile Ser Gln Lys Gly Leu Asp Tyr
 1               5                  10                  15

Ala Ser Gln Gln Gly Thr Ala Ala Leu Gln Lys Glu Leu Lys Arg Ile
                20                  25                  30

Lys Ile Pro Asp Tyr Ser Asp Ser Phe Lys Ile Lys His Leu Gly Lys
            35                  40                  45

Gly His Tyr Ser Phe Tyr Ser Met Asp Ile Arg Glu Phe Gln Leu Pro
        50                  55                  60

Ser Ser Gln Ile Ser Met Val Pro Asn Val Gly Leu Lys Phe Ser Ile
 65                 70                  75                  80

Ser Asn Ala Asn Ile Lys Ile Ser Gly Lys Trp Lys Ala Gln Lys Arg
                85                  90                  95

Phe Leu Lys Met Ser Gly Asn Phe Asp Leu Ser Ile Glu Gly Met Ser
            100                 105                 110

Ile Ser Ala Asp Leu Lys Leu Gly Ser Asn Pro Thr Ser Gly Lys Pro
        115                 120                 125

Thr Ile Thr Cys Ser Ser Cys Ser Ser His Ile Asn Ser Val His Val
    130                 135                 140

His Ile Ser Lys Ser Lys Val Gly Trp Leu Ile Gln Leu Phe His Lys
145                 150                 155                 160
```

```
Lys Ile Glu Ser Ala Leu Arg Asn Lys Met Asn Ser Gln Val Cys Glu
                165                 170                 175

Lys Val Thr Asn Ser Val Ser Ser Glu Leu Gln Pro Tyr Phe Gln Thr
            180                 185                 190

Leu Pro Val Met Thr Lys Ile Asp Ser Val Ala Gly Ile Asn Tyr Gly
        195                 200                 205

Leu Val Ala Pro Pro Ala Thr Thr Ala Glu Thr Leu Asp Val Gln Met
    210                 215                 220

Lys Gly Glu Phe Tyr Ser Glu Asn His His Asn Pro Pro Phe Ala
225                 230                 235                 240

Pro Pro Val Met Glu Phe Pro Ala Ala His Asp Arg Met Val Tyr Leu
                245                 250                 255

Gly Leu Ser Asp Tyr Phe Phe Asn Thr Ala Gly Leu Val Tyr Gln Glu
            260                 265                 270

Ala Gly Val Leu Lys Met Thr Leu Arg Asp Asp Met Ile Pro Lys Glu
        275                 280                 285

Ser Lys Phe Arg Leu Thr Thr Lys Phe Phe Gly Thr Phe Leu Pro Glu
    290                 295                 300

Val Ala Lys Lys Phe Pro Asn Met Lys Ile Gln Ile His Val Ser Ala
305                 310                 315                 320

Ser Thr Pro Pro His Leu Ser Val Gln Pro Thr Gly Leu Thr Phe Tyr
                325                 330                 335

Pro Ala Val Asp Val Gln Ala Phe Ala Val Leu Pro Asn Ser Ser Leu
            340                 345                 350

Ala Ser Leu Phe Leu Ile Gly Met His Thr Thr Gly Ser Met Glu Val
        355                 360                 365

Ser Ala Glu Ser Asn Arg Leu Val Gly Glu Leu Lys Leu Asp Arg Leu
    370                 375                 380

Leu Leu Glu Leu Lys His Ser Asn Ile Gly Pro Phe Pro Val Glu Leu
385                 390                 395                 400

Leu Gln Asp Ile Met Asn Tyr Ile Val Pro Ile Leu Val Leu Pro Arg
                405                 410                 415

Val Asn Glu Lys Leu Gln Lys Gly Phe Pro Leu Pro Thr Pro Ala Arg
            420                 425                 430

Val Gln Leu Tyr Asn Val Val Leu Gln Pro His Gln Asn Phe Leu Leu
        435                 440                 445

Phe Gly Ala Asp Val Val Tyr Lys
    450                 455

<210> SEQ ID NO 12
<211> LENGTH: 456
<212> TYPE: PRT
<213> ORGANISM: Human
<220> FEATURE:
<223> OTHER INFORMATION: lipopolysaccharide binding protein (LBP)
      (Figure 5)

<400> SEQUENCE: 12

Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
        35                  40                  45

Gly Arg Tyr Glu Phe His Ser Leu Asn Ile His Ser Cys Glu Leu Leu
    50                  55                  60
```

-continued

His Ser Ala Leu Arg Pro Val Pro Gly Gln Gly Leu Ser Leu Ser Ile
 65                  70                  75                  80

Ser Asp Ser Ser Ile Arg Val Gln Gly Arg Trp Lys Val Arg Lys Ser
                 85                  90                  95

Phe Phe Lys Leu Gln Gly Ser Phe Asp Val Ser Val Lys Gly Ile Ser
            100                 105                 110

Ile Ser Val Asn Leu Leu Gly Ser Glu Ser Ser Gly Arg Pro Thr
            115                 120                 125

Val Thr Ala Ser Ser Cys Ser Ser Asp Ile Ala Asp Val Glu Val Asp
    130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile Asp Ser Phe Ala Asp Ile Asp Tyr Ser Leu Val
        195                 200                 205

Glu Ala Pro Arg Ala Thr Ala Gln Met Leu Glu Val Met Phe Lys Gly
    210                 215                 220

Glu Ile Phe His Arg Asn His Arg Ser Pro Val Thr Leu Leu Ala Ala
225                 230                 235                 240

Val Met Ser Leu Pro Glu Glu His Asn Lys Met Val Tyr Phe Ala Ile
                245                 250                 255

Ser Asp Tyr Val Phe Asn Thr Ala Ser Leu Val Tyr His Glu Glu Gly
            260                 265                 270

Tyr Leu Asn Phe Ser Ile Thr Asp Asp Met Ile Pro Pro Asp Ser Asn
        275                 280                 285

Ile Arg Leu Thr Thr Lys Ser Phe Arg Pro Phe Val Pro Arg Leu Ala
    290                 295                 300

Arg Leu Tyr Pro Asn Met Asn Leu Glu Leu Gln Gly Ser Val Pro Ser
305                 310                 315                 320

Ala Pro Leu Leu Asn Phe Ser Pro Gly Asn Leu Ser Val Asp Pro Tyr
                325                 330                 335

Met Glu Ile Asp Ala Phe Val Leu Leu Pro Ser Ser Ser Lys Glu Pro
            340                 345                 350

Val Phe Arg Leu Ser Val Ala Thr Asn Val Ser Ala Thr Leu Thr Phe
        355                 360                 365

Asn Thr Ser Lys Ile Thr Gly Phe Leu Lys Pro Gly Lys Val Lys Val
    370                 375                 380

Glu Leu Lys Glu Ser Lys Val Gly Leu Phe Asn Ala Glu Leu Leu Glu
385                 390                 395                 400

Ala Leu Leu Asn Tyr Tyr Ile Leu Asn Thr Phe Tyr Pro Lys Phe Asn
                405                 410                 415

Asp Lys Leu Ala Glu Gly Phe Pro Leu Pro Leu Leu Lys Arg Val Gln
            420                 425                 430

Leu Tyr Asp Leu Gly Leu Gln Ile His Lys Asp Phe Leu Phe Leu Gly
        435                 440                 445

Ala Asn Val Gln Tyr Met Arg Val
    450                 455

<210> SEQ ID NO 13
<211> LENGTH: 476

```
<212> TYPE: PRT
<213> ORGANISM: Human
<220> FEATURE:
<223> OTHER INFORMATION: phospholipid transfer protein (PLTP) (Figure 5)

<400> SEQUENCE: 13
```

| | | | | | | | | | | | | | | | |
|---|---|---|---|---|---|---|---|---|---|---|---|---|---|---|---|
| Glu | Phe | Pro | Gly | Cys | Lys | Ile | Arg | Val | Thr | Ser | Lys | Ala | Leu | Glu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Val | Lys | Gln | Glu | Gly | Leu | Arg | Phe | Leu | Glu | Gln | Glu | Leu | Glu | Thr | Ile |
| | | | 20 | | | | | 25 | | | | | 30 | | |

| | | | | | | | | | | | | | | | |
|---|---|---|---|---|---|---|---|---|---|---|---|---|---|---|---|
| Thr | Ile | Pro | Asp | Leu | Arg | Gly | Lys | Glu | Gly | His | Phe | Tyr | Tyr | Asn | Ile |
| | | 35 | | | | | 40 | | | | | 45 | | | |

| | | | | | | | | | | | | | | | |
|---|---|---|---|---|---|---|---|---|---|---|---|---|---|---|---|
| Ser | Glu | Val | Lys | Val | Thr | Glu | Leu | Gln | Leu | Thr | Ser | Ser | Glu | Leu | Asp |
| | 50 | | | | | 55 | | | | | 60 | | | | |

| | | | | | | | | | | | | | | | |
|---|---|---|---|---|---|---|---|---|---|---|---|---|---|---|---|
| Phe | Gln | Pro | Gln | Gln | Glu | Leu | Met | Leu | Gln | Ile | Thr | Asn | Ala | Ser | Leu |
| 65 | | | | | 70 | | | | | 75 | | | | | 80 |

| | | | | | | | | | | | | | | | |
|---|---|---|---|---|---|---|---|---|---|---|---|---|---|---|---|
| Gly | Leu | Arg | Phe | Arg | Arg | Gln | Leu | Leu | Tyr | Trp | Phe | Phe | Tyr | Asp | Gly |
| | | | | 85 | | | | | 90 | | | | | 95 | |

| | | | | | | | | | | | | | | | |
|---|---|---|---|---|---|---|---|---|---|---|---|---|---|---|---|
| Gly | Tyr | Ile | Asn | Ala | Ser | Ala | Glu | Gly | Val | Ser | Ile | Arg | Thr | Gly | Leu |
| | | | 100 | | | | | 105 | | | | | 110 | | |

| | | | | | | | | | | | | | | | |
|---|---|---|---|---|---|---|---|---|---|---|---|---|---|---|---|
| Glu | Leu | Ser | Arg | Asp | Pro | Ala | Gly | Arg | Met | Lys | Val | Ser | Asn | Val | Ser |
| | | 115 | | | | | 120 | | | | | 125 | | | |

| | | | | | | | | | | | | | | | |
|---|---|---|---|---|---|---|---|---|---|---|---|---|---|---|---|
| Cys | Gln | Ala | Ser | Val | Ser | Arg | Met | His | Ala | Ala | Phe | Gly | Gly | Thr | Phe |
| 130 | | | | | 135 | | | | | 140 | | | | | |

| | | | | | | | | | | | | | | | |
|---|---|---|---|---|---|---|---|---|---|---|---|---|---|---|---|
| Lys | Lys | Val | Tyr | Asp | Phe | Leu | Ser | Thr | Phe | Ile | Thr | Ser | Gly | Met | Arg |
| 145 | | | | | 150 | | | | | 155 | | | | | 160 |

| | | | | | | | | | | | | | | | |
|---|---|---|---|---|---|---|---|---|---|---|---|---|---|---|---|
| Phe | Leu | Leu | Asn | Gln | Gln | Ile | Cys | Pro | Val | Leu | Tyr | His | Ala | Gly | Thr |
| | | | | 165 | | | | | 170 | | | | | 175 | |

| | | | | | | | | | | | | | | | |
|---|---|---|---|---|---|---|---|---|---|---|---|---|---|---|---|
| Val | Leu | Leu | Asn | Ser | Leu | Leu | Asp | Thr | Val | Pro | Val | Arg | Ser | Ser | Val |
| | | | 180 | | | | | 185 | | | | | 190 | | |

| | | | | | | | | | | | | | | | |
|---|---|---|---|---|---|---|---|---|---|---|---|---|---|---|---|
| Asp | Glu | Leu | Val | Gly | Ile | Asp | Tyr | Ser | Leu | Met | Lys | Asp | Pro | Val | Ala |
| | | 195 | | | | | 200 | | | | | 205 | | | |

| | | | | | | | | | | | | | | | |
|---|---|---|---|---|---|---|---|---|---|---|---|---|---|---|---|
| Ser | Thr | Ser | Asn | Leu | Asp | Met | Asp | Phe | Arg | Gly | Ala | Phe | Phe | Pro | Leu |
| | 210 | | | | | 215 | | | | | 220 | | | | |

| | | | | | | | | | | | | | | | |
|---|---|---|---|---|---|---|---|---|---|---|---|---|---|---|---|
| Thr | Glu | Arg | Asn | Trp | Ser | Leu | Pro | Asn | Arg | Ala | Val | Glu | Pro | Gln | Leu |
| 225 | | | | | 230 | | | | | 235 | | | | | 240 |

| | | | | | | | | | | | | | | | |
|---|---|---|---|---|---|---|---|---|---|---|---|---|---|---|---|
| Gln | Glu | Glu | Glu | Arg | Met | Val | Tyr | Val | Ala | Phe | Ser | Glu | Phe | Phe | Phe |
| | | | | 245 | | | | | 250 | | | | | 255 | |

| | | | | | | | | | | | | | | | |
|---|---|---|---|---|---|---|---|---|---|---|---|---|---|---|---|
| Asp | Ser | Ala | Met | Glu | Ser | Tyr | Phe | Arg | Ala | Gly | Ala | Leu | Gln | Leu | Leu |
| | | | 260 | | | | | 265 | | | | | 270 | | |

| | | | | | | | | | | | | | | | |
|---|---|---|---|---|---|---|---|---|---|---|---|---|---|---|---|
| Leu | Val | Gly | Asp | Lys | Val | Pro | His | Asp | Leu | Asp | Met | Leu | Leu | Arg | Ala |
| | | 275 | | | | | 280 | | | | | 285 | | | |

| | | | | | | | | | | | | | | | |
|---|---|---|---|---|---|---|---|---|---|---|---|---|---|---|---|
| Thr | Tyr | Phe | Gly | Ser | Ile | Val | Leu | Leu | Ser | Pro | Ala | Val | Ile | Asp | Ser |
| | 290 | | | | | 295 | | | | | 300 | | | | |

| | | | | | | | | | | | | | | | |
|---|---|---|---|---|---|---|---|---|---|---|---|---|---|---|---|
| Pro | Leu | Lys | Leu | Glu | Leu | Arg | Val | Leu | Ala | Pro | Pro | Arg | Cys | Thr | Ile |
| 305 | | | | | 310 | | | | | 315 | | | | | 320 |

| | | | | | | | | | | | | | | | |
|---|---|---|---|---|---|---|---|---|---|---|---|---|---|---|---|
| Lys | Pro | Ser | Gly | Thr | Thr | Ile | Ser | Val | Thr | Ala | Ser | Val | Thr | Ile | Ala |
| | | | | 325 | | | | | 330 | | | | | 335 | |

| | | | | | | | | | | | | | | | |
|---|---|---|---|---|---|---|---|---|---|---|---|---|---|---|---|
| Leu | Val | Pro | Pro | Asp | Gln | Pro | Glu | Val | Gln | Leu | Ser | Ser | Met | Thr | Met |
| | | | 340 | | | | | 345 | | | | | 350 | | |

| | | | | | | | | | | | | | | | |
|---|---|---|---|---|---|---|---|---|---|---|---|---|---|---|---|
| Asp | Ala | Arg | Leu | Ser | Ala | Lys | Met | Ala | Leu | Arg | Gly | Lys | Ala | Leu | Arg |
| | | 355 | | | | | 360 | | | | | 365 | | | |

| | | | | | | | | | | | | | | | |
|---|---|---|---|---|---|---|---|---|---|---|---|---|---|---|---|
| Thr | Gln | Leu | Asp | Leu | Arg | Arg | Phe | Arg | Ile | Tyr | Ser | Asn | His | Ser | Ala |
| 370 | | | | | 375 | | | | | 380 | | | | | |

-continued

```
Leu Glu Ser Leu Ala Leu Ile Pro Leu Gln Ala Pro Leu Lys Thr Met
385                 390                 395                 400

Leu Gln Ile Gly Val Met Pro Met Leu Asn Glu Arg Thr Trp Arg Gly
            405                 410                 415

Val Gln Ile Pro Leu Pro Glu Gly Ile Asn Phe Val His Glu Val Val
            420                 425                 430

Thr Asn His Ala Gly Phe Leu Thr Ile Gly Ala Asp Leu His Phe Ala
            435                 440                 445

Lys Gly Leu Arg Glu Val Ile Glu Lys Asn Arg Pro Ala Asp Val Arg
450                 455                 460

Ala Ser Thr Ala Pro Thr Pro Ser Thr Ala Ala Val
465                 470                 475

<210> SEQ ID NO 14
<211> LENGTH: 470
<212> TYPE: PRT
<213> ORGANISM: Human
<220> FEATURE:
<223> OTHER INFORMATION: cholesteryl ester transfer protein (CETP)
      (Figure 5)

<400> SEQUENCE: 14

His Glu Ala Gly Ile Val Cys Arg Ile Thr Lys Pro Ala Leu Leu Val
1               5                   10                  15

Leu Asn His Glu Thr Ala Lys Val Ile Gln Thr Ala Phe Gln Arg Ala
            20                  25                  30

Ser Tyr Pro Asp Ile Thr Gly Glu Lys Ala Met Met Leu Leu Gly Gln
        35                  40                  45

Val Lys Tyr Gly Leu His Asn Ile Gln Ile Ser His Leu Ser Ile Ala
    50                  55                  60

Ser Ser Gln Val Glu Leu Val Glu Ala Lys Ser Ile Asp Val Ser Ile
65                  70                  75                  80

Gln Asn Val Ser Val Val Phe Lys Gly Thr Leu Lys Tyr Gly Tyr Thr
                85                  90                  95

Thr Ala Trp Trp Leu Gly Ile Asp Gln Ser Ile Asp Phe Glu Ile Asp
            100                 105                 110

Ser Ala Ile Asp Leu Gln Ile Asn Thr Gln Leu Thr Cys Asp Ser Gly
        115                 120                 125

Arg Val Arg Thr Asp Ala Pro Asp Cys Tyr Leu Ser Phe His Lys Leu
    130                 135                 140

Leu Leu His Leu Gln Gly Glu Arg Glu Pro Gly Trp Ile Lys Gln Leu
145                 150                 155                 160

Phe Thr Asn Phe Ile Ser Phe Thr Leu Lys Leu Val Leu Lys Gly Gln
                165                 170                 175

Ile Cys Lys Glu Ile Asn Val Ile Ser Asn Ile Met Ala Asp Phe Val
            180                 185                 190

Gln Thr Arg Ala Ala Ser Ile Leu Ser Asp Gly Asp Ile Gly Val Asp
        195                 200                 205

Ile Ser Leu Thr Gly Asp Pro Val Ile Thr Ala Ser Tyr Leu Glu Ser
    210                 215                 220

His His Lys Gly His Phe Ile Tyr Lys Asn Val Ser Glu Asp Leu Pro
225                 230                 235                 240

Leu Pro Thr Phe Ser Pro Thr Leu Leu Gly Asp Ser Arg Met Leu Tyr
                245                 250                 255

Phe Trp Phe Ser Glu Arg Val Phe His Ser Leu Ala Lys Val Ala Phe
            260                 265                 270
```

-continued

```
Gln Asp Gly Arg Leu Met Leu Ser Leu Met Gly Asp Glu Phe Lys Ala
        275                 280                 285

Val Leu Glu Thr Trp Gly Phe Asn Thr Asn Gln Glu Ile Phe Gln Glu
        290                 295                 300

Val Val Gly Gly Phe Pro Ser Gln Ala Gln Val Thr Val His Cys Leu
305                     310                 315                 320

Lys Met Pro Lys Ile Ser Cys Gln Asn Lys Gly Val Val Val Asn Ser
                325                 330                 335

Ser Val Met Val Lys Phe Leu Phe Pro Arg Pro Asp Gln Gln His Ser
            340                 345                 350

Val Ala Tyr Thr Phe Glu Glu Asp Ile Val Thr Thr Val Gln Ala Ser
        355                 360                 365

Tyr Ser Lys Lys Lys Leu Phe Leu Ser Leu Leu Asp Phe Gln Ile Thr
        370                 375                 380

Pro Lys Thr Val Ser Asn Leu Thr Glu Ser Ser Glu Ser Ile Gln
385                 390                 395                 400

Ser Phe Leu Gln Ser Met Ile Thr Ala Val Gly Ile Pro Glu Val Met
                405                 410                 415

Ser Arg Leu Glu Val Val Phe Thr Ala Leu Met Asn Ser Lys Gly Val
            420                 425                 430

Ser Leu Phe Asp Ile Ile Asn Pro Glu Ile Ile Thr Arg Asp Gly Phe
        435                 440                 445

Leu Leu Leu Gln Met Asp Phe Gly Phe Pro Glu His Leu Leu Val Asp
    450                 455                 460

Phe Leu Gln Ser Leu Ser
465                 470
```